(12) United States Patent
Matsumoto et al.

(10) Patent No.: US 10,414,761 B2
(45) Date of Patent: **\*Sep. 17, 2019**

(54) CYCLOPROPANAMINE COMPOUND AND USE THEREOF

(71) Applicant: Takeda Pharmaceutical Company Limited, Osaka-shi, Osaka (JP)

(72) Inventors: Shigemitsu Matsumoto, Kanagawa (JP); Yasushi Hattori, Kanagawa (JP); Masashi Toyofuku, Kanagawa (JP); Shinji Morimoto, Kanagawa (JP); Masaki Daini, Kanagawa (JP); Takuto Kojima, Kanagawa (JP); Tomohiro Kaku, Kanagawa (JP); Mitsuhiro Ito, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/882,386

(22) Filed: Jan. 29, 2018

(65) Prior Publication Data

US 2018/0162853 A1    Jun. 14, 2018

Related U.S. Application Data

(63) Continuation of application No. 15/270,863, filed on Sep. 20, 2016, now Pat. No. 9,920,047, which is a (Continued)

(30) Foreign Application Priority Data

Apr. 11, 2014 (JP) ................................. 2014-082057

(51) Int. Cl.
| | | |
|---|---|---|
| *C07D 417/14* | (2006.01) | |
| *C07D 417/12* | (2006.01) | |
| *C07D 409/12* | (2006.01) | |
| *C07D 307/79* | (2006.01) | |
| *C07D 407/12* | (2006.01) | |

(Continued)

(52) U.S. Cl.
CPC ......... *C07D 417/14* (2013.01); *C07D 213/82* (2013.01); *C07D 231/12* (2013.01); *C07D 231/14* (2013.01); *C07D 277/56* (2013.01); *C07D 285/08* (2013.01); *C07D 285/135* (2013.01); *C07D 307/79* (2013.01); *C07D 307/81* (2013.01); *C07D 333/38* (2013.01); *C07D 333/40* (2013.01); *C07D 407/12* (2013.01); *C07D 409/12* (2013.01); *C07D 409/14* (2013.01); *C07D 413/12* (2013.01); (Continued)

(58) Field of Classification Search
CPC .. C07D 417/14; C07D 307/81; C07D 413/12; C07D 409/14; C07D 231/12; C07D 277/56; C07D 413/14; C07D 285/135; C07D 285/08; C07D 333/40; C07D 231/14; C07D 333/38; C07D 407/12; C07D 307/79; C07D 409/12; C07D 417/12; C07D 213/82

See application file for complete search history.

(56) References Cited

U.S. PATENT DOCUMENTS

| | | | |
|---|---|---|---|
| 7,067,507 B2 * | 6/2006 | Pulley | .................. C07D 273/02 514/183 |
| 9,061,966 B2 | 6/2015 | Laria et al. | |

(Continued)

FOREIGN PATENT DOCUMENTS

| | | |
|---|---|---|
| CN | 1882529 | 12/2006 |
| JP | 2012-36124 | 2/2012 |

(Continued)

OTHER PUBLICATIONS

Maes, T., "KDM1 histone lysine demethylases as targets for treatments of oncological and neurodegenerative disease." Epigenomics 7.4 (2015): 609-626.*

(Continued)

*Primary Examiner* — John M Mauro
(74) *Attorney, Agent, or Firm* — Hamre, Schumann, Mueller & Larson, P.C.

(57) ABSTRACT

The present invention provides a compound having a lysine-specific demethylase-1 inhibitory action, and useful as a medicament such as a prophylactic or therapeutic agent for schizophrenia, developmental disorders, particularly diseases having intellectual disability (e.g., autistic spectrum disorders, Rett syndrome, Down's syndrome, Kabuki syndrome, fragile X syndrome, Kleefstra syndrome, neurofibromatosis type 1, Noonan syndrome, tuberous sclerosis), neurodegenerative diseases (e.g., Alzheimer's disease, Parkinson's disease, spinocerebellar degeneration (e.g., dentatorubural pallidoluysian atrophy) and Huntington's disease), epilepsy (e.g., Dravet syndrome) or drug dependence, and the like. A compound represented by the formula

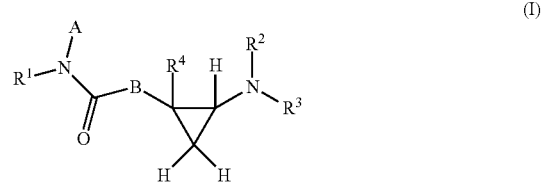

(I)

wherein each symbol is as defined in the present specification, or a salt thereof.

1 Claim, No Drawings
Specification includes a Sequence Listing.

Related U.S. Application Data continuation of application No. 14/682,695, filed on Apr. 9, 2015, now Pat. No. 9,487,511.

(51) Int. Cl.

| | | |
|---|---|---|
| C07D 213/82 | (2006.01) | |
| C07D 333/38 | (2006.01) | |
| C07D 413/14 | (2006.01) | |
| C07D 231/14 | (2006.01) | |
| C07D 333/40 | (2006.01) | |
| C07D 285/08 | (2006.01) | |
| C07D 231/12 | (2006.01) | |
| C07D 277/56 | (2006.01) | |
| C07D 409/14 | (2006.01) | |
| C07D 413/12 | (2006.01) | |
| C07D 307/81 | (2006.01) | |
| C07D 285/135 | (2006.01) | |

(52) U.S. Cl.
CPC ......... *C07D 413/14* (2013.01); *C07D 417/12* (2013.01)

(56) References Cited

U.S. PATENT DOCUMENTS

| | | | |
|---|---|---|---|
| 9,278,931 B2 | 3/2016 | Tomita et al. | |
| 9,487,511 B2* | 11/2016 | Matsumoto | C07D 417/14 |
| 9,714,241 B2* | 7/2017 | Matsumoto | C07D 417/14 |
| 9,718,814 B2* | 8/2017 | Matsumoto | C07D 417/14 |
| 9,751,885 B2* | 9/2017 | Tomita | A61K 45/06 |
| 10,053,456 B2* | 8/2018 | Matsumoto | C07D 417/14 |
| 2008/0132459 A1 | 6/2008 | Moradei et al. | |
| 2010/0324147 A1 | 12/2010 | McCafferty et al. | |
| 2012/0004262 A1 | 1/2012 | Guibourt et al. | |
| 2014/0228405 A1 | 8/2014 | Tomita et al. | |
| 2015/0266881 A1 | 9/2015 | Tomita et al. | |
| 2017/0029417 A1 | 2/2017 | Matsumoto | |

FOREIGN PATENT DOCUMENTS

| | | |
|---|---|---|
| WO | 2005/014552 | 2/2005 |
| WO | 2005/058884 | 6/2005 |
| WO | 2010/043721 | 4/2010 |
| WO | 2010/084160 | 7/2010 |
| WO | 2010/143582 | 12/2010 |
| WO | 2011/035941 | 3/2011 |
| WO | 2011/042217 | 4/2011 |
| WO | 2011/131576 | 10/2011 |
| WO | 2011/131697 | 10/2011 |
| WO | 2012/013727 | 2/2012 |
| WO | 2012/013728 | 2/2012 |
| WO | 2012/135113 | 10/2012 |
| WO | 2012/156531 | 11/2012 |
| WO | 2012/156537 | 11/2012 |
| WO | 2013/022047 | 2/2013 |
| WO | 2013/057320 | 4/2013 |
| WO | 2013/057322 | 4/2013 |
| WO | 2014/058071 | 4/2014 |

OTHER PUBLICATIONS

Dawson, G., "Early behavioral intervention, brain plasticity, and the prevention of autism spectrum disorder." Development and psychopathology 20.3 (2008): 775-803.*

Ricq, E.L., "Toward development of epigenetic drugs for central nervous system disorders: Modulating neuroplasticity via H3K4 methylation." Psychiatry and clinical neurosciences 70.12 (2016): 536-550.*

Alzheimer's Disease Fact Sheet, National Institute on Aging, http://www.nia.nih.gov/publication/alzheimers-disease-fact-sheet 2014; p. 1-4).*

Friedman, L.G., "Meeting report on the Alzheimer's Drug Discovery Foundation 14th International Conference on Alzheimer's Drug Discovery." (2014): 22.*

Lai, M-C., "Subgrouping the autism "Spectrum": reflections on DSM-5." PLoS biology 11.4 (2013): e1001544.*

Binda et al., "Biochemical, Structural, and Biological Evaluation of Tranylcypromine Derivatives as Inhibitors of Histone Demethylases LSD1 and LSD2", J. Am. Chem. Soc. 2010, vol. 132, pp. 6827-6833.

Yang et al., "Structurual Basis for the Inhibition of the LSD1 Histone Demethylase by the Antidepressant trans-2-Phenylcyclopropylamine", Biochemistry, vol. 46, 2007, pp. 8058-8065.

Extended European Search Report issued in corresponding European Patent Application No. 12821416.0, dated Apr. 15, 2015—10 pages.

CAS Registry No. 1026633-98-6, Jun. 8, 2008 (1 page).

Huang et al., "Prefrontal Dysfunction in Schizophrenia Involves Mixed-Lineage Leukemia 1-Regulated Histone Methylation at GABAergic Gene Promoters", The Journal of Neuroscience, Oct. 17, 2007, vol. 27, No. 42, pp. 11254-11262.

The Network and Pathway Analysis Subgroup of the Psychiatric Genomics Consortium, "Psychiatric genome-wide association study analyses implicate neuronal, immune and histone pathways", Nature Neuroscience, Feb. 2015, vol. 18, No. 2, pp. 199-209.

Cui et al., "Nuclear Receptors TR2 and TR4 Recruit Multiple Epigenetic Transcriptional Corepressors That Associate Specifically with the Embryonic β-Type Globin Promoters in Differentiated Adult Erythroid Cells", Molecular and Cellular Biology, Aug. 2011, vol. 31, No. 16, pp. 3298-3311.

International Search Report, dated Jul. 14, 2015; PCT/JP2015/061651 (4 pages).

Written Opinion of the International Searching Authority, dated Jul. 14, 2015; PCT/JP2015/061651 (7 pages).

Gooden et al., "Facile synthesis of substituted trans-2-arylcyclopropylamine inhibitors of the human histone demethylase LSD1 and monoamine oxidases A and B", Bioorganic & Medicinal Chemistry Letters, May 15, 2008, vol. 18, No. 10, pp. 3047-3051.

International Search Report, dated Nov. 19, 2013; PCT/JP2013/077863 (5 pages).

Written Opinion of the International Searching Authority, dated Nov. 19, 2013; PCT/JP2013/077863 ( 8 pages).

Friedman, et al., "Meeting report on the Alzheimer's Drug Discovery Foundation 1th International Conference on Alzheimer's Drug Discovery", Alzheimer's Research & Therapy 6.2 (2014): 22.

Alzheimer's Disease Fact Sheet, National Institute on Aging, http://www.nia.nih.gov/publication/alzheimers-disease-fact-sheet 2014; p. 1-4; accessed online Aug. 13, 2014.

Damasio, A.R., "Alzheimer's disease and related dementias." Cecil Textbook of Medicine, 2, (1996): 1992-1996.

Patani, et al., "Bioisosterism: A Rational Approach in Drug Design", Chem. Rev. 1996, 96, 3147-3176.

Communication issued in the corresponding European patent application No. 15721046.9, dated Jan. 15, 2019, 6 pages.

PubChem Compound Database, NCBI: CID 11599325, 1-12, Create Date Oct. 26, 2006.

* cited by examiner

```
                            SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
agaatcattt aaatggtgat catgtaaccc atcct                              35

<210> SEQ ID NO 2
<211> LENGTH: 44
<212> TYPE: DNA
<213> ORGANISM: Artificial Sequence
<220> FEATURE:
<223> OTHER INFORMATION: primer

<400> SEQUENCE: 2
cgccctgaaa gtacaggttc tcatccgatt ttggaggatg gtcg                    44

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
ataataggat ccgccctgaa agtacaggtt ctc                                33

<210> SEQ ID NO 4
<211> LENGTH: 44
<212> TYPE: DNA
<213> ORGANISM: Artificial Sequence
<220> FEATURE:
<223> OTHER INFORMATION: primer

<400> SEQUENCE: 4
tattatgcta gcgccaccat gttatctggg aagaaggcgg cagc                    44

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
tattatgcgg ccgctcacat gcttggggac tgctgtgc                           38

<210> SEQ ID NO 6
<211> LENGTH: 34
<212> TYPE: DNA
<213> ORGANISM: Artificial Sequence
<220> FEATURE:
<223> OTHER INFORMATION: primer

<400> SEQUENCE: 6
```

```
ataataagat cttcgggtgt ggagggcgca gctt                                  34

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
ataatagcgg ccgccatggc ccccaaaaac tggtctgca                             39

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tgatcttttc cctgctgtca                                                  20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
tcccatgagt aatccagaac g                                                21
```

CYCLOPROPANAMINE COMPOUND AND USE THEREOF

TECHNICAL FIELD

The present invention relates to a cyclopropanamine compound having a lysine-specific demethylase-1 (sometimes to be abbreviated as LSD1 in the present specification) inhibitory action, and useful as a medicament such as a prophylactic or therapeutic agent for cancer, schizophrenia, developmental disorders, particularly diseases having intellectual disability (e.g., autistic spectrum disorders, Rett syndrome, Down's syndrome, Kabuki syndrome, fragile X syndrome, Kleefstra syndrome, neurofibromatosis type 1, Noonan syndrome, tuberous sclerosis), neurodegenerative diseases (e.g., Alzheimer's disease, Parkinson's disease, spinocerebellar degeneration (e.g., dentatorubural pallidoluysian atrophy) and Huntington's disease), epilepsy (e.g., Dravet syndrome) or drug dependence, and the like.

BACKGROUND OF THE INVENTION

LSD1 is a demethylation enzyme of histone, catalyzes a demethylation reaction of a monomethylated product and a dimethylated product of the 4th lysine residue of histone H3 (H3K4me1/2), and forms formaldehyde as a by-product. In addition, LSD1 forms a complex with flavin adenine dinucleotide (FAD) which is a kind of coenzyme, and FAD promotes oxidation of lysine residue by enzymes as a redox mediator.

When a compound having a LSD1 inhibitory activity is applied to neuronal cells, histone H3 methylation especially H3K4 methylation around GAD1 gene promoter is increased through inhibition of histone demethylation activity of LSD1 (Experimental Example 3 to be mentioned later). There are many publications with analyses of relationship between gene expression level and histone H3K4 methylation status, which conclude that promotion of histone H3K4 methylation at a gene promoter leads to an activated transcription of the gene (Becker, Nature 2006, 442: 31-32; Ruthenburg et al., Nature Reviews Molecular Cell Biology 2007, 8: 983-994). Therefore, it is assumed that administration of a compound having an LSD1 inhibitory activity accumulates histone H3K4 methylation in neurons in the brain, which in turn results in the GAD1 mRNA expression in the brain. It is widely known that the induction of GAD1 mRNA expression in the brain is effective for the treatment of central nervous system diseases. For example, intracerebral injection of a GAD1 gene expression vector to Parkinson's disease patients is known to induce GAD1 mRNA expression and improve the symptoms of Parkinson's disease patients (LeWitt et al. Lancet Neurol. 2011, 10: 309-319; Carlson, Physiology of Behavior 11$^{th}$ edition 2013). From the above, it is considered that the administration of an LSD1 inhibitor increases the histone H3K4 methylation and results in increase of the GAD1 expression level in the brain, which may be effective for the treatment of central nervous system diseases.

On the other hand, LSD1 also catalyzes a demethylation reaction of a methylated product of the 9th lysine residue of histone H3 (H3K9me). A decrease of the methylation of H3K9 in animal models of some diseases, for example, animal models of cocaine dependence and Kleefstra syndrome has been reported (Science 8 Jan. 2010, 327, 213-216, Genes Dev. April 2005, 19, 815-826). A decrease of H3K9 methylation is known to cause abnormally enhanced expression of some genes. Therefore, it is assumed that administration of a compound having an LSD1 inhibitory activity accelerates histone H3K9 methylation in neurons in the brain, which in turn decreases the expression of genes abnormally expressed in the brain. From the above, it is considered that LSD1 inhibitor is possibly effective for the treatment of some diseases with a decrease of methylated H3K9.

WO 2010/084160 (patent document 1) discloses a compound of the following formula or a pharmaceutically acceptable salt thereof as an LSD1 inhibitor:

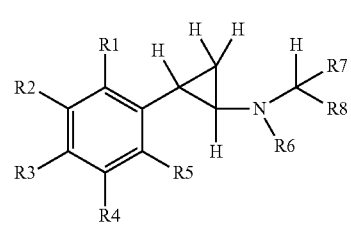

FORMULA I wherein R1-R5 are H, halo and the like; R6 is H or alkyl; R7 is H, alkyl or cycloalkyl; R8 is -L-heterocyclyl or -L-aryl wherein L is —(CH$_2$)$_n$—(CH$_2$)$_n$—, —(CH$_2$)$_n$O(CH$_2$)$_n$— or —(CH$_2$)$_n$S(CH$_2$)$_n$—, and n is 0, 1, 2 or 3.

WO 2010/043721 (patent document 2) discloses a compound of the following formula or a pharmaceutically acceptable salt thereof as an LSD1 inhibitor:

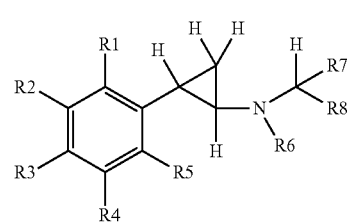

FORMULA I wherein R1-R5 are H, halo and the like; R6 is H or alkyl; R7 is H, alkyl or cycloalkyl; R8 is —C(=O)NRxRy or —C(=O)Rz wherein Rx and Ry are each independently H, alkyl and the like, and Rz is H, alkoxy and the like.

WO 2011/035941 (patent document 3) discloses a compound of the following formula or a pharmaceutically acceptable salt thereof as an LSD1 inhibitor:

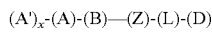

(A')$_x$-(A)-(B)—(Z)-(L)-(D)    I wherein (A') is aryl, arylalkoxy, heterocyclyl and the like; (A) is heteroaryl or aryl; X is 0, 1, 2 or 3; (B) is a cyclopropyl ring; (Z) is —NH—; (L) is —CH$_2$CH$_2$— and the like; (D) is —N(—R1)-R2, —O—R3 or —S—R3 wherein R1 and R2 are each independently H, alkyl and the like; and R3 is H, alkyl and the like.

WO 2011/042217 (patent document 4) discloses a compound of the following formula or a pharmaceutically acceptable salt thereof as an LSD1 inhibitor:

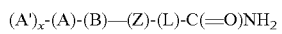

(A')$_x$-(A)-(B)—(Z)-(L)-C(=O)NH$_2$    (I)

wherein (A') is aryl, arylalkoxy, arylalkyl, heterocyclyl and the like; (A) is heteroaryl or aryl; X is 0, 1, 2 or 3; (B) is a cyclopropyl ring; (Z) is —NH—; (L) is —(CH$_2$)$_m$CR1R2— wherein m is 0, 1, 2, 3, 4, 5 or 6; and R1 and R2 are each independently H or C1-6 alkyl.

US 2010/0324147 (patent document 5) discloses a compound of the following formula or a salt thereof as an LSD1 inhibitor:

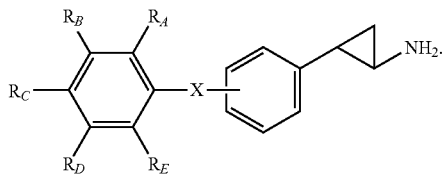

wherein X is a bond, O, S or NH; and $R_A$, $R_B$, $R_C$, $R_D$ and $R_E$ are each independently H, C1-7 alkyl and the like.

WO 2010/143582 (patent document 6) discloses a compound of the following formula or a pharmaceutically acceptable salt thereof as an LSD1 inhibitor:

(I)

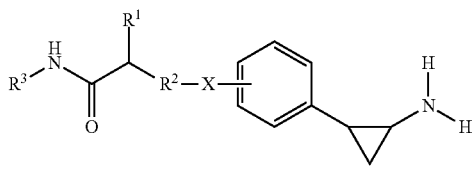

(II)

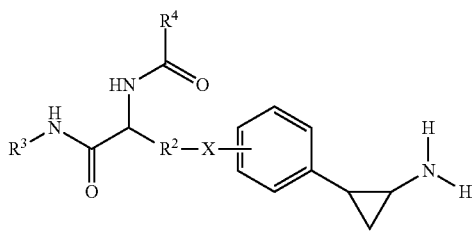

wherein $R^1$ is H, an alkyl group optionally having a substituent attached thereto and the like; $R^2$ is an alkylene group optionally having a substituent attached thereto; $R^3$ is an alkyl group optionally having a substituent attached thereto, a phenyl group optionally having a substituent attached thereto and the like; $R^4$ is an alkyl group optionally having a substituent attached thereto, a phenyl group optionally having a substituent attached thereto and the like; and X is O, $NH_2$, NHCO, CONH, S or $CH_2$.

J. Am. Chem. Soc. 2010, 132, 6827-6833 (non-patent document 1) discloses compounds of the following formulas as an LSD 1/2 inhibitor:

(13b)

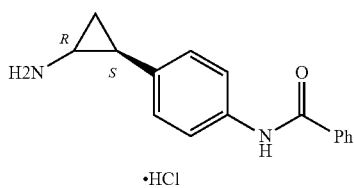

(15e)

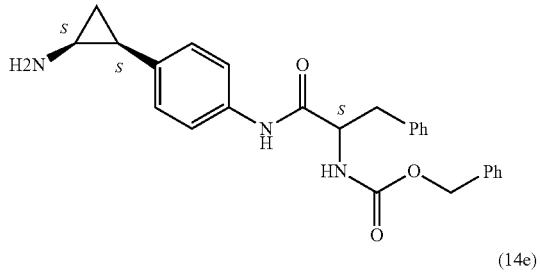

(14e)

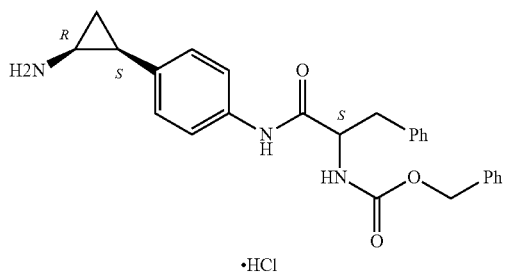

WO 2012/156531 (patent document 7) discloses use of an LSD1 inhibitor for the prophylaxis or treatment of inflammatory diseases.

WO 2012/156537 (patent document 8) discloses use of an LSD1 inhibitor for the prophylaxis or treatment of thrombosis, thrombus formation or circulatory diseases.

WO 2012/135113 (patent document 9) discloses, as an LSD1 inhibitor, a compound of the following formula or a pharmaceutically acceptable salt thereof:

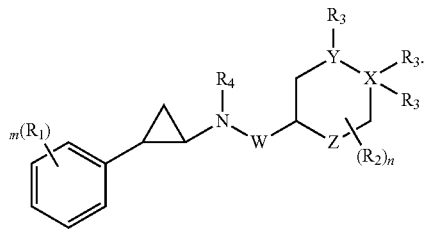

wherein
$R_1$ is selected from the group consisting of $C_{1-6}$ alkyl, —$NSO_2Me$, —$NSO_2Ph$, arylalkoxy, $C_{3-7}$ cycloalkyl, —NC(O)Ra, 1-methyl-1H-pyrazol-4-yl, hydroxy, $C_{1-4}$ alkoxy, halogen, amide, amino, substituted amino and —C(O)ORa;
$R_2$ is H or COOH;
each $R_3$ is independently selected from the group consisting of aryl, heteroaryl, H, $C_{1-6}$ alkyl, —$SO_2Ra$, —NC(O)Ra, —$CH_2C(O)ORa$, —C(O)ORa, —C(O)Ra, —C(O)NRaRb, substituted amino, amino, urea, amide, sulfonamide, arylalkyl and heteroarylalkyl;
each Ra is independently H, phenyl, phenylmethyl, 3,5-dimethylisoxazol-4-yl, 1,2-dimethyl-1H-imidazol-4-yl, $C_{3-7}$ cycloalkyl, $C_{1-6}$ alkyl, $C_{1-4}$ alkoxy, $C_{1-3}$ alkylamino or —NHPh;
Rb is H or $C_{1-3}$ alkyl, or when attached to the same atom, Ra and Rb together form a 5- or 6-membered heterocycloalkyl ring;
$R_4$ is $C_{1-4}$ alkyl, acyl, —C(O)CF$_3$ or H;
W is —$(CH_2)_{1-4}$ or —CH(Rc) $(CH_2)_{0-3}$ wherein Rc is CN or $C_{1-4}$ alkyl;

Y is N or C;
X is N or C;
Z is O or $(CH_2)_q$ wherein q is 0-2, and when q is 0, Z is a bond;
m is 0-3, n is 0-3;
provided that when Z is O, Y is N and X is C;
also provided that when X is C, at least one of the $R_3$ groups attached to X is not H.

WO 2013/022047 (patent document 10) discloses, as an LSD1 inhibitor, the compound of the following formula or a salt thereof.

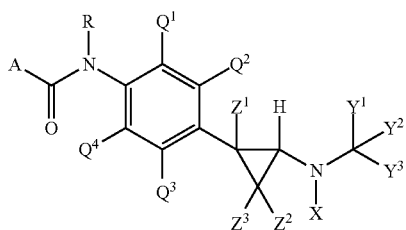

wherein
A is a hydrocarbon group optionally having substituent(s), or a heterocyclic group optionally having substituent(s);
R is a hydrogen atom, a hydrocarbon group optionally having substituent(s), or a heterocyclic group optionally having substituent(s); or
A and R are optionally bonded to each other to form a ring optionally having substituent(s);
$Q^1$, $Q^2$, $Q^3$ and $Q^4$ are each independently a hydrogen atom or a substituent; $Q^1$ and $Q^2$, and $Q^3$ and $Q^4$, are each optionally bonded to each other to form a ring optionally having substituent(s);
X is a hydrogen atom, an acyclic hydrocarbon group optionally having substituent(s), or a saturated cyclic group optionally having substituent(s);
$Y^1$, $Y^2$ and $Y^3$ are each independently a hydrogen atom, a hydrocarbon group optionally having substituent(s), or a heterocyclic group optionally having substituent(s);
X and $Y^1$, and $Y^1$ and $Y^2$, are each optionally bonded to each other to form a ring optionally having substituent(s); and
$Z^1$, $Z^2$ and $Z^3$ are each independently a hydrogen atom or a substituent.

WO 2012/013727 (patent document 11) discloses, as an LSD1 inhibitor, the compound of the following formula or a salt thereof.

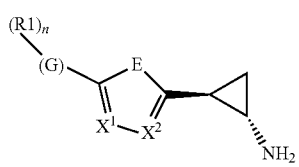

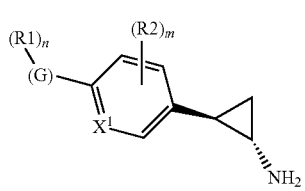

wherein each symbol is as defined in patent document 11.

WO 2013/057322 (patent document 12) discloses, as an LSD1 inhibitor, the compound of the following formula or a salt thereof.

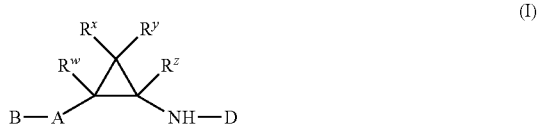

wherein each symbol is as defined in patent document 12.

WO 2013/057320 (patent document 13) discloses, as an LSD1 inhibitor, the compound of the following formula or a salt thereof.

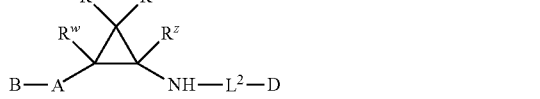

wherein each symbol is as defined in patent document 13.

WO 2014/058071 (patent document 14) discloses, as an LSD1 inhibitor, the compound of the following formula or a salt thereof.

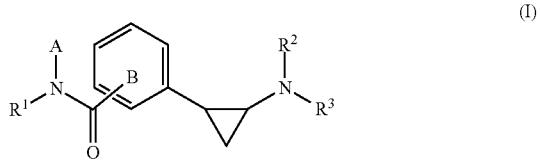

wherein each symbol is as defined in patent document 14.

The Journal of Neuroscience, Oct. 17, 2007, 27(42): 11254-11262 (non-patent document 2) discloses that a decrease in histone H3K4 methylation and a decrease in Gad1 mRNA expression are observed in the brain of schizophrenia patients. In addition, Nature Neuroscience, February 2015, 18, 199-209 (non-patent document 3) discloses that H3K4 methylation pathway is deeply involved in mental diseases such as schizophrenia and the like.

MOLECULAR AND CELLULAR BIOLOGY, August 2011, 31(16), 3298-3311 (non-patent document 4) discloses that LSD1 is a component of a protein complex that regulates transcription of beta globin and potentially involved in the suppression of transcription of beta globin. Activation of beta globin transcription is known to be useful for the treatment of sickle cell anaemia and beta thalassemia, from which it is assumed that LSD1 inhibition results in disinhibition of beta globin transcription, and provides a treatment effect.

DOCUMENT LIST

Patent Documents patent document 1: WO 2010/084160
patent document 2: WO 2010/043721
patent document 3: WO 2011/035941
patent document 4: WO 2011/042217
patent document 5: US 2010/0324147 patent document 6: WO 2010/143582
patent document 7: WO 2012/156531
patent document 8: WO 2012/156537
patent document 9: WO 2012/135113
patent document 10: WO 2013/022047
patent document 11: WO 2012/013727
patent document 12: WO 2013/057322
patent document 13: WO 2013/057320
patent document 14: WO 2014/058071

Non-Patent Documents non-patent document 1: J. Am. Chem. Soc. 2010, 132, 6827-6833
non-patent document 2: The Journal of Neuroscience, Oct. 17, 2007, 27(42):11254-11262
non-patent document 3: Nature Neuroscience, February 2015, 18, 199-209
non-patent document 4: MOLECULAR AND CELLULAR BIOLOGY, August 2011, 31(16), 3298-3311

SUMMARY OF THE INVENTION

Problems to be Solved by the Invention

An object of the present invention is to provide a cyclopropanamine compound having a superior LSD1 inhibitory action and high LSD1 selectivity, and useful as a medicament such as a prophylactic or therapeutic agent for cancer, schizophrenia, developmental disorders, particularly diseases having intellectual disability (e.g., autistic spectrum disorders, Rett syndrome, Down's syndrome, Kabuki syndrome, fragile X syndrome, Kleefstra syndrome, neurofibromatosis type 1, Noonan syndrome, tuberous sclerosis), neurodegenerative diseases (e.g., Alzheimer's disease, Parkinson's disease, spinocerebellar degeneration (e.g., dentatorubural pallidoluysian atrophy) and Huntington's disease (Huntington chorea)), epilepsy (e.g., Dravet syndrome) or drug dependence such as cocaine dependence, and the like.

Means of Solving the Problems

The present inventors have conducted intensive studies in an attempt to solve the aforementioned problems and found that a compound represented by the following formula (I) has a superior LSD1 inhibitory action and high LSD1 selectivity, which resulted in the completion of the present invention.

Accordingly, the present invention relates to the following.

[1] A compound represented by the formula

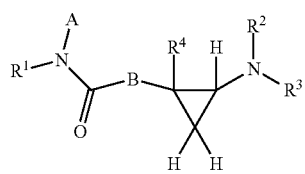
(I)

wherein
A is an optionally substituted heterocyclic group, or an optionally substituted hydrocarbon group;

B is a ring selected from
(1) a 5- or 6-membered aromatic heterocycle optionally fused with an optionally substituted 5- or 6-membered ring, and
(2) a benzene ring fused with an optionally substituted 5- or 6-membered ring,
wherein the ring represented by B is optionally substituted, and binds, via two adjacent carbon atoms with one atom in between, to a group represented by the formula

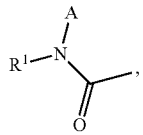
(II)

and
a group represented by the formula

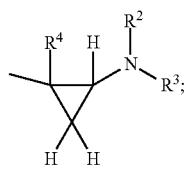
(III)

$R^1$, $R^2$, $R^3$ and $R^4$ are each independently a hydrogen atom, an optionally substituted hydrocarbon group or an optionally substituted heterocyclic group;
A and $R^1$ are optionally bonded with each other to form, together with the adjacent nitrogen atom, an optionally substituted cyclic group; and
$R^2$ and $R^3$ are optionally bonded with each other to form, together with the adjacent nitrogen atom, an optionally substituted cyclic group,
or a salt thereof (hereinafter to be also referred to as compound (I)).
[2] The compound of [1], wherein A is
(1) an optionally substituted heterocyclic group, or
(2) an optionally substituted $C_{3-10}$ cycloalkyl group, or a salt thereof.
[3] The compound of [1] or [2], wherein B is a ring selected from
(1) a 5- or 6-membered aromatic heterocycle, and
(2) a benzene ring fused with an optionally substituted 5- or 6-membered ring,
wherein the ring represented by B is optionally substituted, and binds, via two adjacent carbon atoms with one atom in between, to a group represented by the formula (II), and a group represented by the formula (III),
or a salt thereof.
[4] The compound of [1], [2] or [3], wherein, in the formula

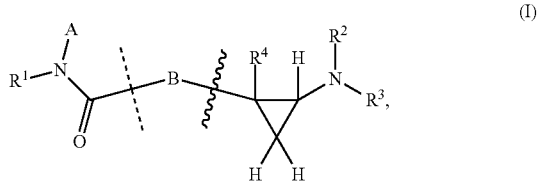
(I)

B is a ring selected from

[chemical structures showing various rings with X, Y, Z substitution positions, and dihydrobenzofuran structures]

and wherein
X¹, X², X³ and X⁴ are each independently a carbon atom or a nitrogen atom;
at least one of X¹, X², X³ and X⁴ is a nitrogen atom;
Y¹, Y² and Y³ are each independently a carbon atom, a nitrogen atom, an oxygen atom or a sulfur atom;
at least one of Y¹, Y² and Y³ is a nitrogen atom, an oxygen atom or a sulfur atom; and
Z¹, Z², Z³ and Z⁴ are each independently a carbon atom or a nitrogen atom, which ring is optionally substituted, or a salt thereof.
[5] The compound of [1], [2], [3] or [4], wherein R, R² and R⁴ are each independently a hydrogen atom or an optionally substituted $C_{1-6}$ alkyl group,
or a salt thereof.
[6] The compound of [1], [2], [3], [4] or [5], wherein R³ is
(1) a hydrogen atom,
(2) an optionally substituted $C_{1-6}$ alkyl group,
(3) an optionally substituted $C_{3-10}$ cycloalkyl group, or
(4) an optionally substituted heterocyclic group,
or a salt thereof.
[7] The compound of [1], wherein, in the formula

[chemical structure of formula (I)]

A is
(1) (i) a 5- or 6-membered aromatic heterocyclic group or (ii) a 4- to 6-membered non-aromatic heterocyclic group, each of which is optionally substituted by $C_{1-6}$ alkyl group(s) optionally substituted by halogen atom(s), or
(2) a $C_{3-10}$ cycloalkyl group optionally substituted by halogen atom(s);

B is a ring selected from

[chemical structures showing various rings with X, Y, Z substitution positions, and dihydrobenzofuran structures]

and wherein
X¹, X², X³ and X⁴ are each independently a carbon atom or a nitrogen atom;
at least one of X¹, X², X³ and X⁴ is a nitrogen atom;
Y¹, Y² and Y³ are each independently a carbon atom, a nitrogen atom, an oxygen atom or a sulfur atom;
at least one of Y¹, Y² and Y³ is a nitrogen atom, an oxygen atom or a sulfur atom; and
Z¹, Z², Z³ and Z⁴ are each independently a carbon atom or a nitrogen atom, which ring is optionally substituted by $C_{1-6}$ alkyl group(s);
R¹ is a hydrogen atom;
R² is a hydrogen atom;
R³ is
(1) a hydrogen atom,
(2) a $C_{1-6}$ alkyl group optionally substituted by substituent(s) selected from
  (a) a $C_{3-10}$ cycloalkyl group,
  (b) a $C_{6-14}$ aryl group optionally substituted by carboxy group(s),
  (c) a 4- to 6-membered non-aromatic heterocyclic group optionally substituted by $C_{1-6}$ alkyl group(s) optionally substituted by substituent(s) selected from a carboxy group, and a $C_{6-14}$ aryl group optionally substituted by carboxy group(s), and
  (d) a 5- or 6-membered aromatic heterocyclic group optionally substituted by amino group(s),
(3) a $C_{3-10}$ cycloalkyl group optionally substituted by substituent(s) selected from an amino group and a halogen atom or
(4) a 4- to 6-membered non-aromatic heterocyclic group optionally substituted by substituent(s) selected from
  (a) a $C_{1-6}$ alkyl group optionally substituted by halogen atom(s),
  (b) a $C_{3-10}$ cycloalkyl group,
  (c) a $C_{1-6}$ alkyl-carbonyl group, and
  (d) a $C_{3-10}$ cycloalkyl-carbonyl group; and
R⁴ is a hydrogen atom,
or a salt thereof.
[7A] The compound of [1], wherein A is
(1) (i) a 5- or 6-membered aromatic heterocyclic group or (ii) a 4- to 6-membered non-aromatic heterocyclic group, each of which is optionally substituted by $C_{1-6}$ alkyl group(s) optionally substituted by halogen atom(s), or
(2) a $C_{3-10}$ cycloalkyl group optionally substituted by halogen atom(s);
B is a ring selected from
thiophene, thiazole, pyrazole, pyridine, naphthalene and 2,3-dihydrobenzofuran, wherein the ring is optionally substituted by $C_{1-6}$ alkyl group(s);
$R^1$ is a hydrogen atom;
$R^2$ is a hydrogen atom;
$R^3$ is
(1) a hydrogen atom,
(2) a $C_{1-6}$ alkyl group optionally substituted by substituent(s) selected from
    (a) a $C_{3-10}$ cycloalkyl group,
    (b) a $C_{6-14}$ aryl group optionally substituted by carboxy group(s),
    (c) a 4- to 6-membered non-aromatic heterocyclic group optionally substituted by $C_{1-6}$ alkyl group(s) optionally substituted by substituent(s) selected from a carboxy group, and a $C_{6-14}$ aryl group optionally substituted by carboxy group(s), and
    (d) a 5- or 6-membered aromatic heterocyclic group optionally substituted by amino group(s),
(3) a $C_{3-10}$ cycloalkyl group optionally substituted by substituent(s) selected from an amino group and a halogen atom or
(4) a 4- to 6-membered non-aromatic heterocyclic group optionally substituted by substituent(s) selected from
    (a) a $C_{1-6}$ alkyl group optionally substituted by halogen atom(s),
    (b) a $C_{3-10}$ cycloalkyl group,
    (c) a $C_{1-6}$ alkyl-carbonyl group, and
    (d) a $C_{3-10}$ cycloalkyl-carbonyl group; and
$R^4$ is a hydrogen atom,
or a salt thereof.

[8] The compound of [1], wherein A is
(1) a piperidinyl group, an isoxazolyl group, a pyrazolyl group, a thiadiazolyl group, a thiazolyl group, a tetrahydropyranyl group, an oxetanyl group, an oxadiazolyl group, a thienyl group, a pyridyl group or an oxazolyl group, each of which is optionally substituted by $C_{1-6}$ alkyl group(s) optionally substituted by halogen atom(s), or
(2) a $C_{3-10}$ cycloalkyl group optionally substituted by halogen atom(s);
B is a ring selected from
thiophene, thiazole, pyrazole, pyridine, naphthalene and 2,3-dihydrobenzofuran, wherein the ring is optionally substituted by $C_{1-6}$ alkyl group(s);
$R^1$ is a hydrogen atom;
$R^2$ is a hydrogen atom;
$R^3$ is
(1) a hydrogen atom,
(2) a $C_{1-6}$ alkyl group optionally substituted by substituent(s) selected from
    (a) a $C_{3-10}$ cycloalkyl group,
    (b) a $C_{6-14}$ aryl group optionally substituted by carboxy group(s),
    (c) a tetrahydropyranyl group or a piperidinyl group each optionally substituted by $C_{1-6}$ alkyl group(s) optionally substituted by substituent(s) selected from a carboxy group, and a $C_{6-14}$ aryl group optionally substituted by carboxy group(s), and
    (d) an oxadiazolyl group optionally substituted by an amino group,
(3) a $C_{3-10}$ cycloalkyl group optionally substituted by substituent(s) selected from an amino group and a halogen atom or
(4) a tetrahydropyranyl group or a piperidinyl group each optionally substituted by substituent(s) selected from
    (a) a $C_{1-6}$ alkyl group optionally substituted by halogen atom(s),
    (b) a $C_{3-10}$ cycloalkyl group,
    (c) a $C_{1-6}$ alkyl-carbonyl group, and
    (d) a $C_{3-10}$ cycloalkyl-carbonyl group; and
$R^4$ is a hydrogen atom,
or a salt thereof.

[8A] The compound of [1], wherein A is
(1) a piperidinyl group, an isoxazolyl group, a pyrazolyl group, a thiadiazolyl group, a thiazolyl group, a tetrahydropyranyl group, an oxetanyl group, an oxadiazolyl group, a thienyl group, a pyridyl group or an oxazolyl group, each of which is optionally substituted by $C_{1-6}$ alkyl group(s) (preferably, 1 or 2 $C_{1-6}$ alkyl groups) optionally substituted by halogen atom(s) (preferably, 1 to 3 halogen atoms), or
(2) a cyclopropyl group, a cyclobutyl group, a cyclopentyl group or a cyclohexyl group, each of which is optionally substituted by halogen atom(s) (preferably, 1 or 2 halogen atoms);
B is a ring selected from
thiophene, thiazole, pyrazole, pyridine, naphthalene and 2,3-dihydrobenzofuran, wherein the ring is optionally substituted by $C_{1-6}$ alkyl group(s) (preferably, one C16 alkyl group);
$R^1$ is a hydrogen atom;
$R^2$ is a hydrogen atom;
$R^3$ is
(1) a hydrogen atom,
(2) a $C_{1-6}$ alkyl group optionally substituted by substituent(s) (preferably, one substituent) selected from
    (a) a cyclopropyl group or cyclobutyl group,
    (b) a phenyl group optionally substituted by carboxy group(s) (preferably, one carboxy group),
    (c) a tetrahydropyranyl group or a piperidinyl group each optionally substituted by $C_{1-6}$ alkyl group(s) (preferably, one $C_{1-6}$ alkyl group) optionally substituted by substituent(s) (preferably, one substituent) selected from a carboxy group, and a phenyl group optionally substituted by carboxy group(s) (preferably, one carboxy group), and
    (d) an oxadiazolyl group optionally substituted by an amino group (one amino group),
(3) a cyclobutyl group or a cyclohexyl group each optionally substituted by substituent(s) (preferably, 1 or 2 substituents) selected from an amino group and a halogen atom, or
(4) a tetrahydropyranyl group or a piperidinyl group each optionally substituted by substituent(s) (preferably, one substituent) selected from
    (a) a $C_{1-6}$ alkyl group optionally substituted by halogen atom(s) (preferably, 1 to 3 halogen atoms),
    (b) a cyclopropyl group,
    (c) a $C_{1-6}$ alkyl-carbonyl group, and
    (d) a cyclopropyl-carbonyl group; and
$R^4$ is a hydrogen atom,
or a salt thereof.

[9] The compound of [1], wherein A is
(1) a pyrazolyl group, a thiadiazolyl group or a tetrahydropyranyl group, each optionally substituted by $C_{1-6}$ alkyl group(s) (preferably, 1 or 2 $C_{1-6}$ alkyl groups), or
(2) a cyclohexyl group optionally substituted by halogen atom(s) (preferably, 1 or 2 halogen atoms);

B is
a thiophene ring, which ring is optionally substituted by $C_{1-6}$ alkyl group(s) (preferably, one $C_{1-6}$ alkyl group);
$R^1$ is a hydrogen atom;
$R^2$ is a hydrogen atom;
$R^3$ is a cyclopropylmethyl group, a tetrahydropyranylmethyl group, a cyclobutylmethyl group, a cyclobutyl group or a tetrahydropyranyl group; and
$R^4$ is a hydrogen atom,
or a salt thereof.
[9A] The compound of [1], wherein A is
a pyrazolyl group, a thiadiazolyl group or a tetrahydropyranyl group, each optionally substituted by $C_{1-6}$ alkyl group(s) (preferably, one $C_{1-6}$ alkyl group),
B is
a thiophene ring, which ring is optionally substituted by $C_{1-6}$ alkyl group(s) (preferably, one $C_{1-6}$ alkyl group);
$R^1$ is a hydrogen atom;
$R^2$ is a hydrogen atom;
$R^3$ is a cyclopropylmethyl group, a tetrahydropyranylmethyl group or a cyclobutyl group; and
$R^4$ is a hydrogen atom,
or a salt thereof.
[10] The compound of [1], wherein A is
a pyrazolyl group, a thiadiazolyl group or a tetrahydropyranyl group, each optionally substituted by $C_{1-6}$ alkyl group(s) (preferably, one $C_{1-6}$ alkyl group),
B is
a thiophene ring, which ring is optionally substituted by $C_1$-6 alkyl group(s) (preferably, one $C_{1-6}$ alkyl group);
$R^1$ is a hydrogen atom;
$R^2$ is a hydrogen atom;
$R^3$ is a cyclopropylmethyl group or a cyclobutyl group; and
$R^4$ is a hydrogen atom,
or a salt thereof.
[11] 5-((1R,2R)-2-(((Cyclopropylmethyl)amino)cyclopropyl)-N-(tetrahydro-2H-pyran-4-yl)thiophene-3-carboxamide or a salt thereof.
[12] 4-((1S,2R)-2-(Cyclobutylamino)cyclopropyl)-N-(5-methyl-1,3,4-thiadiazol-2-yl)thiophene-2-carboxamide or a salt thereof.
[13] 4-((1S,2R)-2-(Cyclobutylamino)cyclopropyl)-5-methyl-N-(1-methyl-1H-pyrazol-4-yl)thiophene-2-carboxamide or a salt thereof.
[14] A medicament comprising the compound of any one of [1] to [13], [7A], [8A] and [9A] or a salt thereof.
[15] The medicament of [14], which is an LSD1 inhibitor.
[15A] The medicament of [14], which is a prophylactic or therapeutic agent for schizophrenia, Alzheimer's disease, Parkinson's disease or Huntington's disease (Huntington chorea).
[16] The medicament of [14], which is a prophylactic or therapeutic agent for schizophrenia, developmental disorders, autistic spectrum disorders, Rett syndrome, Down's syndrome, Kabuki syndrome, fragile X syndrome, Kleefstra syndrome, neurofibromatosis type 1, Noonan syndrome, tuberous sclerosis, Alzheimer's disease, Parkinson's disease, spinocerebellar degeneration, Huntington's disease, epilepsy or drug dependence.
[17] The compound of any one of [1] to [13], [7A], [8A] and [9A] or a salt thereof for use in the prophylaxis or treatment of schizophrenia, developmental disorders, autistic spectrum disorders, Rett syndrome, Down's syndrome, Kabuki syndrome, fragile X syndrome, Kleefstra syndrome, neurofibromatosis type 1, Noonan syndrome, tuberous sclerosis, Alzheimer's disease, Parkinson's disease, spinocerebellar degeneration, Huntington's disease, epilepsy or drug dependence.
[18] A method of inhibiting LSD1 in a mammal, comprising administering an effective amount of the compound of any one of [1] to [13], [7A], [8A] and [9A] or a salt thereof to the mammal.
[19] A method for the prophylaxis or treatment of schizophrenia, developmental disorders, autistic spectrum disorders, Rett syndrome, Down's syndrome, Kabuki syndrome, fragile X syndrome, Kleefstra syndrome, neurofibromatosis type 1, Noonan syndrome, tuberous sclerosis, Alzheimer's disease, Parkinson's disease, spinocerebellar degeneration, Huntington's disease, epilepsy or drug dependence in a mammal, comprising administering an effective amount of the compound of any one of [1] to [13], [7A], [8A] and [9A] or a salt thereof to the mammal.
[20] Use of the compound of any one of [1] to [13], [7A], [8A] and [9A] or a salt thereof in the production of a prophylactic or therapeutic agent for schizophrenia, developmental disorders, autistic spectrum disorders, Rett syndrome, Down's syndrome, Kabuki syndrome, fragile X syndrome, Kleefstra syndrome, neurofibromatosis type 1, Noonan syndrome, tuberous sclerosis, Alzheimer's disease, Parkinson's disease, spinocerebellar degeneration, Huntington's disease, epilepsy or drug dependence.
[7B] The compound of [4], wherein B is a ring represented by the formula

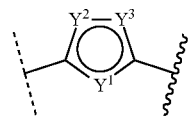

wherein
$Y^1$, $Y^2$ and $Y^3$ are each independently a carbon atom, a nitrogen atom, an oxygen atom or a sulfur atom; and
at least one of $Y^1$, $Y^2$ and $Y^3$ is a nitrogen atom, an oxygen atom or a sulfur atom, which ring is optionally substituted, or a salt thereof.
[8B] The compound of [1], wherein B is a ring selected from thiophene and thiazole, and the ring is optionally substituted, or a salt thereof.
[9B] The compound of [1], [7B] or [8B], wherein $R^2$ is a hydrogen atom and $R^3$ is a cyclopropylmethyl group, or a salt thereof.
[10B] The compound of [1], [7B] or [5B], wherein $R^2$ is a hydrogen atom and $R^3$ is a cyclobutyl group, or a salt thereof.
[11B] The compound of [1], [7B] or [8B], wherein $R^2$ is a hydrogen atom and $R^3$ is a tetrahydropyranyl group, or a salt thereof.
[12B] The compound of [1], [7B] or [8B], wherein $R^2$ is a hydrogen atom and $R^3$ is a tetrahydropyranylmethyl group, or a salt thereof.
[13B] The compound of [1], [7B] or [8B], wherein $R^2$ is a hydrogen atom and $R^3$ is an optionally substituted piperidinyl group (preferably, a piperidinyl group optionally substituted by one $C_{1-6}$ alkyl group optionally substituted by 1 to 3 halogen atoms), or a salt thereof.
[14B] The compound of any one of [1] and [7B] to [13B], wherein $R^1$ is a hydrogen atom, or a salt thereof.
[15B] The compound of any one of [1] and [7B] to [14B], wherein A is (1) a piperidinyl group, an isoxazolyl group, a pyrazolyl group, a thiadiazolyl group, a thiazolyl group or a tetrahydropyranyl group, each optionally substituted by $C_{1-6}$ alkyl group(s) (preferably, one $C_{1-6}$ alkyl group) optionally substituted by halogen atom(s) (preferably, 1 to 3 halogen atoms), or (2) a cyclopentyl group or a cyclohexyl group, each optionally substituted by halogen atom(s) (preferably, 1 or 2 halogen atoms), or a salt thereof.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{1-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, f-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-3-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1}$-6 alkoxy-carbonyl group, a 5- to 14-membered aromatic heterocyclic group, a carbamoyl group, a mono- or di-$C_{1-6}$ alkyl-carbamoyl group and a mono- or di-$C_{1-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{1-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{0-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl)

In the present specification, examples of the "5- or 6-membered aromatic heterocycle" include a 5- or 6-membered aromatic heterocycle containing, as a ring-constituting atom besides carbon atoms, 1 to 4 hetero atoms selected from a nitrogen atom, a sulfur atom and an oxygen atom. Preferable examples of the "5- or 6-membered aromatic heterocycle" include 5- or 6-membered aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, triazine and the like.

A is an optionally substituted heterocyclic group, or an optionally substituted hydrocarbon group.

A is preferably
(1) an optionally substituted heterocyclic group, or
(2) an optionally substituted $C_{3-10}$ cycloalkyl group.

A is more preferably
(1) a heterocyclic group (preferably, (i) a 5- or 6-membered aromatic heterocyclic group or (ii) a 4- to 6-membered non-aromatic heterocyclic group, each containing, as a ring-constituting atom besides carbon atoms, 1 to 4 hetero atoms selected from a nitrogen atom, a sulfur atom and an oxygen atom) (e.g., piperidinyl group, isoxazolyl group, pyrazolyl group, thiadiazolyl group, thiazolyl group, tetrahydropyranyl group, oxetanyl group, oxadiazolyl group, thienyl group, pyridyl group, oxazolyl group) optionally substituted by $C_{1-6}$ alkyl group(s) (preferably, 1 or 2 $C_{1-6}$ alkyl groups) optionally substituted by halogen atom(s) (preferably, 1 to 3 halogen atoms), or
(2) a $C_{3-10}$ cycloalkyl group (e.g., cyclopropyl group, cyclobutyl group, cyclopentyl group, cyclohexyl group) optionally substituted by halogen atom(s) (preferably, 1 or 2 halogen atoms).

A is more preferably
(1) a piperidinyl group, an isoxazolyl group, a pyrazolyl group, a thiadiazolyl group, a thiazolyl group or a tetrahydropyranyl group, each optionally substituted by $C_{1-6}$ alkyl group(s) (preferably, one $C_{1-6}$ alkyl group) optionally substituted by halogen atom(s) (preferably, 1 to 3 halogen atoms), or
(2) a cyclopentyl group or a cyclohexyl group, each optionally substituted by halogen atom(s) (preferably, 1 or 2 halogen atoms).

A is particularly preferably
(1) a pyrazolyl group, a thiadiazolyl group or a tetrahydropyranyl group, each optionally substituted by $C_{1-6}$ alkyl group(s) (preferably, one $C_{1-6}$ alkyl group), or
(2) a cyclopentyl group or a cyclohexyl group, each optionally substituted by halogen atom(s) (preferably, 1 or 2 halogen atoms).

B is a ring selected from
(1) a 5- or 6-membered aromatic heterocycle optionally fused with an optionally substituted 5- or 6-membered ring, and
(2) a benzene ring fused with an optionally substituted 5- or 6-membered ring,
and the ring represented by B is optionally substituted and binds, via two adjacent carbon atoms with one atom in between, to a group represented by the formula

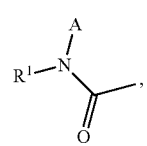

(II)

and a group represented by the formula

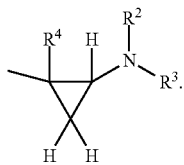
(III)

Examples of the "optionally substituted 5- or 6-membered ring" include a 5- or 6-membered ring optionally having substituent(s) selected from the aforementioned substituent group A.

The number of the substituents for the "optionally substituted 5- or 6-membered ring" is, for example, 1 to 3. When the number of the substituents is two or more, respective substituents may be the same or different.

The substituent that B optionally has is, for example, a substituent selected from the aforementioned substituent group A.

The number of the substituents that B optionally has is, for example, 1 to 3, preferably 1 or 2, more preferably 1. When the number of the substituents is two or more, respective substituents may be the same or different.

B is preferably a ring selected from
(1) a 5- or 6-membered aromatic heterocycle, and
(2) a benzene ring fused with an optionally substituted 5- or 6-membered ring,
and the ring represented by B is optionally substituted, via two adjacent carbon atoms with one atom in between, and binds to a group represented by the formula (II), and a group represented by the formula (III).

In the formula

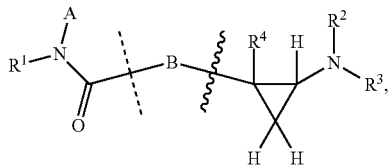
(I)

B is more preferably, a ring selected from

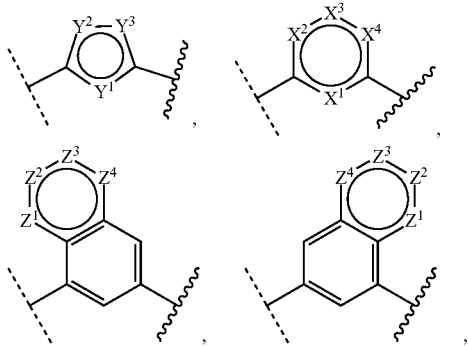

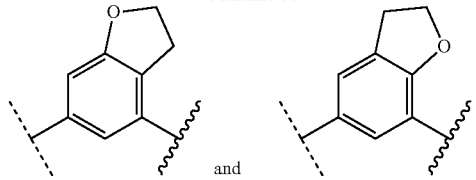

wherein
$X^1$, $X^2$, $X^3$ and $X^4$ are each independently a carbon atom or a nitrogen atom;
at least one of $X^1$, $X^2$, $X^3$ and $X^4$ is a nitrogen atom;
$Y^1$, $Y^2$ and $Y^3$ are each independently a carbon atom, a nitrogen atom, an oxygen atom or a sulfur atom;
at least one of $Y^1$, $Y^2$ and $Y^3$ is a nitrogen atom, an oxygen atom or a sulfur atom; and
$Z^1$, $Z^2$, $Z^3$ and $Z^4$ are each independently a carbon atom or a nitrogen atom, which ring is optionally substituted.

Preferable examples of B include a ring selected from

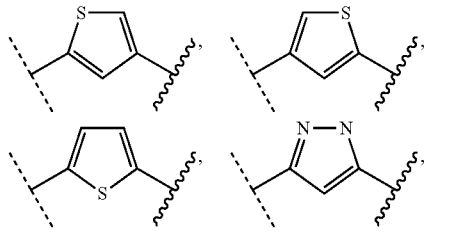

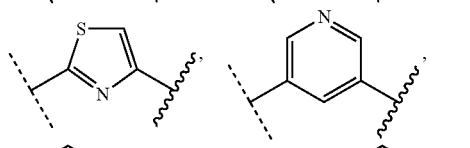

The ring is optionally substituted by 1 or 2 (preferably 1) $C_{1-6}$ alkyl groups.

B is more preferably a ring represented by the formula

wherein
$Y^1$, $Y^2$ and $Y^3$ are each independently a carbon atom, a nitrogen atom, an oxygen atom or a sulfur atom; and
at least one of $Y^1$, $Y^2$ and $Y^3$ is a nitrogen atom, an oxygen atom or a sulfur atom, and the ring is optionally substituted.

B is particularly preferably a ring selected from thiophene and thiazole, and the ring is optionally substituted.

Another preferable embodiment of B is thiophene or thiazole each optionally substituted by 1 or 2 (preferably 1) $C_{1-6}$ alkyl groups.

A still another preferable embodiment of B is thiophene optionally substituted by one $C_{1-6}$ alkyl group.

A yet another preferable embodiment of B is

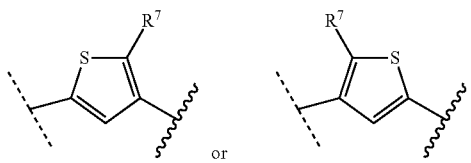

wherein $R^7$ is a hydrogen atom or a $C_{1-6}$ alkyl group.

$R^1$, $R^2$, $R^3$ and $R^4$ are each independently a hydrogen atom, an optionally substituted hydrocarbon group or an optionally substituted heterocyclic group.

$R^1$ is preferably a hydrogen atom or an optionally substituted $C_{1-6}$ alkyl group, more preferably, a hydrogen atom or a $C_{1-6}$ alkyl group, particularly preferably a hydrogen atom.

A and $R^1$ are optionally bonded with each other to form, together with the adjacent nitrogen atom optionally substituted cyclic group.

Examples of the "cyclic group" of the "optionally substituted cyclic group", which is formed, together with the adjacent nitrogen atom, by A and $R^1$ bonded to each other include a 4- to 10-membered heterocyclic group containing one nitrogen atom as a ring-constituting atom besides carbon atom, and optionally further containing one hetero atom selected from a nitrogen atom, a sulfur atom and an oxygen atom, and the like. Examples of the "4- to 10-membered heterocyclic group" include azetidin-1-yl, pyrrolidin-1-yl, pyrrolin-1-yl, pyrazolin-1-yl, imidazolin-1-yl, thiazolidin-3-yl, oxazolidin-3-yl, isothiazolidin-2-yl, isoxazolidin-2-yl, thiazolin-3-yl, oxazolin-3-yl, isothiazolin-2-yl, isoxazolin-2-yl, piperidin-1-yl, piperazin-1-yl, morpholin-4-yl, thiomorpholin-4-yl, azepan-1-yl, diazepan-1-yl, 1,4-oxazepan-4-yl, 1,4-thiazepan-4-yl, 5,7-dihydro-6H-pyrrolo[3,4-b]pyridin-6-yl and the like.

Examples of the substituent of the "optionally substituted cyclic group", which is formed, together with the adjacent nitrogen atom, by A and $R^1$ bonded to each other, include substituents selected from the aforementioned substituent group A.

The number of the substituents in "optionally substituted cyclic group", which is formed, together with the adjacent nitrogen atom, by A and $R^1$ bonded to each other, is, for example, 1 to 3. When the number of the substituents is two or more, the respective substituents may be the same or different.

Preferable examples of the "optionally substituted cyclic group", which is formed, together with the adjacent nitrogen atom, by A and $R^1$ bonded to each other include a 4- to 10-membered heterocyclic group containing one nitrogen atom as a ring-constituting atom besides carbon atoms, and optionally further containing one hetero atom selected from a nitrogen atom, a sulfur atom and an oxygen atom (e.g., azetidin-1-yl, pyrrolidin-1-yl, piperidin-1-yl, 5,7-dihydro-6H-pyrrolo[3,4-b]pyridin-6-yl), and the heterocyclic group is optionally substituted by 1 to 3 substituents selected from a hydroxy group and a cyano group, As regards —N(R')(A) moiety,
$R^1$ is preferably a hydrogen atom.
A is preferably
(1) a piperidinyl group, an isoxazolyl group, a pyrazolyl group, a thiadiazolyl group, a thiazolyl group or a tetrahydropyranyl group each optionally substituted by $C_{1-6}$ alkyl group(s) (preferably, one $C_{1-6}$ alkyl group) optionally substituted by halogen atom(s) (preferably, 1 to 3 halogen atoms), or
(2) a cyclopentyl group or a cyclohexyl group each optionally substituted by halogen atom(s) (preferably, 1 or 2 halogen atoms).

$R^2$ is preferably a hydrogen atom or an optionally substituted $C_{1-6}$ alkyl group, more preferably, a hydrogen atom or a $C_{1-6}$ alkyl group, particularly preferably a hydrogen atom.

$R^3$ is preferably
(1) a hydrogen atom,
(2) an optionally substituted $C_{1-6}$ alkyl group,
(3) an optionally substituted $C_{3-10}$ cycloalkyl group, or
(4) an optionally substituted heterocyclic group.

$R^3$ is more preferably
(1) a hydrogen atom,
(2) a $C_{1-6}$ alkyl group substituted by one $C_{3-10}$ cycloalkyl group (e.g., cyclopropylmethyl group),
(3) a $C_{1-6}$ alkyl group substituted by one 4- to 6-membered non-aromatic heterocyclic group (preferably, a 4- to 6-membered non-aromatic heterocyclic group containing, as a ring-constituting atom besides carbon atoms, 1 or 2 hetero atoms selected from a nitrogen atom, a sulfur atom and an oxygen atom) (e.g., tetrahydropyranylmethyl group),
(4) a $C_{3-10}$ cycloalkyl group (e.g., cyclobutyl group, cyclohexyl group) optionally substituted by one amino group, or
(5) a 4- to 6-membered non-aromatic heterocyclic group (preferably, a 4- to 6-membered non-aromatic heterocyclic group containing, as a ring-constituting atom besides carbon atoms, 1 or 2 hetero atoms selected from a nitrogen atom, a sulfur atom and an oxygen atom) (e.g., tetrahydropyranyl group, piperidinyl group), and the heterocyclic group is optionally substituted by one substituent selected from
(a) a $C_{1-6}$ alkyl group optionally substituted by halogen atom(s) (preferably, 1 to 3 halogen atoms), and
(b) a $C_{3-10}$ cycloalkyl group (e.g., cyclopropyl group).

$R^3$ is more preferably a hydrogen atom, a cyclopropylmethyl group, a tetrahydropyranylmethyl group, a cyclobutyl group or a tetrahydropyranyl group.

$R^3$ is particularly preferably a cyclopropylmethyl group, a tetrahydropyranylmethyl group, a cyclobutyl group or a tetrahydropyranyl group.

$R^2$ and $R^3$ are optionally bonded with each other to form, together with the adjacent nitrogen atom, an optionally substituted cyclic group.

Examples of the "cyclic group" of the "optionally substituted cyclic group", which is formed, together with the adjacent nitrogen atom, by $R^2$ and $R^3$ bonded to each other include a 4- to 10-membered heterocyclic group containing one nitrogen atom as a ring-constituting atom besides carbon atom, and optionally further containing one hetero atom selected from a nitrogen atom, a sulfur atom and an oxygen atom, and the like. Examples of the "4- to 10-membered heterocyclic group" include azetidin-1-yl, pyrrolidin-1-yl, pyrrolin-1-yl, pyrazolin-1-yl, imidazolin-1-yl, thiazolidin-3-yl, oxazolidin-3-yl, isothiazolidin-2-yl, isoxazolidin-2-yl, thiazolin-3-yl, oxazolin-3-yl, isothiazolin-2-yl, isoxazolin-2-yl, piperidin-1-yl, piperazin-1-yl, morpholin-4-yl, thiomorpholin-4-yl, azepan-1-yl, diazepan-1-yl, 1,4-oxazepan-4-yl, 1,4-thiazepan-4-yl, 5,7-dihydro-6H-pyrrolo[3,4-b]pyridin-6-yl and the like.

Examples of the substituent of the "optionally substituted cyclic group", which is formed, together with the adjacent nitrogen atom, by $R^2$ and $R^3$ bonded to each other include substituents selected from the aforementioned substituent group A.

The number of the substituents in "optionally substituted cyclic group", which is formed, together with the adjacent nitrogen atom, by $R^2$ and $R^3$ bonded to each other is, for example, 1 to 3. When the number of the substituents is two or more, the respective substituents may be the same or different.

Preferable examples of the "optionally substituted cyclic group", which is formed, together with the adjacent nitrogen atom, by $R^2$ and $R^3$ bonded to each other include a 4- to 10-membered heterocyclic group containing one nitrogen atom as a ring-constituting atom besides carbon atom, and optionally further containing one hetero atom selected from a nitrogen atom, a sulfur atom and an oxygen atom (e.g., pyrrolidin-1-yl, piperidin-1-yl, morpholin-4-yl, thiomorpholin-4-yl), and the heterocyclic group is optionally substituted by 1 to 3 oxo groups.

A preferable combination of $R^2$ and $R^3$ is a hydrogen atom and a cyclopropylmethyl group, a hydrogen atom and a cyclobutyl group, a hydrogen atom and a tetrahydropyranyl group, a hydrogen atom and a tetrahydropyranylmethyl group, or a hydrogen atom and an optionally substituted piperidinyl group (preferably, a piperidinyl group optionally substituted by one $C_{1-6}$ alkyl group optionally substituted by 1 to 3 halogen atoms).

$R^4$ is preferably a hydrogen atom or an optionally substituted $C_{1-6}$ alkyl group, more preferably, a hydrogen atom or a $C_{1-6}$ alkyl group, particularly preferably a hydrogen atom.

In the formula (I), the relative configuration of the substituent represented by the formula $(R^1)(A)N—CO—B—$ and the substituent represented by the formula $—N(R^2)(R^3)$ on the cyclopropane ring is cis or trans, preferably trans.

A compound of the formula (I) having a preferable relative configuration is shown by the following formula (IA).

Relative Configuration

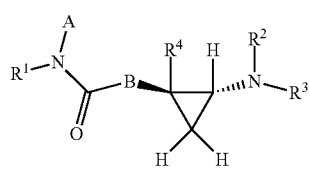

(IA)

wherein A, B, $R^1$, $R^2$, $R^3$ and $R^4$ are as defined above.

Compound (I) encompasses a compound having the absolute configuration represented by the following formula (IB) or (IC), and a mixture thereof at any ratio.

Absolute Configuration

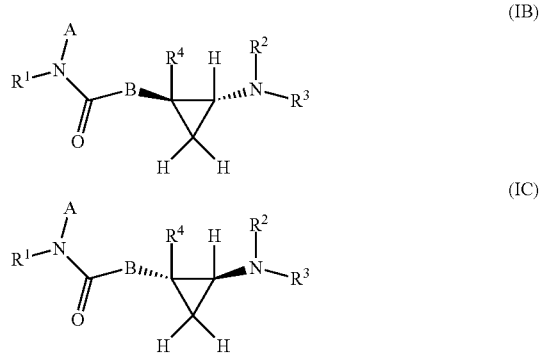

wherein A, B, $R^1$, $R^2$, $R^3$ and $R^4$ are as defined above.

Preferable examples of compound (I) include the following compounds.

[Compound A]

Compound (I) wherein

B is a ring selected from thiophene, thiazole, pyrazole, pyridine, naphthalene and 2,3-dihydrobenzofuran, and the ring is optionally substituted by $C_{1-6}$ alkyl group(s) (preferably, one $C_{1-6}$ alkyl group);

A is (1) a heterocyclic group (preferably, (i) a 5- or 6-membered aromatic heterocyclic group or (ii) a 4- to 6-membered non-aromatic heterocyclic group, each containing, as a ring-constituting atom besides carbon atoms, 1 to 4 hetero atoms selected from a nitrogen atom, a sulfur atom and an oxygen atom) (e.g., piperidinyl group, isoxazolyl group, pyrazolyl group, thiadiazolyl group, thiazolyl group, tetrahydropyranyl group, oxetanyl group, oxadiazolyl group, thienyl group, pyridyl group, oxazolyl group) optionally substituted by $C_{1-6}$ alkyl group(s) (preferably, 1 or 2 $C_{1-6}$ alkyl groups) optionally substituted by halogen atom(s) (preferably, 1 to 3 halogen atoms) or (2) a $C_{3-10}$ cycloalkyl group (e.g., cyclopropyl group, cyclobutyl group, cyclopentyl group, cyclohexyl group) optionally substituted by halogen atom(s) (preferably, 1 or 2 halogen atoms);

$R^1$ is a hydrogen atom;

$R^2$ is a hydrogen atom;

$R^3$ is (1) a hydrogen atom, (2) a $C_{1-6}$ alkyl group substituted by one $C_{3-10}$ cycloalkyl group (e.g., cyclopropylmethyl group), (3) a $C_{1-6}$ alkyl group substituted by one 4- to 6-membered non-aromatic heterocyclic group (preferably, a 4- to 6-membered non-aromatic heterocyclic group containing, as a ring-constituting atom besides carbon atoms, 1 or 2 hetero atoms selected from a nitrogen atom, a sulfur atom and an oxygen atom) (e.g., tetrahydropyranylmethyl group), (4) a $C_{3-10}$ cycloalkyl group (e.g., cyclobutyl group, cyclohexyl group) optionally substituted by one amino group, or (5) a 4- to 6-membered non-aromatic heterocyclic group (preferably, a 4- to 6-membered non-aromatic heterocyclic group containing, as a ring-constituting atom besides carbon atoms, 1 or 2 hetero atoms selected from a nitrogen atom, a sulfur atom and an oxygen atom) (e.g., tetrahydropyranyl group, piperidinyl group) optionally substituted by one substituent selected from (a) a $C_{1-6}$ alkyl group optionally substituted by halogen atom(s) (preferably, 1 to 3 halogen atoms), and (b) a $C_{3-10}$ cycloalkyl group (e.g., cyclopropyl group); and
$R^4$ is a hydrogen atom.
[Compound B]
  Compound (I) wherein
B is a ring selected from
thiophene, thiazole, pyrazole, pyridine, naphthalene and 2,3-dihydrobenzofuran, wherein the ring is optionally substituted by $C_{1-6}$ alkyl group(s) (preferably, one $C_{1-6}$ alkyl group); A is
(1) a pyrazolyl group, a thiadiazolyl group or a tetrahydropyranyl group, each optionally substituted by $C_{1-6}$ alkyl group(s) (preferably, one $C_{1-6}$ alkyl group), or
(2) a cyclopentyl group or a cyclohexyl group, each optionally substituted by halogen atom(s) (preferably, 1 or 2 halogen atoms);
$R^1$ is a hydrogen atom;
$R^2$ is a hydrogen atom;
$R^3$ is a hydrogen atom, a cyclopropylmethyl group, a tetrahydropyranylmethyl group, a cyclobutyl group or a tetrahydropyranyl group; and
$R^4$ is a hydrogen atom.
[Compound C]
  Compound (I) wherein
B is a ring selected from thiophene and thiazole, and the ring is optionally substituted by $C_{1-6}$ alkyl group(s) (preferably, one $C_{1-6}$ alkyl group);
  A is
(1) a pyrazolyl group, a thiadiazolyl group or a tetrahydropyranyl group, each optionally substituted by $C_{1-6}$ alkyl group(s) (preferably, one $C_{1-6}$ alkyl group), or
(2) a cyclopentyl group or a cyclohexyl group, each optionally substituted by halogen atom(s) (preferably, 1 or 2 halogen atoms);
$R^1$ is a hydrogen atom;
$R^2$ is a hydrogen atom;
$R^3$ is a cyclopropylmethyl group, a tetrahydropyranylmethyl group, a cyclobutyl group or a tetrahydropyranyl group; and
$R^4$ is a hydrogen atom.
[Compound D]
  A compound represented by the formula (IA)

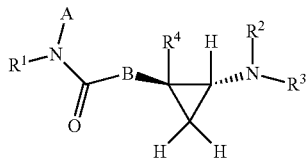

(IA)

wherein A, B, $R^1$, $R^2$, $R^3$ and $R^4$ are as defined for compound A, and the steric configuration shows a relative configuration, or a salt thereof.
[Compound E]
  A compound represented by the formula (IA)

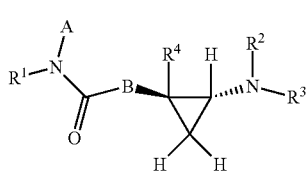

(IA)

wherein A, B, $R^1$, $R^2$, $R^3$ and $R^4$ are as defined for compound B, and the steric configuration shows a relative configuration, or a salt thereof.
[Compound F]
  A compound represented by the formula (IA)

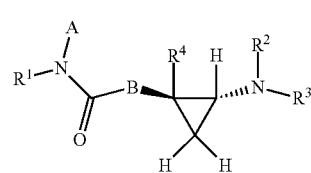

(IA)

wherein A, B, $R^1$, $R^2$, $R^3$ and $R^4$ are as defined for compound C, and the steric configuration shows a relative configuration, or a salt thereof.

The salt of compound (I) is preferably a pharmacologically acceptable salt. Examples of such salt include salts with inorganic bases, salts with organic bases, salts with inorganic acids, salts with organic acids, and salts with basic or acidic amino acids.

Preferable examples of salts with inorganic bases include alkali metal salts such as sodium salts, potassium salts and the like; alkali earth metal salts such as calcium salts, magnesium salts and the like; aluminum salts; and ammonium salts.

Preferable examples of salts with organic bases include salts with trimethylamine, triethylamine, pyridine, picoline, ethanolamine, diethanolamine, triethanolamine, dicyclohexylamine, N,N-dibenzylethylenediamine and the like.

Preferable examples of salts with inorganic acids include salts with hydrochloric acid, hydrobromic acid, nitric acid, sulfuric acid, phosphoric acid and the like.

Preferable examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of salts with basic amino acids include salts with arginine, lysine, ornithine and the like.

Preferable examples of salts with acidic amino acids include salts with aspartic acid, glutamic acid and the like.

The salt of compound (I) is preferably a salt with an inorganic acid (preferably, hydrochloric acid) or an organic acid (preferably, trifluoroacetic acid).

Compound (I) may also be used as a prodrug. A prodrug of compound (I) means a compound which is converted to compound (I) due to a reaction due to an enzyme, gastric acid, etc. under the physiological condition in the living body, that is, a compound which is converted to compound (I) with oxidation, reduction, hydrolysis, and the like according to an enzyme; a compound which is converted to compound (I) by hydrolysis etc. due to gastric acid, and the like. A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation and dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation) and the like. Any of these compounds can be produced from compound (I) by a method known per se.

The prodrug of compound (I) may be a compound that converts to compound (I) under physiological conditions as described in Development of Pharmaceutical Products, vol. 7, Molecular Design, 163-198, Hirokawa Shoten (1990).

Compound (I) may be labeled with an isotope (e.g., $^2$H, $^3$H, $^{14}$C, $^{35}$S, $^{125}$I, $^{11}$C, $^{18}$F) and the like.

Compound (I) labeled with or substituted by an isotope can be used, for example, as a tracer used for Positron Emission Tomography (PET) (PET tracer), and is useful in the field of medical diagnosis and the like.

Compound (I) may be an anhydrate or a hydrate. Compound (I) may be a solvate or a non-solvate. Furthermore, compound (I) may be a deuterated compound.

Compound (I) may be a crystal, and both a single crystal and crystal mixtures are encompassed in compound (I). Crystals can be produced by crystallization according to crystallization methods known per se.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, and stability). The cocrystal and cocrystal salt can be produced by cocrystallization method known per se.

When compound (I) includes isomers such as optical isomers, stereoisomers, regioisomers, rotational isomers, geometrical isomers, and the like, one of the isomers and mixture are also encompassed in compound (I).

Compound (I) or a prodrug thereof (hereinafter sometimes to be simply abbreviated as the compound of the present invention) has low toxicity (e.g., acute toxicity, chronic toxicity, genetic toxicity, reproductive toxicity, cardiotoxicity, carcinogenicity), and can be used as it is or in the form of a pharmaceutical composition (in the present specification, sometimes to be abbreviated as "medicament of the present invention") after mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As a pharmaceutical acceptable carrier here, common organic or inorganic carrier substances are used as formulation raw materials. Carriers are added as vehicles, lubricants, binders and disintegrants in the solid formulations; and as solvents, solubilizing agents, suspending Jo agents, isotonization agents, buffering agents, soothing agents etc. in the liquid formulations. If desired, formulation additives such as preservatives, antioxidants, colorants, sweeteners, etc. can be used.

Preferable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light anhydrous silicic acid, synthetic aluminum silicate, and magnesium metasilicic aluminate.

Preferable examples of the lubricant include magnesium stearate, calcium stearate, talc, colloidal silica, and the like.

Preferable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methylcellulose, and polyvinylpyrrolidone.

Preferable examples of the disintegrants are as follows: lactose, sucrose, starch, carboxymethylcellulose, calcium carboxymethylcellulose, croscarmellose sodium, sodium carboxymethyl starch, light anhydrous silicic acid, and low-substituted hydroxypropylcellulose.

Preferable examples of the solvents are as follows: water for injection, physiological saline, Linger solution, alcohol, propylene glycol, polyethylene glycol, sesame oil, corn oil, olive oil, and cottonseed oil.

Preferable examples of the solubilizing agents are as follows: polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate.

Preferable examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, and polyoxyethylene hydrogenated castor oil.

Preferable examples of the isotonization agents include sodium chloride, glycerin, D-mannitol, D-sorbitol, and glucose.

Preferable examples of the buffering agent include buffer solutions such as phosphates, acetates, carbonates, and citrates.

Preferable examples of the soothing agent include benzyl alcohol.

Preferable examples of the preservative include p-hydroxybenzoates, chlorobutanol, benzyl alcohol, phenethyl alcohol, dehydroacetic acid, and sorbic acid.

Preferable examples of antioxidants include sulfites and ascorbates.

Preferable examples of the colorants include water soluble edible tar dyes (e.g., edible dyes such as Food Red No. 2 and No. 3, Food Yellow No. 4 and No. 5, Food Blue No. 1 and 2, etc.); water insoluble lake dyes (e.g., aluminum salts of the aforementioned water soluble edible tar dyes), and natural dyes (e.g., β-carotene, chlorophyll, ferric oxide red).

Preferable examples of the sweeteners include sodium saccharin, dipotassium glycyrrhizinate, aspartame and stevia.

Examples of the dosage form of the medicament of the present invention include oral preparations such as tablet (including sublingual tablet, orally disintegrating tablet), capsule (including soft capsule, microcapsule), granule, powder, troche, syrup, emulsion, suspension and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparation, pulmonary preparation (inhalant), eye drop and the like, which can be respectively safely administered orally or parenterally.

These preparations may be a release control preparation (e.g., sustained-release microcapsule) such as an immediate-release preparation, a sustained-release preparation and the like.

The medicament of the present invention can be manufactured by the common methods in the field of formulation technology, for example, methods listed in the Japanese Pharmacopoeia, and the like.

The content of the compound of the present invention in the medicament of the present invention varies based on the dosage forms, dosages of the compound of the present invention, and the like. For example, it is approximately about 0.1 to 100 wt %.

The compound of the present invention has a superior LSD1 inhibitory action and can be used as a prophylactic or therapeutic agent for various diseases in mammals (e.g., human, mouse, rat, rabbit, dog, cat, bovine, horse, swine, monkey). Moreover, since the compound of the present invention shows low monoamine oxidase A (MAO-A) and monoamine oxidase B (MAO-B) inhibitory activity and high LSD1 selectivity, it causes fewer side effects.

In addition, the compound of the present invention is expected to show, after transfer into the brain, suppression of a decrease in histone H3K4 methylation and suppression of a decrease in Gad1 mRNA expression, which are derived from the inhibition of LSD1. As a result, it is also useful as a medicament based on superior actions such as neuronal function, enhancement of neural plasticity, promotion of neurogenesis, and promotion of BDNF production.

In addition, the compound of the present invention can, after transfer into the brain, suppress a decrease in histone H3K9 methylation derived from LSD1 inhibition. As a result, it is effective for the treatment of some diseases associated with a decrease in the methylation of H3K9.

The compound of the present invention can be used as a prophylactic or therapeutic agent for cancer. Examples of the cancer include breast cancer, prostate cancer, pancreatic cancer, gastric cancer, lung cancer, colorectal cancer, rectal cancer, esophagus cancer, duodenal cancer, tongue cancer, pharyngeal cancer, brain tumor, schwannoma, non-small cell lung cancer, small cell lung cancer, liver cancer, kidney cancer, bile duct cancer, uterine body cancer, cervical cancer, ovarian cancer, urinary bladder cancer, skin cancer, hemangioma, malignant lymphoma, malignant melanoma, thyroid cancer, bone tumor, angiofibroma, retinoblastoma, penile cancer, childhood solid cancer, Kaposi's sarcoma, AIDS-related Kaposi's sarcoma, tumor of maxillary sinus, fibrous histiocytoma, leiomyosarcoma, rhabdomyosarcoma, and leukemia. Among these, the compound can be preferably used for prostate cancer, leukemia, and malignant lymphoma.

It is known that the level of H3K4me2, which is a substrate of LSD1, and memory improvement are correlated (Nature 2007, Vol. 447, page 175), and the compound of the present invention having a superior LSD1 inhibitory action can also be used as a prophylactic or therapeutic agent for neurodegenerative diseases.

The compound of the present invention can be used as a therapeutic agent for anemia. Examples of anemia include sickle cell anaemia and beta thalassemia.

The compound of the present invention can be used as a prophylactic or therapeutic agent for central nervous system diseases. It is useful as a prophylactic or therapeutic agent for diseases such as (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, mood disorder, panic disorder, phobia, social phobia, social anxiety disorder, obsessive disorder, post-traumatic stress syndrome, post-traumatic stress disorder, Tourette syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, anxiety symptom, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington's disease (Huntington chorea), multi-infarct dementia, frontotemporal dementia, frontotemporal dementia with Parkinsonism, progressive supranuclear palsy, Pick's syndrome, Niemann-Pick syndrome, corticobasal degeneration, vascular dementia, postencephalitic parkinsonism, dementia with Lewy body, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, spinocerebellar degeneration (e.g., dentatorubural pallidoluysian atrophy)], (3) developmental disorders, particularly, diseases with intellectual disability (e.g., autistic spectrum disorders, Rett syndrome, Down's syndrome, Kabuki syndrome, fragile X syndrome, Kleefstra syndrome, neurofibromatosis type 1, Noonan syndrome, tuberous sclerosis), (4) age-related cognition and memory disorders [e.g., age-related memory disorders, senile dementia], (5) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake disorder and the like), parasomnia, sleep disorders associated with internal medical or psychiatric disorder (e.g., chronic obstructive pulmonary disease, Alzheimer's disease, Parkinson's disease, cerebrovascular dementia, schizophrenia, depression, anxiety neurosis), stress insomnia, insomnia, insomniac neurosis, sleep apnea syndrome], (6) respiratory depression caused by anesthetics, traumatic disease, or neurodegenerative disease and the like, (7) epilepsy (e.g., Dravet syndrome), traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol intoxication, alcoholic jealousy, alcoholic mania, alcohol-dependent psychiatric disorder, alcoholic insanity, drug dependence, drug intoxication, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hearing loss, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, stress ulcer, diarrhea, constipation, postoperative ileus, and the like.

The compound of the present invention is particularly useful as an agent for the prophylaxis or treatment of diseases such as schizophrenia, developmental disorders, particularly diseases having intellectual disability (e.g., autistic spectrum disorders, Rett syndrome, Down's syndrome, Kabuki syndrome, fragile X syndrome, Kleefstra syndrome, neurofibromatosis type 1, Noonan syndrome, tuberous sclerosis), neurodegenerative diseases (e.g., Alzheimer's disease, Parkinson's disease, spinocerebellar degeneration (e.g., dentatorubural pallidoluuysian atrophy) and Huntington's disease (Huntington chorea)), epilepsy (e.g., Dravet syndrome) or drug dependence, and the like.

Since the compound of the present invention has a superior LSD1 inhibitory activity, it is expected to show a superior treatment effects for the above-mentioned diseases.

The dosage of the compound of the present invention varies depending on the administration subjects, administration routes, target diseases, symptoms, and the like. For example, for oral administration to adult patients with cancer, generally a single dose is about 0.01 to 100 mg/kg body weight, preferably 0.1 to 50 mg/kg body weight, further preferably 0.5 to 20 mg/kg body weight, and this dosage is preferably administered 1 to 3 times daily.

The compound of the present invention can be used in combination with a medicament such as chemotherapeutic agent, immunotherapeutic agent, medicament inhibiting actions of cell growth factor and receptor thereof (hereinafter to be abbreviated as a concomitant drug).

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

Examples of the chemotherapeutic agent include alkylating agents (e.g., nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin), metabolic antagonists (e.g., mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine), antitumor antibiotics (e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride), and plant-derived antitumor agents (e.g., etoposide, etoposide phosphate, vinblastine sulfate, vincristine sulfate, vindesine sulfate, teniposide, paclitaxel, docetaxel, vinorelbine).

Examples of the immunotherapeutic agent include picibanil, krestin, schizophyllan, lentinan, ubenimex, interferon, interleukin, macrophage colony stimulating factor, granulocyte colony stimulating factor, erythropoietin, lymphotoxin, BCG vaccine, corynebacterium parvum, levamisole, polysaccharide K, procodazole and anti-CTLA4 antibody.

Examples of the "medicament inhibiting actions of cell growth factor and receptor thereof" include anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-primido[5,4-d] [2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2 (R),3-dihydroxypropoxy]-3,4-difluoro-2-(2-fluoro-4-iodophenylamino)benzamide (PD-0325901) and everolimus (RAD001)

Examples of the concomitant drug for the central nervous system diseases include the following.
benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-HT1A agonist, (buspirone hydrochloride, tandospirone citrate, osemozotan hydrocloride etc.), 5-HT$_3$ antagonist (cyamemazine etc.), non-cardioselective β blocker (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH (Hirtonin, Ceredist), MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcohol dependence, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance dependence (varenicline etc.), therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for Huntington's disease (Huntington chorea), therapeutic drug for ALS (riluzole etc., neurotrophic factor etc.), antiepileptic drug (phenobarbital, phenytoin, valproic acid, clonazepam, topiramate, gabapentin, phenobarbital ethosuximide etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, anti-anxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin, indomethacin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug, and the like.

The above-mentioned concomitant drug may be used in a combination of two or more kinds at an appropriate ratio.

When the compound of the present invention is used in combination with a concomitant drug, the respective dosages can be reduced within a safe range in consideration of the opposite effects of the respective drugs. As a result, the opposite effect caused by these agents can be prevented safely.

The compound of the present invention can also be used in combination with a non-medication therapy. Specific examples of the non-medication therapy include (1) operation; (2) hypertensive chemical therapy using angiotensin II and the like; (3) gene therapy; (4) hyperthermic therapy; (5) cryotherapy; (6) laser ablation method; (7) radiation therapy; and (8) immunotherapy.

[Production Method]

The production method of the compound of the present invention is explained below. Those of ordinary skill in the art can produce compound (I) according to the methods shown in each step of the following production methods and Examples, or a method analogous thereto.

The starting materials and reagents used in each step of the following production methods, as well as the obtained compounds may each form a salt. Examples of such salt include those similar to the salts of the aforementioned compounds of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

While the compounds obtained in each step can be directly used for the next reaction in the form of a reaction mixture or as a crude product, the compound obtained in each step can be isolated and/or purified according to a conventional method from the reaction mixture by separation means such as concentration, crystallization, recrystallization, distillation, solvent extraction, fractionation, chromatography and the like.

When the compound of a starting material or a reagent for each step is commercially available, the commercially available product can be directly used.

In the reaction of each step, while the reaction time varies depending on the reagents and solvents to be used, unless particularly indicated, it is generally 1 min to 72 hr, preferably 10 min to 8 hr.

In the reaction of each step, while the reaction temperature varies depending on the reagents and solvents to be used, unless particularly indicated, it is generally −78° C. to 300° C., preferably −78° C. to 150° C.

In the reaction of each step, while the pressure varies depending on the reagents and solvents to be used, unless particularly indicated, it is generally 1 atm to 20 atm, preferably 1 atm to 3 atm.

In the reaction of each step, microwave synthesizers such as Initiator manufactured by Biotage and the like are sometimes used. While the reaction temperature varies depending on the reagents and solvents to be used, unless particularly indicated, it is generally room temperature to 300° C., preferably 50° C. to 250° C. While the reaction time varies depending on the reagents and solvents to be used, unless particularly indicated, it is generally 1 min to 48 hr, preferably 1 min to 8 hr.

In the reaction of each step, unless particularly indicated, the reagents are used in 0.5 equivalent to 20 equivalents, preferably 0.8 equivalent to 5 equivalents, relative to the substrate. When a reagent is used as a catalyst, the reagent is used in 0.001 equivalent to 1 equivalent, preferably 0.01 equivalent to 0.2 equivalent, relative to the substrate. When the reagent is also used as a reaction solvent, the reagent is used in a solvent amount.

In the reaction of each step, unless particularly indicated, the reaction is performed without solvent, or by dissolving or suspending a starting material in a suitable solvent. Specific examples of the solvent include the solvents described in Examples, and the following.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
hydrocarbon halides: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

Two or more kinds of the above-mentioned solvents may be mixed and used at appropriate ratios.

When a base is used in the reaction of each step, for example, the bases shown below or the bases described in the Examples are used.

inorganic bases: sodium hydroxide, magnesium hydroxide, lithium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acidic catalyst is used in the reaction of each step, for example, the acids or acidic catalysts shown below or those described in the Examples are used.

inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed by a method known per se, for example, the methods described in Jikken Kagaku Koza (Courses in Experimental Chemistry), 5th Edition, Volumes 13-19 (The Chemical Society of Japan ed.); Shin Jikken Kagaku Koza (New Experimental Chemistry Course), Volumes 14-15 (The Chemical Society of Japan ed.); Seimitsu Yuki Gosei (Reactions and Syntheses: In the Organic Chemistry Laboratory), Revised 2nd Edition (L. F. Tietze, Th. Eicher, Nankodo Co., Ltd.); Revised Edition Organic Name Reactions; The Reaction Mechanism and Essence (Hideo Togo, Kodansha Ltd.); ORGANIC SYNTHESES Collective Volumes I-VII (John Wiley & Sons, Inc.); Modern Organic Synthesis in the Laboratory A Collection of Standard Experimental Procedures (Jie Jack Li, OXFORD UNIVERSITY PRESS); Comprehensive Heterocyclic Chemistry III, Vol. 1-Vol. 14 (Elsevier Japan KK); Strategic Applications of Named Reactions in Organic Synthesis (translated by Kiyoshi Tomioka, Kagaku-Dojin Publishing Company, INC); Comprehensive Organic Transformations (VCH Publishers Inc.) 1989 and the like, or the methods described in the Examples.

In each step, protection or deprotection of functional groups is performed according to a method known per se, for example, the methods described in Wiley-Interscience, 2007, "Protective Groups in Organic Synthesis, 4th Ed." (Theodora W. Greene, Peter G. M. Wuts); Thieme, 2004, "Protecting Groups 3rd Ed." (P. J. Kocienski) and the like, or the methods described in the Examples.

Examples of the protecting group for hydroxyl group of alcohol and the like and phenolic hydroxyl group include ether-type protecting groups such as methoxymethyl ether, benzyl ether, t-butyldimethylsilyl ether, tetrahydropyranyl ether and the like; carboxylate-type protecting groups such as acetate and the like; sulfonate-type protecting groups such as methanesulfonate and the like; carbonate-type protecting groups such as t-butyl carbonate and the like; and the like.

Examples of the protecting group for carbonyl group of aldehyde include acetal-type protecting groups such as dimethyl acetal and the like; cyclic acetal-type protecting groups such as cyclic 1,3-dioxane and the like; and the like.

Examples of the protecting group for carbonyl group of ketone include ketal-type protecting groups such as dimethyl ketal and the like; cyclic ketal-type protecting groups such as cyclic 1,3-dioxane and the like; oxime-type protecting groups such as O-methyloxime and the like; hydrazone-type protecting groups such as N,N-dimethylhydrazone and the like; and the like.

Examples of the protecting group for carboxyl group include ester-type protecting groups such as methyl ester and the like; amide-type protecting groups such as N,N-dimethylamide and the like; and the like.

Examples of the protecting group for thiol include ether-type protecting groups such as benzyl thioether and the like; ester-type protecting groups such as thioacetate, thiocarbonate, thiocarbamate and the like; and the like.

Examples of the protecting group for amino group, and aromatic heterocycle such as imidazole, pyrrole, indole and the like include carbamate-type protecting groups such as benzyl carbamate, tert-butyl carbamate and the like; amide-type protecting groups such as acetamide and the like; alkylamine-type protecting groups such as N-triphenylmethylamine and the like; sulfonamide-type protecting groups such as methanesulfonamide and the like; and the like.

Protecting groups can be removed by a method known per se, for example, methods using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), reduction methods and the like.

When a reduction reaction is performed in each step, the reducing agent to be used includes metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane-tetrahydrofuran complex and the like; Raney-nickel; Raney-cobalt; hydrogen; formic acid and the like. When a carbon-carbon double bond or triple bond is reduced, a method using a catalyst such as palladium-carbon, Lindlar catalyst and the like can be used.

When oxidation reaction is performed in each step, the oxidizing agent to be used includes peracids such as m-chloroperbenzoic acid (MCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents having manganese such as manganese dioxide, potassium permanganate and the like; lead compounds such as lead tetraacetate and the like; reagents having chrome such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is performed in each step, the radical initiator to be used includes azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. The radical reaction reagent to be used includes tributylstannane, tris(trimethylsilyl)silane, 1,1,2,2-tetraphenyldisilane, diphenylsilane, samarium iodide and the like.

When the Wittig reaction is performed in each step, the Wittig reagent to be used includes alkylidene phosphoranes and the like. Alkylidene phosphoranes can be prepared by a method known per se, for example, by reacting a phosphonium salt with a strong base.

When the Horner-Emmons reaction is performed in each step, the reagent to be used includes phosphonoacetates such as methyl dimethylphosphonoacetate, ethyl diethylphosphonoacetate, tert-butyl diethylphosphonoacetate and the like; bases such as alkali metal hydrides, organic lithiums, 1,8-diazabicyclo[5.4.0]undec-7-ene and the like; lithium chloride, sodium iodide and the like.

When the Friedel-Crafts reaction is performed in each step, the reagent to be used includes Lewis acid and acid chloride or alkylating agents (e.g., alkyl halides, alcohol, olefins and the like). Alternatively, organic acid and inorganic acid can also be used instead of Lewis acid, and acid anhydrides such as acetic anhydride and the like can also be used instead of acid chloride.

When an aromatic nucleophilic substitution reaction is performed in each step, nucleophilic agents (e.g., amines, imidazole and the like) and bases (e.g., basic salts, organic bases and the like) are used as the reagents.

When a nucleophilic addition reaction by a nucleophilic agent, a nucleophilic addition reaction by carbanion, a nucleophilic 1,4-addition reaction by carbanion (Michael addition) or a nucleophilic substitution reaction by carbanion is performed in each step, a base used to generate carbanion includes organic lithiums, metal alkoxides, inorganic bases, organic bases and the like.

When the Grignard reaction is performed in each step, the Grignard reagent includes arylmagnesium halides such as phenylmagnesium bromide and the like; alkylmagnesium halides such as methylmagnesium bromide and the like. Grignard reagents can be prepared by a method known per se, for example, by reacting alkyl halide or aryl halide with metal magnesium in ether or tetrahydrofuran as a solvent.

When the Knoevenagel condensation is performed in each step, active methylene compounds (e.g., malonic acid, diethyl malonate, malononitrile and the like) and bases (e.g., organic bases, metal alkoxides, inorganic bases) sandwiched between two electron withdrawing groups are used as the reagents.

When the Vilsmeier-Haack reaction is performed in each step, phosphoryl chloride and amide derivative (e.g., N,N-dimethylformamide and the like) are used as the reagents.

When an azidation reaction of alcohols, alkyl halides or sulfonates is performed in each step, the azidating agent to be used includes diphenylphosphoryl azide (DPPA), trimethylsilyl azide, sodium azide and the like. For example, when alcohols are azidated, a method using diphenylphosphoryl azide and 1,8-diazabicyclo[5.4.0]undec-7-ene (DBU), a method using trimethylsilyl azide and Lewis acid, and the like can be used.

When a reductive amination reaction is performed in each step, the reducing agent to be used includes sodium triacetoxyborohydride, sodium cyanoborohydride, hydrogen, formic acid, sodium borohydride, 2-picoline-borane complex and the like. When the substrate is an amine compound, a carbonyl compound to be used includes paraformaldehyde, aldehydes such as acetaldehyde and the like, and ketones such as cyclohexanone and the like. When the substrate is a carbonyl compound, amines to be used includes primary amines such as ammonia, methylamine and the like; secondary amines such as dimethylamine and the like, and the like. An additive such as trimethyl orthoformate and the like may be added to the reaction.

When the Mitsunobu reaction is performed in each step, azodicarboxylates (e.g., diethyl azodicarboxylate (DEAD), diisopropyl azodicarboxylate (DIAD) and the like) and triphenylphosphine are used as the reagents.

When an esterification reaction, an amidation reaction or a ureation reaction is performed in each step, the reagent to be used includes acyl halides such as acid chloride, acid bromide and the like; and activated carboxylic acids such as acid anhydride, active ester form, sulfuric acid ester form and the like. An activator of carboxylic acid includes carbodiimide-type condensing agents such as 1-ethyl-3-(3-dimethylaminopropyl)carbodiimide hydrochloride (WSCD) and the like; triazine-type condensing agents such as 4-(4,6-dimethoxy-1,3,5-triazin-2-yl)-4-methylmorpholinium chloride-n-hydrate (DMT-MM) and the like; carbonate-type condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; or combinations of these and the like.

When a carbodiimide-type condensing agent is used, an additive such as 1-hydroxybenzotriazole (HOBt), N-hydroxysuccinimide (HOSu), dimethylaminopyridine (DMAP) and the like may be further added to the reaction.

When a coupling reaction is performed in each step, the metal catalyst to be used includes palladium compounds such as palladium(II) acetate, tetrakis(triphenylphosphine)palladium(0), dichlorobis(triphenylphosphine)palladium (II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; nickel compounds such as tetrakis(triphenylphosphine)nickel(0) and the like; rhodium compounds such as tris(triphenylphosphine)rhodium(III) chloride and the like; cobalt compound; copper compounds such as copper oxide, copper(I) iodide and the like; platinum compound and the like. Furthermore, a base may be added to the reaction, and examples of such base include inorganic bases, basic salts and the like.

When a thiocarbonylation reaction is performed in each step, diphosphorus pentasulfide is typically used as a thiocarbonylating agent. However, a reagent having a 1,3,2,4-dithiadiphosphetane-2,4-disulfide structure such as 2,4-bis (4-methoxyphenyl-1,3,2,4-dithiadiphosphetane-2,4-disulfide (Lawesson's reagent) and the like may be used besides diphosphorus pentasulfide.

When the Wohl-Ziegler reaction is performed in each step, the halogenating agent to be used includes N-iodosuccinimide, N-bromosuccinimide (NBS), N-chlorosuccinimide (NCS), bromine, sulfuryl chloride and the like. Furthermore, the reaction can be accelerated by adding a radical initiator such as heat, light, benzoyl peroxide, azobisisobutyronitrile and the like to the reaction.

When halogenation of hydroxy group is performed in each step, the halogenating agent to be used includes hydrohalic acid and acid halide of inorganic acid, specifically, hydrochloric acid, thionyl chloride, phosphorus oxychloride and the like for chlorination, and 48% hydrobromic acid and the like for bromination. In addition, a method for obtaining alkyl halide from alcohol by a reaction of triphenylphosphine and carbon tetrachloride or carbon tetrabromide and the like may be used. Alternatively, a method for synthesizing alkyl halide by a two-step reaction including converting alcohol to sulfonate and reacting same with lithium bromide, lithium chloride or sodium iodide may be used.

When the Arbuzov reaction is performed in each step, the reagent to be used includes alkyl halides such as ethyl bromoacetate and the like; and phosphites such as triethyl phosphite, tri(isopropyl)phosphite and the like.

When a sulfonylation reaction is performed in each step, the sulfonylating agent to be used includes methanesulfonyl chloride, p-toluenesulfonyl chloride, methanesulfonic anhydride, p-toluenesulfonic anhydride and the like.

When hydrolysis is performed in each step, an acid or a base is used as a reagent. When acid hydrolysis of t-butyl ester is performed, formic acid, triethylsilane and the like are sometimes added to reductively trap the by-produced t-butyl cation.

When a dehydration reaction is performed in each step, the dehydrating agent to be used includes sulfuric acid, phosphorus pentoxide, phosphorus oxychloride, N,N'-dicyclohexylcarbodiimide, alumina, polyphosphoric acid and the like.

When the Corey-Chaykovsky cyclopropanation reaction is performed in each step, the reagent to be used includes trimethylsulfoxonium iodide, potassium tert-butoxide, sodium hydride and the like.

When a carbon monoxide insertion reaction and a subsequent nucleophilic substitution reaction by alcohol are performed in each step, the metal catalyst to be used includes palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; and examples of the phosphine ligand include triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-1,1'-biphenyl, 2-(dicyclohexylphosphino)-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine) and the like.

Examples of the alcohol include methanol, ethanol, 2-propanol, benzyl alcohol and the like.

This reaction is performed using, as necessary, a phosphine ligand generally under a carbon monoxide atmosphere from normal pressure to about 10 atm in an inert solvent.

When the Curtius rearrangement reaction is performed in each step, the reagents to be used includes diphenylphosphoryl azide and tert-butyl alcohol and the like. As reagents, ethyl chloroformate, a base, sodium azide, tert-butyl alcohol and the like can also be used.

When a diastereomeric salt resolution method is performed in each step, the optically active organic base to be used includes, for example, ((1R,4aS,10aR)-7-isopropyl-1,4a-dimethyl-1,2,3,4,4a,9,10,10a-octahydrophenanthren-1-yl)methanamine, (R)-2-amino-3-phenylpropan-1-ol and the like.

The compound obtained in each step may be used after optical resolution by a known means such as chiral column chromatography, optical fractional crystallization, diastereomer derivatization and the like.

In the schemes, $R^5$ and $R^6$ are alkyl groups such as methyl group, ethyl group, tert-butyl group and the like, and other symbols are each as defined above. Compound (Ia) to compound (Ik), compound (Iaa) and compound (Iga) are included in the aforementioned compound (I), and each of them shows a compound group of compound (I) wherein $R^3$=H. The thiophene ring, pyrazole ring, naphthalene ring, dihydrobenzofuran ring, pyridine ring and thiazole ring each optionally has substituent(s) on the ring.

<Reaction Scheme 1>

Compound (Ia) can be produced from compound (1) by the following method.

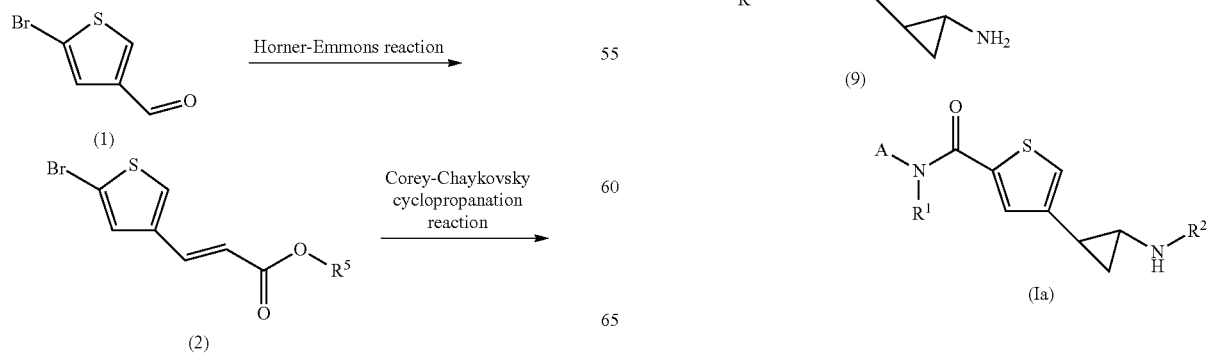

<Reaction Scheme 2>

Compound (Ib) can be produced from compound (10) by the following method.

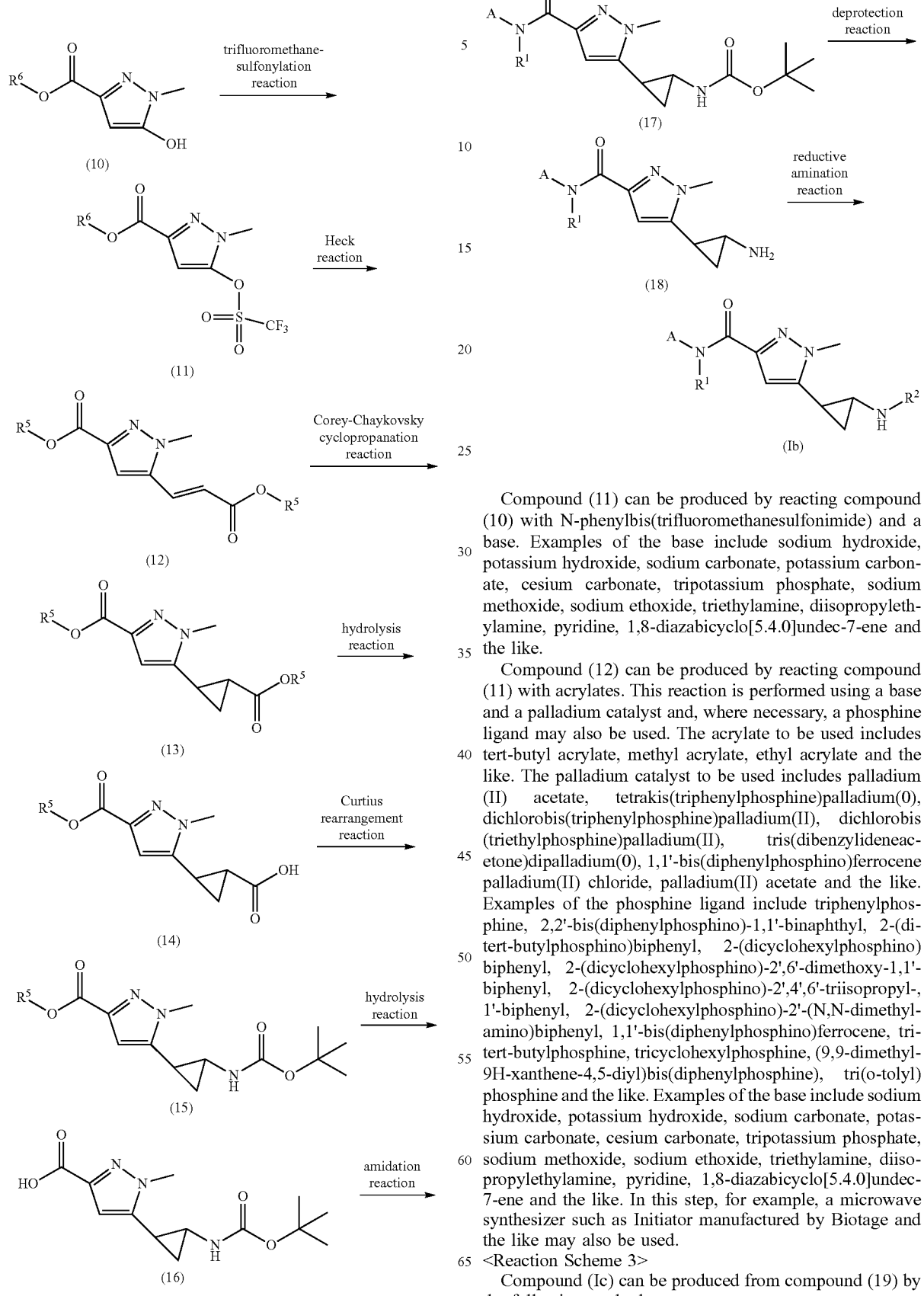

Compound (11) can be produced by reacting compound (10) with N-phenylbis(trifluoromethanesulfonimide) and a base. Examples of the base include sodium hydroxide, potassium hydroxide, sodium carbonate, potassium carbonate, cesium carbonate, tripotassium phosphate, sodium methoxide, sodium ethoxide, triethylamine, diisopropylethylamine, pyridine, 1,8-diazabicyclo[5.4.0]undec-7-ene and the like.

Compound (12) can be produced by reacting compound (11) with acrylates. This reaction is performed using a base and a palladium catalyst and, where necessary, a phosphine ligand may also be used. The acrylate to be used includes tert-butyl acrylate, methyl acrylate, ethyl acrylate and the like. The palladium catalyst to be used includes palladium (II) acetate, tetrakis(triphenylphosphine)palladium(0), dichlorobis(triphenylphosphine)palladium(II), dichlorobis (triethylphosphine)palladium(II), tris(dibenzylideneacetone)dipalladium(0), 1,1'-bis(diphenylphosphino)ferrocene palladium(II) chloride, palladium(II) acetate and the like. Examples of the phosphine ligand include triphenylphosphine, 2,2'-bis(diphenylphosphino)-1,1'-binaphthyl, 2-(di-tert-butylphosphino)biphenyl, 2-(dicyclohexylphosphino) biphenyl, 2-(dicyclohexylphosphino)-2',6'-dimethoxy-1,1'-biphenyl, 2-(dicyclohexylphosphino)-2',4',6'-triisopropyl-, 1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine), tri(o-tolyl) phosphine and the like. Examples of the base include sodium hydroxide, potassium hydroxide, sodium carbonate, potassium carbonate, cesium carbonate, tripotassium phosphate, sodium methoxide, sodium ethoxide, triethylamine, diisopropylethylamine, pyridine, 1,8-diazabicyclo[5.4.0]undec-7-ene and the like. In this step, for example, a microwave synthesizer such as Initiator manufactured by Biotage and the like may also be used.

<Reaction Scheme 3>

Compound (Ic) can be produced from compound (19) by the following method.

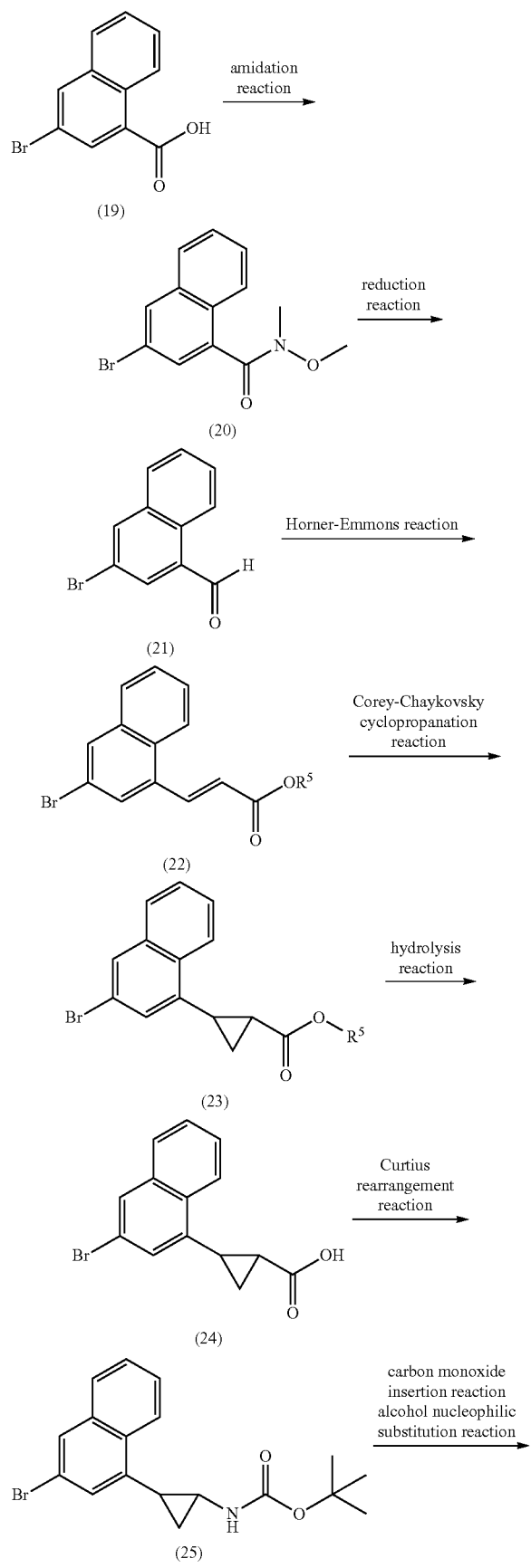
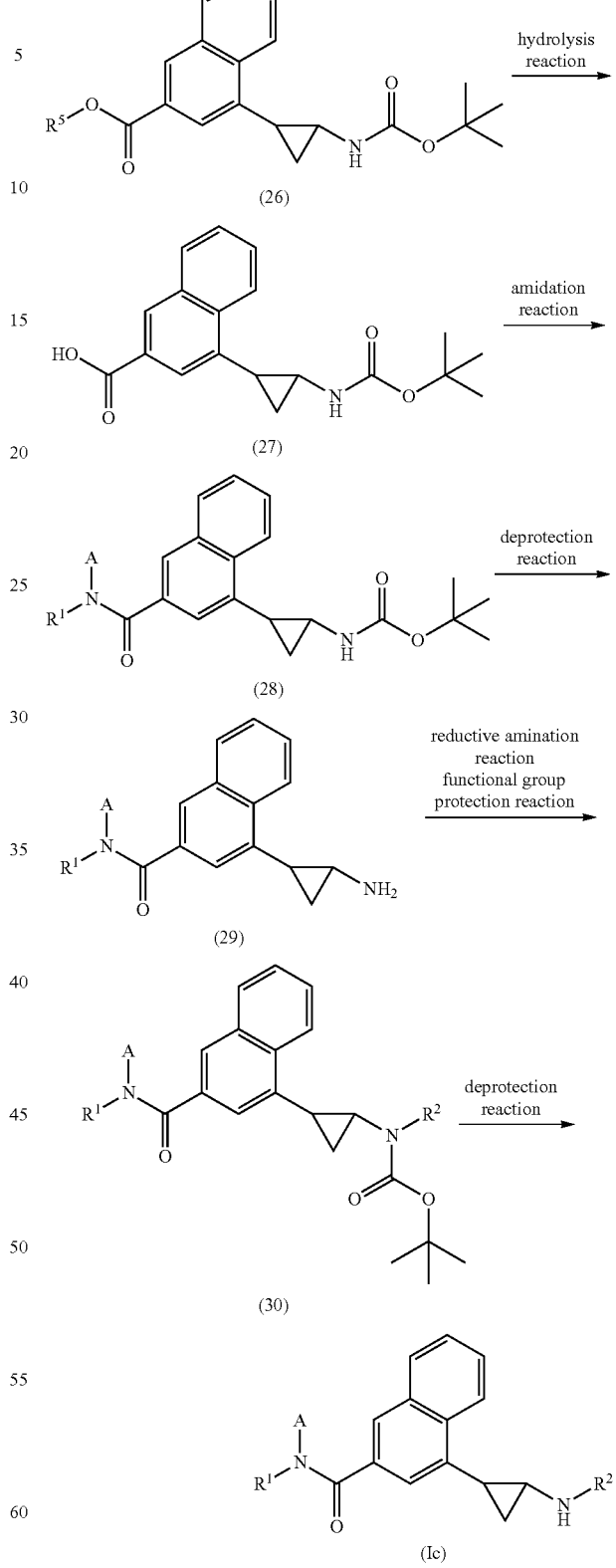
<Reaction Scheme 4>
Compound (Id) can be produced from compound (31) by the following method.

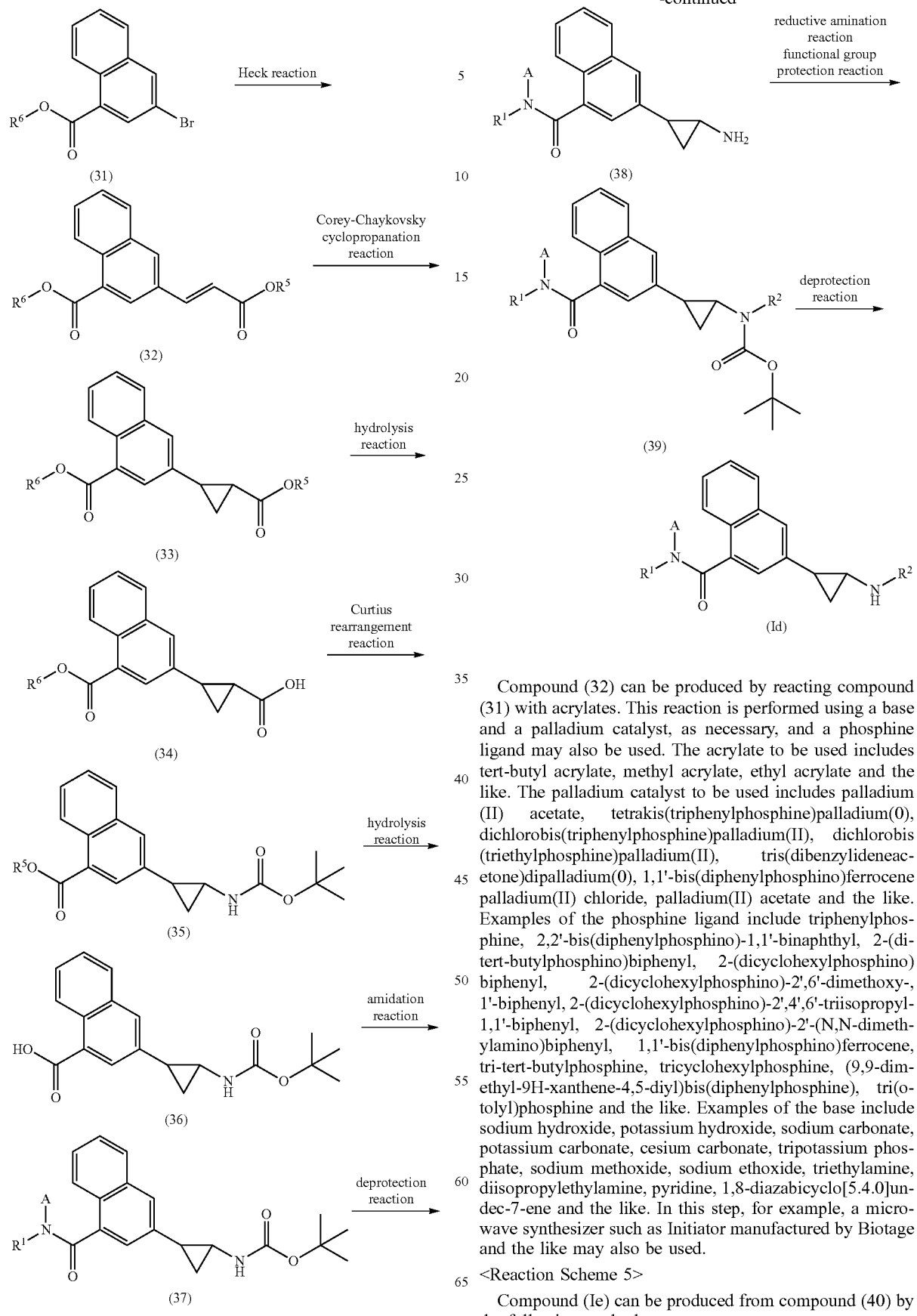

Compound (32) can be produced by reacting compound (31) with acrylates. This reaction is performed using a base and a palladium catalyst, as necessary, and a phosphine ligand may also be used. The acrylate to be used includes tert-butyl acrylate, methyl acrylate, ethyl acrylate and the like. The palladium catalyst to be used includes palladium (II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like. Examples of the phosphine ligand include triphenylphosphine, 2,2'-bis(diphenylphosphino)-1,1'-binaphthyl, 2-(di-tert-butylphosphino)biphenyl, 2-(dicyclohexylphosphino)biphenyl, 2-(dicyclohexylphosphino)-2',6'-dimethoxy-,1'-biphenyl, 2-(dicyclohexylphosphino)-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, (9,9-dimethyl-9H-xanthene-4,5-diyl)bis(diphenylphosphine), tri(o-tolyl)phosphine and the like. Examples of the base include sodium hydroxide, potassium hydroxide, sodium carbonate, potassium carbonate, cesium carbonate, tripotassium phosphate, sodium methoxide, sodium ethoxide, triethylamine, diisopropylethylamine, pyridine, 1,8-diazabicyclo[5.4.0]undec-7-ene and the like. In this step, for example, a microwave synthesizer such as Initiator manufactured by Biotage and the like may also be used.

<Reaction Scheme 5>

Compound (Ie) can be produced from compound (40) by the following method.

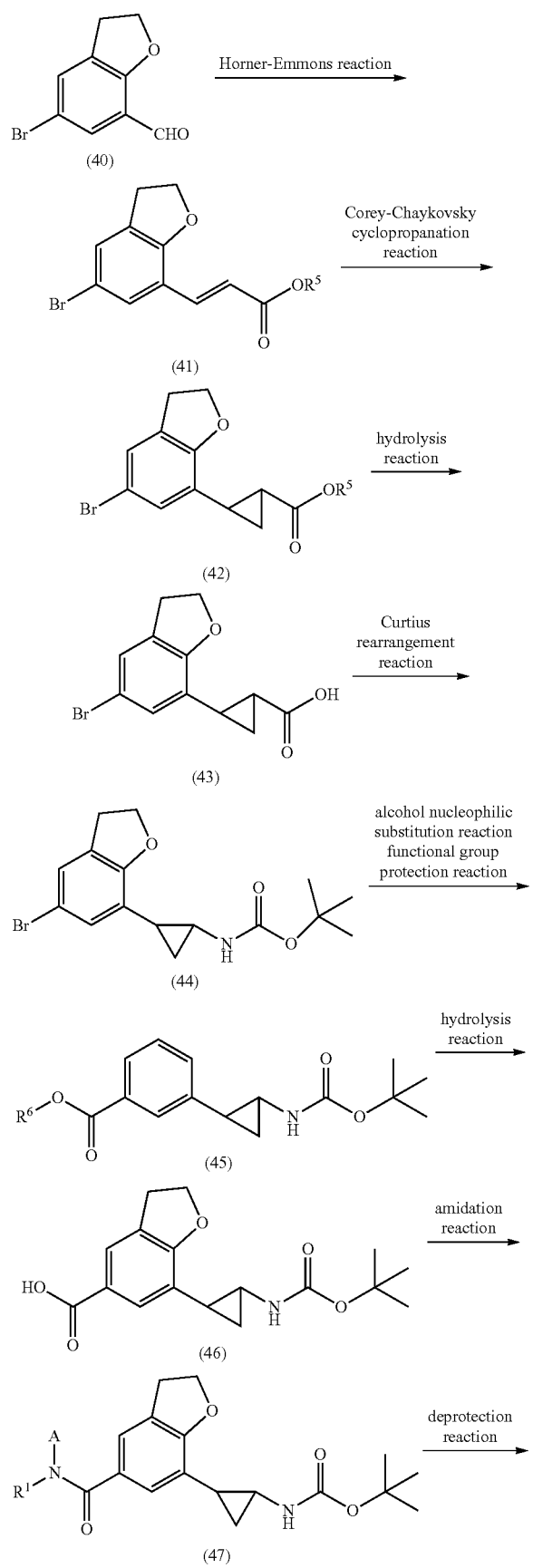
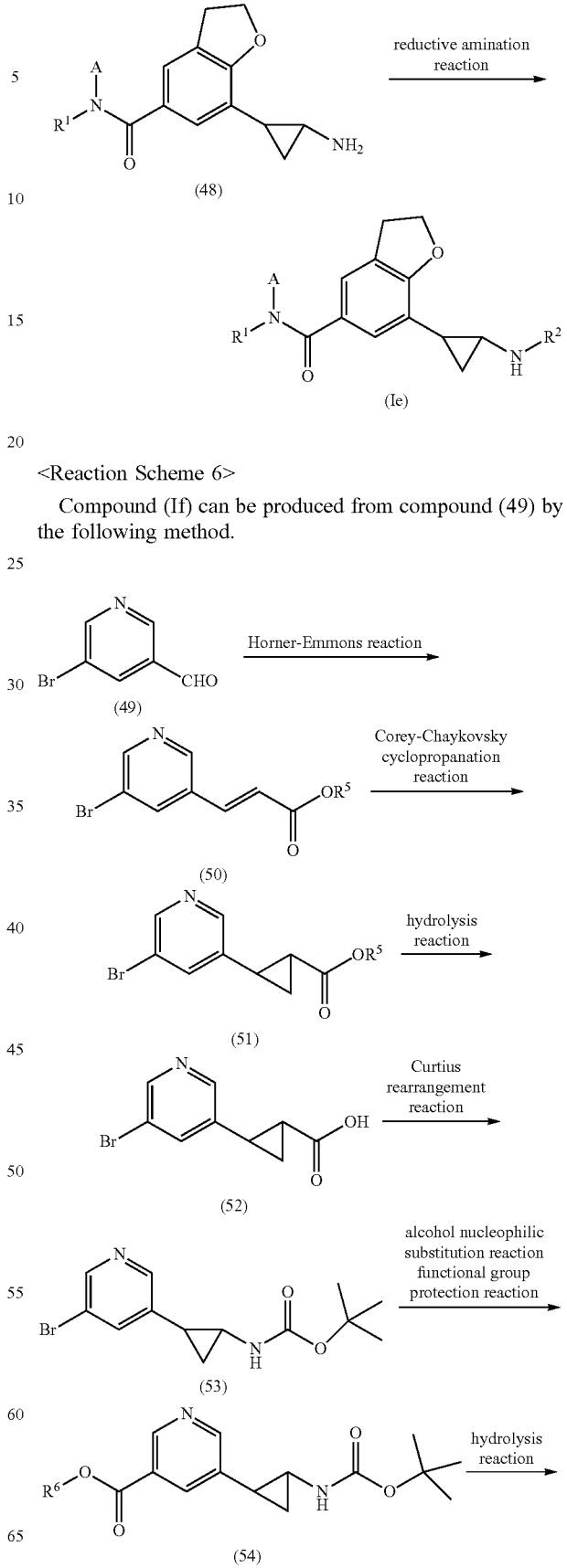
<Reaction Scheme 6>
Compound (If) can be produced from compound (49) by the following method.

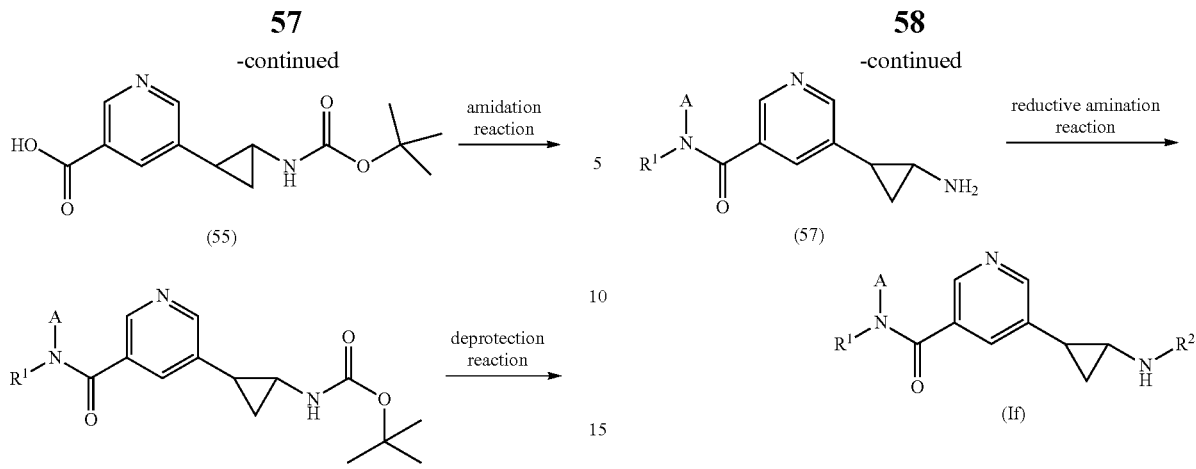
<Reaction Scheme 7>
Compound (Ig) can be produced from compound (58) by the following method.
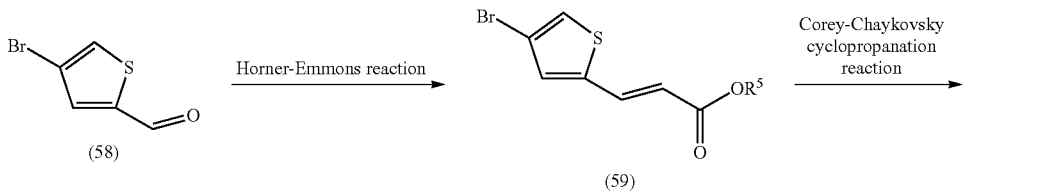
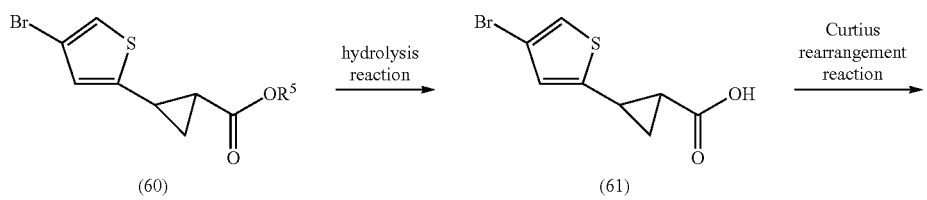
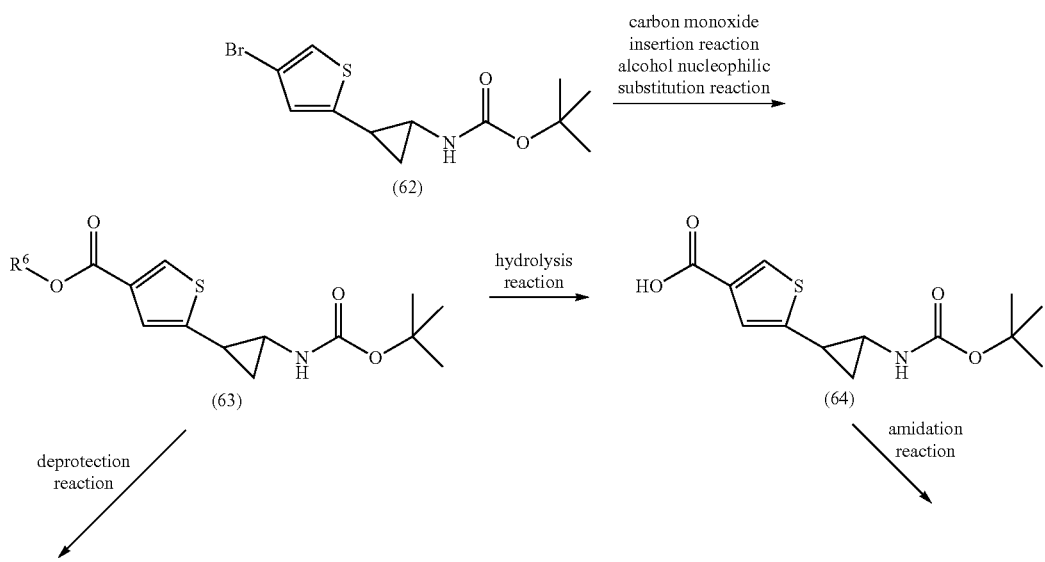

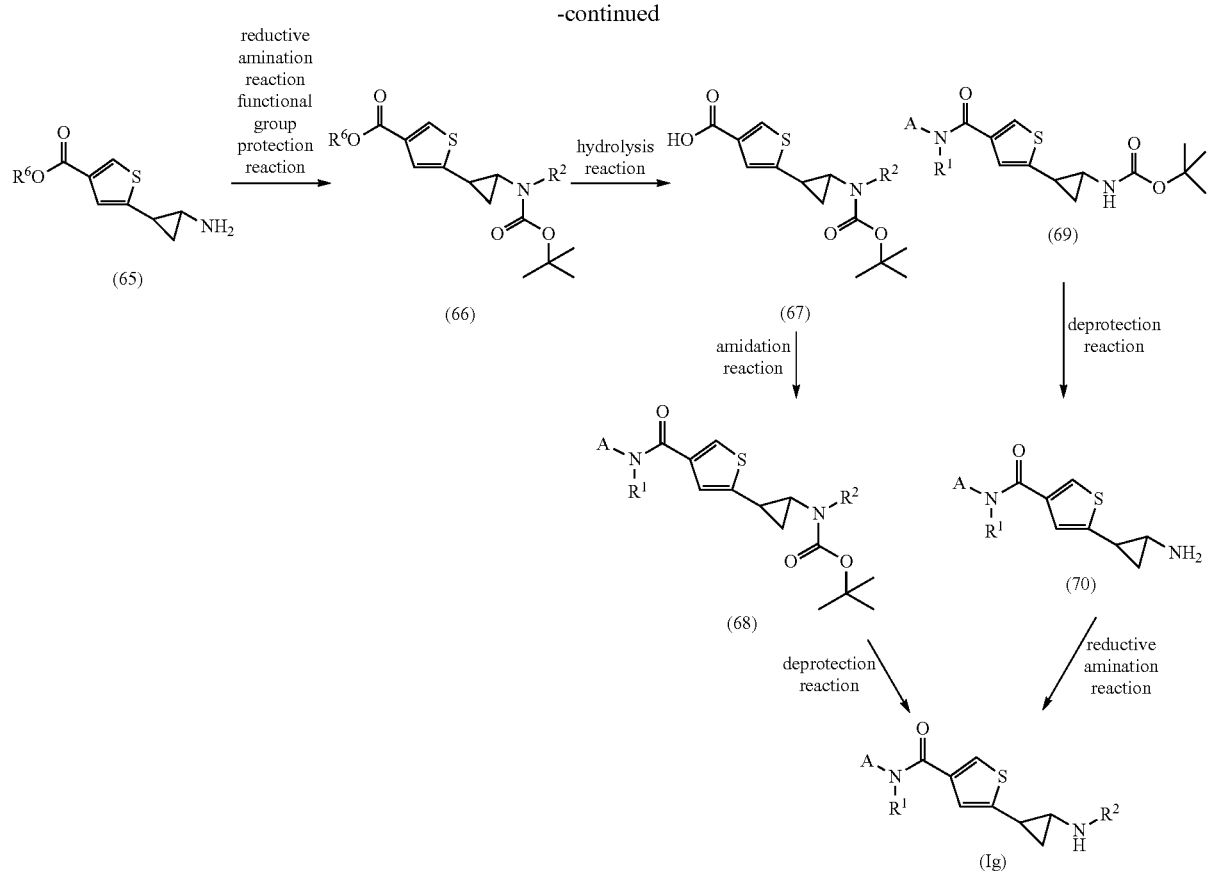
<Reaction Scheme 8>
Compound (Ih) can be produced from compound (71) by the following method.
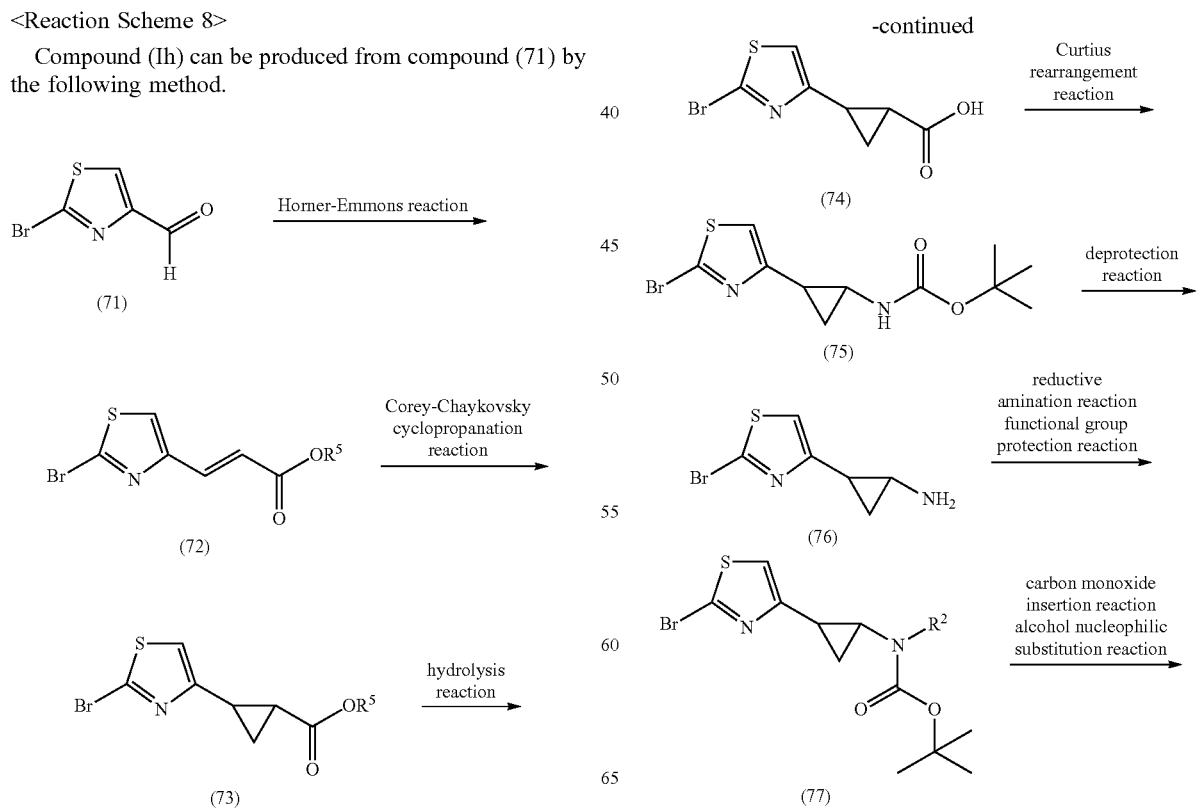

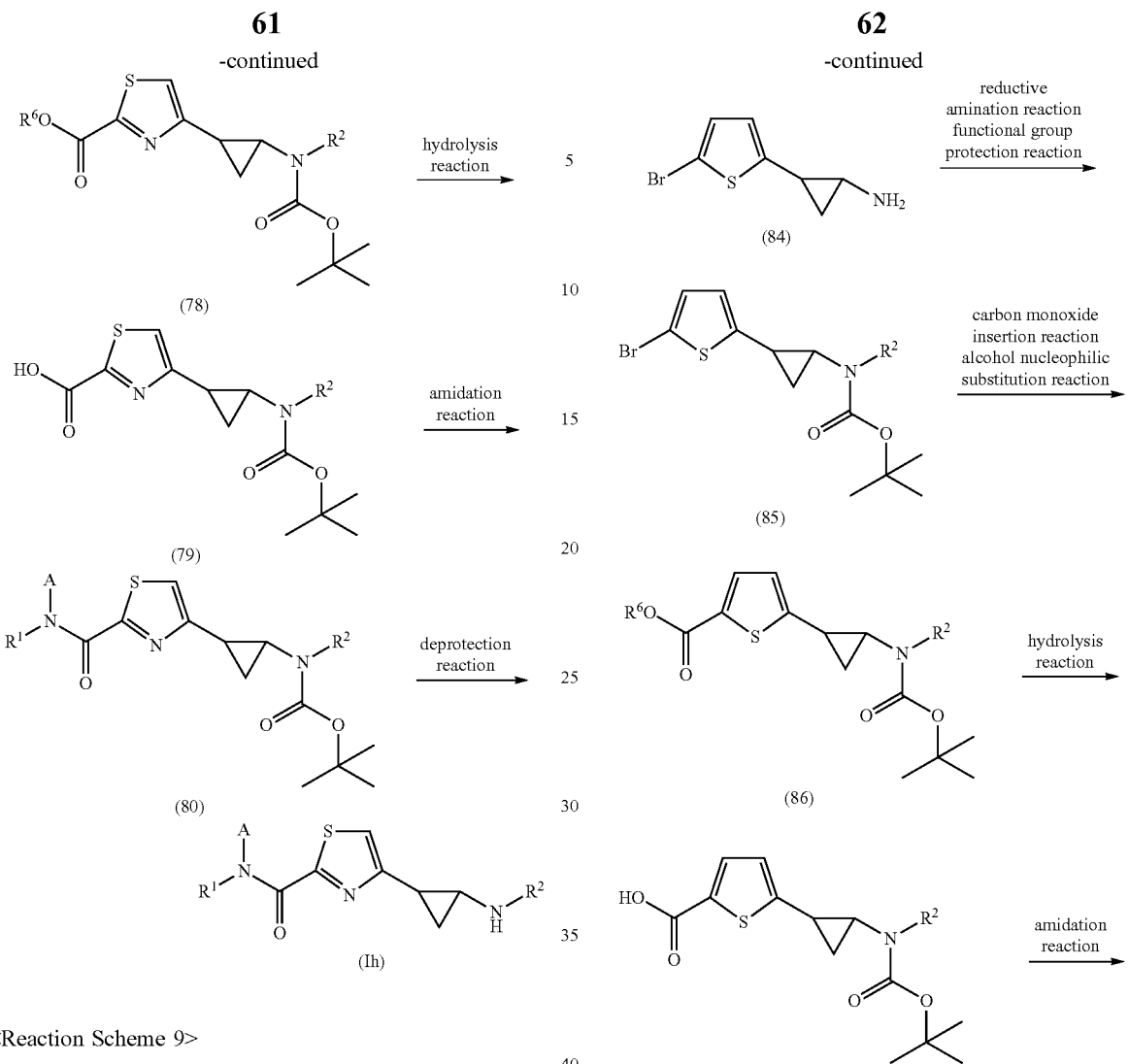
(78) (79) (80) (Ih)
<Reaction Scheme 9>
Compound (Ii) can be produced from compound (81) by the following method.
(81) (82) (83)
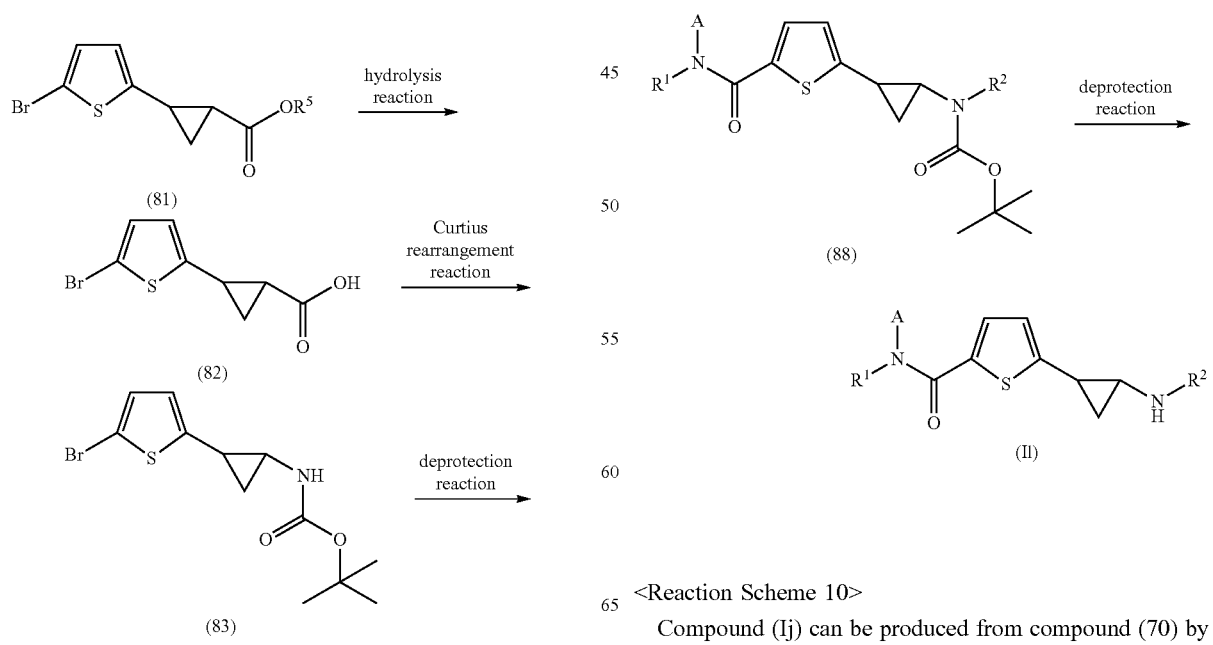
(84) (85) (86) (87) (88) (Il)
<Reaction Scheme 10>
Compound (Ij) can be produced from compound (70) by the following method.

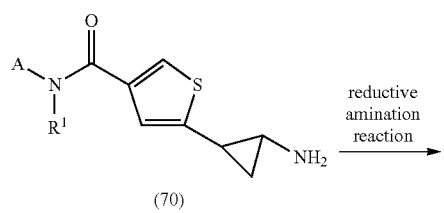
(70)
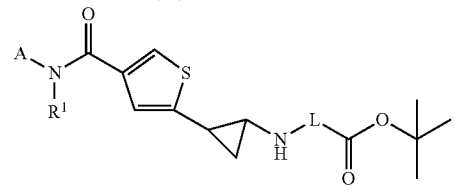
(89)
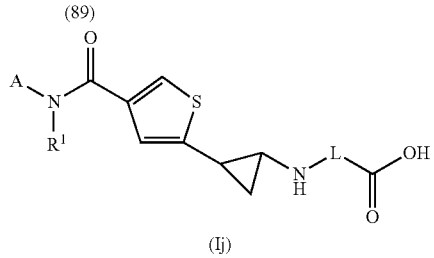
(Ij)
<Reaction Scheme 11>
Compound (Ik) can be produced from compound (89) by the following method.
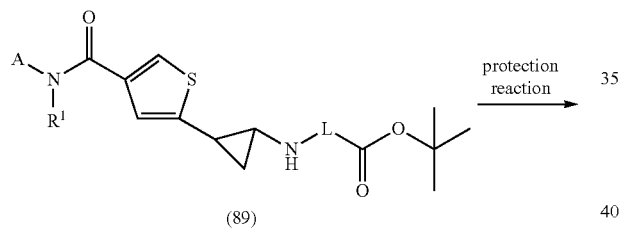
(89)
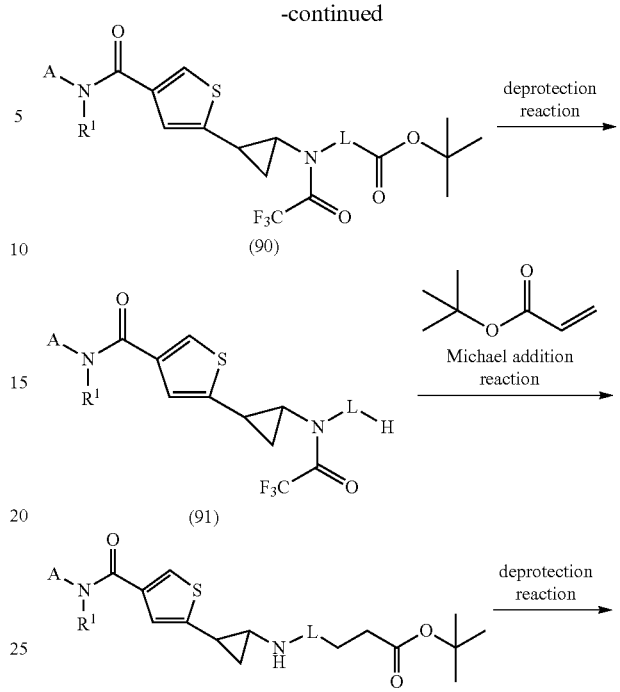
(Ik)
<Reaction Scheme 12>
Compound (Iaa) can be produced from compound (6) or compound (4) by the following method.

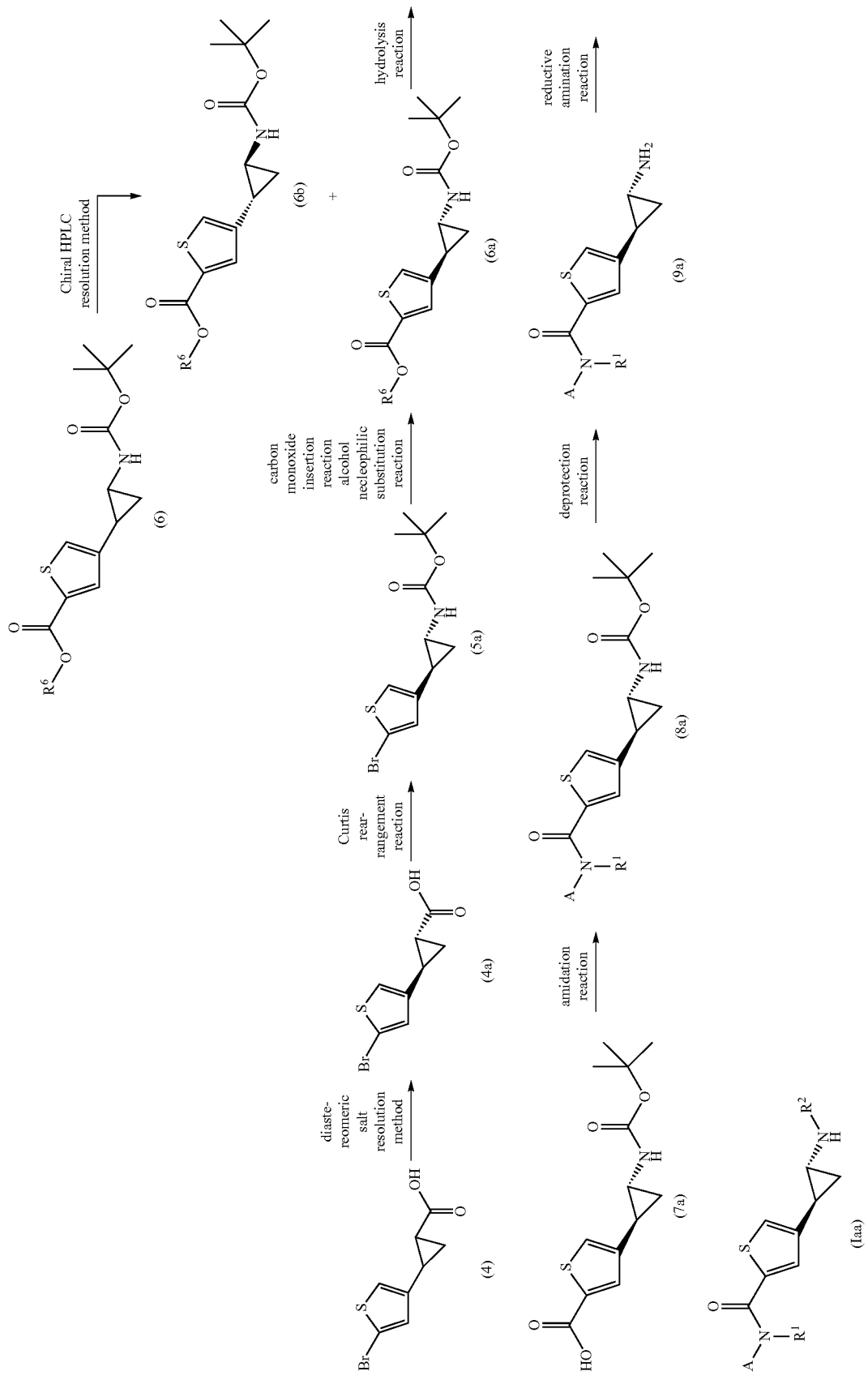

<Reaction Scheme 13>

Compound (Iga) can be produced from compound (61) or compound (63) by the following method.

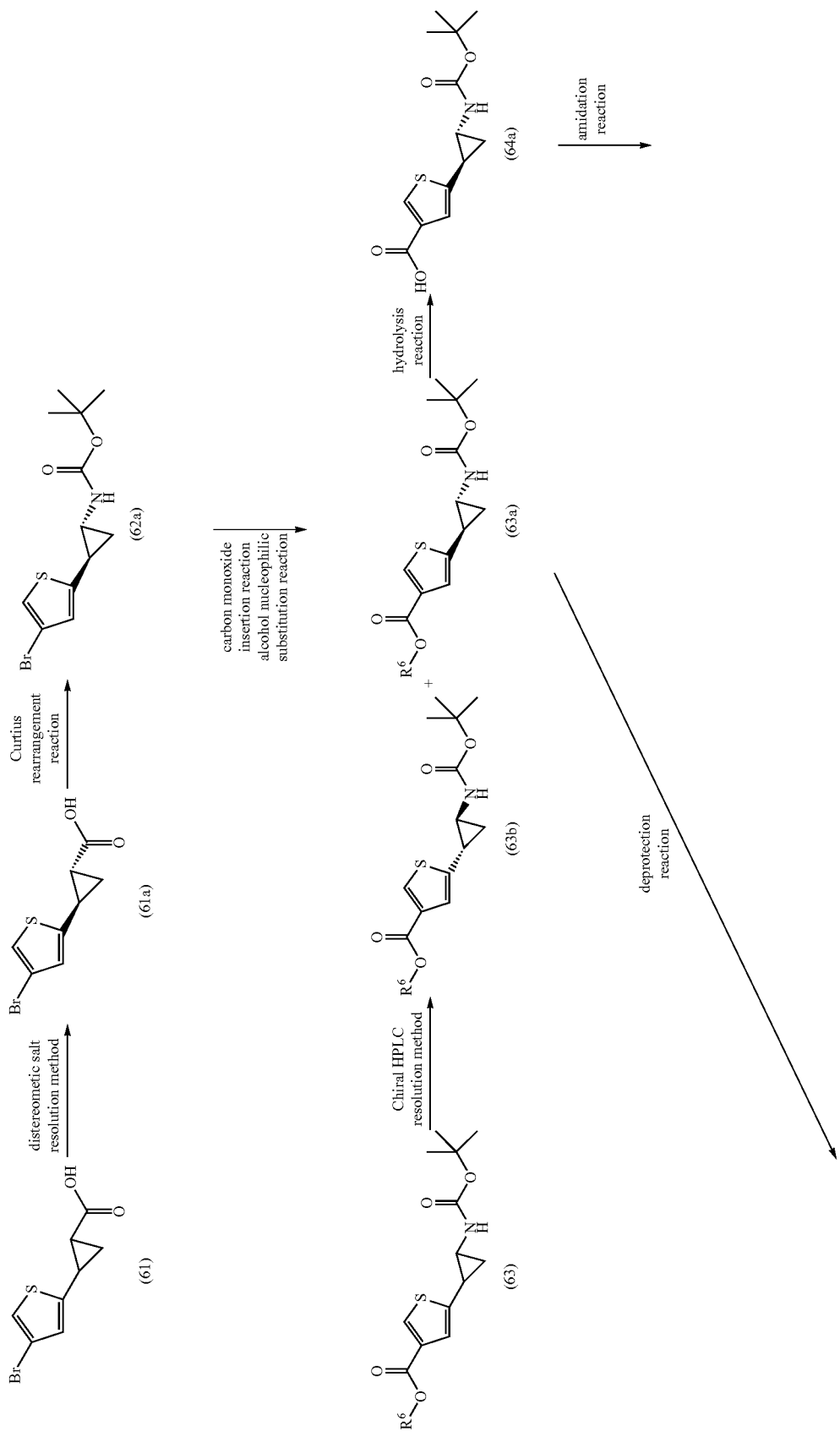

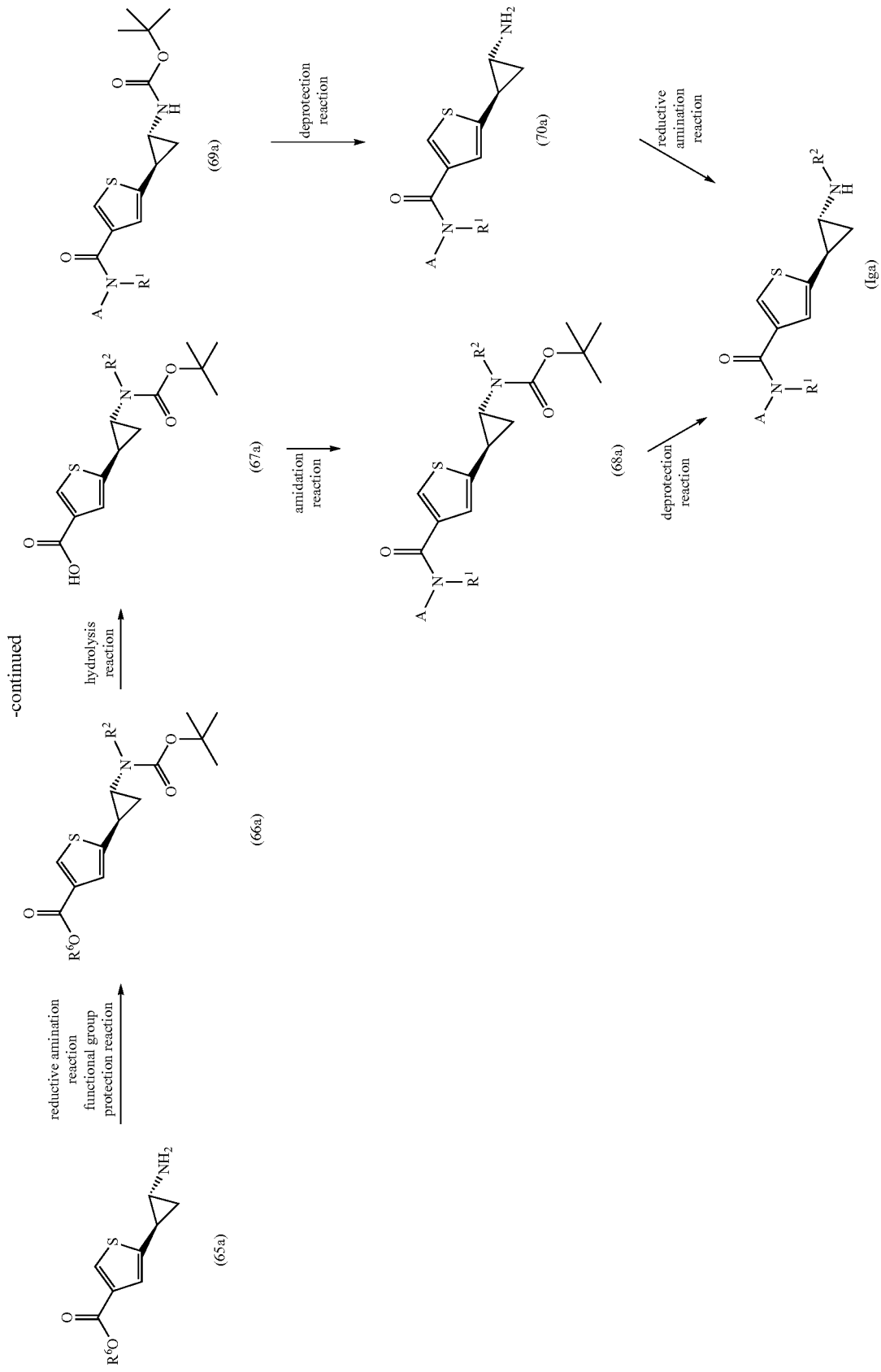

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. Unless otherwise specified, the ratio of elution solvents is a volume mixing ratio.

In the following Examples, the following abbreviations are used.

mp: melting point
MS: mass spectrum
[M+H]$^+$, [M−H]$^-$: molecular ion peak
M: molar concentration
N: normality
CDCl$_3$: deuterated chloroform
DMSO-d$_6$: deuterated dimethyl sulfoxide
$^1$H NMR: proton nuclear magnetic resonance
LC/MS: liquid chromatography mass spectrometer
ESI: ElectroSpray Ionization
APCI: Atmospheric Pressure Chemical Ionization
THF: tetrahydrofuran
DMF: N,N-dimethylformamide
DMSO: dimethyl sulfoxide
TFA: trifluoroacetic acid
SFC: supercritical fluid chromatography
TEA: triethylamine
AA: acetic acid
DMAP: 4-dimethylaminopyridine $^1$H NMR was measured by Fourier-transform NMR. For the analyses, ACD/SpecManager (trade name) and the like were used. A peak showing very mild proton of hydroxyl group, amino group or the like is not described.

MS was measured by LC/MS. As the ionization method, ESI method or APCI method was used. The data indicates measured values (found). Generally, a molecular ion peak is observed. However, when a compound has a tert-butoxycarbonyl group, a peak free of a tert-butoxycarbonyl group or tert-butyl group may be observed as a fragment ion. When a compound has a hydroxyl group, a peak free of H$_2$O may be observed as a fragment ion. In the case of a salt, a molecular ion peak or a fragment ion peak of a free form is generally observed.

The unit of the sample concentration (c) in optical rotation ([α]$_D$) is g/100 mL.

As the elemental analytical values (Anal.), Calculated (Calcd) and measured values (Found) are described.

Example 1

4-(trans-2-aminocyclopropyl)-5-methyl-N-(5-methyl-1,3,4-thiadiazol-2-yl)thiophene-2-carboxamide dihydrochloride A) (E)-ethyl 3-(5-bromo-2-methylthiophene-3-yl)acrylate To a mixture of potassium tert-butoxide (4.59 g) and dry THF (60 mL) was added ethyl diethylphosphonoacetate (7.5 mL) at −5° C., and the mixture was stirred for 20 min. To the reaction mixture was added a mixture of 5-bromo-2-methylthiophene-3-carbaldehyde (7.0 g) and dry THF (10 mL) at −5° C., and the mixture was stirred for 30 min. To the reaction mixture was added water (100 mL), and the mixture was extracted twice with ethyl acetate (100 mL each). The extracts were combined, dried over anhydrous sodium sulfate, and concentrated under reduced pressure to give the title compound (7.2 g).

$^1$H NMR (400 MHz, DMSO-d$_6$) δ 1.17-1.35 (3H, m), 2.45 (3H, s), 4.19 (2H, q, J=5.8 Hz), 6.40 (1H, d, J=15.7 Hz), 7.48 (1H, d, J=15.7 Hz), 7.78 (1H, s).

B) ethyl trans-2-(5-bromo-2-methylthiophen-3-yl)cyclopropanecarboxylate

To a suspension of sodium hydride (50% in oil, 2.26 g) in DMSO (50 mL) was added trimethylsulfoxonium iodide (10.4 g), and the mixture was stirred at room temperature for 1 hr. To the reaction mixture was added a mixture of ethyl (E)-ethyl 3-(5-bromo-2-methylthiophen-3-yl)acrylate (6.5 g) and DMSO (30 mL), and the mixture was stirred at room temperature for 4 hr. To the reaction mixture was added ice water (200 mL), and the mixture was extracted with ethyl acetate (100 mL, twice). The extracts were combined, washed with saturated brine (100 mL), dried over anhydrous sodium sulfate, and concentrated under reduced pressure. The residue was purified by silica gel column chromatography (hexane/ethyl acetate) to give the title compound (3.5 g).

$^1$H NMR (400 MHz, DMSO-d$_6$) δ 1.23 (3H, t, J=5.2 Hz), 1.24-1.29 (1H, m), 1.30-1.40 (1H, m), 1.86-1.90 (1H, m), 2.23-2.28 (1H, m), 2.33 (3H, s), 4.09 (2H, q, J=7.1 Hz), 6.82 (1H, s).

C) trans-2-(5-bromo-2-methylthiophen-3-yl)cyclopropanecarboxylic acid

Ethyl trans-2-(5-bromo-2-methylthiophen-3-yl)cyclopropanecarboxylate (500 mg) was dissolved in methanol (8 mL), a mixture of sodium hydroxide (138 mg) and water (2 mL) was added at 0° C., and the mixture was stirred at room temperature for 2 hr. The reaction mixture was concentrated under reduced pressure, and adjusted to pH 6 with 2 mol/L hydrochloric acid at an inside temperature of not more than 10° C. The precipitated solid was collected by filtration and dried under reduced pressure to give the title compound (350 mg).

$^1$H NMR (400 MHz, DMSO-d$_6$) δ 1.22-1.27 (1H, m), 1.31-1.36 (1H, m), 1.72-1.76 (1H, m), 2.19-2.24 (1H, m), 2.34 (3H, s), 6.79 (1H, s), 12.31 (1H, brs).

D) tert-butyl (trans-2-(5-bromo-2-methylthiophen-3-yl)cyclopropyl)carbamate

To a mixture of trans-2-(5-bromo-2-methylthiophen-3-yl)cyclopropanecarboxylic acid (1.5 g) and tert-butyl alcohol (70 mL) were added triethylamine (8.3 mL) and diphenylphosphoryl azide (3.7 mL) at room temperature, and the mixture was stirred at 90° C. for 16 hr. The reaction mixture was cooled to room temperature, and concentrated under reduced pressure. To the residue was added water (100 mL), and the mixture was extracted twice with ethyl acetate (200 mL each). The extracts were combined, washed with saturated brine (100 mL), dried over anhydrous sodium sulfate, and concentrated under reduced pressure. The residue was purified by silica gel column chromatography (hexane/ethyl acetate) to give the title compound (0.75 g).

$^1$H NMR (400 MHz, DMSO-$d_6$) δ 0.99-1.05 (2H, m), 1.38 (9H, s), 1.72-1.76 (1H, m), 2.35 (3H, s), 2.52-2.54 (1H, m), 6.72 (1H, s), 7.20 (1H, s).

E) methyl 4-(trans-2-((tert-butoxycarbonyl)amino)cyclopropyl)-5-methylthiophene-2-carboxylate A mixture of tert-butyl (trans-2-(5-bromo-2-methylthiophen-3-yl)cyclopropyl)carbamate (1.3 g), diisopropylethylamine (3.42 mL), dichloro(1,1'-bis(diphenylphosphino)ferrocene)palladium (0.96 g) and methanol (45 mL) was heated under a carbon monoxide atmosphere (10 atm) at 80° C. for 16 hr. After cooling to room temperature, the insoluble material was filtered off, and the filtrate was concentrated under reduced pressure. The residue was purified by silica gel column chromatography (hexane/ethyl acetate) to give the title compound (0.90 g).

$^1$H NMR (400 MHz, DMSO-$d_6$) δ 1.05-1.15 (2H, m), 1.36 (9H, s), 1.73-1.78 (1H, m), 2.47 (3H, s), 2.50-2.55 (1H, m), 3.76 (3H, s), 7.25 (1H, brs), 7.34 (1H, s)

F) 4-(trans-2-((tert-butoxycarbonyl)amino)cyclopropyl)-5-methylthiophene-2-carboxylic acid Methyl 4-(trans-2-((tert-butoxycarbonyl)amino)cyclopropyl)-5-methylthiophene-2-carboxylate (900 mg) was dissolved in methanol (45 mL), a mixture of sodium hydroxide (1160 mg) and water (15 mL) was added at 0° C., and the mixture was stirred at room temperature for 16 hr. The reaction mixture was concentrated under reduced pressure, and water (10 mL) was added to the residue. The mixture was adjusted to pH 6 with 2 mol/L hydrochloric acid at an inside temperature of not more than 10° C., and extracted with 20% methanol-dichloromethane solution (100 mL each). The extracts were combined, dried over anhydrous sodium sulfate, and concentrated under reduced pressure to give the title compound (660 mg).

$^1$H NMR (400 MHz, DMSO-$d_6$) δ 1.02-1.07 (2H, m), 1.38 (9H, s), 1.72-1.76 (1H, m), 2.45 (3H, s), 2.49-2.54 (1H, m), 7.24 (2H, s), 12.79 (1H, s).

G) tert-butyl (trans-2-(2-methyl-5-((5-methyl-1,3,4-thiadiazol-2-yl)carbamoyl)thiophen-3-yl)cyclopropyl)carbamate 4-(trans-2-((tert-Butoxycarbonyl)amino)cyclopropyl)-5-methylthiophene-2-carboxylic acid (100 mg), 5-methyl-1,3,4-thiadiazol-2-amine (44.8 mg) and triethylamine (0.187 mL) were dissolved in DMF (3.0 mL), and the mixture was cooled to 0° C. O-(7-Azabenzotriazol-1-yl)-N,N,N',N'-tetramethyluronium hexafluorophosphate (153 mg) was added, and the mixture was stirred at room temperature overnight. The reaction mixture was poured into water, and the mixture was extracted with ethyl acetate. The extract was successively washed with saturated aqueous sodium hydrogen carbonate solution and saturated brine, dried over anhydrous sodium sulfate, and concentrated under reduced pressure. The obtained residue was purified by silica gel column chromatography (hexane/ethyl acetate) and concentrated under reduced pressure. The obtained residue was diluted with ethyl acetate-THF, successively washed with water and saturated brine, dried over anhydrous sodium sulfate, and concentrated under reduced pressure to give the title compound (64 mg).

MS: [M+H]$^+$ 395.2.

H) 4-(trans-2-aminocyclopropyl)-5-methyl-N-(5-methyl-1,3,4-thiadiazol-2-yl)thiophene-2-carboxamide dihydrochloride To a mixture of tert-butyl (trans-2-(2-methyl-5-((5-methyl-1,3,4-thiadiazol-2-yl)carbamoyl)thiophen-3-yl)cyclopropyl)carbamate (64 mg), ethyl acetate (5 mL) and methanol (2 mL) was added 4 mol/L hydrogen chloride/ethyl acetate solution (0.811 mL) at room temperature, and the mixture was stirred at room temperature for 3 days. The precipitated solid was collected by filtration and dried under reduced pressure to give the title compound (45 mg).

Example 2

4-(trans-2-((cyclopropylmethyl)amino)cyclopropyl)-5-methyl-N-(5-methyl-1,3,4-thiadiazol-2-yl)thiophene-2-carboxamide dihydrochloride To a mixture of 4-(trans-2-aminocyclopropyl)-5-methyl-N-(5-methyl-1,3,4-thiadiazol-2-yl)thiophene-2-carboxamide dihydrochloride (42 mg), sodium hydrogen carbonate (38.4 mg), THF (0.5 mL) and methanol (0.5 mL) was added cyclopropanecarbaldehyde (13 μL) at room temperature. Under a nitrogen atmosphere, the reaction mixture was stirred at 50° C. for 1.5 hr and at room temperature for 1 hr. To the reaction mixture was added cyclopropanecarbaldehyde (8.8 μL) at room temperature, and the mixture was stirred at 50° C. for 1.5 hr under a nitrogen atmosphere and at room temperature for 30 min. Sodium borohydride (8.7 mg) was added under ice-cooling and the reaction mixture was stirred for 30 min under a nitrogen atmosphere. Under ice-cooling, to the reaction mixture were added ethyl acetate (5 mL), water and saturated aqueous sodium hydrogen carbonate solution, and the mixture was extracted with ethyl acetate. The extract was washed with saturated brine, and the aqueous layer was extracted with a mixture of ethyl acetate and THF. The combined organic layer was dried over anhydrous sodium sulfate, and the solvent was evaporated under reduced pressure. The residue was washed with a mixture of ethyl acetate and diisopropyl ether, and dissolved in methanol. A 2 mol/L hydrogen chloride/methanol solution (2 mL) was added, and the mixture was concentrated under reduced pressure. The residue was crystallized from ethanol/diisopropyl ether to give the title compound (25.9 mg).

$^1$H NMR (300 MHz, DMSO-$d_6$) δ 0.33-0.43 (2H, m), 0.55-0.65 (2H, m), 1.06-1.14 (1H, m), 1.16-1.27 (1H, m), 1.53-1.62 (1H, m), 2.40-2.47 (1H, m), 2.52 (3H, s), 2.62 (3H, s), 2.85-3.02 (3H, m), 7.85 (1H, brs), 9.24 (2H, brs), 12.66 (1H, brs).

Example 3

5-(trans-2-((cyclopropylmethyl)amino)cyclopropyl)-N-(4,4-difluorocyclohexyl)-1-methyl-1H-pyrazole-3-carboxamide hydrochloride A) methyl 1-methyl-5-(((trifluoromethyl)sulfonyl)oxy)-1H-pyrazole-3-carboxylate To a mixture of methyl 5-hydroxy-1-methyl-1H-pyrazole-3-carboxylate (2.404 g), diisopropylethylamine (5.38 mL) and DMF (24 mL) was added N-phenylbis(trifluoromethanesulfonimide) (6.05 g) at 0° C., and the mixture was stirred at room temperature overnight under a nitrogen atmosphere. The reaction mixture was poured into water, extracted with ethyl acetate, washed with saturated brine, dried over anhydrous sodium sulfate, and concentrated under reduced pressure. The obtained residue was purified by silica gel column chromatography (hexane/ethyl acetate) and concentrated under reduced pressure to give the title compound (3.92 g).

$^1$H NMR (300 MHz, CDCl$_3$) δ 3.92 (3H, s), 3.94 (3H, s), 6.69 (1H, s).

B) methyl 5-((1E)-3-tert-butoxy-3-oxoprop-1-en-1-yl)-1-methyl-1H-pyrazole-3-carboxylate A mixture of methyl 1-methyl-5-(((trifluoromethyl)sulfonyl)oxy)-1H-pyrazole-3-carboxylate (890 mg), tert-butyl acrylate (1.35 mL), tri(o-tolyl)phosphine (188 mg), palladium acetate (69.3 mg), triethylamine (1.29 mL) and DMF (8 mL) was stirred at 80° C. for 3 hr under a nitrogen atmosphere. The reaction mixture was poured into water at room temperature, and the mixture was extracted with ethyl acetate, washed with saturated brine, dried over anhydrous sodium sulfate, and concentrated under reduced pressure. The obtained residue was purified by silica gel column chromatography (hexane/ethyl acetate) and concentrated under reduced pressure to give the title compound (144 mg).

$^1$H NMR (300 MHz, CDCl$_3$) δ 1.53 (9H, s), 3.93 (3H, s), 4.02 (3H, s), 6.34 (1H, d, J=15.9 Hz), 7.07 (1H, s), 7.45 (1H, d, J=15.9 Hz).

C) methyl 5-(trans-2-((tert-butoxycarbonyl)amino)cyclopropyl)-1-methyl-1H-pyrazole-3-carboxylate By a method similar to that of Example 1, step B, the title compound was obtained.

MS: [M+H]$^+$ 281.2.

D) 2-(3-(methoxycarbonyl)-1-methyl-1H-pyrazol-5-yl)cyclopropanecarboxylic acid

To methyl 5-(trans-2-((tert-butoxycarbonyl)amino)cyclopropyl)-1-methyl-1H-pyrazole-3-carboxylate (135 mg) was added trifluoroacetic acid (2 mL) at 0° C., and the mixture was stirred at room temperature for 4 hr and concentrated under reduced pressure. Water was added to the residue, and the mixture was extracted with ethyl acetate, successively washed with water and saturated brine, dried over anhydrous sodium sulfate, and concentrated under reduced pressure. The obtained residue was diluted with ethyl acetate and saturated aqueous sodium hydrogen carbonate solution. The aqueous layer was separated, acidified with 2 mol/L hydrochloric acid, and extracted with ethyl acetate. The extract was successively washed with water and saturated brine, dried over anhydrous sodium sulfate, and concentrated under reduced pressure. The residue was diluted with toluene and concentrated under reduced pressure to give the title compound (100 mg).

MS: [M+H]$^+$ 225.1.

E) 5-(trans-2-((cyclopropylmethyl)amino)cyclopropyl)-N-(4,4-difluorocyclohexyl)-1-methyl-1H-pyrazole-3-carboxamide hydrochloride By a method similar to that of Example 1, steps D, F, G and H and Example 2, the title compound was obtained.

Example 4

5-(trans-2-aminocyclopropyl)-N-(4,4-difluorocyclohexyl)-1-methyl-1H-pyrazole-3-carboxamide hydrochloride By a method similar to that of Example 3, steps A, B, C and D and Example 1, steps D, F, G and H, the title compound was obtained.

Example 5

4-(trans-2-aminocyclopropyl)-N-(5-methyl-1,3,4-thiadiazol-2-yl)-2-naphthamide dihydrochloride A) 3-bromo-N-methoxy-N-methyl-1-naphthamide 3-Bromo-1-naphthoic acid (3.00 g), N,O-dimethylhydroxylamine hydrochloride (1.32 g), 1-ethyl-3-(3-dimethylaminopropyl)carbodiimide hydrochloride (2.80 g) and anhydrous 1-hydroxybenzotriazole (1.94 g) were dissolved in anhydrous DMF (60.0 mL), triethylamine (4.16 mL) was added, and the mixture was stirred at room temperature for 16 hr. Water was added to the reaction mixture, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (2.69 g).

MS: [M+H]$^+$ 293.9.

B) 3-bromo-1-naphthaldehyde

To a solution of 3-bromo-N-methoxy-N-methyl-1-naphthamide (2.69 g) in THF (50.0 mL) was slowly added 1.5 mol/L diisobutylaluminum hydride toluene solution (9.15 mL) at 0° C., and the mixture was stirred at 0° C. for 2 hr under a nitrogen atmosphere. To the reaction mixture was added 1 mol/L hydrochloric acid at 0° C., and the mixture was extracted with ethyl acetate. The extract was successively washed with water and saturated brine, dried over anhydrous sodium sulfate, and concentrated under reduced pressure. The obtained residue was purified by silica gel column chromatography (hexane/ethyl acetate) to give the title compound (1.52 g).

$^1$H NMR (300 MHz, CDCl$_3$) δ 7.57-7.66 (1H, m), 7.67-7.74 (1H, m), 7.84 (1H, d, J=8.3 Hz), 8.06 (1H, d, J=2.3 Hz), 8.26 (1H, s), 9.16 (1H, d, J=8.7 Hz), 10.36 (1H, s).

C) (E)-tert-butyl 3-(3-bromonaphthalen-1-yl)acrylate

Lithium chloride (0.28 g) was dried in vacuo, and acetonitrile (20.0 mL) was added. To the mixture were added 3-bromo-1-naphthaldehyde (1.52 g) and tert-butyl diethylphosphonoacetate (1.71 g) at 0° C., and the mixture was stirred at 0° C. for 5 min under a nitrogen atmosphere. To the reaction mixture was added 1,8-diazabicyclo[5.4.0]undec-7-ene (1.02 mL) at 0° C., and the mixture was stirred at room temperature for 18 hr under a nitrogen atmosphere. Water was added to the reaction mixture at room temperature, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (1.93 g).

$^1$H NMR (300 MHz, CDCl$_3$) δ 1.57 (9H, s), 6.46 (1H, d, J=15.9 Hz), 7.51-7.61 (2H, m), 7.75-7.82 (2H, m), 8.02 (1H, d, J=1.5 Hz), 8.10-8.16 (1H, m), 8.32 (1H, d, J=15.9 Hz).

D) 4-(trans-2-aminocyclopropyl)-N-(5-methyl-1,3,4-thiadiazol-2-yl)-2-naphthamide dihydrochloride By a method similar to that of Example 1, steps B, D, E, F, G and H and Example 3, step D, the title compound was obtained.

Example 6

N-(5-methyl-1,3,4-thiadiazol-2-yl)-4-(trans-2-((tetrahydro-2H-pyran-4-ylmethyl)amino)cyclopropyl)-2-naphthamide hydrochloride A) tert-butyl (trans-2-(3-((5-methyl-1,3,4-thiadiazol-2-yl)carbamoyl)naphthalen-1-yl)cyclopropyl) ((tetrahydro-2H-pyran-4-yl)methyl)carbamate 4-(trans-2-Aminocyclopropyl)-N-(5-methyl-1,3,4-thiadiazol-2-yl)-2-naphthamide dihydrochloride (56.6 mg) and sodium hydrogen carbonate (35.9 mg) were dissolved in THF (5.00 mL)/methanol (5.00 mL), and tetrahydro-2H-pyran-4-carbaldehyde (19.5 mg) was added. Under a nitrogen atmosphere, the reaction mixture was stirred at 60° C. for 3 hr, and sodium borohydride (10.8 mg) was added at 0° C. The reaction mixture was stirred at room temperature for 2 hr, to the reaction mixture was added di-tert-butyl dicarbonate (0.099 mL), and the mixture was stirred at room temperature for 16 hr. Water was added to the reaction mixture, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (33.5 mg).

MS: [M+H]$^+$ 523.1.

B) N-(5-methyl-1,3,4-thiadiazol-2-yl)-4-(trans-2-((tetrahydro-2H-pyran-4-ylmethyl)amino)cyclopropyl)-2-naphthamide hydrochloride By a method similar to that of Example 1, step H, the title compound was obtained.

Anal. Calcd for C$_{23}$H$_{26}$N$_4$O$_2$S HCl: C, 60.19; H, 5.93; N, 12.21. Found: C, 59.52; H, 5.87; N, 11.88.

Example 7

4-(trans-2-((cyclopropylmethyl)amino)cyclopropyl)-N-(5-methyl-1,3,4-thiadiazol-2-yl)-2-naphthamide dihydrochloride By a method similar to that of Example 6, the title compound was obtained.

Anal. Calcd for C$_{21}$H$_{22}$N$_4$OS 2HCl: C, 55.88; H, 5.36; N, 12.41. Found: C, 56.60; H, 5.56; N, 12.39.

Example 8

N-(4,4-difluorocyclohexyl)-5-methyl-4-(trans-2-((tetrahydro-2H-pyran-4-ylmethyl)amino)cyclopropyl)thiophene-2-carboxamide hydrochloride A) tert-butyl (trans-2-(5-((4,4-difluorocyclohexyl)carbamoyl)-2-methylthiophen-3-yl)cyclopropyl)carbamate 4-(trans-2-((tert-Butoxycarbonyl)amino)cyclopropyl)-5-methylthiophene-2-carboxylic acid (100 mg), 4,4-difluorocyclohexanamine hydrochloride (63.5 mg) and triethylamine (0.187 mL) were dissolved in DMF (1.0 mL), 0-(7-azabenzotriazol-1-yl)-N,N,N',N'-tetramethyluronium hexafluorophosphate (153 mg) was added at room temperature, and the mixture was stirred overnight. Water was added to the reaction mixture, and the resulting precipitate was collected by filtration to give the title compound (140 mg).

MS: [M+H]$^+$ 415.3.

B) 4-(trans-2-aminocyclopropyl)-N-(4,4-difluorocyclohexyl)-5-methylthiophene-2-carboxamide hydrochloride To a solution (2.0 mL) of tert-butyl (trans-2-(5-((4,4-difluorocyclohexyl)carbamoyl)-2-methylthiophen-3-yl)cyclopropyl)carbamate (140 mg) in ethyl acetate was added 4 mol/L hydrogen chloride/ethyl acetate solution (2.0 mL) at room temperature, and the mixture was stirred at room temperature for 3 days. The resulting precipitate was collected by filtration to give the title compound (90 mg).

MS: [M-HCl+H]$^+$ 315.2.

C) N-(4,4-difluorocyclohexyl)-5-methyl-4-(trans-2-((tetrahydro-2H-pyran-4-ylmethyl)amino)cyclopropyl)thiophene-2-carboxamide hydrochloride To a mixture of 4-(trans-2-aminocyclopropyl)-N-(4,4-difluorocyclohexyl)-5-methylthiophene-2-carboxamide hydrochloride (48.9 mg), sodium hydrogen carbonate (46.8 mg), THF (1 mL) and methanol (1 mL) was added tetrahydro-2H-pyran-4-carbaldehyde (19.1 mg) at room temperature. The reaction mixture was stirred at 60° C. for 1.5 hr and at room temperature for 30 min, and sodium borohydride (7.91 mg) was added at 0° C. Under a nitrogen atmosphere, the reaction mixture was stirred at room temperature for 1 hr. To the reaction mixture were added ethyl acetate, water and saturated aqueous sodium hydrogen carbonate solution under ice-cooling, and the mixture was extracted with ethyl acetate. The extract was washed with water and saturated brine. The organic layer was dried over anhydrous sodium sulfate, and the solvent was evaporated under reduced pressure. The obtained residue was purified by silica gel column chromatography (ethyl acetate/methanol). To the obtained fraction was added 4 mol/L hydrogen chloride/ethyl acetate solution and the mixture was concentrated under reduced pressure to give the title compound (42.3 mg).

$^1$H NMR (300 MHz, DMSO-d$_6$) δ 1.11-1.34 (3H, m), 1.54-2.12 (13H, m), 2.83-3.04 (4H, m), 3.21-3.34 (2H, m), 3.86 (3H, dd, J=11.3, 2.3 Hz), 7.40 (1H, s), 8.12 (1H, d, J=7.9 Hz), 8.56 (1H, brs), 9.39 (2H, brs).

Example 9

7-(trans-2-aminocyclopropyl)-N-(5-methyl-1,3,4-thiadiazol-2-yl)-2,3-dihydro-1-benzofuran-5-carboxamide dihydrochloride By a method similar to that of Example 1, the title compound was obtained.

Example 10

7-(trans-2-((cyclopropylmethyl)amino)cyclopropyl)-N-(5-methyl-1,3,4-thiadiazol-2-yl)-2,3-dihydro-1-benzofuran-5-carboxamide dihydrochloride By a method similar to that of Example 2, the title compound was obtained.

Example 11

7-(trans-2-((cyclopropylmethyl)amino)cyclopropyl)-N-(4,4-difluorocyclohexyl)-2,3-dihydro-1-benzofuran-5-carboxamide hydrochloride By a method similar to that of Example 1, steps G and H and Example 2, the title compound was obtained.

Example 12

N-(4,4-difluorocyclohexyl)-7-(trans-2-((tetrahydro-2H-pyran-4-ylmethyl)amino)cyclopropyl)-2,3-dihydro-1-benzofuran-5-carboxamide hydrochloride By a method similar to that of Example 2, the title compound was obtained.

Example 13

5-(trans-2-aminocyclopropyl)-N-(4,4-difluorocyclohexyl)-6-methylnicotinamide dihydrochloride By a method similar to that of Example 1, the title compound was obtained.

Example 14

5-(trans-2-((cyclopropylmethyl)amino)cyclopropyl)-N-(4,4-difluorocyclohexyl)-6-methylnicotinamide dihydrochloride By a method similar to that of Example 2, the title compound was obtained.

Example 15

3-(trans-2-aminocyclopropyl)-N-(5-methyl-1,3,4-thiadiazol-2-yl)-1-naphthamide dihydrochloride A) (E)-methyl 3-(3-(tert-butoxy)-3-oxoprop-1-en-1-yl)-1-naphthoate A mixture of methyl 3-bromo-1-naphthoate (500 mg), tert-butyl acrylate (0.422 mL), tri(o-tolyl)phosphine (114 mg), palladium acetate (43.2 mg), triethylamine (0.781 mL) and anhydrous DMF (3.00 mL) was heated at 100° C. for 1 hr under microwave irradiation. The reaction mixture was poured into water and the mixture was extracted with ethyl acetate. The extract was washed with water and saturated brine, dried over anhydrous sodium sulfate, and concentrated under reduced pressure. The obtained residue was purified by silica gel column chromatography (hexane/ethyl acetate) and concentrated under reduced pressure to give the title compound (575 mg).

$^1$H NMR (300 MHz, CDCl$_3$) δ1.56 (9H, s), 4.03 (3H, s), 6.55 (1H, d, J=15.8 Hz), 7.52-7.59 (1H, m), 7.60-7.67 (1H, m), 7.74 (1H, d, J=15.8 Hz), 7.89 (1H, d, J=7.5 Hz), 8.07 (1H, s), 8.37 (1H, d, J=1.9 Hz), 8.87 (1H, d, J=8.7 Hz).

B) 3-(trans-2-aminocyclopropyl)-N-(5-methyl-1,3,4-thiadiazol-2-yl)-1-naphthamide dihydrochloride By a method similar to that of Example 1, steps B, D, F, G and H and Example 3, step D, the title compound was obtained.

Anal. Calcd for C$_{17}$H$_{16}$N$_4$OS 2HCl H$_2$O: C, 49.16; H, 4.85; N, 13.49. Found: C, 49.12; H, 5.47; N, 13.12.

Example 16

N-(5-methyl-1,3,4-thiadiazol-2-yl)-3-(trans-2-((tetrahydro-2H-pyran-4-ylmethyl)amino)cyclopropyl)-1-naphthamide dihydrochloride By a method similar to that of Example 6, the title compound was obtained.

Anal. Calcd for C$_{23}$H$_{26}$N$_4$O$_2$S, 2HCl 1.4H$_2$O: C, 53.06; H, 5.96; N, 10.76. Found: C, 52.93; H, 5.96; N, 10.31.

Example 17

4-(trans-2-(cyclobutylamino)cyclopropyl)-5-methyl-N-(5-methyl-1,3,4-thiadiazol-2-yl)thiophene-2-carboxamide 1/2 fumarate To a mixture of 4-(trans-2-aminocyclopropyl)-5-methyl-N-(5-methyl-1,3,4-thiadiazol-2-yl)thiophene-2-carboxamide dihydrochloride (45 mg), triethylamine (0.034 mL), trimethyl orthoformate (0.027 mL) and methanol (2.0 mL) was added cyclobutanone (0.014 mL) at room temperature, and the mixture was stirred at room temperature overnight. Sodium borohydride (9.3 mg) was added under ice-cooling, and the reaction mixture was stirred at 0° C. for 10 min. After stirring, water was added under ice-cooling, and the mixture was extracted with ethyl acetate. The extract was washed with water and saturated brine. The organic layer was dried over anhydrous magnesium sulfate, and the solvent was evaporated under reduced pressure. The obtained residue was purified by silica gel column chromatography (ethyl acetate/methanol) and concentrated under reduced pressure. The obtained residue was suspended in ethyl acetate, and a solution of fumaric acid (14.2 mg) in ethanol was added at room temperature. The reaction mixture was stirred for 30 min, and the resulting precipitate was collected by filtration to give the title compound (23 mg).

$^1$H NMR (300 MHz, DMSO-d$_6$) δ 0.78-0.88 (1H, m), 0.91-1.02 (1H, m), 1.52-1.83 (5H, m), 2.05-2.19 (2H, m), 2.20-2.30 (2H, m), 2.47 (3H, s), 2.61 (3H, s), 6.57-6.62 (1H, m), 7.70-7.77 (1H, m).

Example 18

4-(trans-2-((cyclopropylmethyl)amino)cyclopropyl)-N-(4,4-difluorocyclohexyl)-5-methylthiophene-2-carboxamide fumarate By a method similar to that of Example 19, the title compound was synthesized.

Example 19

4-(trans-2-((cyclopropylmethyl)amino)cyclopropyl)-5-methyl-N-(tetrahydro-2H-pyran-4-yl)thiophene-2-carboxamide fumarate A) tert-butyl (trans-2-(2-methyl-5-((tetrahydro-2H-pyran-4-yl)carbamoyl)thiophen-3-yl)cyclopropyl)carbamate 4-(trans-2-((tert-Butoxycarbonyl)amino)cyclopropyl)-5-methylthiophene-2-carboxylic acid (100 mg), tetrahydro-2H-pyran-4-amine (37.4 mg) and triethylamine (0.187 mL) were dissolved in DMF (1.0 mL), O-(7-azabenzotriazol-1-yl)-N,N,N',N'-tetramethyluronium hexafluorophosphate (153 mg) was added at room temperature, and the mixture was stirred overnight. The reaction mixture was poured into water, and the resulting precipitate was collected by filtration to give the title compound (122 mg).
MS: [M+H]$^+$ 381.2.

B) 4-(trans-2-aminocyclopropyl)-5-methyl-N-(tetrahydro-2H-pyran-4-yl)thiophene-2-carboxamide hydrochloride To a mixture of tert-butyl (trans-2-(2-methyl-5-((tetrahydro-2H-pyran-4-yl)carbamoyl)thiophen-3-yl)cyclopropyl)carbamate (122 mg) and ethyl acetate (2 mL) was added 4 mol/L hydrogen chloride/ethyl acetate solution (1.60 mL) at room temperature, and the mixture was stirred at room temperature overnight. The resulting precipitate was collected by filtration to give the title compound (95 mg).
MS: [M-HCl+H]$^+$ 281.2.

C) 4-(trans-2-((cyclopropylmethyl)amino) cyclopropyl)-5-methyl-N-(tetrahydro-2H-pyran-4-yl)thiophene-2-carboxamide fumarate To a mixture of 4-(trans-2-aminocyclopropyl)-5-methyl-N-(tetrahydro-2H-pyran-4-yl)thiophene-2-carboxamide hydrochloride (45 mg), triethylamine (0.040 mL) and methanol (2.0 mL) was added cyclopropanecarbaldehyde (14.9 mg) at room temperature, and the reaction mixture was stirred at room temperature overnight. Sodium borohydride (10.8 mg) was added under ice-cooling, and the reaction mixture was stirred at 0° C. for 10 min. After stirring, water was added under ice-cooling, and the mixture was extracted with ethyl acetate. The extract was washed with water and saturated brine. The organic layer was dried over anhydrous magnesium sulfate, and the solvent was evaporated under reduced pressure. The obtained residue was purified by silica gel column chromatography (ethyl acetate/methanol) and concentrated under reduced pressure. The obtained residue was suspended in ethyl acetate, a solution of fumaric acid (13.5 mg) in ethanol was added at room temperature, and the reaction mixture was stirred for 30 min. After stirring, the resulting precipitate was collected by filtration to give the title compound (40 mg).

$^1$H NMR (300 MHz, DMSO-d$_6$) δ 0.09-0.18 (2H, m), 0.38-0.47 (2H, m), 0.82-0.98 (2H, m), 1.02-1.13 (1H, m), 1.41-1.59 (2H, m), 1.66-1.77 (2H, m), 1.79-1.90 (1H, m), 2.36-2.45 (4H, m), 2.57 (2H, dd, J=6.82, 1.89 Hz), 3.28-3.42 (2H, m), 3.80-3.96 (3H, m), 6.57 (2H, s), 7.26 (1H, s), 8.04 (1H, d, J=7.57 Hz).

Example 20

5-methyl-N-(5-methyl-1,3,4-thiadiazol-2-yl)-4-(trans-2-((tetrahydro-2H-pyran-4-ylmethyl)amino)cyclopropyl)thiophene-2-carboxamide dihydrochloride By a method similar to that of Example 2, the title compound was synthesized.

Example 21

N-(4,4-difluorocyclohexyl)-5-methyl-4-(trans-2-(tetrahydro-2H-pyran-4-ylamino)cyclopropyl)thiophene-2-carboxamide fumarate 4-(trans-2-Aminocyclopropyl)-N-(4,4-difluorocyclohexyl)-5-methylthiophene-2-carboxamide hydrochloride (49 mg) and borane-2-methylpyridine complex (44.8 mg) were dissolved in methanol (2.0 mL)/acetic acid (0.20 mL), tetrahydro-4H-pyran-4-one (21.0 mg) was added, and the mixture was stirred at room temperature overnight. Under ice-cooling, to the reaction mixture was added saturated aqueous sodium hydrogen carbonate solution, and the mixture was extracted with ethyl acetate. The extract was washed with water and saturated brine, dried over anhydrous magnesium sulfate and concentrated under reduced pressure. The residue was purified by silica gel column chromatography (hexane/ethyl acetate) and concentrated under reduced pressure. The obtained residue was dissolved in ethyl acetate, a solution of fumaric acid (9.32 mg) in ethanol was added at room temperature, and the reaction mixture was stirred for 30 min. After stirring, the mixture was concentrated under reduced pressure to give the title compound (12 mg).

$^1$H NMR (300 MHz, METHANOL-d$_4$) δ 1.04-1.15 (1H, m), 1.21-1.33 (1H, m), 1.41-2.16 (14H, m), 2.40 (3H, s), 2.64-2.74 (1H, m), 3.30-3.42 (2H, m), 3.77-3.96 (3H, m), 6.58-6.64 (2H, m), 7.14-7.17 (1H, m).

Example 22

4-(trans-2-(cyclobutylamino)cyclopropyl)-5-methyl-N-(1-methyl-1H-pyrazol-4-yl)thiophene-2-carboxamide dihydrochloride To a mixture of 4-(trans-2-aminocyclopropyl)-5-methyl-N-(1-methyl-1H-pyrazol-4-yl)thiophene-2-carboxamide dihydrochloride (50 mg), triethylamine (0.040 mL), trimethyl orthoformate (0.032 mL) and methanol (2.0 mL) was added cyclobutanone (15.1 mg) at room temperature, and the mixture was stirred at room temperature overnight. Sodium borohydride (10.8 mg) was added under ice-cooling, and the reaction mixture was stirred for 10 min. Water was added under ice-cooling, and the mixture was extracted with ethyl acetate. The extract was washed with water and saturated brine. The organic layer was dried over anhydrous magnesium sulfate, and the solvent was evaporated under reduced pressure. The obtained residue was purified by silica gel column chromatography (ethyl acetate/methanol). To the obtained fraction was added 4 mol/L hydrogen chloride/ethyl acetate solution and the reaction mixture was concentrated under reduced pressure. The obtained residue was crystallized from ethanol/heptane to give the title compound (10 mg).

$^1$H NMR (300 MHz, DMSO-$d_6$) δ 1.12-1.22 (1H, m), 1.47-1.58 (1H, m), 1.75-1.91 (2H, m), 2.14-2.32 (4H, m), 2.35-2.44 (1H, m), 2.47-2.49 (3H, m), 2.71-2.85 (1H, m), 3.80 (3H, s), 3.82-3.92 (1H, m), 7.47-7.50 (1H, m), 7.50-7.53 (1H, m), 7.89-7.95 (1H, m), 9.47-9.67 (2H, m) 10.25-10.32 (1H, m).

Example 23

5-(trans-2-((cyclopropylmethyl)amino)cyclopropyl)-N-(5-methyl-1,3,4-thiadiazol-2-yl)thiophene-3-carboxamide dihydrochloride A) ethyl (2E)-3-(4-bromothiophen-2-yl)acrylate Lithium chloride (453 mg) was dried in high vacuo, and acetonitrile (40 mL) was added. To this mixture were added 4-bromothiophene-2-carbaldehyde (2.00 g) and ethyl diethylphosphonoacetate (2.46 g) at 0° C., and the mixture was stirred at 0° C. for 5 min under a nitrogen atmosphere. To the reaction mixture was added 1,8-diazabicyclo[5.4.0]undec-7-ene (1.66 mL) at 0° C., and the mixture was stirred at room temperature overnight under a nitrogen atmosphere. Water was added to the reaction mixture, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (2.52 g).

$^1$H NMR (300 MHz, DMSO-$d_6$) δ 1.18-1.31 (3H, m), 4.18 (2H, q, J=7.07 Hz), 6.37 (1H, d, J=15.90 Hz), 7.58-7.89 (3H, m).

B) ethyl trans-2-(4-bromothiophen-2-yl)cyclopropanecarboxylate

To a suspension of trimethylsulfoxonium iodide (2.54 g) in DMSO (20 mL) was added sodium hydride (60% in oil, 461 mg), and the mixture was stirred at room temperature for 30 min. To the reaction mixture was added a solution of ethyl (2E)-3-(4-bromothiophen-2-yl)acrylate (2.51 g) in DMSO (10 mL), and the mixture was stirred at room temperature overnight under a nitrogen atmosphere. Water was added to the reaction mixture at 0° C., and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (1.27 g).

$^1$H NMR (300 MHz, DMSO-$d_6$) δ 1.20 (3H, t, J=7.19 Hz), 1.35-1.54 (2H, m), 1.97 (1H, ddd, J=8.42, 5.40, 3.98 Hz), 2.58-2.67 (1H, m), 4.05-4.16 (2H, m), 6.98 (1H, dd, J=1.51, 0.76 Hz), 7.46 (1H, d, J=1.51 Hz).

C) trans-2-(4-bromothiophen-2-yl)cyclopropanecarboxylic acid

Ethyl trans-2-(4-bromothiophen-2-yl)cyclopropanecarboxylate (1.27 g) was dissolved in THF (5 mL) and ethanol (5 mL), 8 mol/L aqueous sodium hydroxide solution (1.44 mL) was added at 0° C., and the mixture was stirred at room temperature overnight. The reaction mixture was acidified with 1 mol/L hydrochloric acid at 0° C., and extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (1.11 g).

$^1$H NMR (300 MHz, DMSO-$d_6$) δ 1.29-1.50 (2H, m), 1.78-1.87 (1H, m), 2.54-2.63 (1H, m), 6.97 (1H, dd, J=1.51, 0.76 Hz), 7.45 (1H, d, J=1.51 Hz), 12.49 (1H, brs).

D) tert-butyl (trans-2-(4-bromothiophen-2-yl)cyclopropyl)carbamate

To a mixture of trans-2-(4-bromothiophen-2-yl)cyclopropanecarboxylic acid (1.10 g) and tert-butyl alcohol (10 mL) were added triethylamine (0.745 mL) and diphenylphosphoryl azide (1.15 mL) at room temperature, and the mixture was stirred at room temperature for 2 hr, and then at 80° C. overnight. The reaction mixture was cooled to room temperature, water was added, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (930 mg).

$^1$H NMR (300 MHz, DMSO-$d_6$) δ 1.04-1.23 (2H, m), 1.38 (9H, s), 2.07 (1H, ddd, J=9.09, 6.06, 3.03 Hz), 2.61 (1H, brs), 6.80 (1H, d, J=0.76 Hz), 7.22-7.34 (1H, m), 7.38 (1H, d, J=1.51 Hz).

E) methyl 5-(trans-2-((tert-butoxycarbonyl)amino)cyclopropyl)thiophene-3-carboxylate A mixture of tert-butyl (trans-2-(4-bromothiophen-2-yl)cyclopropyl)carbamate (925 mg), triethylamine (0.810 mL), dichloro(1,1'-bis(diphenylphosphino)ferrocene)palladium (425 mg) and methanol (100 mL) was stirred at 90° C. for 8 hr under a carbon monoxide atmosphere (3 atm). The insoluble material was filtered off and washed with methanol, and the filtrate was concentrated under reduced pressure. The residue was extracted with ethyl acetate and water, and the organic layer was washed with saturated brine, dried over anhydrous sodium sulfate, and concentrated under reduced pressure. The residue was purified by silica gel column chromatography (hexane/ethyl acetate) to give the title compound (813 mg).

$^1$H NMR (300 MHz, DMSO-$d_6$) δ 1.08-1.23 (2H, m), 1.39 (9H, s), 2.08 (1H, ddd, J=9.18, 6.34, 3.03 Hz), 2.60 (1H, brs), 3.76 (3H, s), 7.08-7.15 (1H, m), 7.29 (1H, brs), 8.07 (1H, d, J=1.51 Hz).

F) methyl 5-(trans-2-aminocyclopropyl)thiophene-3-carboxylate hydrochloride

To a mixture of methyl 5-(trans-2-((tert-butoxycarbonyl)amino)cyclopropyl)thiophene-3-carboxylate (450 mg) and ethyl acetate (5 mL) was added 4 mol/L hydrogen chloride/ethyl acetate solution (3.78 mL) at 0° C., and the mixture was stirred at room temperature overnight. The reaction mixture was concentrated under reduced pressure, the residue was dissolved in methanol, and ethyl acetate was added. The precipitated solid was collected by filtration and washed with ethyl acetate to give the title compound (320 mg)

$^1$H NMR (300 MHz, DMSO-$d_6$) δ 1.29 (1H, dt, J=7.76, 6.15 Hz), 1.47 (1H, ddd, J=10.13, 5.96, 4.73 Hz), 2.56 (1H, ddd, J=9.75, 6.15, 3.79 Hz), 2.81-2.94 (1H, m), 3.73-3.80 (3H, m), 7.23 (1H, d, J=0.76 Hz), 8.12-8.18 (1H, m), 8.51 (3H, brs).

G) methyl 5-(trans-2-((tert-butoxycarbonyl)(cyclopropylmethyl)amino)cyclopropyl)thiophene-3-carboxylate A mixture of methyl 5-(trans-2-aminocyclopropyl)thiophene-3-carboxylate hydrochloride (50.0 mg), sodium hydrogen carbonate (44.9 mg), THF (2 mL) and methanol (2 mL) was stirred at room temperature for 30 min, and cyclopropanecarbaldehyde (18.0 mg) was added. Under a nitrogen atmosphere, the reaction mixture was stirred at 60° C. for 2 hr, and sodium borohydride (12.1 mg) was added at 0° C. Under a nitrogen atmosphere, the reaction mixture was stirred at room temperature for 1.5 hr, and to the reaction mixture were added ethyl acetate and water under ice-cooling. The mixture was extracted with ethyl acetate, and the extract was washed with water and saturated brine and dried over anhydrous sodium sulfate. The solvent was evaporated under reduced pressure, and the obtained residue was dissolved in THF (3 mL). Triethylamine (0.037 mL) and di-tert-butyl dicarbonate (0.077 mL) were added, and the reaction mixture was stirred at room temperature overnight. Water was added, and the mixture was extracted with ethyl acetate. The organic layer was washed with saturated brine, and dried over anhydrous sodium sulfate, and the solvent was evaporated under reduced pressure. The residue was purified by silica gel column chromatography (hexane/ethyl acetate) to give the title compound (75.7 mg).

$^1$H NMR (300 MHz, DMSO-$d_6$) δ 0.09-0.30 (2H, m), 0.34-0.52 (2H, m), 0.91-1.01 (1H, m), 1.20-1.28 (1H, m), 1.28-1.43 (10H, m), 2.23-2.38 (1H, m), 2.70-2.81 (1H, m), 2.92 (1H, dd, J=14.39, 7.19 Hz), 3.22 (1H, dd, J=14.20, 7.00 Hz), 3.73-3.80 (3H, m), 7.19 (1H, dd, J=1.51, 0.76 Hz), 8.08 (1H, d, J=1.51 Hz).

H) 5-(trans-2-((tert-butoxycarbonyl)(cyclopropylmethyl)amino)cyclopropyl)thiophene-3-carboxylic acid Methyl 5-(trans-2-((tert-butoxycarbonyl)(cyclopropylmethyl)amino)cyclopropyl)thiophene-3-carboxylate (73.0 mg) was dissolved in THF (1.5 mL) and methanol (1.5 mL), 2 mol/L aqueous sodium hydroxide solution (0.260 mL) was added at 0° C., and the mixture was stirred at room temperature overnight. The reaction mixture was acidified with 1 mol/L hydrochloric acid, and extracted with ethyl acetate. The extract was successively washed with water and saturated brine, dried over anhydrous sodium sulfate, and concentrated under reduced pressure to give the title compound (66.5 mg).

MS: [M+2H-Boc]$^+$ 238.2.

I) tert-butyl (cyclopropylmethyl) (trans-2-(4-((5-methyl-1,3,4-thiadiazol-2-yl)carbamoyl)thiophen-2-yl)cyclopropyl)carbamate 5-(trans-2-((tert-Butoxycarbonyl)(cyclopropylmethyl)amino)cyclopropyl)thiophene-3-carboxylic acid (33.0 mg), 5-methyl-1,3,4-thiadiazol-2-amine (12.4 mg) and triethylamine (0.027 mL) were dissolved in DMF (2 mL), O-(7-azabenzotriazol-1-yl)-N,N,N',N'-tetramethyluronium hexafluorophosphate (44.6 mg) was added, and the mixture was stirred at room temperature overnight. Water was added to the reaction mixture, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (27.4 mg).

MS: [M+H]$^+$ 435.3.

J) 5-(trans-2-((cyclopropylmethyl)amino)cyclopropyl)-N-(5-methyl-1,3,4-thiadiazol-2-yl)thiophene-3-carboxamide dihydrochloride To a mixture of tert-butyl (cyclopropylmethyl) (trans-2-(4-((5-methyl-1,3,4-thiadiazol-2-yl)carbamoyl)thiophen-2-yl)cyclopropyl)carbamate (27.0 mg) and ethyl acetate (2 mL) was added 4 mol/L hydrogen chloride/ethyl acetate solution (0.310 mL) at 0° C., and the mixture was stirred at room temperature overnight. The reaction mixture was concentrated under reduced pressure, and the residue was fractionated with LC/MS (C18, mobile phase: water/acetonitrile (containing 0.1% TFA)). The obtained fraction was extracted with ethyl acetate and saturated aqueous sodium hydrogen carbonate solution. The organic layer was successively washed with water and saturated brine, dried over anhydrous sodium sulfate, and concentrated under reduced pressure. The residue was dissolved in ethyl acetate, 4 mol/L hydrogen chloride/ethyl acetate solution was added, and the mixture was stirred at room temperature for 2 hr. The precipitated solid was collected by filtration and washed with ethyl acetate to give the title compound (22.9 mg)

$^1$H NMR (300 MHz, DMSO-$d_6$) δ 0.35-0.44 (2H, m), 0.53-0.64 (2H, m), 1.28-1.39 (1H, m), 1.63-1.75 (1H, m), 2.63 (3H, s), 2.80 (1H, ddd, J=9.75, 6.15, 3.79 Hz), 2.90-2.99 (2H, m), 7.51 (1H, s), 8.45 (1H, d, J=1.51 Hz), 9.57 (2H, brs), 10.08 (1H, brs), 12.36-13.00 (1H, m).

Example 24

N-(4,4-difluorocyclohexyl)-5-(trans-2-((tetrahydro-2H-pyran-4-ylmethyl)amino)cyclopropyl)thiophene-3-carboxamide hydrochloride

A) 5-(trans-2-((tert-butoxycarbonyl)amino)cyclopropyl)thiophene-3-carboxylic acid Methyl 5-(trans-2-((tert-butoxycarbonyl)amino)cyclopropyl)thiophene-3-carboxylate (450 mg) was dissolved in methanol (5 mL) and THF (5 mL), 2 mol/L aqueous sodium hydroxide solution (1.89 mL) was added at 0° C., and the mixture was stirred at room temperature overnight. The reaction mixture was acidified with 1 mol/L hydrochloric acid at 0° C. and extracted with ethyl acetate. The extract was washed with saturated brine, dried over anhydrous sodium sulfate, and concentrated under reduced pressure to give the title compound (385 mg).

$^1$H NMR (300 MHz, DMSO-$d_6$) δ 1.02-1.23 (2H, m), 1.39 (9H, s), 2.07 (1H, ddd, J=9.09, 6.25, 3.22 Hz), 2.59 (1H, brs), 7.07 (1H, d, J=0.76 Hz), 7.28 (1H, brs), 7.97 (1H, d, J=1.51 Hz), 12.61 (1H, brs).

B) N-(4,4-difluorocyclohexyl)-5-(trans-2-((tetrahydro-2H-pyran-4-ylmethyl)amino)cyclopropyl)thiophene-3-carboxamide hydrochloride By a method similar to that of Example 1, steps G and H and Example 2, the title compound was obtained.

Example 25

4-(trans-2-aminocyclopropyl)-5-methyl-N-(1-methyl-1H-pyrazol-4-yl)thiophene-2-carboxamide dihydrochloride 4-(trans-2-((tert-Butoxycarbonyl)amino)cyclopropyl)-5-methylthiophene-2-carboxylic acid (50 mg), 1-methyl-1H-pyrazol-4-amine hydrochloride (27 mg) and triethylamine (0.094 mL) were dissolved in DMF (1.0 mL), O-(7-azabenzotriazol-1-yl)-N,N,N',N'-tetramethyluronium hexafluorophosphate (77 mg) was added at room temperature, and the mixture was stirred at room temperature overnight. The reaction mixture was poured into water, extracted with ethyl acetate, washed with water and saturated brine, dried over anhydrous magnesium sulfate and concentrated under reduced pressure. To a mixture of the obtained residue and ethyl acetate (2.0 mL) was added 4 mol/L hydrogen chloride/ethyl acetate solution (2.0 mL) at room temperature, and the mixture was stirred at room temperature overnight. The resulting precipitate was collected by filtration to give the title compound (55 mg).
MS: [M-2HCl+H]$^+$ 277.1.

Example 26

4-(trans-2-((cyclopropylmethyl)amino) cyclopropyl)-5-methyl-N-(5-methyl-1,3,4-thiadiazol-2-yl)thiophene-2-carboxamide fumarate To a mixture of 4-(trans-2-((cyclopropylmethyl)amino)cyclopropyl)-5-methyl-N-(5-methyl-1,3,4-thiadiazol-2-yl)thiophene-2-carboxamide dihydrochloride (15 mg) and ethyl acetate was added saturated aqueous sodium hydrogen carbonate solution, and the mixture was extracted with ethyl acetate. The extract was washed with water and saturated brine, dried over anhydrous magnesium sulfate and concentrated under reduced pressure. To a mixture of the obtained residue and ethyl acetate was added a solution of fumaric acid (4.13 mg) in ethanol at room temperature, and the reaction mixture was stirred for 30 min. The resulting precipitate was collected by filtration to give the title compound (9.0 mg).
$^1$H NMR (300 MHz, METHANOL-d$_4$) δ 0.26-0.36 (2H, m), 0.58-0.69 (2H, m), 1.01-1.12 (1H, m), 1.13-1.22 (1H, m), 1.30-1.40 (1H, m), 2.10-2.20 (1H, m), 2.55 (3H, s), 2.67 (3H, s), 2.72-2.79 (1H, m), 2.83-2.90 (2H, m), 6.63-6.72 (1H, m), 7.52-7.65 (1H, m).

Example 27

4-(trans-2-((cyclopropylmethyl)amino)cyclopropyl)-N-(5-methyl-1,3,4-thiadiazol-2-yl)thiophene-2-carboxamide dihydrochloride A) ethyl (E)-3-(5-bromothiophen-3-yl)acrylate To a suspension of lithium chloride (174 mg) and acetonitrile (15 mL) were added 5-bromothiophene-3-carbaldehyde (770 mg) and ethyl diethylphosphonoacetate (0.840 mL) at 0° C., and the mixture was stirred at 0° C. for 10 min. To the reaction mixture was added 1,8-diazabicyclo[5.4.0]undec-7-ene (0.638 mL), and the mixture was stirred at room temperature overnight. Water was added to the reaction mixture, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (1.01 g).
$^1$H NMR (300 MHz, DMSO-d$_6$) δ 1.19-1.29 (3H, m), 4.11-4.23 (2H, m), 6.48 (1H, d, J=15.90 Hz), 7.53 (1H, d, J=15.0 Hz), 7.74 (1H, d, J=1.51 Hz), 7.98 (1H, d, J=1.51 Hz).

B) ethyl trans-2-(5-bromothiophen-3-yl)cyclopropanecarboxylate

To a suspension of trimethylsulfoxonium iodide (1.01 g) in DMSO (10 mL) was added sodium hydride (60% in oil, 184 mg) under a nitrogen atmosphere, and the mixture was stirred at room temperature for 30 min. To the reaction mixture was added a mixture of ethyl (E)-3-(5-bromothiophen-3-yl)acrylate (1.00 g) and DMSO (5 mL), and the mixture was stirred at room temperature overnight under a nitrogen atmosphere. Water was added to the reaction mixture at room temperature, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (263 mg).
$^1$H NMR (300 MHz, DMSO-d$_6$) δ 1.16-1.24 (3H, m), 1.27-1.42 (2H, m), 1.92 (1H, ddd, J=8.33, 5.30, 4.16 Hz), 2.44 (1H, ddd, J=9.18, 6.72, 4.16 Hz), 4.03-4.14 (2H, m), 7.09 (1H, d, J=1.89 Hz), 7.32 (1H, d, J=1.51 Hz).

C) trans-2-(5-bromothiophen-3-yl)cyclopropanecarboxylic acid

Ethyl trans-2-(5-bromothiophen-3-yl)cyclopropanecarboxylate (260 mg) was dissolved in THF (2 mL) and ethanol (2 mL), 2 mol/L aqueous sodium hydroxide solution (1.18 mL) was added at 0° C., and the mixture was stirred at room temperature overnight. The reaction mixture was acidified with 1 mol/L hydrochloric acid, and extracted with ethyl acetate. The extract was successively washed with water and saturated brine, dried over anhydrous sodium sulfate, and concentrated under reduced pressure to give the title compound (215 mg).
$^1$H NMR (300 MHz, DMSO-d$_6$) δ 1.22-1.40 (2H, m), 1.78 (1H, ddd, J=8.33, 5.30, 4.16 Hz), 2.39 (1H, ddd, J=9.09, 6.44, 4.16 Hz), 7.08 (1H, d, J=1.51 Hz), 7.30 (1H, d, J=1.51 Hz), 12.35 (1H, brs).

D) tert-butyl (trans-2-(5-bromothiophen-3-yl)cyclopropyl)carbamate

To a mixture of trans-2-(5-bromothiophen-3-yl)cyclopropanecarboxylic acid (230 mg) and tert-butyl alcohol (3 mL) were added triethylamine (0.156 mL) and diphenylphosphoryl azide (0.241 mL) at room temperature, and the mixture was stirred at room temperature for 2 hr and then at 80° C. overnight. The reaction mixture was cooled to room temperature, water was added, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (205 mg).
$^1$H NMR (300 MHz, DMSO-d$_6$) δ 0.92-1.10 (2H, m), 1.34-1.41 (9H, m), 1.87 (1H, ddd, J=9.28, 6.25, 3.41 Hz), 2.53-2.65 (1H, m), 7.00 (1H, d, J=1.51 Hz), 7.12 (1H, d, J=1.51 Hz), 7.20 (1H, brs).

E) methyl 4-(trans-2-((tert-butoxycarbonyl)amino) cyclopropyl)thiophene-2-carboxylate A mixture of tert-butyl (trans-2-(5-bromothiophen-3-yl) cyclopropyl)carbamate (330 mg), triethylamine (0.289 mL), dichloro(1,1'-bis(diphenylphosphino)ferrocene)palladium (152 mg) and methanol (30 mL) was stirred at 90° C. for 8 hr under a carbon monoxide atmosphere (3 atm). The insoluble material was filtered off, and the filtrate was concentrated under reduced pressure. The residue was extracted with ethyl acetate and water, and the organic layer was washed with saturated brine, dried over anhydrous sodium sulfate, and concentrated under reduced pressure. The residue was purified by silica gel column chromatography (hexane/ethyl acetate) to give the title compound (253 mg).
$^1$H NMR (300 MHz, DMSO-$d_6$) δ 0.99-1.12 (2H, m), 1.38 (9H, s), 1.88-1.98 (1H, m), 2.60 (1H, brs), 3.80 (3H, s), 7.22 (1H, brs), 7.50 (1H, d, J=1.51 Hz), 7.59 (1H, d, J=1.51 Hz).

F) 4-(trans-2-((tert-butoxycarbonyl)amino)cyclopropyl)thiophene-2-carboxylic acid Methyl 4-(trans-2-((tert-butoxycarbonyl)amino)cyclopropyl)thiophene-2-carboxylate (250 mg) was dissolved in THF (4 mL) and methanol (4 mL), 2 mol/L aqueous sodium hydroxide solution (1.05 mL) was added at 0° C., and the mixture was stirred at room temperature overnight. The reaction mixture was acidified with 1 mol/L hydrochloric acid at 0° C., and the mixture was extracted with ethyl acetate. The extract was successively washed with water and saturated brine, dried over anhydrous sodium sulfate, and concentrated under reduced pressure to give the title compound (235 mg).
$^1$H NMR (300 MHz, DMSO-$d_6$) δ 0.96-1.12 (2H, m), 1.38 (9H, s), 1.92 (1H, ddd, J=9.18, 6.34, 3.03 Hz), 2.58 (1H, brs), 7.22 (1H, brs), 7.39-7.46 (1H, m), 7.50 (1H, d, J=1.51 Hz), 12.99 (1H, brs).

G) tert-butyl (trans-2-(5-((5-methyl-1,3,4-thiadiazol-2-yl)carbamoyl)thiophen-3-yl)cyclopropyl)carbamate 4-(trans-2-((tert-Butoxycarbonyl)amino)cyclopropyl) thiophene-2-carboxylic acid (80.0 mg), 5-methyl-1,3,4-thiadiazol-2-amine (35.8 mg) and triethylamine (0.079 mL) were dissolved in DMF (3 mL), O-(7-azabenzotriazol-1-yl)-N,N,N',N'-tetramethyluronium hexafluorophosphate (129 mg) was added, and the mixture was stirred at room temperature overnight. Water was added to the reaction mixture, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (58.2 mg).
MS: [M+H]$^+$ 381.2.

H) 4-(trans-2-aminocyclopropyl)-N-(5-methyl-1,3,4-thiadiazol-2-yl)thiophene-2-carboxamide dihydrochloride To a mixture of tert-butyl (trans-2-(5-((5-methyl-1,3,4-thiadiazol-2-yl)carbamoyl)thiophen-3-yl)cyclopropyl)carbamate (55.0 mg) and ethyl acetate (3 mL) was added 4 mol/L hydrogen chloride/ethyl acetate solution (0.361 mL) at 0° C., and the mixture was stirred at room temperature overnight. The precipitated solid was collected by filtration and washed with ethyl acetate to give the title compound (26.3 mg).
$^1$H NMR (300 MHz, DMSO-$d_6$) δ 1.11-1.23 (1H, m), 1.44 (1H, ddd, J=10.03, 5.87, 4.54 Hz), 2.43 (1H, ddd, J=9.75, 6.15, 3.41 Hz), 2.62 (3H, s), 2.81 (1H, dd, J=7.76, 3.98 Hz), 7.73 (1H, s), 7.92-8.19 (1H, m), 8.54 (3H, brs).

I) 4-(trans-2-((cyclopropylmethyl)amino)cyclopropyl)-N-(5-methyl-, 3,4-thiadiazol-2-yl)thiophene-2-carboxamide dihydrochloride To a mixture of 4-(trans-2-aminocyclopropyl)-N-(5-methyl-1,3,4-thiadiazol-2-yl)thiophene-2-carboxamide dihydrochloride (24.0 mg), sodium hydrogen carbonate (14.3 mg), THF (1.5 mL) and methanol (1.5 mL) was added cyclopropanecarbaldehyde (5.71 mg) at room temperature. Under a nitrogen atmosphere, the reaction mixture was stirred at 60° C. for 1.5 hr and at room temperature for 30 min, and sodium borohydride (3.86 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine, and dried over anhydrous sodium sulfate. The solvent was evaporated under reduced pressure and the residue was purified by silica gel column chromatography (ethyl acetate/methanol). To the obtained fraction was added 4 mol/L hydrogen chloride/ethyl acetate solution and the reaction mixture was stirred at room temperature overnight. The precipitated solid was collected by filtration and washed with ethyl acetate to give the title compound (17.6 mg).
$^1$H NMR (300 MHz, DMSO-$d_6$) δ 0.30-0.44 (2H, m), 0.50-0.68 (2H, m), 1.05-1.17 (1H, m), 1.19-1.32 (1H, m), 1.52-1.66 (1H, m), 2.55-2.67 (4H, m), 2.86-3.00 (3H, m), 7.75 (1H, s), 8.07 (1H, brs), 9.37-9.60 (2H, m).

Example 28

4-(trans-2-((cyclopropylmethyl)amino)cyclopropyl)-N-(4,4-difluorocyclohexyl)thiophene-2-carboxamide hydrochloride

A) tert-butyl (trans-2-(5-((4,4-difluorocyclohexyl)carbamoyl)thiophen-3-yl)cyclopropyl)carbamate 4-(trans-2-((tert-Butoxycarbonyl)amino)cyclopropyl) thiophene-2-carboxylic acid (150 mg), 4,4-difluorocyclohexanamine hydrochloride (100 mg) and triethylamine (0.295 mL) were dissolved in DMF (6 mL), O-(7-azabenzotriazol-1-yl)-N,N,N',N'-tetramethyluronium hexafluorophosphate (242 mg) was added at room temperature, and the mixture was stirred overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (211 mg).
$^1$H NMR (300 MHz, DMSO-$d_6$) δ 0.92-1.12 (2H, m), 1.33-1.42 (9H, m), 1.48-1.69 (2H, m), 1.79-2.14 (7H, m), 2.62 (1H, brs), 3.92 (1H, d, J=7.57 Hz), 7.22 (1H, brs), 7.31 (1H, s), 7.55 (1H, d, J=1.14 Hz), 8.20 (1H, d, J=7.95 Hz).

B) 4-(trans-2-aminocyclopropyl)-N-(4,4-difluorocyclohexyl)thiophene-2-carboxamide hydrochloride To a mixture of tert-butyl (trans-2-(5-((4,4-difluorocyclohexyl)carbamoyl)thiophen-3-yl)cyclopropyl)carbamate (210 mg) and ethyl acetate (3 mL) was added 4 mol/L hydrogen chloride/ethyl acetate solution (1.31 mL) at 0° C., and the mixture was stirred at room temperature overnight. The precipitated solid was collected by filtration, washed with ethyl acetate, and dried under reduced pressure to give the title compound (108 mg).
MS: [M-HCl+H]$^+$ 301.2.

C) 4-(trans-2-((cyclopropylmethyl)amino)cyclopropyl)-N-(4,4-difluorocyclohexyl)thiophene-2-carboxamide hydrochloride To a mixture of 4-(trans-2-aminocyclopropyl)-N-(4,4-difluorocyclohexyl)thiophene-2-carboxamide hydrochloride (30.0 mg), sodium hydrogen carbonate (18.7 mg), THF (1.5 mL) and methanol (1.5 mL) was added cyclopropanecarbaldehyde (7.49 mg) at room temperature. Under a nitrogen atmosphere, the reaction mixture was stirred at 60° C. for 1.5 hr and at room temperature for 30 min, and sodium borohydride (5.05 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine, and dried over anhydrous sodium sulfate. The solvent was evaporated under reduced pressure. The residue was purified by silica gel column chromatography (hexane/ethyl acetate), and to the obtained fraction was added 4 mol/L hydrogen chloride/ethyl acetate solution. The reaction mixture was stirred at room temperature overnight, and the precipitated solid was collected by filtration, washed with ethyl acetate and dried under reduced pressure to give the title compound (18.1 mg).
$^1$H NMR (300 MHz, DMSO-d$_6$) δ 0.36 (2H, brs), 0.59 (2H, brs), 0.97-1.34 (2H, m), 1.45-1.68 (3H, m), 1.80-2.13 (6H, m), 2.94 (3H, d, J=7.57 Hz), 3.92 (2H, brs), 7.44-7.75 (2H, m), 8.23 (1H, d, J=8.33 Hz), 9.19 (1H, brs).

Example 29

N-(4,4-difluorocyclohexyl)-4-(trans-2-(tetrahydro-2H-pyran-4-ylamino)cyclopropyl)thiophene-2-carboxamide hydrochloride To a mixture of 4-(trans-2-aminocyclopropyl)-N-(4,4-difluorocyclohexyl)thiophene-2-carboxamide hydrochloride (30.0 mg), sodium hydrogen carbonate (18.7 mg), THF (1.5 mL) and methanol (1.5 mL) was added dihydro-2H-pyran-4(3H)-one (10.7 mg). Under a nitrogen atmosphere, the reaction mixture was stirred at 60° C. for 1.5 hr and at room temperature for 30 min, and sodium borohydride (5.05 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine, and dried over anhydrous sodium sulfate. The solvent was evaporated under reduced pressure. The residue was purified by silica gel column chromatography (methanol/ethyl acetate), and to the obtained fraction was added 4 mol/L hydrogen chloride/ethyl acetate solution. The reaction mixture was stirred at room temperature overnight, and the precipitated solid was collected by filtration, and washed with ethyl acetate to give the title compound (14.8 mg).
$^1$H NMR (300 MHz, DMSO-d$_6$) δ 1.11-1.33 (1H, m), 1.42-2.20 (15H, m), 2.93 (1H, brs), 3.38-3.55 (2H, m), 3.92 (3H, d, J=10.60 Hz), 7.43-7.71 (2H, m), 8.23 (1H, d, J=6.82 Hz), 9.43 (1H, brs).

Example 30

5-(trans-2-((cyclopropylmethyl)amino)cyclopropyl)-N-(4,4-difluorocyclohexyl)thiophene-3-carboxamide hydrochloride A) tert-butyl (trans-2-(4-((4,4-difluorocyclohexyl)carbamoyl)thiophen-2-yl)cyclopropyl)carbamate 5-(trans-2-((tert-Butoxycarbonyl)amino)cyclopropyl)thiophene-3-carboxylic acid (100 mg), 4,4-difluorocyclohexanamine hydrochloride (66.6 mg) and triethylamine (0.197 mL) were dissolved in DMF (4 mL), O-(7-azabenzotriazol-1-yl)-N,N,N',N'-tetramethyluronium hexafluorophosphate (161 mg) was added, and the mixture was stirred at room temperature overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (92.1 mg).
MS: [M+H]$^+$ 401.2.

B) 5-(trans-2-aminocyclopropyl)-N-(4,4-difluorocyclohexyl)thiophene-3-carboxamide hydrochloride To a mixture of tert-butyl (trans-2-(4-((4,4-difluorocyclohexyl)carbamoyl)thiophen-2-yl)cyclopropyl)carbamate (90.0 mg) and ethyl acetate (3 mL) was added 4 mol/L hydrogen chloride/ethyl acetate solution (0.562 mL) at 0° C., and the mixture was stirred at room temperature overnight. The precipitated solid was collected by filtration and washed with ethyl acetate to give the title compound (76.8 mg).
MS: [M-HCl+H]$^+$ 301.2.

C) 5-(trans-2-((cyclopropylmethyl)amino)cyclopropyl)-N-(4,4-difluorocyclohexyl)thiophene-3-carboxamide hydrochloride To a mixture of 5-(trans-2-aminocyclopropyl)-N-(4,4-difluorocyclohexyl)thiophene-3-carboxamide hydrochloride (30.0 mg), sodium hydrogen carbonate (18.7 mg), THF (1.5 mL) and methanol (1.5 mL) was added cyclopropanecarbaldehyde (7.49 mg) at room temperature. Under a nitrogen atmosphere, the reaction mixture was stirred at 60° C. for 1.5 hr and at room temperature for 30 min, and sodium borohydride (5.05 mg) was added at 0° C. Under a nitrogen atmosphere, the reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine, and dried over anhydrous sodium sulfate. The solvent was evaporated under reduced pressure. The residue was purified by silica gel column chromatography (hexane/ethyl acetate), and to the obtained fraction was added 4 mol/L hydrogen chloride/ethyl acetate solution. The reaction mixture was stirred at room temperature overnight, and the precipitated solid was collected by filtration, and washed with ethyl acetate to give the title compound (14.6 mg).

$^1$H NMR (300 MHz, DMSO-d$_6$) δ 0.38 (2H, m, J=3.41 Hz), 0.58 (2H, d, J=6.44 Hz), 1.07 (1H, brs), 1.20-1.38 (1H, m), 1.45-1.68 (3H, m), 1.86 (3H, m), 2.03 (3H, m), 2.69 (2H, m), 2.95 (2H, d, J=7.19 Hz), 3.93 (1H, brs), 7.28 (1H, s), 7.95 (1H, s), 8.05 (1H, d, J=7.95 Hz), 9.26 (2H, brs).

Example 31

N-(4,4-difluorocyclohexyl)-5-(trans-2-(tetrahydro-2H-pyran-4-ylamino)cyclopropyl)thiophene-3-carboxamide hydrochloride To a mixture of 5-(trans-2-aminocyclopropyl)-N-(4,4-difluorocyclohexyl)thiophene-3-carboxamide hydrochloride (30.0 mg), sodium hydrogen carbonate (18.7 mg), THF (1.5 mL) and methanol (1.5 mL) was added dihydro-2H-pyran-4(3H)-one (10.7 mg) at room temperature. Under a nitrogen atmosphere, the reaction mixture was stirred at 60° C. for 1.5 hr and at room temperature for 30 min, and sodium borohydride (5.05 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine, and dried over anhydrous sodium sulfate. The solvent was evaporated under reduced pressure. The residue was purified by silica gel column chromatography (methanol/ethyl acetate), and to the obtained fraction was added 4 mol/L hydrogen chloride/ethyl acetate solution. The reaction mixture was stirred at room temperature overnight, and the precipitated solid was collected by filtration, and washed with ethyl acetate to give the title compound (18.1 mg).

$^1$H NMR (300 MHz, DMSO-d$_6$) δ 1.25-1.41 (1H, m), 1.62 (5H, d, J=10.60 Hz), 1.77-2.15 (9H, m), 2.62-2.80 (1H, m), 2.89-3.08 (1H, m), 3.39-3.59 (1H, m), 3.92 (3H, d, J=9.47 Hz), 7.28 (1H, s), 7.95 (1H, s), 8.04 (1H, d, J=7.95 Hz), 9.44 (2H, brs).

Example 32

5-(trans-2-((cyclopropylmethyl)amino)cyclopropyl)-N-(tetrahydro-2H-pyran-4-yl)thiophene-3-carboxamide hydrochloride A) tert-butyl (2-(4-((tetrahydro-2H-pyran-4-yl)carbamoyl)thiophen-2-yl)cyclopropyl)carbamate 5-(trans-2-((tert-Butoxycarbonyl)amino)cyclopropyl) thiophene-3-carboxylic acid (50.0 mg), tetrahydro-2H-pyran-4-amine (19.6 mg) and triethylamine (0.049 mL) were dissolved in DMF (2 mL), 0-(7-azabenzotriazol-1-yl)-N,N,N',N'-tetramethyluronium hexafluorophosphate (81.0 mg) was added at room temperature, and the mixture was stirred overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (61.8 mg).

$^1$H NMR (300 MHz, DMSO-d$_6$) δ 0.99-1.11 (1H, m), 1.12-1.21 (1H, m), 1.39 (9H, s), 1.44-1.62 (2H, m), 1.72 (2H, dd, J=12.49, 2.27 Hz), 2.06 (1H, ddd, J=8.99, 5.77, 3.41 Hz), 2.62 (1H, brs), 3.33-3.42 (2H, m), 3.80-4.00 (3H, m), 7.17 (1H, s), 7.28 (1H, brs), 7.83 (1H, d, J=1.51 Hz), 8.00 (1H, d, J=7.95 Hz).

B) 5-(trans-2-aminocyclopropyl)-N-(tetrahydro-2H-pyran-4-yl)thiophene-3-carboxamide hydrochloride To a mixture of tert-butyl (2-(4-((tetrahydro-2H-pyran-4-yl)carbamoyl)thiophen-2-yl)cyclopropyl)carbamate (59.0 mg) and ethyl acetate (3 mL) was added 4 mol/L hydrogen chloride/ethyl acetate solution (0.402 mL) at 0° C., and the mixture was stirred at room temperature overnight. The precipitated solid was collected by filtration and washed with ethyl acetate to give the title compound (45.5 mg).

$^1$H NMR (300 MHz, DMSO-d$_6$) δ 1.17-1.31 (1H, m), 1.40-1.62 (3H, m), 1.64-1.79 (2H, m), 2.55 (1H, td, J=6.44, 3.41 Hz), 2.75-2.88 (1H, m), 3.29-3.45 (2H, m), 3.79-4.01 (3H, m), 7.24-7.32 (1H, m), 7.94 (1H, d, J=1.51 Hz), 8.08 (1H, d, J=7.95 Hz), 8.55 (3H, d, J=2.65 Hz).

C) 5-(trans-2-((cyclopropylmethyl)amino)cyclopropyl)-N-(tetrahydro-2H-pyran-4-yl)thiophene-3-carboxamide hydrochloride To a mixture of 5-(trans-2-aminocyclopropyl)-N-(tetrahydro-2H-pyran-4-yl)thiophene-3-carboxamide hydrochloride (43.0 mg), sodium hydrogen carbonate (29.8 mg), THF (2 mL) and methanol (2 mL) was added cyclopropanecarbaldehyde (11.9 mg). Under a nitrogen atmosphere, the reaction mixture was stirred at 60° C. for 1.5 hr and at room temperature for 30 min, and sodium borohydride (8.06 mg) was added at 0° C. Under a nitrogen atmosphere, the reaction mixture was stirred at room temperature for 1 hr, and ethyl acetate, water and saturated aqueous sodium hydrogen carbonate solution were added to the reaction mixture. The mixture was extracted with ethyl acetate, and the extract was washed successively with water and saturated brine. The extract was dried over anhydrous sodium sulfate, and the solvent was evaporated under reduced pressure. The residue was purified by silica gel column chromatography (hexane/ethyl acetate), and to the obtained fraction was added 4 mol/L hydrogen chloride/ethyl acetate solution under ice-cooling. The reaction mixture was stirred at room temperature for 2 hr. The precipitated solid was collected by filtration and washed with ethyl acetate to give the title compound (29.8 mg).

$^1$H NMR (300 MHz, DMSO-d$_6$) δ 0.31-0.44 (2H, m), 0.51-0.66 (2H, m), 0.98-1.15 (1H, m), 1.21-1.38 (1H, m), 1.42-1.66 (3H, m), 1.66-1.81 (2H, m), 2.70 (1H, ddd, J=9.66, 6.25, 3.41 Hz), 2.91-3.01 (3H, m), 3.33-3.45 (2H, m), 3.78-4.04 (3H, m), 7.28 (1H, s), 7.95 (1H, d, J=1.51 Hz), 8.06 (1H, d, J=7.57 Hz), 9.30 (2H, brs).

Example 33

5-(trans-2-(cyclobutylamino)cyclopropyl)-N-(5-methyl-1,3,4-thiadiazol-2-yl)thiophene-3-carboxamide dihydrochloride A) methyl 5-(trans-2-((tert-butoxycarbonyl)(cyclobutyl)amino)cyclopropyl)thiophene-3-carboxylate To a mixture of methyl 5-(trans-2-aminocyclopropyl) thiophene-3-carboxylate hydrochloride (100 mg), sodium hydrogen carbonate (90.0 mg), THF (4 mL) and methanol (4 mL) was added cyclobutanone (36.0 mg). Under a nitrogen atmosphere, the reaction mixture was stirred at 60° C. for 1.5 hr and at room temperature for 30 min, and sodium borohydride (24.3 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine, and dried over anhydrous sodium sulfate. The solvent was evaporated under reduced pressure. The obtained residue was dissolved in THF (3 mL), and triethylamine (0.090 mL) and di-tert-butyl dicarbonate (0.120 mL) were added. The reaction mixture was stirred at room temperature overnight, and the mixture was extracted with ethyl acetate and water. The organic layer was washed with saturated brine, and dried over anhydrous sodium sulfate, and the solvent was evaporated under reduced pressure. The residue was purified by silica gel column chromatography (hexane/ethyl acetate) to give the title compound (98.9 mg).

$^1$H NMR (300 MHz, DMSO-$d_6$) δ 1.23-1.33 (2H, m), 1.37 (9H, s), 1.45-1.68 (2H, m), 2.01-2.32 (5H, m), 2.62 (1H, ddd, J=7.10, 5.02, 3.41 Hz), 3.77 (3H, s), 3.92-4.09 (1H, m), 7.14-7.21 (1H, m), 8.08 (1H, d, J=1.51 Hz).

B) 5-(trans-2-((tert-butoxycarbonyl) (cyclobutyl) amino)cyclopropyl)thiophene-3-carboxylic acid Methyl 5-(trans-2-((tert-butoxycarbonyl) (cyclobutyl) amino)cyclopropyl)thiophene-3-carboxylate (95.0 mg) was dissolved in THF (2 mL) and methanol (2 mL), 2 mol/L aqueous sodium hydroxide solution (0.338 mL) was added at 0° C., and the mixture was stirred at room temperature overnight. The reaction mixture was acidified with 1 mol/L hydrochloric acid at 0° C., and extracted with ethyl acetate. The extract was successively washed with water and saturated brine, dried over anhydrous sodium sulfate, and concentrated under reduced pressure to give the title compound (90.1 mg).

$^1$H NMR (300 MHz, DMSO-$d_6$) δ 1.22-1.32 (2H, m), 1.38 (9H, s), 1.48-1.67 (2H, m), 2.04-2.30 (5H, m), 2.61 (1H, ddd, J=7.29, 4.45, 3.41 Hz), 3.94-4.07 (1H, m), 7.11-7.15 (1H, m), 7.99 (1H, d, J=1.51 Hz), 12.60 (1H, brs).

C) tert-butyl cyclobutyl(trans-2-(4-((5-methyl-1,3,4-thiadiazol-2-yl)carbamoyl)thiophen-2-yl)cyclopropyl)carbamate 5-(trans-2-((tert-Butoxycarbonyl) (cyclobutyl)amino) cyclopropyl)thiophene-3-carboxylic acid (45.0 mg), 5-methyl-1,3,4-thiadiazol-2-amine (18.4 mg) and triethylamine (0.028 mL) were dissolved in DMF (3 mL), O-(7-azabenzotriazol-1-yl)-N,N,N',N'-tetramethyluronium hexafluorophosphate (60.8 mg) was added, and the mixture was stirred at room temperature overnight. The reaction mixture was extracted with ethyl acetate and water, and the organic layer was washed with saturated brine, dried over anhydrous sodium sulfate, and concentrated under reduced pressure. The residue was purified by silica gel column chromatography (hexane/ethyl acetate) to give the title compound (38.3 mg)

$^1$H NMR (300 MHz, DMSO-$d_6$) δ 1.14-1.43 (11H, m), 1.48-1.69 (2H, m), 2.04-2.34 (5H, m), 2.58-2.67 (4H, m), 4.03 (1H, quin, J=8.52 Hz), 7.47 (1H, s), 8.36 (1H, d, J=1.14 Hz), 12.64 (1H, brs).

D) 5-(trans-2-(cyclobutylamino)cyclopropyl)-N-(5-methyl-1,3,4-thiadiazol-2-yl)thiophene-3-carboxamide dihydrochloride To a mixture of tert-butyl cyclobutyl(trans-2-(4-((5-methyl-1,3,4-thiadiazol-2-yl)carbamoyl)thiophen-2-yl)cyclopropyl)carbamate (36.0 mg) and ethyl acetate (2 mL) was added 4 mol/L hydrogen chloride/ethyl acetate solution (0.207 mL) at 0° C., and the mixture was stirred at room temperature overnight. The precipitated solid was collected by filtration and washed with ethyl acetate to give the title compound (26.5 mg).

$^1$H NMR (300 MHz, DMSO-$d_6$) δ 1.17 (1H, t, J=7.00 Hz), 1.26-1.42 (1H, m), 1.56-1.68 (1H, m), 1.74-1.92 (2H, m), 2.29 (4H, d, J=13.63), 2.69-3.11 (3H, m), 3.60-4.26 (2H, m), 7.42 (1H, s), 8.45 (1H, brs), 9.67-10.18 (1H, m), 13.03 (1H, brs).

Example 34

5-(trans-2-(cyclobutylamino)cyclopropyl)-N-(1-methyl-H-pyrazol-4-yl)thiophene-3-carboxamide hydrochloride A) tert-butyl cyclobutyl(trans-2-(4-((1-methyl-1H-pyrazol-4-yl)carbamoyl)thiophen-2-yl)cyclopropyl) carbamate 5-(trans-2-((tert-Butoxycarbonyl) (cyclobutyl)amino)cyclopropyl)thiophene-3-carboxylic acid (45.0 mg), 1-methyl-1H-pyrazol-4-amine (15.5 mg) and triethylamine (0.028 mL) were dissolved in DMF (3 mL), O-(7-azabenzotriazol-1-yl)-N,N,N',N'-tetramethyluronium hexafluorophosphate (60.8 mg) was added, and the mixture was stirred at room temperature overnight. Water was added to the reaction mixture, and the mixture was extracted with ethyl acetate. The organic layer was washed with saturated brine, dried over anhydrous sodium sulfate, and concentrated under reduced pressure. The residue was purified by silica gel column chromatography (hexane/ethyl acetate) to give the title compound (24.0 mg).

$^1$H NMR (300 MHz, DMSO-$d_6$) δ 1.20-1.35 (2H, m), 1.36-1.42 (9H, m), 1.47-1.70 (2H, m), 2.01-2.34 (5H, m), 2.57-2.67 (1H, m), 3.76-3.85 (3H, m), 3.93-4.15 (1H, m), 7.30 (1H, d, J=0.76 Hz), 7.50 (1H, s), 7.93 (2H, s), 10.11 (1H, s).

B) 5-(trans-2-(cyclobutylamino)cyclopropyl)-N-(1-methyl-1H-pyrazol-4-yl)thiophene-3-carboxamide hydrochloride To a mixture of tert-butyl cyclobutyl(trans-2-(4-((1-methyl-1H-pyrazol-4-yl)carbamoyl)thiophen-2-yl)cyclopropyl)carbamate (22.0 mg) and ethyl acetate (1 mL) was added 4 mol/L hydrogen chloride/ethyl acetate solution (0.132 mL) at 0° C., and the mixture was stirred at room temperature overnight. The precipitated solid was collected by filtration and washed with ethyl acetate to give the title compound (11.2 mg).

$^1$H NMR (300 MHz, DMSO-$d_6$) δ 1.24-1.38 (1H, m), 1.51-1.66 (1H, m), 1.72-1.90 (2H, m), 2.12-2.40 (4H, m), 2.74 (1H, ddd, J=9.94, 6.15, 3.22 Hz), 2.82-2.96 (1H, m), 3.75-3.95 (4H, m), 7.29-8.12 (4H, m), 9.76 (2H, brs), 10.26 (1H, s).

Example 35

4-(trans-2-((cyclopropylmethyl)amino) cyclopropyl)-N-(4,4-difluorocyclohexyl) thiazole-2-carboxamide hydrochloride

A) ethyl (E)-3-(2-bromothiazol-4-yl)acrylate

To a suspension of lithium chloride (450 mg) in acetonitrile (30 mL) were added 2-bromothiazole-4-carbaldehyde (2.00 g) and ethyl diethylphosphonoacetate (2.17 mL) at 0° C., and the mixture was stirred under a nitrogen atmosphere at 0° C. for 5 min. To the reaction mixture was added 1,8-diazabicyclo[5.4.0]undec-7-ene (1.65 mL) at 0° C., and the mixture was stirred under a nitrogen atmosphere at room temperature overnight. Water was added to the reaction mixture, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (2.34 g).
$^1$H NMR (300 MHz, DMSO-$d_6$) δ 1.25 (3H, t, J=7.00 Hz), 4.19 (2H, q, J=6.94 Hz), 6.54 (1H, d, J=15.52 Hz), 7.60 (1H, d, J=15.52 Hz), 8.14 (1H, s).

B) ethyl trans-2-(2-bromothiazol-4-yl)cyclopropanecarboxylate

To a suspension of trimethylsulfoxonium iodide (2.35 g) in DMSO (20 mL) was added sodium hydride (50% in oil, 512 mg) under a nitrogen atmosphere, and the mixture was stirred at room temperature for 30 min. To the reaction mixture was added a mixture of ethyl (E)-3-(2-bromothiazol-4-yl)acrylate (2.33 g) and DMSO (10 mL), and the mixture was stirred at room temperature overnight. Water was added to the reaction mixture at 0° C., and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (912 mg).
$^1$H NMR (300 MHz, DMSO-$d_6$) δ 1.16-1.23 (3H, m), 1.39-1.48 (2H, m), 1.93-2.03 (1H, m), 2.56-2.65 (1H, m), 4.09 (2H, q, J=6.94 Hz), 7.56 (1H, s).

C) trans-2-(2-bromothiazol-4-yl)cyclopropanecarboxylic acid

Ethyl trans-2-(2-bromothiazol-4-yl)cyclopropanecarboxylate (905 mg) was dissolved in THF (5 mL) and ethanol (5 mL), 2 mol/L aqueous sodium hydroxide solution (4.10 mL) was added at 0° C., and the mixture was stirred at room temperature overnight. The reaction mixture was acidified with 1 mol/L hydrochloric acid, and extracted with ethyl acetate. The extract was successively washed with water and saturated brine, dried over anhydrous sodium sulfate, and concentrated under reduced pressure to give the title compound (809 mg).
$^1$H NMR (300 MHz, DMSO-$d_6$) δ 1.32-1.45 (2H, m), 1.88 (1H, ddd, J=8.24, 5.40, 4.16 Hz), 2.53-2.60 (1H, m), 7.54 (1H, s), 12.42 (1H, brs).

D) tert-butyl (trans-2-(2-bromothiazol-4-yl)cyclopropyl)carbamate

To a mixture of trans-2-(2-bromothiazol-4-yl)cyclopropanecarboxylic acid (805 mg) and tert-butyl alcohol (10 mL) were added triethylamine (0.543 mL) and diphenylphosphoryl azide (0.838 mL) at room temperature, and the mixture was stirred at room temperature for 2 hr and then at 80° C. overnight. The reaction mixture was cooled to room temperature, water was added, and the mixture was extracted with ethyl acetate. The extract was successively washed with water and saturated brine, dried over anhydrous sodium sulfate, and concentrated under reduced pressure. The residue was purified by silica gel column chromatography (hexane/ethyl acetate) to give the title compound (514 mg).
$^1$H NMR (300 MHz, DMSO-$d_6$) δ 1.05-1.14 (2H, m), 1.37 (9H, s), 2.06 (1H, td, J=7.57, 3.03 Hz), 2.79 (1H, brs), 7.24 (1H, brs), 7.36 (1H, s).

E) trans-2-(2-bromothiazol-4-yl)cyclopropanamine hydrochloride

To a mixture of tert-butyl (trans-2-(2-bromothiazol-4-yl)cyclopropyl)carbamate (200 mg) and ethyl acetate (3 mL) was added 4 mol/L hydrogen chloride/ethyl acetate solution (1.57 mL) at 0° C., and the mixture was stirred at room temperature overnight. The precipitated solid was collected by filtration and washed with ethyl acetate to give the title compound (158 mg).
$^1$H NMR (300 MHz, DMSO-$d_6$) δ 1.24 (1H, dt, J=7.95, 6.06 Hz), 1.36-1.46 (1H, m), 2.56 (1H, ddd, J=9.75, 6.15, 3.41 Hz), 2.81-2.95 (1H, m), 7.56 (1H, s), 8.54 (3H, brs).

F) trans-2-(2-bromothiazol-4-yl)-N-(cyclopropylmethyl)cyclopropanamine

A mixture of trans-2-(2-bromothiazol-4-yl)cyclopropanamine hydrochloride (100 mg), sodium hydrogen carbonate (131 mg), THF (3 mL) and methanol (3 mL) was stirred at room temperature for 30 min, and cyclopropanecarbaldehyde (32.9 mg) was added. Under a nitrogen atmosphere, the reaction mixture was stirred at 60° C. for 2 hr, and sodium borohydride (22.2 mg) was added at 0° C. Under a nitrogen atmosphere, the reaction mixture was stirred at room temperature for 1.5 hr, and ethyl acetate and water were added to the reaction mixture under ice-cooling. The mixture was extracted with ethyl acetate, and the extract was successively washed with water and saturated brine, and dried over anhydrous sodium sulfate. The solvent was evaporated under reduced pressure. The residue was purified by silica gel column chromatography (NH, hexane/ethyl acetate) to give the title compound (84.4 mg).
$^1$H NMR (300 MHz, DMSO-$d_6$) δ 0.02-0.09 (2H, m), 0.33-0.41 (2H, m), 0.76-0.89 (1H, m), 0.90-1.03 (2H, m), 1.87-2.02 (1H, m), 2.36-2.47 (4H, m), 7.27 (1H, s).

G) tert-butyl (trans-2-(2-bromothiazol-4-yl)cyclopropyl) (cyclopropylmethyl)carbamate trans-2-(2-Bromothiazol-4-yl)-N-(cyclopropylmethyl)cyclopropanamine (81.0 mg) was dissolved in THF (4 mL), and triethylamine (0.062 mL) and di-tert-butyl dicarbonate (0.103 mL) were added. The reaction mixture was stirred at room temperature overnight, and extracted with ethyl acetate and water. The organic layer was washed with water and saturated brine, dried over anhydrous sodium sulfate, and the solvent was evaporated under reduced pressure. The residue was purified by silica gel column chromatography (hexane/ethyl acetate) to give the title compound (106 mg).
$^1$H NMR (300 MHz, DMSO-$d_6$) δ 0.06-0.28 (2H, m), 0.33-0.53 (2H, m), 0.87-1.03 (1H, m), 1.24 (2H, dd, J=7.57, 6.44 Hz), 1.35 (9H, s), 2.18-2.33 (1H, m), 2.79-2.99 (2H, m), 3.21 (1H, dd, J=14.39, 6.82 Hz), 7.44 (1H, s).

H) methyl 4-(trans-2-((tert-butoxycarbonyl)(cyclopropylmethyl)amino)cyclopropyl)thiazole-2-carboxylate A mixture of tert-butyl (trans-2-(2-bromothiazol-4-yl)cyclopropyl) (cyclopropylmethyl)carbamate (80.0 mg), triethylamine (0.060 mL), dichloro(1,1'-bis(diphenylphosphino)ferrocene)palladium (31.4 mg) and methanol (15 mL) was stirred at 90° C. for 8 hr under a carbon monoxide atmosphere (3 atm). After cooling to room temperature, the insoluble material was filtered off, and the filtrate was concentrated under reduced pressure. The residue was extracted with ethyl acetate and water, and the organic layer was washed with saturated brine, dried over anhydrous sodium sulfate, and concentrated under reduced pressure. The residue was purified by silica gel column chromatography (hexane/ethyl acetate) to give the title compound (76.0 mg).
$^1$H NMR (300 MHz, DMSO-$d_6$) δ 0.05-0.28 (2H, m), 0.32-0.53 (2H, m), 0.87-1.05 (1H, m), 1.27-1.37 (11H, m), 2.36 (1H, td, J=7.86, 3.22 Hz), 2.87-3.03 (2H, m), 3.22 (1H, dd, J=14.39, 6.82 Hz), 3.82-3.93 (3H, m), 7.85 (1H, s).

I) 4-(trans-2-((tert-butoxycarbonyl)(cyclopropylmethyl)amino)cyclopropyl)thiazole-2-carboxylic acid Methyl 4-(trans-2-((tert-butoxycarbonyl)(cyclopropylmethyl)amino)cyclopropyl)thiazole-2-carboxylate (93.0 mg) was dissolved in methanol (5 mL), 2 mol/L aqueous sodium hydroxide solution (0.330 mL) was added at 0° C., and the mixture was stirred at room temperature for 1 hr. The reaction mixture was acidified with 1 mol/L hydrochloric acid at 0° C., and extracted with ethyl acetate. The extract was successively washed with water and saturated brine, dried over anhydrous sodium sulfate, and concentrated under reduced pressure to give the title compound (78.9 mg).
MS: [M+H]$^+$ 339.2.

J) tert-butyl (cyclopropylmethyl) (trans-2-(2-((4,4-difluorocyclohexyl)carbamoyl)thiazol-4-yl)cyclopropyl)carbamate 4-(trans-2-((tert-Butoxycarbonyl) (cyclopropylmethyl)amino)cyclopropyl)thiazole-2-carboxylic acid (38.0 mg), 4,4-difluorocyclohexanamine hydrochloride (21.2 mg) and triethylamine (0.063 mL) were dissolved in DMF (3 mL), O-(7-azabenzotriazol-1-yl)-N,N,N',N'-tetramethyluronium hexafluorophosphate (51.2 mg) was added, and the mixture was stirred at room temperature overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (17.6 mg).
$^1$H NMR (300 MHz, DMSO-$d_6$) δ 0.07-0.28 (2H, m), 0.32-0.54 (2H, m), 0.90-1.04 (1H, m), 1.23-1.42 (11H, m), 1.64-1.95 (5H, m), 1.99-2.12 (3H, m), 2.29 (1H, ddd, J=9.47, 6.25, 3.22 Hz), 2.94-3.07 (1H, m), 3.10-3.25 (1H, m), 3.96 (1H, d, J=7.95 Hz), 7.66 (1H, s), 8.54 (1H, d, J=8.71 Hz).

K) 4-(trans-2-((cyclopropylmethyl)amino) cyclopropyl)-N-(4,4-difluorocyclohexyl)thiazole-2-carboxamide hydrochloride To a mixture of tert-butyl (cyclopropylmethyl) (trans-2-(2-((4,4-difluorocyclohexyl)carbamoyl)thiazol-4-yl)cyclopropyl)carbamate (16.0 mg) and ethyl acetate (1.5 mL) was added 4 mol/L hydrogen chloride/ethyl acetate solution (0.088 mL) at 0° C., and the mixture was stirred at room temperature overnight. The precipitated solid was collected by filtration and washed with ethyl acetate to give the title compound (10.1 mg).
$^1$H NMR (300 MHz, DMSO-$d_6$) δ 0.36 (2H, d, J=4.16 Hz), 0.57 (2H, d, J=6.44 Hz), 1.00-1.18 (1H, m), 1.33-1.49 (1H, m), 1.55-1.67 (1H, m), 1.68-1.87 (4H, m), 2.05 (3H, brs), 2.76-2.85 (1H, m), 2.94 (2H, d, J=6.44 Hz), 3.13 (1H, brs), 3.97 (2H, brs), 7.78 (1H, s), 8.59 (1H, d, J=8.71 Hz), 9.33-9.67 (2H, m).

Example 36

5-(trans-2-((cyclopropylmethyl)amino)cyclopropyl)-N-(4,4-difluorocyclohexyl)thiophene-2-carboxamide hydrochloride

A) trans-2-(5-bromothiophen-2-yl)cyclopropanecarboxylic acid

To a mixture of lithium hydroxide monohydrate (12.7 g), water (100 mL) and methanol (100 mL) was added ethyl trans-2-(5-bromothiophen-2-yl)cyclopropanecarboxylate (16.7 g) at room temperature. After stirring at room temperature for 24 hr, methanol was evaporated under reduced pressure. The aqueous layer was washed with dichloromethane, acidified with 2 mol/L hydrochloric acid, and extracted with ethyl acetate. The extract was dried over anhydrous sodium sulfate, and concentrated under reduced pressure to give the title compound (14.7 g).
$^1$H NMR (400 MHz, CDCl$_3$) δ 1.35-1.40 (1H, m), 1.65-1.69 (1H, m), 1.90-1.94 (1H, m), 2.67-2.72 (1H, m), 6.61 (1H, d, J=3.6 Hz), 6.87 (1H, d, J=3.6 Hz).

B) tert-butyl (2-(5-bromothiophen-2-yl)cyclopropyl)carbamate trans-2-(5-Bromothiophen-2-yl)cyclopropanecarboxylic acid (14.7 g) was dissolved in acetone (150 mL), triethylamine (9.03 g) was added, and then ethyl chloroformate (9.68 g) was added at −20° C. After stirring at −10° C. to −20° C. for 2 hr, a mixture of sodium azide (6.57 g) and water (20 mL) was added, and the mixture was stirred at −10° C. to −20° C. for 3 hr. Acetone was evaporated by concentration under reduced pressure, and water (150 mL) and toluene (150 mL) were added. The aqueous layer was extracted twice with toluene (100 mL). The combined extract was dried over anhydrous sodium sulfate and concentrated to 150 mL under reduced pressure. To the obtained mixture was added tert-butyl alcohol (25 mL), and the mixture was heated under reflux for 18 hr. The mixture was concentrated under reduced pressure, and the residue was purified by silica gel column chromatography (petroleum ether/ethyl acetate) to give the title compound (8.66 g).
$^1$H NMR (400 MHz, CDCl$_3$) δ 1.15 (2H, t, J=6.8 Hz), 1.46 (9H, s), 2.08-2.13 (1H, m), 2.67-2.74 (1H, m), 4.81 (1H, s), 6.57 (1H, d, J=3.2 Hz), 6.82 (1H, d, J=3.2 Hz).

C)

trans-2-(5-bromothiophen-2-yl)cyclopropanamine hydrochloride

To a mixture of tert-butyl (2-(5-bromothiophen-2-yl)cyclopropyl)carbamate (200 mg) and ethyl acetate (5 mL) was added 4 mol/L hydrogen chloride/ethyl acetate solution (1.57 mL) at 0° C., and the mixture was stirred at room temperature overnight. The precipitated solid was collected by filtration and washed with ethyl acetate to give the title compound (135 mg).

$^1$H NMR (300 MHz, DMSO-$d_6$) δ 1.23 (1H, dt, J=7.95, 6.25 Hz), 1.36-1.51 (1H, m), 2.47-2.54 (1H, m), 2.73-2.85 (1H, m), 6.75 (1H, dd, J=3.79, 1.14 Hz), 6.99-7.10 (1H, m), 8.50 (2H, brs).

D) tert-butyl (2-trans-(5-bromothiophen-2-yl)cyclopropyl) (cyclopropylmethyl)carbamate To a mixture of trans-2-(5-bromothiophen-2-yl)cyclopropanamine hydrochloride (130 mg), sodium hydrogen carbonate (107 mg), THF (4 mL) and methanol (4 mL) was added cyclopropanecarbaldehyde (43.0 mg) at room temperature. Under a nitrogen atmosphere, the reaction mixture was stirred at 60° C. for 1.5 hr and then at room temperature for 30 min, and sodium borohydride (29.0 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine and dried over anhydrous sodium sulfate. The solvent was evaporated under reduced pressure. The obtained residue was dissolved in THF (5 mL), triethylamine (0.094 mL) and di-tert-butyl dicarbonate (0.156 mL) were added, and the mixture was stirred at room temperature overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (160 mg).

$^1$H NMR (300 MHz, DMSO-$d_6$) δ 0.08-0.27 (2H, m), 0.35-0.52 (2H, m), 0.88-1.06 (1H, m), 1.14-1.24 (1H, m), 1.25-1.34 (1H, m), 1.39 (9H, s), 2.20-2.32 (1H, m), 2.65-2.77 (1H, m), 2.93 (1H, dd, J=14.39, 6.82 Hz), 3.18 (1H, dd, J=14.39, 6.82 Hz), 6.71 (1H, dd, J=3.79, 0.76 Hz), 7.02 (1H, d, J=3.79 Hz).

E) methyl 5-(trans-2-((tert-butoxycarbonyl)(cyclopropylmethyl)amino)cyclopropyl)thiophene-2-carboxylate A mixture of tert-butyl (2-trans-(5-bromothiophen-2-yl)cyclopropyl) (cyclopropylmethyl)carbamate (155 mg), triethylamine (0.116 mL), dichloro(1,1'-bis(diphenylphosphino)ferrocene)palladium (60.9 mg) and methanol (15 mL) was stirred at 90° C. for 8 hr under a carbon monoxide atmosphere (3 atm). After cooling to room temperature, the insoluble material was filtered off, and the filtrate was concentrated under reduced pressure. The residue was extracted with ethyl acetate and water, and the organic layer was washed with saturated brine, dried over anhydrous sodium sulfate, and concentrated under reduced pressure. The residue was purified by silica gel column chromatography (hexane/ethyl acetate) to give the title compound (138 mg).

$^1$H NMR (300 MHz, DMSO-$d_6$) δ 0.06-0.30 (2H, m), 0.33-0.52 (2H, m), 0.84-1.05 (1H, m), 1.23-1.33 (1H, m), 1.35-1.49 (10H, m), 2.39 (1H, ddd, J=9.47, 6.25, 3.22 Hz), 2.76-2.87 (1H, m), 2.88-3.02 (1H, m), 3.20 (1H, dd, J=14.20, 7.00 Hz), 3.73-3.82 (3H, m), 6.96 (1H, d, J=3.79 Hz), 7.63 (1H, d, J=3.79 Hz).

F) 5-(trans-2-((tert-butoxycarbonyl) (cyclopropylmethyl)amino)cyclopropyl)thiophene-2-carboxylic acid Methyl 5-(trans-2-((tert-butoxycarbonyl)(cyclopropylmethyl)amino)cyclopropyl)thiophene-2-carboxylate (130 mg) was dissolved in methanol (5 mL), 2 mol/L aqueous sodium hydroxide solution (0.462 mL) was added at 0° C., and the mixture was stirred at room temperature overnight. The reaction mixture was acidified with 1 mol/L hydrochloric acid at 0° C., and extracted with ethyl acetate. The extract was successively washed with water and saturated brine, dried over anhydrous sodium sulfate, and concentrated under reduced pressure to give the title compound (125 mg).

MS: [M+2H-(Boc)]$^+$ 238.2.

G) tert-butyl (cyclopropylmethyl) (trans-2-(5-((4,4-difluorocyclohexyl)carbamoyl)thiophen-2-yl)cyclopropyl)carbamate 5-(trans-2-((tert-Butoxycarbonyl) (cyclopropylmethyl)amino)cyclopropyl)thiophene-2-carboxylic acid (35.0 mg), 4,4-difluorocyclohexanamine hydrochloride (19.6 mg) and triethylamine (0.058 mL) were dissolved in DMF (3 mL), O-(7-azabenzotriazol-1-yl)-N,N,N',N'-tetramethyluronium hexafluorophosphate (47.3 mg) was added, and the mixture was stirred at room temperature overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (42.3 mg).

$^1$H NMR (300 MHz, DMSO-$d_6$) δ 0.08-0.28 (2H, m), 0.34-0.52 (2H, m), 0.88-1.04 (1H, m), 1.18-1.27 (1H, m), 1.32-1.42 (10H, m), 1.50-1.69 (2H, m), 1.77-1.96 (3H, m), 1.97-2.13 (3H, m), 2.32 (1H, m), 2.70-2.80 (1H, m), 2.89-3.04 (1H, m), 3.10-3.26 (1H, m), 3.91 (1H, d, J=7.57 Hz), 6.86 (1H, d, J=3.79 Hz), 7.58 (1H, d, J=3.79 Hz), 8.16 (1H, d, J=7.57 Hz).

H) 5-(trans-2-((cyclopropylmethyl)amino)cyclopropyl)-N-(4,4-difluorocyclohexyl)thiophene-2-carboxamide hydrochloride tert-Butyl (cyclopropylmethyl) (trans-2-(5-((4,4-difluorocyclohexyl)carbamoyl)thiophen-2-yl)cyclopropyl)carbamate (40.0 mg) was dissolved in ethyl acetate (3 mL), 4 mol/L hydrogen chloride/ethyl acetate solution (0.220 mL) was added at 0° C., and the mixture was stirred at room temperature for 4 hr. The precipitated solid was collected by filtration and washed with ethyl acetate to give the title compound (22.1 mg).

$^1$H NMR (300 MHz, DMSO-$d_6$) δ 0.31-0.44 (2H, m), 0.51-0.64 (2H, m), 0.97-1.15 (1H, m), 1.23-1.40 (1H, m), 1.50-1.72 (3H, m), 1.78-2.10 (6H, m), 2.74 (1H, ddd, J=9.84, 6.25, 3.60 Hz), 2.87-3.05 (3H, m), 3.82-4.00 (1H, m), 6.93 (1H, d, J=3.79 Hz), 7.63 (1H, d, J=3.79 Hz), 8.25 (1H, d, J=7.95 Hz), 9.39 (2H, brs).

Example 37

5-(trans-2-((cyclopropylmethyl)amino) cyclopropyl)-N-(5-methyl-1,3,4-thiadiazol-2-yl)thiophene-2-carboxamide dihydrochloride A) tert-butyl (cyclopropylmethyl) (trans-2-(5-((5-methyl-1,3,4-thiadiazol-2-yl)carbamoyl)thiophen-2-yl)cyclopropyl)carbamate 5-(trans-2-((tert-Butoxycarbonyl) (cyclopropylmethyl) amino)cyclopropyl)thiophene-2-carboxylic acid (35.0 mg), 5-methyl-1,3,4-thiadiazol-2-amine (13.1 mg) and triethylamine (0.029 mL) were dissolved in DMF (3 mL), O-(7-azabenzotriazol-1-yl)-N,N,N',N'-tetramethyluronium hexafluorophosphate (47.3 mg) was added, and the mixture was stirred at room temperature overnight. To the reaction mixture were added ethyl acetate and water, and the mixture was extracted with ethyl acetate. The extract was washed with saturated brine, dried over anhydrous sodium sulfate, and concentrated under reduced pressure. The residue was purified by silica gel column chromatography (hexane/ethyl acetate) to give the title compound (23.7 mg).
$^1$H NMR (300 MHz, DMSO-d$_6$) δ 0.08-0.31 (2H, m), 0.35-0.53 (2H, m), 0.90-1.07 (1H, m), 1.20-1.50 (11H, m), 2.33-2.45 (1H, m), 2.62 (3H, s), 2.78-2.88 (1H, m), 2.90-3.07 (1H, m), 3.19 (1H, dd, J=14.39, 6.82 Hz), 6.98 (1H, d, J=3.79 Hz), 8.08 (1H, brs), 12.85 (1H, brs).

B) 5-(trans-2-((cyclopropylmethyl)amino)cyclopropyl)-N-(5-methyl-1,3,4-thiadiazol-2-yl)thiophene-2-carboxamide dihydrochloride To a mixture of tert-butyl (cyclopropylmethyl) (trans-2-(5-((5-methyl-1,3,4-thiadiazol-2-yl)carbamoyl)thiophen-2-yl)cyclopropyl)carbamate (22.0 mg) and ethyl acetate (2 mL) was added 4 mol/L hydrogen chloride/ethyl acetate solution (0.127 mL) at 0° C., and the mixture was stirred at room temperature overnight. The precipitated solid was collected by filtration, and washed with ethyl acetate and methanol to give the title compound (10.2 mg).
$^1$H NMR (300 MHz, DMSO-d$_6$) δ 0.32-0.44 (2H, m), 0.51-0.65 (2H, m), 0.97-1.19 (1H, m), 1.30-1.45 (1H, m), 1.65-1.81 (1H, m), 2.62 (3H, s), 2.78-2.90 (1H, m), 2.96 (2H, d, J=5.68 Hz), 3.01-3.11 (1H, m), 3.86 (2H, s), 7.06 (1H, d, J=3.79 Hz), 8.09 (1H, s), 9.55 (2H, brs).

Example 38

N-cyclopentyl-5-(trans-2-(tetrahydro-2H-pyran-4-ylamino)cyclopropyl)thiophene-3-carboxamide hydrochloride [Optical Isomer, Compound Derived from methyl 5-(trans-2-((tert-butoxycarbonyl) amino)cyclopropyl)thiophene-3-carboxylate (Optical Isomer, Retention Time Long)]

A) methyl 5-(trans-2-((tert-butoxycarbonyl)amino) cyclopropyl)thiophene-3-carboxylate (Optical Isomer, Retention Time Long)

B) methyl 5-(trans-2-((tert-butoxycarbonyl)amino) cyclopropyl)thiophene-3-carboxylate (Optical Isomer, Retention Time Short)

A racemate (16.9 g) of methyl 5-(trans-2-((tert-butoxycarbonyl)amino)cyclopropyl)thiophene-3-carboxylate was fractionated by SFC (column: CHIRALPAK AD, 20 mmID× 250 mmL, manufactured by Daicel Corporation, mobile phase: carbon dioxide/methanol=820/180), and the obtained fraction was concentrated under reduced pressure to give the title compound (7.23 g) having a short retention time and the title compound (7.39 g) having a long retention time.

methyl 5-(trans-2-((tert-butoxycarbonyl)amino)cyclopropyl)thiophene-3-carboxylate (Optical Isomer, Retention Time Long)

$^1$H NMR (300 MHz, DMSO-d$_6$) δ 1.07-1.25 (2H, m), 1.39 (9H, s), 2.08 (1H, ddd, J=9.09, 6.25, 3.22 Hz), 2.60 (1H, d, J=5.30 Hz), 3.76 (3H, s), 7.08-7.14 (1H, m), 7.29 (1H, brs), 8.07 (1H, d, J=1.14 Hz).
HPLC retention time 2.859 min (column: CHIRALPAK ADH (trade name), 4.6 mmID×150 mmL, mobile phase: carbon dioxide/methanol=820/180, flow rate: 4.0 mL/min, temperature: 35° C., detection: UV 220 nm, concentration: 0.5 mg/mL, injection volume: 0.005 mL).

methyl 5-(trans-2-((tert-butoxycarbonyl)amino)cyclopropyl)thiophene-3-carboxylate (optical isomer, retention time short)

$^1$H NMR (300 MHz, DMSO-d$_6$) δ 1.08-1.24 (2H, m), 1.39 (9H, s), 2.08 (1H, ddd, J=8.99, 6.15, 3.03 Hz), 2.60 (1H, brs), 3.77 (3H, s), 7.12 (1H, dd, J=1.51, 0.76 Hz), 7.29 (1H, brs), 8.07 (1H, d, J=1.14 Hz).
HPLC retention time 1.950 min (column: CHIRALPAK ADH (trade name), 4.6 mmID×150 mmL, mobile phase: carbon dioxide/methanol=820/180, flow rate: 4.0 mL/min, temperature: 35° C., detection: UV 220 nm, concentration: 0.5 mg/mL, injection volume: 0.005 mL).
Methyl 5-(trans-2-((tert-butoxycarbonyl)amino)cyclopropyl)thiophene-3-carboxylate (optical isomer, retention time long) was clarified to be methyl 5-((1R,2R)-2-((tert-butoxycarbonyl)amino)cyclopropyl)thiophene-3-carboxylate.
Methyl 5-(trans-2-((tert-butoxycarbonyl)amino)cyclopropyl)thiophene-3-carboxylate (optical isomer, retention time short) was clarified to be methyl 5-((1S,2S)-2-((tert-butoxycarbonyl)amino)cyclopropyl)thiophene-3-carboxylate.

C) 5-(trans-2-((tert-butoxycarbonyl)amino)cyclopropyl)thiophene-3-carboxylic acid [Optical Isomer, Compound Derived from methyl 5-(trans-2-((tert-butoxycarbonyl)amino)cyclopropyl)thiophene-3-carboxylate (Optical Isomer, Retention Time Long)]

Methyl 5-(trans-2-((tert-butoxycarbonyl)amino)cyclopropyl)thiophene-3-carboxylate (optical isomer, retention time long) (458 mg) was dissolved in methanol (5 mL), 2 mol/L aqueous sodium hydroxide solution (1.93 mL) was added at 0° C., and the mixture was stirred at room temperature overnight. The reaction mixture was acidified with 1 mol/L hydrochloric acid at 0° C., and extracted with ethyl acetate. The extract was successively washed with water and saturated brine, dried over anhydrous sodium sulfate, and concentrated under reduced pressure to give the title compound (435 mg).
$^1$H NMR (300 MHz, DMSO-d$_6$) δ 1.05-1.22 (2H, m), 1.39 (9H, s), 2.07 (1H, ddd, J=9.09, 6.06, 3.03 Hz), 2.59 (1H, d, J=7.57 Hz), 7.05-7.09 (1H, m), 7.28 (1H, brs), 7.97 (1H, d, J=1.51 Hz), 12.61 (1H, brs).
5-(trans-2-((tert-butoxycarbonyl)amino)cyclopropyl) thiophene-3-carboxylic acid [optical isomer, compound derived from methyl 5-(trans-2-((tert-butoxycarbonyl)

amino)cyclopropyl)thiophene-3-carboxylate (optical isomer, retention time long)] was clarified to be 5-(((1R,2R)-2-((tert-butoxycarbonyl)amino)cyclopropyl)thiophene-3-carboxylic acid.

D) tert-butyl (trans-2-(4-(cyclopentylcarbamoyl)thiophen-2-yl)cyclopropyl)carbamate [Optical Isomer, Compound Derived from methyl 5-(trans-2-((tert-butoxycarbonyl)amino)cyclopropyl)thiophene-3-carboxylate (Optical Isomer, Retention Time Long)]

5-(trans-2-((tert-Butoxycarbonyl)amino)cyclopropyl)thiophene-3-carboxylic acid [optical isomer, compound derived from methyl 5-(trans-2-((tert-butoxycarbonyl)amino)cyclopropyl)thiophene-3-carboxylate (optical isomer, retention time long)] (70.0 mg), cyclopentanamine (23.1 mg) and triethylamine (0.069 mL) were dissolved in DMF (3 mL), O-(7-azabenzotriazol-1-yl)-N,N,N',N'-tetramethyluronium hexafluorophosphate (113 mg) was added, and the mixture was stirred at room temperature overnight. Water was added to the reaction mixture, and the mixture was extracted with ethyl acetate. The organic layer was successively washed with water and saturated brine, dried over anhydrous sodium sulfate, and concentrated under reduced pressure. The residue was purified by silica gel column chromatography (hexane/ethyl acetate) to give the title compound (77.8 mg).

MS: $[M+H]^+$ 351.3.

tert-Butyl (trans-2-(4-(cyclopentylcarbamoyl)thiophen-2-yl)cyclopropyl)carbamate [optical isomer, compound derived from methyl 5-(trans-2-((tert-butoxycarbonyl)amino)cyclopropyl)thiophene-3-carboxylate (optical isomer, retention time long)] was clarified to be tert-butyl ((1R,2R)-2-(4-(cyclopentylcarbamoyl)thiophen-2-yl)cyclopropyl)carbamate.

E) 5-(trans-2-aminocyclopropyl)-N-cyclopentylthiophene-3-carboxamide hydrochloride [Optical Isomer, Compound Derived from methyl 5-(trans-2-((tert-butoxycarbonyl)amino)cyclopropyl)thiophene-3-carboxylate (Optical Isomer, Retention Time Long)]

To a mixture of tert-butyl (trans-2-(4-(cyclopentylcarbamoyl)thiophen-2-yl)cyclopropyl)carbamate [optical isomer, compound derived from methyl 5-(trans-2-((tert-butoxycarbonyl)amino)cyclopropyl)thiophene-3-carboxylate (optical isomer, retention time long)] (75.0 mg) and ethyl acetate (2 mL) was added 4 mol/L hydrogen chloride/ethyl acetate solution (0.535 mL) at 0° C., and the mixture was stirred at room temperature overnight. The precipitated solid was collected by filtration and washed with ethyl acetate to give the title compound (56.2 mg).

MS: $[M+H-(HCl)]^+$ 251.2.

5-(trans-2-Aminocyclopropyl)-N-cyclopentylthiophene-3-carboxamide hydrochloride [optical isomer, compound derived from methyl 5-(trans-2-((tert-butoxycarbonyl)amino)cyclopropyl)thiophene-3-carboxylate (optical isomer, retention time long)] was clarified to be 5-(((1R,2R)-2-aminocyclopropyl)-N-cyclopentylthiophene-3-carboxamide hydrochloride.

F) N-cyclopentyl-5-(trans-2-(tetrahydro-2H-pyran-4-ylamino)cyclopropyl)thiophene-3-carboxamide hydrochloride [Optical Isomer, Compound Derived from methyl 5-(trans-2-((tert-butoxycarbonyl)amino)cyclopropyl)thiophene-3-carboxylate (Optical Isomer, Retention Time Long)]

To a mixture of 5-(trans-2-aminocyclopropyl)-N-cyclopentylthiophene-3-carboxamide hydrochloride [optical isomer, compound derived from methyl 5-(trans-2-((tert-butoxycarbonyl)amino)cyclopropyl)thiophene-3-carboxylate (optical isomer, retention time long)] (53.0 mg), sodium hydrogen carbonate (38.8 mg), THF (3 mL) and methanol (3 mL) was added dihydro-2H-pyran-4(3H)-one (22.2 mg) at room temperature. Under a nitrogen atmosphere, the reaction mixture was stirred at 60° C. for 1.5 hr and at room temperature for 30 min, and sodium borohydride (10.5 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine and dried over anhydrous sodium sulfate. The solvent was evaporated under reduced pressure. The residue was purified by silica gel column chromatography (ethyl acetate/methanol), and to the obtained fraction was added 4 mol/L hydrogen chloride/ethyl acetate solution. The reaction mixture was stirred at room temperature overnight, and the precipitated solid was collected by filtration, and washed with ethyl acetate to give the title compound (38.9 mg).

$^1$H NMR (300 MHz, DMSO-$d_6$) δ 1.28-1.39 (1H, m), 1.39-1.75 (9H, m), 1.78-1.92 (2H, m), 1.93-2.06 (2H, m), 2.73 (1H, ddd, J=9.75, 6.34, 3.60 Hz), 2.99 (1H, brs), 3.24-3.34 (2H, m), 3.47 (1H, brs), 3.85-4.02 (2H, m), 4.15 (1H, sxt, J=6.74 Hz), 7.29 (1H, s), 7.94 (1H, d, J=1.14 Hz), 8.02 (1H, d, J=7.19 Hz), 9.54 (2H, brs).

N-Cyclopentyl-5-(trans-2-(tetrahydro-2H-pyran-4-ylamino)cyclopropyl)thiophene-3-carboxamide hydrochloride [optical isomer, compound derived from methyl 5-(trans-2-((tert-butoxycarbonyl)amino)cyclopropyl)thiophene-3-carboxylate (optical isomer, retention time long)] was clarified to be N-cyclopentyl-5-((1R,2R)-2-(tetrahydro-2H-pyran-4-ylamino)cyclopropyl)thiophene-3-carboxamide hydrochloride

Example 39

N-cyclopentyl-5-(trans-2-(tetrahydro-2H-pyran-4-ylamino)cyclopropyl)thiophene-3-carboxamide hydrochloride [Optical Isomer, Compound Derived from methyl 5-(trans-2-((tert-butoxycarbonyl)amino)cyclopropyl)thiophene-3-carboxylate (Optical Isomer, Retention Time Short)]

By a method similar to that of Example 38, the title compound was obtained.

N-Cyclopentyl-5-(trans-2-(tetrahydro-2H-pyran-4-ylamino)cyclopropyl)thiophene-3-carboxamide hydrochloride [optical isomer, compound derived from methyl 5-(trans-2-((tert-butoxycarbonyl)amino)cyclopropyl)thiophene-3-carboxylate (optical isomer, retention time short)]

was clarified to be N-cyclopentyl-5-((1S,2S)-2-(tetrahydro-2H-pyran-4-ylamino)cyclopropyl)thiophene-3-carboxamide.

Example 40

N-(5-methyl-1,3,4-thiadiazol-2-yl)-5-(trans-2-((tetrahydro-2H-pyran-4-ylmethyl)amino)cyclopropyl)thiophene-3-carboxamide dihydrochloride [Optical Isomer, Compound Derived from methyl 5-(trans-2-((tert-butoxycarbonyl)amino)cyclopropyl)thiophene-3-carboxylate (Optical Isomer, Retention Time Long)]

A) tert-butyl (trans-2-(4-((5-methyl-1,3,4-thiadiazol-2-yl)carbamoyl)thiophen-2-yl)cyclopropyl)carbamate [Optical Isomer, Compound Derived from methyl 5-(trans-2-((tert-butoxycarbonyl)amino)cyclopropyl)thiophene-3-carboxylate (Optical Isomer, Retention Time Long)]

5-(trans-2-((tert-Butoxycarbonyl)amino)cyclopropyl)thiophene-3-carboxylic acid [optical isomer, compound derived from methyl 5-(trans-2-((tert-butoxycarbonyl)amino)cyclopropyl)thiophene-3-carboxylate (optical isomer, retention time long)] (70.0 mg), 5-methyl-1,3,4-thiadiazol-2-amine (31.3 mg) and triethylamine (0.069 mL) were dissolved in DMF (3 mL), O-(7-azabenzotriazol-1-yl)-N,N,N',N'-tetramethyluronium hexafluorophosphate (113 mg) was added, and the mixture was stirred at room temperature overnight. Water was added to the reaction mixture, and the mixture was extracted with ethyl acetate. The organic layer was successively washed with water and saturated brine, dried over anhydrous sodium sulfate, and concentrated under reduced pressure. The residue was purified by silica gel column chromatography (hexane/ethyl acetate) to give the title compound (37.6 mg).
MS: [M+H]$^+$ 381.2.
tert-Butyl (trans-2-(4-((5-methyl-1,3,4-thiadiazol-2-yl)carbamoyl)thiophen-2-yl)cyclopropyl)carbamate [optical isomer, compound derived from methyl 5-(trans-2-((tert-butoxycarbonyl)amino)cyclopropyl)thiophene-3-carboxylate (optical isomer, retention time long)] was clarified to be tert-butyl ((1R,2R)-2-(4-((5-methyl-1,3,4-thiadiazol-2-yl)carbamoyl)thiophen-2-yl)cyclopropyl)carbamate.

B) 5-(trans-2-aminocyclopropyl)-N-(5-methyl-1,3,4-thiadiazol-2-yl)thiophene-3-carboxamide dihydrochloride [Optical Isomer, Compound Derived from methyl 5-(trans-2-((tert-butoxycarbonyl)amino)cyclopropyl)thiophene-3-carboxylate (Optical Isomer, Retention Time Long)]

To a mixture of tert-butyl (trans-2-(4-((5-methyl-1,3,4-thiadiazol-2-yl)carbamoyl)thiophen-2-yl)cyclopropyl)carbamate [optical isomer, compound derived from methyl 5-(trans-2-((tert-butoxycarbonyl)amino)cyclopropyl)thiophene-3-carboxylate (optical isomer, retention time long)] (37.6 mg), ethyl acetate (2 mL) and methanol (2 mL) was added 4 mol/L hydrogen chloride/ethyl acetate solution (0.247 mL) at 0° C., and the mixture was stirred at room temperature overnight. The precipitated solid was collected by filtration and washed with ethyl acetate to give the title compound (34.5 mg).
MS: [M+H-(2HCl)]$^+$ 281.1.
5-(trans-2-Aminocyclopropyl)-N-(5-methyl-1,3,4-thiadiazol-2-yl)thiophene-3-carboxamide dihydrochloride [optical isomer, compound derived from methyl 5-(trans-2-((tert-butoxycarbonyl)amino)cyclopropyl)thiophene-3-carboxylate (optical isomer, retention time long)] was clarified to be 5-((1R,2R)-2-aminocyclopropyl)-N-(5-methyl-1,3,4-thiadiazol-2-yl)thiophene-3-carboxamide dihydrochloride.

C) N-(5-methyl-1,3,4-thiadiazol-2-yl)-5-(trans-2-((tetrahydro-2H-pyran-4-ylmethyl)amino)cyclopropyl)thiophene-3-carboxamide dihydrochloride [Optical Isomer, Compound Derived from methyl 5-(trans-2-((tert-butoxycarbonyl)amino)cyclopropyl)thiophene-3-carboxylate (Optical Isomer, Retention Time Long)]

To a mixture of 5-(trans-2-aminocyclopropyl)-N-(5-methyl-1,3,4-thiadiazol-2-yl)thiophene-3-carboxamide dihydrochloride [optical isomer, compound derived from methyl 5-(trans-2-((tert-butoxycarbonyl)amino)cyclopropyl)thiophene-3-carboxylate (optical isomer, retention time long)] (33.0 mg), sodium hydrogen carbonate (19.6 mg), THF (2 mL) and methanol (2 mL) was added tetrahydro-2H-pyran-4-carbaldehyde (12.8 mg) at room temperature. Under a nitrogen atmosphere, the reaction mixture was stirred at 60° C. for 1.5 hr and at room temperature for 30 min, and sodium borohydride (5.30 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine and dried over anhydrous sodium sulfate. The solvent was evaporated under reduced pressure. The residue was purified by silica gel column chromatography (ethyl acetate/methanol), and to the obtained fraction was added 4 mol/L hydrogen chloride/ethyl acetate solution. The reaction mixture was stirred at room temperature overnight. The precipitated solid was collected by filtration and washed with ethyl acetate to give the title compound (19.6 mg).
$^1$H NMR (300 MHz, DMSO-d$_6$) δ 1.16-1.41 (3H, m), 1.60-1.77 (3H, m), 1.84-2.06 (1H, m), 2.63 (3H, s), 2.70-2.84 (1H, m), 2.94-3.11 (3H, m), 3.29 (2H, t, J=11.93 Hz), 3.90-4.00 (2H, m), 7.51 (1H, s), 8.46 (1H, s), 9.26 (2H, brs).
N-(5-Methyl-1,3,4-thiadiazol-2-yl)-5-(trans-2-((tetrahydro-2H-pyran-4-ylmethyl)amino)cyclopropyl)thiophene-3-carboxamide dihydrochloride [optical isomer, compound derived from methyl 5-(trans-2-((tert-butoxycarbonyl)amino)cyclopropyl)thiophene-3-carboxylate (optical isomer, retention time long)] was clarified to be N-(5-methyl-1,3,4-thiadiazol-2-yl)-5-((1R,2R)-2-((tetrahydro-2H-pyran-4-ylmethyl)amino)cyclopropyl)thiophene-3-carboxamide dihydrochloride.

Example 41

N-(5-methyl-1,3,4-thiadiazol-2-yl)-5-(trans-2-((tetrahydro-2H-pyran-4-ylmethyl)amino)cyclopropyl)thiophene-3-carboxamide dihydrochloride [Optical Isomer, Compound Derived from methyl 5-(trans-2-((tert-butoxycarbonyl)amino)cyclopropyl)thiophene-3-carboxylate (Optical Isomer, Retention Time Short)]

By a method similar to that of Example 40, the title compound was obtained.
N-(5-Methyl-1,3,4-thiadiazol-2-yl)-5-(trans-2-((tetrahydro-2H-pyran-4-ylmethyl)amino)cyclopropyl)thiophene- 3-carboxamide dihydrochloride [optical isomer, compound derived from methyl 5-(trans-2-((tert-butoxycarbonyl)amino)cyclopropyl)thiophene-3-carboxylate (optical isomer, retention time short)] was clarified to be N-(5-methyl-1,3,4-thiadiazol-2-yl)-5-((1S,2S)-2-((tetrahydro-2H-pyran-4-ylmethyl)amino)cyclopropyl)thiophene-3-carboxamide dihydrochloride.

Example 42

5-(trans-2-(cyclobutylamino)cyclopropyl)-N-(tetrahydro-2H-pyran-4-yl)thiophene-3-carboxamide hydrochloride [Optical Isomer, Compound Derived from methyl 5-(trans-2-((tert-butoxycarbonyl)amino)cyclopropyl)thiophene-3-carboxylate (Optical Isomer, Retention Time Long)]

A) tert-butyl (trans-2-(4-((tetrahydro-2H-pyran-4-yl)carbamoyl)thiophen-2-yl)cyclopropyl)carbamate [Optical Isomer, Compound Derived from methyl 5-(trans-2-((tert-butoxycarbonyl)amino)cyclopropyl)thiophene-3-carboxylate (Optical Isomer, Retention Time Long)]

5-(trans-2-((tert-Butoxycarbonyl)amino)cyclopropyl)thiophene-3-carboxylic acid [optical isomer, compound derived from methyl 5-(trans-2-((tert-butoxycarbonyl)amino)cyclopropyl)thiophene-3-carboxylate (optical isomer, retention time long)] (70.0 mg) was dissolved in DMF (3 mL). Tetrahydro-2H-pyran-4-amine (27.5 mg), triethylamine (0.069 mL) and O-(7-azabenzotriazol-1-yl)-N,N,N',N'-tetramethyluronium hexafluorophosphate (113 mg) were added, and the mixture was stirred at room temperature overnight. Water was added to the reaction mixture, and the mixture was extracted with ethyl acetate. The organic layer was successively washed with water and saturated brine, dried over anhydrous sodium sulfate, and concentrated under reduced pressure. The residue was purified by silica gel column chromatography (hexane/ethyl acetate) to give the title compound (71.8 mg).
MS: [M+H]$^+$ 367.2.
tert-Butyl (trans-2-(4-((tetrahydro-2H-pyran-4-yl)carbamoyl)thiophen-2-yl)cyclopropyl)carbamate [optical isomer, compound derived from methyl 5-(trans-2-((tert-butoxycarbonyl)amino)cyclopropyl)thiophene-3-carboxylate (optical isomer, retention time long)] was clarified to be tert-butyl ((1R,2R)-2-(4-((tetrahydro-2H-pyran-4-yl)carbamoyl)thiophen-2-yl)cyclopropyl)carbamate.

B) 5-(trans-2-aminocyclopropyl)-N-(tetrahydro-2H-pyran-4-yl)thiophene-3-carboxamide dihydrochloride [Optical Isomer, Compound Derived from methyl 5-(trans-2-((tert-butoxycarbonyl)amino)cyclopropyl)thiophene-3-carboxylate (Optical Isomer, Retention Time Long)]

To a mixture of tert-butyl (trans-2-(4-((tetrahydro-2H-pyran-4-yl)carbamoyl)thiophen-2-yl)cyclopropyl)carbamate [optical isomer, compound derived from methyl 5-(trans-2-((tert-butoxycarbonyl)amino)cyclopropyl)thiophene-3-carboxylate (optical isomer, retention time long)] (69.5 mg) and ethyl acetate (2 mL) was added 4 mol/L hydrogen chloride/ethyl acetate solution (0.474 mL) at 0° C., and the mixture was stirred at room temperature overnight. The precipitated solid was collected by filtration and washed with ethyl acetate to give the title compound (53.6 mg).
MS: [M+H-(2HCl)]$^+$ 267.2.

5-(trans-2-Aminocyclopropyl)-N-(tetrahydro-2H-pyran-4-yl)thiophene-3-carboxamide dihydrochloride [optical isomer, compound derived from methyl 5-(trans-2-((tert-butoxycarbonyl)amino)cyclopropyl)thiophene-3-carboxylate (optical isomer, retention time long)] was clarified to be 5-((1R,2R)-2-aminocyclopropyl)-N-(tetrahydro-2H-pyran-4-yl)thiophene-3-carboxamide dihydrochloride.

C) 5-(trans-2-(cyclobutylamino)cyclopropyl)-N-(tetrahydro-2H-pyran-4-yl)thiophene-3-carboxamide hydrochloride [Optical Isomer, Compound Derived from methyl 5-(trans-2-((tert-butoxycarbonyl)amino)cyclopropyl)thiophene-3-carboxylate (Optical Isomer, Retention Time Long)]

To a mixture of 5-(trans-2-aminocyclopropyl)-N-(tetrahydro-2H-pyran-4-yl)thiophene-3-carboxamide dihydrochloride [optical isomer, compound derived from methyl 5-(trans-2-((tert-butoxycarbonyl)amino)cyclopropyl)thiophene-3-carboxylate (optical isomer, retention time long)] (51.0 mg), sodium hydrogen carbonate (35.4 mg), THF (2 mL) and methanol (2 mL) was added cyclobutanone (14.2 mg) at room temperature. Under a nitrogen atmosphere, the reaction mixture was stirred at 60° C. for 1.5 hr and at room temperature for 30 min, and sodium borohydride (9.56 mg) was added at 0° C. The reaction mixture was stirred at room temperature for 1 hr, and ethyl acetate, water and saturated aqueous sodium hydrogen carbonate solution were added to the reaction mixture. The mixture was extracted with ethyl acetate, and the extract was successively washed with water and saturated brine and dried over anhydrous sodium sulfate. The solvent was evaporated under reduced pressure. The residue was purified by silica gel column chromatography (ethyl acetate/methanol), and to the obtained fraction was added 4 mol/L hydrogen chloride/ethyl acetate solution. The reaction mixture was stirred at room temperature overnight. The precipitated solid was collected by filtration and washed with ethyl acetate to give the title compound (28.7 mg).
$^1$H NMR (300 MHz, DMSO-d$_6$) δ 1.03 (2H, d, J=6.06 Hz), 1.22-1.36 (1H, m), 1.43-1.62 (3H, m), 1.65-1.91 (4H, m), 2.11-2.32 (4H, m), 2.65 (1H, brs), 2.85 (1H, d, J=3.41 Hz), 3.77-4.00 (4H, m), 7.26 (1H, s), 7.95 (1H, s), 8.05 (1H, d, J=7.95 Hz), 9.49 (2H, brs).
5-(trans-2-(Cyclobutylamino)cyclopropyl)-N-(tetrahydro-2H-pyran-4-yl)thiophene-3-carboxamide hydrochloride [optical isomer, compound derived from methyl 5-(trans-2-((tert-butoxycarbonyl)amino)cyclopropyl)thiophene-3-carboxylate (optical isomer, retention time long)] was clarified to be 5-((1R,2R)-2-(cyclobutylamino)cyclopropyl)-N-(tetrahydro-2H-pyran-4-yl)thiophene-3-carboxamide hydrochloride.

Example 43

5-(trans-2-(cyclobutylamino)cyclopropyl)-N-(tetrahydro-2H-pyran-4-yl)thiophene-3-carboxamide hydrochloride [Optical Isomer, Compound Derived from methyl 5-(trans-2-((tert-butoxycarbonyl)amino)cyclopropyl)thiophene-3-carboxylate (Optical Isomer, Retention Time Short)]

By a method similar to that of Example 42, the title compound was obtained.
5-(trans-2-(Cyclobutylamino)cyclopropyl)-N-(tetrahydro-2H-pyran-4-yl)thiophene-3-carboxamide hydrochloride [optical isomer, compound derived from methyl 5-(trans-2-((tert-butoxycarbonyl)amino)cyclopropyl)thiophene-3-carboxylate (optical isomer, retention time short)] was clarified to be 5-((1S,2S)-2-(cyclobutylamino)cyclopropyl)-N-(tetrahydro-2H-pyran-4-yl)thiophene-3-carboxamide hydrochloride.

Example 44

N-(4,4-difluorocyclohexyl)-5-((1R,2R)-2-(tetrahydro-2H-pyran-4-ylamino)cyclopropyl)thiophene-3-carboxamide hydrochloride A) tert-butyl ((1R,2R)-2-(4-((4,4-difluorocyclohexyl)carbamoyl)thiophen-2-yl)cyclopropyl)carbamate 5-((1R,2R)-2-((tert-Butoxycarbonyl)amino)cyclopropyl)thiophene-3-carboxylic acid (400 mg) was dissolved in DMF (10 mL), 4,4-difluorocyclohexanamine hydrochloride (291 mg), triethylamine (0.59 mL) and O-(7-azabenzotriazol-1-yl)-N,N,N',N'-tetramethyluronium hexafluorophosphate (644 mg) were added, and the mixture was stirred at room temperature overnight. Water was added to the reaction mixture, and the mixture was extracted with ethyl acetate. The organic layer was successively washed with water and saturated brine, dried over anhydrous sodium sulfate, and concentrated under reduced pressure to give the title compound (680 mg). The title compound was used for the next reaction without further purification.
MS: [M-tBu($C_4H_9$)+2H]$^+$ 345.1.

B) 5-((1R,2R)-2-aminocyclopropyl)-N-(4,4-difluorocyclohexyl)thiophene-3-carboxamide hydrochloride tert-Butyl ((1R,2R)-2-(4-((4,4-difluorocyclohexyl)carbamoyl)thiophen-2-yl)cyclopropyl)carbamate (680 mg) and 4 mol/L hydrogen chloride/ethyl acetate solution (1.7 mL) were stirred at room temperature overnight. The precipitated solid was collected by filtration to give the title compound (500 mg).
MS: [M+H-(HCl)]$^+$ 301.1.

C) N-(4,4-difluorocyclohexyl)-5-((1R,2R)-2-(tetrahydro-2H-pyran-4-ylamino)cyclopropyl)thiophene-3-carboxamide hydrochloride To a mixture of 5-((1R,2R)-2-aminocyclopropyl)-N-(4,4-difluorocyclohexyl)thiophene-3-carboxamide hydrochloride (62.0 mg), borane-2-picoline complex (29.5 mg), methanol (2.0 mL) and acetic acid (0.2 mL) was added dihydro-2H-pyran-4(3H)-one (58.2 mg) at room temperature. The reaction mixture was stirred at room temperature for 18 hr, and saturated aqueous sodium hydrogen carbonate solution was added at 0° C. The mixture was extracted with ethyl acetate, and the extract was successively washed with water and saturated brine and dried over anhydrous sodium sulfate. The solvent was evaporated under reduced pressure. The residue was purified by NH silica gel column chromatography (ethyl acetate/hexane), and to the obtained fraction was added 4 mol/L hydrogen chloride/ethyl acetate solution. The reaction mixture was concentrated under reduced pressure, and the obtained residue was crystallized from ethanol/heptane to give the title compound (40.0 mg).
$^1$H NMR (300 MHz, DMSO-$d_6$) δ 1.27-1.41 (1H, m), 1.49-1.72 (5H, m), 1.77-2.16 (8H, m), 2.61-2.73 (1H, m), 2.89-3.08 (1H, m), 3.26-3.39 (2H, m), 3.40-3.55 (1H, m), 3.83-4.02 (3H, m), 7.24-7.31 (1H, m), 7.92-7.98 (1H, m), 7.99-8.08 (1H, m), 8.99-9.48 (2H, m).

The compounds of Examples 45 to 59 could be produced according to the production methods described in the present specification, a method shown in the Examples, or a method analogous thereto.

Example 45

5-((1R,2R)-2-(cis-(4-aminocyclohexyl)amino)cyclopropyl)-N-(4,4-difluorocyclohexyl)thiophene-3-carboxamide dihydrochloride or 5-((1R,2R)-2-(trans-(4-aminocyclohexyl)amino)cyclopropyl)-N-(4,4-difluorocyclohexyl)thiophene-3-carboxamide dihydrochloride Example 46

5-((1R,2R)-2-(trans-(4-aminocyclohexyl)amino)cyclopropyl)-N-(4,4-difluorocyclohexyl)thiophene-3-carboxamide dihydrochloride or 5-((1R,2R)-2-(cis-(4-aminocyclohexyl)amino)cyclopropyl)-N-(4,4-difluorocyclohexyl)thiophene-3-carboxamide dihydrochloride Example 47

5-((1R,2R)-2-((4,4-difluorocyclohexyl)amino)cyclopropyl)-N-(tetrahydro-2H-pyran-4-yl)thiophene-3-carboxamide hydrochloride Example 48

5-((1R,2R)-2-((1-cyclopropylpiperidin-4-yl)amino)cyclopropyl)-N-(5-methyl-1,3,4-thiadiazol-2-yl)thiophene-3-carboxamide dihydrochloride Example 49

N-(5-methyl-1,3,4-thiadiazol-2-yl)-5-((1R,2R)-2-(tetrahydro-2H-pyran-4-ylamino)cyclopropyl)thiophene-3-carboxamide hydrochloride Example 50

N-(2-methyl-1,3-thiazol-5-yl)-5-((1R,2R)-2-(tetrahydro-2H-pyran-4-ylamino)cyclopropyl)thiophene-3-carboxamide hydrochloride Example 51

N-(4,4-difluorocyclohexyl)-5-((1R,2R)-2-((tetrahydro-2H-pyran-4-ylmethyl)amino)cyclopropyl)thiophene-3-carboxamide hydrochloride Example 52

5-((1R,2R)-2-((tetrahydro-2H-pyran-4-ylmethyl)amino)cyclopropyl)-N-(1-(2,2,2-trifluoroethyl)piperidin-4-yl)thiophene-3-carboxamide hydrochloride

Example 53

N-(2-methyl-1,3-thiazol-5-yl)-5-((1R,2R)-2-((tetrahydro-2H-pyran-4-ylmethyl)amino)cyclopropyl)thiophene-3-carboxamide dihydrochloride

Example 54

N-(1,3-dimethyl-1H-pyrazol-4-yl)-5-((1R,2R)-2-((tetrahydro-2H-pyran-4-ylmethyl)amino)cyclopropyl)thiophene-3-carboxamide dihydrochloride

Example 55

N-(1,5-dimethyl-1H-pyrazol-4-yl)-5-((1R,2R)-2-((tetrahydro-2H-pyran-4-ylmethyl)amino)cyclopropyl)thiophene-3-carboxamide dihydrochloride

Example 56

N-cyclopropyl-5-((1R,2R)-2-((tetrahydro-2H-pyran-4-ylmethyl)amino)cyclopropyl)thiophene-3-carboxamide hydrochloride

Example 57

4-(trans-2-(cyclobutylamino)cyclopropyl)-N-(5-methyl-1,3,4-thiadiazol-2-yl)thiophene-2-carboxamide hydrochloride

Example 58

N-(5-methyl-1,3,4-thiadiazol-2-yl)-4-(trans-2-((tetrahydro-2H-pyran-4-ylmethyl)amino)cyclopropyl)thiophene-2-carboxamide hydrochloride

Example 59

4-(trans-2-((1-cyclopropylpiperidin-4-yl)amino)cyclopropyl)-N-(5-methyl-1,3,4-thiadiazol-2-yl)thiophene-2-carboxamide dihydrochloride

Example 60

3-(4-(((((1R,2R)-2-(4-((5-methyl-1,3,4-thiadiazol-2-yl)carbamoyl)-2-thienyl)cyclopropyl)amino)methyl)piperidin-1-yl)propanoic acid trihydrochloride A) tert-butyl 4-(((((1R,2R)-2-(4-((5-methyl-1,3,4-thiadiazol-2-yl)carbamoyl)thiophen-2-yl)cyclopropyl)amino)methyl)piperidine-1-carboxylate By a method similar to that of Example 2, the title compound was obtained.
MS: [M+H]+ 478.3.

B) tert-butyl 4-((2,2,2-trifluoro-N-((1R,2R)-2-(4-((5-methyl-1,3,4-thiadiazol-2-yl)carbamoyl)thiophen-2-yl)cyclopropyl)acetamido)methyl)piperidine-1-carboxylate To a mixture of tert-butyl 4-(((((1R,2R)-2-(4-((5-methyl-1,3,4-thiadiazol-2-yl)carbamoyl)thiophen-2-yl)cyclopropyl)amino)methyl)piperidine-1-carboxylate (301 mg), triethylamine (127.0 mg) and THF (4.0 mL) was added trifluoroacetic anhydride (355.0 mg) at room temperature. The reaction mixture was stirred at room temperature for 18 hr, and saturated aqueous sodium hydrogen carbonate solution was added at 0° C. The mixture was extracted with ethyl acetate, and the extract was successively washed with water and saturated brine and dried over anhydrous sodium sulfate. The solvent was evaporated under reduced pressure. The residue was purified by NH silica gel column chromatography (ethyl acetate/hexane) to give the title compound (213.0 mg).
MS: [M+H]+ 574.1.

C) N-(5-methyl-1,3,4-thiadiazol-2-yl)-5-((1R,2R)-2-(2,2,2-trifluoro-N-(piperidin-4-ylmethyl)acetamido)cyclopropyl)thiophene-3-carboxamide hydrochloride By a method similar to that of Example 1, step H, the title compound was obtained.
MS: [M-HCl+H]+ 474.1.

D) tert-butyl 3-(4-((2,2,2-trifluoro-N-((1R,2R)-2-(4-((5-methyl-1,3,4-thiadiazol-2-yl)carbamoyl)thiophen-2-yl)cyclopropyl)acetamido)methyl)piperidin-1-yl)propanoate To a mixture of N-(5-methyl-1,3,4-thiadiazol-2-yl)-5-((1R,2R)-2-(2,2,2-trifluoro-N-(piperidin-4-ylmethyl)acetamido)cyclopropyl)thiophene-3-carboxamide hydrochloride (50.0 mg), triethylamine (10.9 mg) and ethanol (2.0 mL) was added tert-butyl acrylate (12.6 mg) at room temperature. The reaction mixture was stirred at room temperature overnight, and the solvent was evaporated under reduced pressure. To the residue were added ethyl acetate and saturated aqueous sodium hydrogen carbonate solution, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/hexane) to give the title compound (44.0 mg).
MS: [M+H]+ 602.1.

E) tert-butyl 3-(4-(((((1R,2R)-2-(4-((5-methyl-1,3,4-thiadiazol-2-yl)carbamoyl)thiophen-2-yl)cyclopropyl)amino)methyl)piperidin-1-yl)propanoate To a mixture of tert-butyl 3-(4-((2,2,2-trifluoro-N-((1R,2R)-2-(4-((5-methyl-1,3,4-thiadiazol-2-yl)carbamoyl)thiophen-2-yl)cyclopropyl)acetamido)methyl)piperidin-1-yl)propanoate (44.0 mg), methanol (1.0 mL) and THF (1.0 mL) was added 1 mol/L aqueous sodium hydroxide solution (1.0 mL) at room temperature. The reaction mixture was stirred at room temperature for 10 min, and water was added at room temperature. The mixture was extracted with ethyl acetate, and the extract was washed with saturated brine and dried over anhydrous magnesium sulfate. The solvent was evaporated under reduced pressure to give the title compound (30.0 mg).
MS: [M+H]+ 506.2.

F) 3-(4-(((((1R,2R)-2-(4-((5-methyl-1,3,4-thiadiazol-2-yl)carbamoyl)-2-thienyl)cyclopropyl)amino)methyl)piperidin-1-yl)propanoic acid trihydrochloride A mixture of tert-butyl 3-(4-(((((1R,2R)-2-(4-((5-methyl-1,3,4-thiadiazol-2-yl)carbamoyl)thiophen-2-yl)cyclopropyl)amino)methyl)piperidin-1-yl)propanoate (30.0 mg) and 4 mol/L hydrogen chloride/ethyl acetate solution (1.0 mL) was stirred at room temperature overnight, and the solvent was evaporated under reduced pressure to give the title compound (33.0 mg).

$^1$H NMR (300 MHz, DMSO-d$_6$) δ 1.29-1.41 (1H, m), 1.44-1.64 (2H, m), 1.72 (1H, brs), 2.01 (3H, d, J=12.49), 2.63 (3H, s), 2.76-3.08 (7H, m), 3.17-3.35 (3H, m), 3.42-3.56 (2H, m), 7.51 (1H, s), 8.46 (1H, d, J=1.14), 9.36-9.73 (2H, m), 9.96-12.92 (2H, m).

The compounds of Examples 61 to 66 could be produced according to the production methods described in the present specification, a method shown in the Examples, or a method analogous thereto.

Example 61

4-(trans-2-(cyclobutylamino)cyclopropyl)-N-(1-methyl-1H-pyrazol-4-yl)thiophene-2-carboxamide dihydrochloride

Example 62

4-(trans-2-((cyclopropylmethyl)amino)cyclopropyl)-N-(1-methyl-1H-pyrazol-4-yl)thiophene-2-carboxamide dihydrochloride

Example 63

4-(trans-2-(cyclobutylamino)cyclopropyl)-N-(tetrahydro-2H-pyran-4-yl)thiophene-2-carboxamide hydrochloride

Example 64

4-(trans-2-((cyclopropylmethyl)amino)cyclopropyl)-N-(tetrahydro-2H-pyran-4-yl)thiophene-2-carboxamide hydrochloride

Example 65

5-(trans-2-((cyclopropylmethyl)amino)cyclopropyl)-N-(4,4-difluorocyclohexyl)-2-methylthiophene-3-carboxamide hydrochloride

Example 66

N-(4,4-difluorocyclohexyl)-2-methyl-5-(trans-2-((tetrahydro-2H-pyran-4-ylmethyl)amino)cyclopropyl)thiophene-3-carboxamide hydrochloride

Example 67

N-(4,4-difluorocyclohexyl)-2-methyl-5-(trans-2-(tetrahydro-2H-pyran-4-ylamino)cyclopropyl)thiophene-3-carboxamide hydrochloride To a mixture of 5-(trans-2-aminocyclopropyl)-N-(4,4-difluorocyclohexyl)-2-methylthiophene-3-carboxamide hydrochloride (30.0 mg), sodium hydrogen carbonate (10.8 mg), THF (1.5 mL) and methanol (1.5 mL) was added dihydro-2H-pyran-4(3H)-one (9.48 μL). Under a nitrogen atmosphere, the reaction mixture was stirred at 60° C. for 1.5 hr and at room temperature for 30 min, and sodium borohydride (4.85 mg) was added under ice-cooling. The reaction mixture was stirred at room temperature for 1 hr, and diluted with ethyl acetate. Water and saturated aqueous sodium hydrogen carbonate solution were added, and the mixture was extracted with ethyl acetate. The extract was successively washed with water and saturated brine, dried over anhydrous sodium sulfate, and the solvent was evaporated under reduced pressure. The obtained residue was purified by silica gel column chromatography (ethyl acetate/methanol). To the obtained fraction was added 4 mol/L hydrogen chloride/ethyl acetate solution, and the mixture was stirred overnight. The precipitated solid was collected by filtration and washed with ethyl acetate to give the title compound (15.6 mg).

$^1$H NMR (300 MHz, DMSO-d$_6$) δ 1.22-1.36 (1H, m), 1.49-1.75 (5H, m), 1.78-2.09 (9H, m), 2.53 (3H, s), 2.64 (1H, brs), 2.89 (1H, brs), 3.45 (1H, brs), 3.93 (3H, d, J=10.98 Hz), 7.06 (1H, s), 7.83 (1H, d, J=7.95 Hz), 9.50 (2H, brs).

Example 68

5-(trans-2-((cyclopropylmethyl)amino)cyclopropyl)-2-methyl-N-(tetrahydro-2H-pyran-4-yl)thiophene-3-carboxamide hydrochloride The title compound could be produced according to the production methods described in the present specification, a method shown in the Examples, or a method analogous thereto.

Example 69

5-(trans-2-((cyclopropylmethyl)amino)cyclopropyl)-2-methyl-N-(5-methyl-1,3,4-thiadiazol-2-yl)thiophene-3-carboxamide dihydrochloride To a mixture of 5-(trans-2-aminocyclopropyl)-2-methyl-N-(5-methyl-1,3,4-thiadiazol-2-yl)thiophene-3-carboxamide dihydrochloride (30.0 mg), sodium hydrogen carbonate (17.2 mg), THF (1.5 mL) and methanol (1.5 mL) was added cyclopropanecarbaldehyde (7.32 μL). Under a nitrogen atmosphere, the reaction mixture was stirred at 60° C. for 1.5 hr and at room temperature for 30 min. Sodium borohydride (4.63 mg) was added under ice-cooling, and the reaction mixture was stirred at room temperature for 1 hr and diluted with ethyl acetate. Water and saturated aqueous sodium hydrogen carbonate solution were added, and the mixture was extracted with ethyl acetate. The extract was successively washed with water and saturated brine, dried over anhydrous sodium sulfate, and the solvent was evaporated under reduced pressure. The obtained residue was purified by silica gel column chromatography (ethyl acetate/methanol). To the obtained fraction was added 4 mol/L hydrogen chloride/ethyl acetate solution, and the mixture was stirred overnight. The precipitated solid was collected by filtration and washed with ethyl acetate to give the title compound (22.1 mg).

$^1$H NMR (300 MHz, DMSO-d$_6$) δ 0.35-0.45 (2H, m), 0.55-0.65 (2H, m), 1.03-1.20 (1H, m), 1.24-1.36 (1H, m), 1.59-1.70 (1H, m), 2.60-2.75 (8H, m), 2.86-3.02 (3H, m), 7.47 (1H, s), 9.51 (2H, d, J=4.54 Hz).

Example 70

2-methyl-N-(5-methyl-1,3,4-thiadiazol-2-yl)-5-(trans-2-((tetrahydro-2H-pyran-4-ylmethyl)amino)cyclopropyl)thiophene-3-carboxamide dihydrochloride The title compound could be produced according to the production methods described in the present specification, a method shown in the Examples, or a method analogous thereto.

Example 71

5-((1R,2R)-2-((cyclopropylmethyl)amino)cyclopropyl)-N-(tetrahydro-2H-pyran-4-yl)thiophene-3-carboxamide hydrochloride

A) ((1R,4aS,10aR)-7-isopropyl-1,4a-dimethyl-1,2,3,4,4a,9,10,10a-octahydrophenanthren-1-yl)methanamine (1R,2R)-2-(4-bromothiophen-2-yl)cyclopropanecarboxylate ((1R,4aS,10aR)-7-Isopropyl-1,4a-dimethyl-1,2,3,4,4a,9,10,10a-octahydrophenanthren-1-yl)methanamine (1.040 g) was dissolved in methanol (3.2 mL) and diisopropyl ether (15.7 mL) at 40° C., and trans-2-(4-bromothiophen-2-yl)cyclopropanecarboxylic acid (900 mg) was added. The reaction mixture was stirred for 5 min at the same temperature, and methanol (8 mL) was added. The reaction mixture was heated to 53° C. to dissolve the precipitate. The reaction mixture was cooled to 46° C. and stirred at 46-47° C. for 2 hr. The reaction mixture was slowly cooled to room temperature (28° C.) and stirred overnight. The precipitate was collected by filtration, and the obtained solid was washed with a mixed solvent of ethyl acetate/hexane (1/5=ethyl acetate/hexane (v/v), 4 mL) to give the title compound (594 mg, 95.7% d.e.).

MS: [M−H—($C_{20}H_{31}$N)]$^-$ 245.0.
Column: CHIROBIOTIC R 4.6 mmID×250 mmL
Eluent solvent: Methanol/TEA/AA=1000/3/1 (v/v/v)
Flow rate: 1.0 mL/min
Retention time: 4.4 min.
Temperature: 300° C.
Detection: UV 254 nm
Concentration: 0.5 mg/mL
Injection volume: 0.010 mL

B) ((1R,4aS,10aR)-7-isopropyl-1,4a-dimethyl-1,2,3,4,4a,9,10,10a-octahydrophenanthren-1-yl)methanamine (1R,2R)-2-(4-bromothiophen-2-yl)cyclopropanecarboxylate ((1R,4aS,10aR)-7-Isopropyl-1,4a-dimethyl-1,2,3,4,4a,9,10,10a-octahydrophenanthren-1-yl)methanamine (1R,2R)-2-(4-bromothiophen-2-yl)cyclopropanecarboxylate (290 mg, 95.7% d.e.) was dissolved in ethanol (3.77 mL) and diisopropyl ether (1.45 mL) at 62° C., and diisopropyl ether (8.12 mL) was further added dropwise at 62° C. The mixture was cooled to 46° C. and stirred at 45-47° C. for 2 hr. The mixture was slowly cooled to room temperature (28° C.) and stirred overnight. Furthermore, the mixture was stirred at 0° C. for 1 hr. The precipitate was collected by filtration, and the obtained solid was washed with ethyl acetate/hexane (1/5=ethyl acetate/hexane (v/v), 2 mL) to give the title compound (246 mg, 99.6% d.e.).

$^1$H NMR (300 MHz, DMSO-$d_6$) δ 0.84 (3H, s), 1.00-1.76 (19H, m), 2.21-2.38 (2H, m), 2.39-2.47 (2H, m), 2.71-2.87 (2H, m), 3.38-3.50 (2H, m), 6.81-6.86 (1H, m), 6.88-6.92 (1H, m), 6.92-6.98 (1H, m), 7.10-7.19 (1H, m), 7.40 (1H, d, J=1.5 Hz).
Column: CHIROBIOTIC R 4.6 mmID×250 mmL
Eluent solvent: Methanol/TEA/AA=1000/3/1 (v/v/v)
Flow rate: 1.0 mL/min
Retention time: 4.3 min.
Temperature: 300° C.
Detection: UV 254 nm
Concentration: 0.5 mg/mL
Injection volume: 0.010 mL

C) (1R,2R)-2-(4-bromothiophen-2-yl)cyclopropanecarboxylic acid

To a suspension of ((1R,4aS,10aR)-7-isopropyl-1,4a-dimethyl-1,2,3,4,4a,9,10,10a-octahydrophenanthren-1-yl)methanamine (1R,2R)-2-(4-bromothiophen-2-yl)cyclopropanecarboxylate (26.8 g) in ethyl acetate (300 mL) were added 1 mol/L aqueous sodium hydroxide solution (60.4 mL) and water (200 mL) at room temperature, and the mixture was stirred at room temperature for 5 min. The aqueous layer was separated and washed with ethyl acetate (200 mL, twice). To the aqueous layer was added 2 mol/L hydrochloric acid (35.2 mL) under ice-cooling at 0° C. to adjust the mixture from pH 2 to pH 3, and the mixture was extracted with ethyl acetate (100 mL, twice). The organic layer was separated, and the extract was washed with saturated brine, and dried over magnesium sulfate. The solvent was evaporated under reduced pressure to give the title compound (11.7 g).

$^1$H NMR (300 MHz, CDCl$_3$) δ 1.39 (1H, ddd, J=8.5, 6.4, 4.7 Hz), 1.64-1.73 (1H, m), 1.90-1.98 (1H, m), 2.66-2.78 (1H, m), 6.75 (1H, dd, J=1.5, 0.8 Hz), 7.02 (1H, d, J=1.5 Hz).

D) tert-butyl ((1R,2R)-2-(4-bromothiophen-2-yl)cyclopropyl)carbamate

To a solution of (1R,2R)-2-(4-bromothiophen-2-yl)cyclopropanecarboxylic acid (15 g) and tert-butyl alcohol (150 mL) were added triethylamine (10.15 mL) and diphenylphosphoryl azide (13.07 mL) at room temperature, and the mixture was stirred at room temperature for 1 hr, and then at 80° C. overnight. The reaction mixture was cooled to room temperature, saturated aqueous sodium hydrogen carbonate solution was added, and the mixture was extracted with ethyl acetate. The organic layer was separated, successively washed with water and saturated brine, dried over anhydrous sodium sulfate, and concentrated under reduced pressure. The residue was purified by silica gel column chromatography (hexane/ethyl acetate) to give the title compound (14.6 g).

$^1$H NMR (300 MHz, DMSO-$d_6$) δ 1.04-1.24 (2H, m), 1.38 (9H, s), 2.07 (1H, ddd, J=9.18, 6.15, 3.22 Hz), 2.61 (1H, brs), 6.80 (1H, d, J=0.76 Hz), 7.27 (1H, brs), 7.38 (1H, d, J=1.51 Hz).

E) methyl 5-((1R,2R)-2-((tert-butoxycarbonyl)amino)cyclopropyl)thiophene-3-carboxylate To a solution of tert-butyl ((1R,2R)-2-(4-bromothiophen-2-yl)cyclopropyl)carbamate (7.2 g) in methanol (180 mL) were added triethylamine (6.31 mL) and dichloro(1,1'-bis(diphenylphosphino)ferrocene)palladium (828 mg) at room temperature, and the mixture was stirred at 90° C. for 6 hr under a carbon monoxide atmosphere (3 atm). The reaction mixture was filtered through celite and washed with methanol. The filtrate was concentrated under reduced pressure, water was added to the residue, and the mixture was extracted with ethyl acetate. The contaminants in the organic layer were removed by filtration, and the filtrate was concentrated under reduced pressure to give residue A.

To a solution of tert-butyl ((1R,2R)-2-(4-bromothiophen-2-yl)cyclopropyl)carbamate (7.2 g) in methanol (180 mL)

were added triethylamine (6.31 mL) and dichloro(1,1'-bis(diphenylphosphino)ferrocene)palladium (828 mg) at room temperature, and the mixture was stirred at 90° C. for 6 hr under a carbon monoxide atmosphere (3 atm). The reaction mixture was filtered through celite, and washed with methanol. The filtrate was concentrated under reduced pressure, water was added to the residue, and the mixture was extracted with ethyl acetate. The contaminants in the organic layer were removed by filtration, and the filtrate was concentrated under reduced pressure to give residue B.

The residues A and B were combined and purified by silica gel column chromatography (hexane/ethyl acetate) to give the title compound (11.1 g).

$^1$H NMR (300 MHz, DMSO-$d_6$) δ 1.05-1.25 (2H, m), 1.35-1.42 (9H, m), 2.08 (1H, ddd, J=9.18, 6.34, 3.03 Hz), 2.60 (1H, brs), 3.76 (3H, s), 7.12 (1H, d, J=0.76 Hz), 7.28 (1H, brs), 8.07 (1H, d, J=1.51 Hz).

F) 5-((1R,2R)-2-((tert-butoxycarbonyl)amino)cyclopropyl)thiophene-3-carboxylic acid By a method similar to that of Example 38, step C, the title compound was obtained.

G) tert-butyl ((1R,2R)-2-(4-((tetrahydro-2H-pyran-4-yl)carbamoyl)thiophen-2-yl)cyclopropyl)carbamate By a method similar to that of Example 42, step A, the title compound was obtained.

H) 5-((1R,2R)-2-aminocyclopropyl)-N-(tetrahydro-2H-pyran-4-yl)thiophene-3-carboxamide dihydrochloride By a method similar to that of Example 42, step B, the title compound was obtained.

I) 5-((1R,2R)-2-((cyclopropylmethyl)amino)cyclopropyl)-N-(tetrahydro-2H-pyran-4-yl)thiophene-3-carboxamide hydrochloride To a mixture of 5-((1R,2R)-2-aminocyclopropyl)-N-(tetrahydro-2H-pyran-4-yl)thiophene-3-carboxamide dihydrochloride (1.54 g), triethylamine (2.12 mL), THF (20 mL) and methanol (20 mL) was added cyclopropanecarbaldehyde (0.428 g) at room temperature. The reaction mixture was stirred at room temperature for 2 hr, and sodium borohydride (0.231 g) was added at 0° C. The reaction mixture was stirred at 0° C. for 10 min and added to water. The methanol and tetrahydrofuran were evaporated under reduced pressure, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/methanol). To the obtained fraction was added 4 mol/L hydrogen chloride/ethyl acetate solution and the mixture was concentrated under reduced pressure. The obtained residue was crystallized from ethanol/heptane to give the title compound (1.04 g).

$^1$H NMR (300 MHz, DMSO-$d_6$) δ 0.33-0.43 (2H, m), 0.51-0.64 (2H, m), 0.99-1.15 (1H, m), 1.24-1.37 (1H, m), 1.42-1.65 (3H, m), 1.67-1.78 (2H, m), 2.64-2.75 (1H, m), 2.90-3.04 (3H, m), 3.32-3.42 (2H, m), 3.79-4.00 (3H, m), 7.28 (1H, s), 7.95 (1H, d, J=1.5 Hz), 8.05 (1H, d, J=8.0 Hz), 9.25 (2H, brs).

The compounds of Examples 72 to 80 could be produced according to the production methods described in the present specification, a method shown in the Examples, or a method analogous thereto.

Example 72

N-(5-methyl-1,3,4-thiadiazol-2-yl)-4-((1S,2R)-2-((tetrahydro-2H-pyran-4-ylmethyl)amino)cyclopropyl)thiophene-2-carboxamide hydrochloride Example 73

4-((1R,2S)-2-(cyclobutylamino)cyclopropyl)-N-(tetrahydro-2H-pyran-4-yl)thiophene-2-carboxamide hydrochloride Example 74

N-(5-methyl-1,3,4-thiadiazol-2-yl)-4-((1R,2S)-2-((tetrahydro-2H-pyran-4-ylmethyl)amino)cyclopropyl)thiophene-2-carboxamide hydrochloride Example 75

4-((1R,2S)-2-((cyclopropylmethyl)amino)cyclopropyl)-N-(tetrahydro-2H-pyran-4-yl)thiophene-2-carboxamide hydrochloride Example 76

4-((1S,2R)-2-(cyclobutylamino)cyclopropyl)-N-(tetrahydro-2H-pyran-4-yl)thiophene-2-carboxamide hydrochloride Example 77

4-((1S,2R)-2-((cyclopropylmethyl)amino)cyclopropyl)-N-(tetrahydro-2H-pyran-4-yl)thiophene-2-carboxamide hydrochloride Example 78

4-((1S,2R)-2-((1-cyclopropylpiperidin-4-yl)amino)cyclopropyl)-N-(5-methyl-1,3,4-thiadiazol-2-yl)thiophene-2-carboxamide dihydrochloride Example 79

4-((1R,2S)-2-((1-cyclopropylpiperidin-4-yl)amino)cyclopropyl)-N-(5-methyl-1,3,4-thiadiazol-2-yl)thiophene-2-carboxamide dihydrochloride Example 80

5-((1R,2R)-2-((1-cyclopropylpiperidin-4-yl)amino)cyclopropyl)-N-(4,4-difluorocyclohexyl)thiophene-3-carboxamide hydrochloride Example 81

N-(5-methyl-1,2-oxazol-3-yl)-5-((1R,2R)-2-((tetrahydro-2H-pyran-4-ylmethyl)amino)cyclopropyl)thiophene-3-carboxamide hydrochloride A) tert-butyl ((1R,2R)-2-(4-((5-methylisoxazol-3-yl)carbamoyl)thiophen-2-yl)cyclopropyl) ((tetrahydro-2H-pyran-4-yl)methyl)carbamate To a mixture of 5-((1R,2R)-2-((tert-butoxycarbonyl) ((tetrahydro-2H-pyran-4-yl)methyl)amino)cyclopropyl)thiophene-3-carboxylic acid (50.0 mg) and THF (2 mL) was added oxalyl chloride (0.014 mL) at 0° C., and the mixture was stirred at 0° C. for 1 hr. The solvent was evaporated under reduced pressure to give an acid chloride intermediate.

To a mixture of 5-methylisoxazol-3-amine (19.3 mg), DMAP (8.01 mg) and pyridine (2 mL) was added a mixture of the aforementioned acid chloride and THF (1.5 mL) at 60° C., and the mixture was stirred at 60° C. for 2 hr. The reaction mixture was neutralized with saturated aqueous sodium hydrogen carbonate solution, and extracted with ethyl acetate. The extract was successively washed with water and saturated brine, and dried over magnesium sulfate, and the solvent was evaporated under reduced pressure. The residue was purified by silica gel column chromatography (hexane/ethyl acetate) to give the title compound (17.2 mg).

MS: [M-Boc+H]$^+$ 362.3.

B) N-(5-methyl-1,2-oxazol-3-yl)-5-((1R,2R)-2-((tetrahydro-2H-pyran-4-ylmethyl)amino)cyclopropyl)thiophene-3-carboxamide hydrochloride By a method similar to that of Example 1, step H, the title compound was obtained.

Example 82

4-((1S,2R)-2-((cyclopropylmethyl)amino)cyclopropyl)-N-(5-methyl-1,3,4-thiadiazol-2-yl)thiophene-2-carboxamide dihydrochloride

A) (R)-2-amino-3-phenylpropan-1-ol (1R,2R)-2-(5-bromothiophen-3-yl)cyclopropanecarboxylate trans-2-(5-Bromothiophen-3-yl)cyclopropanecarboxylic acid (47.8 g) and (R)-2-amino-3-phenylpropan-1-ol (29.2 g) were dissolved in ethanol (480 mL) at 57° C., diisopropyl ether (480 mL) was added, and the mixture was cooled to 53° C. The reaction mixture was stirred at 53° C. for 1 hr, cooled to room temperature, and stirred overnight. The reaction mixture was cooled to 0° C. and stirred for 1 hr. The precipitate was collected by filtration, and washed with a mixed solvent of ethyl acetate/hexane (1/2=ethyl acetate/hexane (v/v)) to give the title compound (32.6 g, >99% d.e.).

MS: [M-H—$C_9H_{13}NO$]$^-$ 246.8.

B) (R)-2-amino-3-phenylpropan-1-ol (1R,2R)-2-(5-bromothiophen-3-yl)cyclopropanecarboxylate (R)-2-Amino-3-phenylpropan-1-ol (1R,2R)-2-(5-bromothiophen-3-yl)cyclopropanecarboxylate (32.5 g) was dissolved in ethanol (430 mL) at 60° C., diisopropyl ether (850 mL) was added, and the mixture was cooled to 55° C. The reaction mixture was stirred at 55° C. for 1 hr, cooled to room temperature, and stirred overnight. The reaction mixture was cooled to 0° C., stirred for 1 hr, and the precipitate was collected by filtration and washed with a mixed solvent of ethyl acetate/hexane (1/2=ethyl acetate/hexane (v/v)) to give the title compound (27.5 g, >99% d.e.).

MS: [M-H—$C_9H_{13}NO$]$^-$ 246.8.

C) (1R,2R)-2-(5-bromothiophen-3-yl)cyclopropanecarboxylic acid

To a mixture of (R)-2-amino-3-phenylpropan-1-ol (1R,2R)-2-(5-bromothiophen-3-yl)cyclopropanecarboxylate (26.0 g) and ethyl acetate was added 1 mol/L aqueous hydrochloric acid solution, and the mixture was extracted with ethyl acetate. The extract was successively washed with water and saturated brine, and dried over anhydrous sodium sulfate. The solvent was evaporated under reduced pressure. Toluene was added to the residue, and the mixture was concentrated under reduced pressure to give the title compound (16.1 g).

MS: [M–H]$^-$ 246.8.

D) tert-butyl ((1R,2S)-2-(5-bromothiophen-3-yl)cyclopropyl)carbamate

To a mixture of (1R,2R)-2-(5-bromothiophen-3-yl)cyclopropanecarboxylic acid (16.0 g) and tert-butyl alcohol (200 mL) were added triethylamine (10.8 mL) and diphenylphosphoryl azide (16.7 mL) at room temperature, and the mixture was stirred at room temperature for 2 hr and at 80° C. overnight. Water was added to the reaction mixture, and the mixture was extracted with ethyl acetate. The extract was successively washed with water and saturated brine, and dried over anhydrous sodium sulfate. The solvent was evaporated under reduced pressure, and the residue was purified by silica gel column chromatography (hexane/ethyl acetate) to give the title compound (18.1 g).

$^1$H NMR (300 MHz, DMSO-d$_6$) δ 0.91-1.11 (2H, m), 1.37 (9H, s), 1.87 (1H, ddd, J=9.28, 6.25, 3.41 Hz), 2.56 (1H, s), 7.00 (1H, d, J=1.89 Hz), 7.12 (1H, d, J=1.89 Hz), 7.18 (1H, brs).

E) methyl 4-((1S,2R)-2-((tert-butoxycarbonyl)amino)cyclopropyl)thiophene-2-carboxylate To a mixture of tert-butyl ((1R,2S)-2-(5-bromothiophen-3-yl)cyclopropyl)carbamate (9.00 g) and methanol (200 mL) were added triethylamine (7.88 mL) and 1,1'-bis(diphenylphosphino)ferrocene-palladium(II) dichloride (1.04 g), and the mixture was heated at 90° C. for 6 hr under a carbon monoxide atmosphere (3 atm). The insoluble material was filtered off by celite and washed with methanol, and the filtrate was concentrated under reduced pressure and extracted with ethyl acetate and water. The extract was washed with saturated brine, and dried over anhydrous sodium sulfate. The solvent was evaporated under reduced pressure to give residue A.

To a mixture of tert-butyl ((1R,2S)-2-(5-bromothiophen-3-yl)cyclopropyl)carbamate (9.00 g) and methanol (200 mL) were added triethylamine (7.88 mL) and 1,1'-bis(diphenylphosphino)ferrocene-palladium(II) dichloride (1.04 g), and the mixture was stirred at 90° C. for 6 hr under a carbon monoxide atmosphere (3 atm). The insoluble material was filtered off by celite and washed with methanol, and the filtrate was concentrated under reduced pressure and extracted with ethyl acetate and water. The extract and the residues A were combined, washed with 5% ammonia water (twice), N-acetyl-L-cysteine aqueous solution (twice), water and saturated brine, and dried over anhydrous sodium sulfate. The solvent was evaporated under reduced pressure. The residue was purified by silica gel column chromatography (hexane/ethyl acetate) to give the title compound (15.2 g).

MS: [M-Boc+2H]$^+$ 198.1.

F) 4-((1S,2R)-2-((tert-butoxycarbonyl)amino)cyclopropyl)thiophene-2-carboxylic acid To a solution of methyl 4-((1S,2R)-2-((tert-butoxycarbonyl)amino)cyclopropyl)thiophene-2-carboxylate (15.2 g) in THF (50 mL)/methanol (50 mL) was added 2 mol/L aqueous sodium hydroxide solution (63.9 mL) at 0° C., and the mixture was stirred at room temperature overnight. The reaction mixture was acidified with 1 mol/L hydrochloric acid at 0° C., and extracted with ethyl acetate. The extract was successively washed with water and saturated brine, dried over anhydrous sodium sulfate, and concentrated under reduced pressure. The obtained residue was washed with diisopropyl ether to give the title compound (13.4 g).

$^1$H NMR (300 MHz, DMSO-$d_6$) δ 1.00-1.11 (2H, m), 1.34-1.42 (9H, m), 1.92 (1H, ddd, J=9.09, 6.25, 3.22 Hz), 2.54-2.66 (1H, m), 7.21 (1H, br. s.), 7.42 (1H, d, J=1.14 Hz), 7.50 (1H, d, J=1.51 Hz), 12.99 (1H, brs).

G) tert-butyl ((1R,2S)-2-(5-((5-methyl-1,3,4-thiadiazol-2-yl)carbamoyl)thiophen-3-yl)cyclopropyl) carbamate To a solution of 4-((1S,2R)-2-((tert-butoxycarbonyl)amino)cyclopropyl)thiophene-2-carboxylic acid (13.3 g) in DMF (200 mL) were added 5-methyl-1,3,4-thiadiazol-2-amine (6.49 g), triethylamine (13.08 mL) and O-(7-azabenzotriazol-1-yl)-N,N,N',N'-tetramethyluronium hexafluorophosphate (21.42 g), and the mixture was stirred at room temperature overnight. To the reaction mixture were added water and ethyl acetate, and the precipitate was collected by filtration and washed with ethyl acetate to give the title compound (12.1 g). The filtrate was extracted with ethyl acetate. The organic layer was successively washed with 0.1 mol/L hydrochloric acid, saturated aqueous sodium hydrogen carbonate solution, water and saturated brine, dried over anhydrous sodium sulfate, and concentrated under reduced pressure. To the residue was added ethyl acetate, and the precipitate was collected by filtration. The obtained solid was washed with ethyl acetate to give the title compound (2.86 g).

MS: [M+H]$^+$ 381.1.

H) 4-((1S,2R)-2-aminocyclopropyl)-N-(5-methyl-1,3,4-thiadiazol-2-yl)thiophene-2-carboxamide dihydrochloride To a suspension of tert-butyl ((1R,2S)-2-(5-((5-methyl-1,3,4-thiadiazol-2-yl)carbamoyl)thiophen-3-yl)cyclopropyl) carbamate (1.67 g) in ethyl acetate (10 mL) and methanol (10 mL) was added 4 mol/L hydrogen chloride/ethyl acetate solution (10.97 mL) at 0° C., and the mixture was stirred at room temperature overnight. The precipitated solid was collected by filtration, and washed with ethyl acetate to give the title compound (1.55 g).

MS: [M+H-(2HCl)]$^+$ 281.0.

I) 4-((1S,2R)-2-((cyclopropylmethyl)amino)cyclopropyl)-N-(5-methyl-1,3,4-thiadiazol-2-yl)thiophene-2-carboxamide dihydrochloride To a mixture of 4-((1S,2R)-2-aminocyclopropyl)-N-(5-methyl-1,3,4-thiadiazol-2-yl)thiophene-2-carboxamide dihydrochloride (1.00 g), sodium hydrogen carbonate (549 mg), THF (15 mL) and methanol (15 mL) was added cyclopropanecarbaldehyde (254 µL). Under a nitrogen atmosphere, the reaction mixture was stirred at 60° C. for 1.5 hr and at room temperature for 30 min. Sodium borohydride (161 mg) was added under ice-cooling, and the reaction mixture was stirred at room temperature for 1 hr. The reaction mixture was diluted with ethyl acetate, water and saturated aqueous sodium hydrogen carbonate solution were added, and the mixture was extracted with ethyl acetate. The extract was successively washed with water and saturated brine, and dried over anhydrous sodium sulfate. The solvent was evaporated under reduced pressure, and the obtained residue was purified by silica gel column chromatography (ethyl acetate/methanol). To the obtained fraction was added 4 mol/L hydrogen chloride/ethyl acetate solution, and the mixture was stirred overnight and concentrated under reduced pressure. The residue was crystallized from methanol/diisopropyl ether to give the title compound (723 mg).

$^1$H NMR (300 MHz, DMSO-$d_6$) δ 0.33-0.42 (2H, m), 0.54-0.65 (2H, m), 1.01-1.17 (1H, m), 1.20-1.32 (1H, m), 1.53-1.66 (1H, m), 2.56-2.65 (4H, m), 2.86-3.02 (3H, m), 7.75 (1H, s), 8.07 (1H, brs), 9.26-9.56 (2H, m).

Example 83

4-((1R,2S)-2-((cyclopropylmethyl)amino)cyclopropyl)-N-(5-methyl-1,3,4-thiadiazol-2-yl)thiophene-2-carboxamide dihydrochloride The title compound could be produced according to the production methods described in the present specification, a method shown in the Examples, or a method analogous thereto.

Example 84

4-((1S,2R)-2-(cyclobutylamino)cyclopropyl)-N-(5-methyl-1,3,4-thiadiazol-2-yl)thiophene-2-carboxamide dihydrochloride To a mixture of (1S,2R)-4-(2-aminocyclopropyl)-N-(5-methyl-1,3,4-thiadiazol-2-yl)thiophene-2-carboxamide dihydrochloride (3.36 g), THF (30 mL) and methanol (30 mL) was added triethylamine (3.31 mL), triethyl orthoformate (2.10 mL) and cyclobutanone (0.856 mL) at room temperature, and the mixture was stirred at room temperature overnight. Sodium borohydride (540 mg) was added under ice-cooling, and the reaction mixture was stirred at room temperature for 1 hr. The reaction mixture was diluted with ethyl acetate, water and saturated aqueous sodium hydrogen carbonate solution were added, and the mixture was extracted with ethyl acetate. The extract was successively washed with water and saturated brine, and dried over anhydrous sodium sulfate. The solvent was evaporated under reduced pressure and the obtained residue was purified by silica gel column chromatography (ethyl acetate/methanol). To the obtained fraction was added 4 mol/L hydrogen chloride/ethyl acetate solution, and the mixture was stirred overnight and concentrated under reduced pressure. The residue was crystallized from ethanol/water/ethyl acetate to give the title compound (2.17 g).

$^1$H NMR (300 MHz, DMSO-$d_6$) δ 1.18-1.29 (1H, m), 1.48-1.60 (1H, m), 1.72-1.89 (2H, m), 2.12-2.39 (4H, m), 2.54-2.67 (4H, m), 2.74-2.86 (1H, m), 3.74-3.92 (1H, m), 7.74 (1H, d, J=1.14 Hz), 8.06 (1H, s), 9.79 (2H, brs).

The compounds of Examples 85 to 92 could be produced according to the production methods described in the present specification, a method shown in the Examples, or a method analogous thereto.

Example 85

4-((1R,2S)-2-(cyclobutylamino)cyclopropyl)-N-(5-methyl-1,3,4-thiadiazol-2-yl)thiophene-2-carboxamide dihydrochloride

Example 86

N-(1-ethyl-1H-pyrazol-4-yl)-5-((1R,2R)-2-((tetrahydro-2H-pyran-4-ylmethyl)amino)cyclopropyl)thiophene-3-carboxamide dihydrochloride

Example 87

4-((1S,2R)-2-((cyclopropylmethyl)amino)cyclopropyl)-N-(1-methyl-1H-pyrazol-4-yl)thiophene-2-carboxamide dihydrochloride

Example 88

4-((1R,2S)-2-((cyclopropylmethyl)amino)cyclopropyl)-N-(1-methyl-1H-pyrazol-4-yl)thiophene-2-carboxamide dihydrochloride

Example 89

4-((1S,2R)-2-(cyclobutylamino)cyclopropyl)-N-(1-methyl-1H-pyrazol-4-yl)thiophene-2-carboxamide dihydrochloride

Example 90

4-((1R,2S)-2-(cyclobutylamino)cyclopropyl)-N-(1-methyl-1H-pyrazol-4-yl)thiophene-2-carboxamide dihydrochloride

Example 91

5-((1R,2R)-2-((1-acetylpiperidin-4-yl)amino)cyclopropyl)-N-(4,4-difluorocyclohexyl)thiophene-3-carboxamide hydrochloride

Example 92

5-((1R,2R)-2-((1-(cyclopropylcarbonyl)piperidin-4-yl)amino)cyclopropyl)-N-(4,4-difluorocyclohexyl)thiophene-3-carboxamide hydrochloride

Example 93

N-(4,4-difluorocyclohexyl)-5-methyl-4-((1S,2R)-2-(tetrahydro-2H-pyran-4-ylamino)cyclopropyl)thiophene-2-carboxamide fumarate A) 4-((1S,2R)-2-aminocyclopropyl)-N-(4,4-difluorocyclohexyl)-5-methylthiophene-2-carboxamide hydrochloride 4-((1S,2R)-2-((tert-Butoxycarbonyl)amino)cyclopropyl)-5-methylthiophene-2-carboxylic acid (50 mg), 4,4-difluorocyclohexanamine (27.3 mg) and triethylamine (0.094 mL) were dissolved in DMF (1 mL), O-(7-azabenzotriazol-1-yl)-N,N,N',N'-tetramethyluronium hexafluorophosphate (77 mg) was added, and the mixture was stirred at room temperature overnight. Water was added to the reaction mixture, and the mixture was extracted with ethyl acetate. The organic layer was successively washed with water and saturated brine, dried over magnesium sulfate, and concentrated under reduced pressure. The obtained residue (70.5 mg) and 4 mol/L hydrogen chloride/ethyl acetate solution (4.0 mL) were stirred at room temperature overnight. The precipitated solid was collected by filtration and washed with ethyl acetate to give the title compound (51 mg).

MS: [M-HCl+H]$^+$ 315.1.

B) N-(4,4-difluorocyclohexyl)-5-methyl-4-((1S,2R)-2-(tetrahydro-2H-pyran-4-ylamino)cyclopropyl)thiophene-2-carboxamide fumarate To a mixture of 4-((1S,2R)-2-aminocyclopropyl)-N-(4,4-difluorocyclohexyl)-5-methylthiophene-2-carboxamide hydrochloride (40.0 mg), borane-2-picoline complex (36.7 mg), methanol (2.0 mL) and acetic acid (0.2 mL) was added dihydro-2H-pyran-4(3H)-one (17.1 mg) at room temperature. The reaction mixture was stirred at room temperature for 18 hr, and saturated aqueous sodium hydrogen carbonate solution was added at 0° C. The mixture was extracted with ethyl acetate, and the extract was successively washed with water and saturated brine, and dried over anhydrous sodium sulfate. The solvent was evaporated under reduced pressure. The residue was purified by silica gel column chromatography (ethyl acetate/hexane), the obtained residue was dissolved in ethyl acetate, and a solution of fumaric acid (9.3 mg) in ethanol was added at room temperature. The reaction mixture was stirred at room temperature for 30 min, and the solvent was evaporated under reduced pressure to give the title compound (40.0 mg).

$^1$H NMR (300 MHz, DMSO-d6) δ 0.76-0.91 (1H, m), 0.95-1.04 (1H, m), 1.21-1.40 (2H, m), 1.48-1.66 (2H, m), 1.69-2.11 (9H, m), 2.26-2.34 (1H, m), 2.40 (3H, s), 2.75-2.87 (1H, m), 3.23-3.34 (2H, m), 3.76-3.96 (3H, m), 6.60 (2H, s), 7.21 (1H, s), 7.94-8.05 (1H, m).

Example 94

N-(4,4-difluorocyclohexyl)-5-methyl-4-((1R,2S)-2-(tetrahydro-2H-pyran-4-ylamino)cyclopropyl)thiophene-2-carboxamide fumarate The title compound could be produced according to the production methods described in the present specification, a method shown in the Examples, or a method analogous thereto.

Example 95

4-((1S,2R)-2-((cyclopropylmethyl)amino)cyclopropyl)-5-methyl-N-(5-methyl-1,3,4-thiadiazol-2-yl)thiophene-2-carboxamide fumarate A) 4-((1S,2R)-2-aminocyclopropyl)-5-methyl-N-(5-methyl-1,3,4-thiadiazol-2-yl)thiophene-2-carboxamide 4-((1S,2R)-2-((tert-Butoxycarbonyl)amino)cyclopropyl)-5-methylthiophene-2-carboxylic acid (150 mg), 5-methyl-1,3,4-thiadiazol-2-amine (69.7 mg) and triethylamine (0.281 mL) were dissolved in DMF (5 mL), O-(7-azabenzotriazol-1-yl)-N,N,N',N'-tetramethyluronium hexafluorophosphate (230 mg) was added, and the mixture was stirred at room temperature overnight. Water was added to the reaction mixture, and the precipitate was collected by filtration to give solid A. The filtrate was extracted with ethyl acetate. The organic layer was successively washed with water and saturated brine, dried over magnesium sulfate, and concentrated under reduced pressure to give solid B. The solid (197 mg) combined with the obtained solids A and B, and 4 mol/L hydrogen chloride/ethyl acetate solution (4 mL) were stirred at room temperature overnight. The precipitated solid was collected by filtration, and washed with ethyl acetate to give the title compound (120 mg).

MS: [M-HCl+H]$^+$ 295.1.

B) 4-((1S,2R)-2-((cyclopropylmethyl)amino)cyclopropyl)-5-methyl-N-(5-methyl-1,3,4-thiadiazol-2-yl)thiophene-2-carboxamide fumarate To a mixture of 4-((1S,2R)-2-aminocyclopropyl)-5-methyl-N-(5-methyl-1,3,4-thiadiazol-2-yl)thiophene-2-carboxamide hydrochloride (40.0 mg), triethylamine (22.0 mg), THF (1.0 mL) and methanol (1.0 mL) was added cyclopropanecarbaldehyde (11.8 mg) at room temperature. The reaction mixture was stirred at 50° C. for 1.5 hr, and stirred at room temperature for 1 hr. Sodium borohydride (8.2 mg) was added at 0° C., the reaction mixture was stirred at 0° C. for 30 min, and ethyl acetate, water and saturated aqueous sodium hydrogen carbonate solution were added to the reaction mixture. The mixture was extracted with ethyl acetate/THF, and the extract was washed with saturated brine, and dried over anhydrous sodium sulfate. The solvent was evaporated under reduced pressure. The residue was purified by silica gel column chromatography (methanol/ethyl acetate), the obtained residue was suspended in ethyl acetate, and a solution of fumaric acid (8.4 mg) in ethanol was added at room temperature. The reaction mixture was stirred at room temperature for 30 min, and the solid was collected by filtration to give the title compound (28.0 mg).

$^1$H NMR (300 MHz, DMSO-$d_6$) δ 0.10-0.21 (2H, m), 0.37-0.49 (2H, m), 0.85-1.00 (2H, m), 1.04-1.16 (1H, m), 1.80-1.92 (1H, m), 2.40-2.46 (1H, m), 2.48 (3H, s), 2.56-2.60 (2H, m), 2.61 (3H, s), 6.58 (2H, s), 7.76 (1H, s).

Example 96

4-((1R,2S)-2-((cyclopropylmethyl)amino)cyclopropyl)-5-methyl-N-(5-methyl-1,3,4-thiadiazol-2-yl)thiophene-2-carboxamide fumarate The title compound could be produced according to the production methods described in the present specification, a method shown in the Examples, or a method analogous thereto.

Example 97

5-methyl-N-(5-methyl-1,3,4-thiadiazol-2-yl)-4-((1S,2R)-2-((tetrahydro-2H-pyran-4-ylmethyl)amino)cyclopropyl)thiophene-2-carboxamide hydrochloride To a mixture of 4-((1S,2R)-2-aminocyclopropyl)-5-methyl-N-(5-methyl-1,3,4-thiadiazol-2-yl)thiophene-2-carboxamide hydrochloride (40.0 mg), triethylamine (22.0 mg), THF (1.0 mL) and methanol (1.0 mL) was added tetrahydro-2H-pyran-4-carbaldehyde (18.6 mg) at room temperature. The reaction mixture was stirred at room temperature overnight, sodium borohydride (8.2 mg) was added at 0° C., and the reaction mixture was stirred at 0° C. for 10 min. To the reaction mixture were added ethyl acetate and water, and the mixture was extracted with ethyl acetate. The extract was dried over anhydrous sodium sulfate, and the solvent was evaporated under reduced pressure. The residue was purified by silica gel column chromatography (methanol/ethyl acetate), and to the obtained fraction was added 4 mol/L hydrogen chloride/ethyl acetate solution. The reaction mixture was concentrated under reduced pressure, and the obtained residue was crystallized from ethanol/heptane to give the title compound (31.0 mg).

$^1$H NMR (300 MHz, DMSO-$d_6$) δ 1.14-1.35 (4H, m), 1.52-1.63 (1H, m), 1.64-1.76 (2H, m), 1.86-2.06 (1H, m), 2.53 (3H, s), 2.62 (3H, s), 2.86-3.09 (3H, m), 3.21-3.30 (2H, m), 3.79-3.95 (2H, m), 7.70-8.03 (1H, m), 8.94-9.41 (2H, m), 12.34-12.97 (1H, m).

Example 98

5-methyl-N-(5-methyl-1,3,4-thiadiazol-2-yl)-4-((1R,2S)-2-((tetrahydro-2H-pyran-4-ylmethyl)amino)cyclopropyl)thiophene-2-carboxamide hydrochloride The title compound could be produced according to the production methods described in the present specification, a method shown in the Examples, or a method analogous thereto.

Example 99

4-((1S,2R)-2-(cyclobutylamino)cyclopropyl)-5-methyl-N-(5-methyl-1,3,4-thiadiazol-2-yl)thiophene-2-carboxamide hydrochloride To a mixture of 4-((1S,2R)-2-aminocyclopropyl)-5-methyl-N-(5-methyl-1,3,4-thiadiazol-2-yl)thiophene-2-carboxamide dihydrochloride (40.0 mg), triethylamine (22.0 mg), trimethyl orthoformate (17.3 mg), methanol (1.0 mL) and THF (1.0 mL) was added cyclobutanone (11.8 mg) at room temperature, and the mixture was stirred at room temperature for 3 hr. Sodium borohydride (8.2 mg) was added under ice-cooling, the reaction mixture was stirred for 30 min, and ethyl acetate and saturated aqueous sodium hydrogen carbonate solution were added. The mixture was extracted with ethyl acetate/THF, and the extract was washed with saturated brine. The organic layer was dried over anhydrous sodium sulfate, and the solvent was evaporated under reduced pressure. The obtained residue was purified by silica gel column chromatography (ethyl acetate/methanol), and to the obtained fraction was added 4 mol/L hydrogen chloride/ethyl acetate solution. The reaction mixture was concentrated under reduced pressure, and the obtained residue was washed with ethyl acetate to give the title compound (18.0 mg).

$^1$H NMR (300 MHz, DMSO-$d_6$) δ 1.12-1.24 (1H, m), 1.45-1.57 (1H, m), 1.74-1.92 (2H, m), 2.17-2.31 (4H, m), 2.34-2.46 (1H, m), 2.62 (3H, s), 2.71-2.86 (1H, m), 3.31 (3H, s), 3.76-3.94 (1H, m), 7.70-7.91 (1H, m), 9.06-9.71 (2H, m), 12.20-13.03 (1H, m).

Example 100

4-((1R,2S)-2-(cyclobutylamino)cyclopropyl)-5-methyl-N-(5-methyl-1,3,4-thiadiazol-2-yl)thiophene-2-carboxamide hydrochloride The title compound could be produced according to the production methods described in the present specification, a method shown in the Examples, or a method analogous thereto.

Example 101

4-((4-((((1R,2R)-2-(4-((4,4-difluorocyclohexyl)carbamoyl)-2-thienyl)cyclopropyl)amino)methyl)piperidin-1-yl)methyl)benzoic acid dihydrochloride The title compound could be produced according to the production methods described in the present specification, a method shown in the Examples, or a method analogous thereto.

Example 102

4-((1S,2R)-2-((cyclopropylmethyl)amino)cyclopropyl)-5-methyl-N-(1-methyl-1H-pyrazol-4-yl)thiophene-2-carboxamide dihydrochloride To a mixture of 4-((1S,2R)-2-aminocyclopropyl)-5-methyl-N-(1-methyl-1H-pyrazol-4-yl)thiophene-2-carboxamide dihydrochloride (35.0 mg), sodium hydrogen carbonate (21.0 mg), THF (1.5 mL) and methanol (1.5 mL) was added cyclopropanecarbaldehyde (8.99 µL). Under a nitrogen atmosphere, the reaction mixture was stirred at 60° C. for 1.5 hr and at room temperature for 30 min, sodium borohydride (5.69 mg) was added under ice-cooling, and the reaction mixture was stirred at room temperature for 1 hr. The reaction mixture was diluted with ethyl acetate, water and saturated aqueous sodium hydrogen carbonate solution were added, and the mixture was extracted with ethyl acetate. The extract was successively washed with water and saturated brine, and dried over anhydrous sodium sulfate. The solvent was evaporated under reduced pressure. The obtained residue was purified by silica gel column chromatography (ethyl acetate/methanol), and to the obtained fraction was added 4 mol/L hydrogen chloride/ethyl acetate solution. The mixture was stirred overnight, and the precipitated solid was collected by filtration, and washed with ethyl acetate to give the title compound (32.6 mg).

$^1$H NMR (300 MHz, DMSO-$d_6$) δ 0.33-0.45 (2H, m), 0.50-0.66 (2H, m), 1.00-1.26 (2H, m), 1.50-1.65 (1H, m), 2.49 (3H, s), 2.82-3.05 (3H, m), 3.80 (3H, s), 7.49-7.58 (2H, m), 7.92 (1H, s), 9.41 (2H, brs), 10.34 (1H, s).
MS: [M-2HCl+H]$^+$ 331.2.

Example 103

4-((1R,2S)-2-((cyclopropylmethyl)amino)cyclopropyl)-5-methyl-N-(1-methyl-1H-pyrazol-4-yl)thiophene-2-carboxamide dihydrochloride The title compound could be produced according to the production methods described in the present specification, a method shown in the Examples, or a method analogous thereto.

Example 104

4-((1S,2R)-2-(cyclobutylamino)cyclopropyl)-5-methyl-N-(1-methyl-1H-pyrazol-4-yl)thiophene-2-carboxamide dihydrochloride To a mixture of 4-((1S,2R)-2-aminocyclopropyl)-5-methyl-N-(1-methyl-1H-pyrazol-4-yl)thiophene-2-carboxamide dihydrochloride (35.0 mg), sodium hydrogen carbonate (21.0 mg), THF (1.5 mL) and methanol (1.5 mL) was added cyclobutanone (9.01 µL). Under a nitrogen atmosphere, the reaction mixture was stirred at 60° C. for 1.5 hr and at room temperature for 30 min, sodium borohydride (5.69 mg) was added under ice-cooling, and the reaction mixture was stirred at room temperature for 1 hr. The reaction mixture was diluted with ethyl acetate, water and saturated aqueous sodium hydrogen carbonate solution were added, and the mixture was extracted with ethyl acetate. The extract was successively washed with water and saturated brine, and dried over anhydrous sodium sulfate. The solvent was evaporated under reduced pressure. The obtained residue was purified by silica gel column chromatography (ethyl acetate/methanol), and to the obtained fraction was added 4 mol/L hydrogen chloride/ethyl acetate solution. The mixture was stirred overnight, and the precipitated solid was collected by filtration, and washed with ethyl acetate to give the title compound (29.6 mg).

$^1$H NMR (300 MHz, DMSO-$d_6$) δ 1.10-1.24 (1H, m), 1.49-1.60 (1H, m), 1.72-1.89 (2H, m), 2.15-2.35 (4H, m), 2.39-2.48 (4H, m), 2.73-2.84 (1H, m), 3.76-3.91 (4H, m), 7.50-7.56 (2H, m), 7.92 (1H, s), 9.72 (2H, d, J=3.79 Hz), 10.33 (1H, s).

The compounds of Examples 105 to 107 could be produced according to the production methods described in the present specification, a method shown in the Examples, or a method analogous thereto.

Example 105

4-((1R,2S)-2-(cyclobutylamino)cyclopropyl)-5-methyl-N-(1-methyl-1H-pyrazol-4-yl)thiophene-2-carboxamide dihydrochloride [Optical Isomer, Compound Derived from methyl 4-(trans-2-((tert-butoxycarbonyl)amino)cyclopropyl)-5-methylthiophene-2-carboxylate (Optical Isomer, Retention Time Long)]

Example 106

4-((1S,2R)-2-((cyclopropylmethyl)amino)cyclopropyl)-5-methyl-N-(tetrahydro-2H-pyran-4-yl)thiophene-2-carboxamide hydrochloride

Example 107

4-((1R,2S)-2-((cyclopropylmethyl)amino)cyclopropyl)-5-methyl-N-(tetrahydro-2H-pyran-4-yl)thiophene-2-carboxamide hydrochloride

Example 108

4-((1S,2R)-2-(cyclobutylamino)cyclopropyl)-5-methyl-N-(tetrahydro-2H-pyran-4-yl)thiophene-2-carboxamide hydrochloride A) tert-butyl ((1R,2S)-2-(2-methyl-5-((tetrahydro-2H-pyran-4-yl)carbamoyl)thiophen-3-yl)cyclopropyl)carbamate 4-((1S,2R)-2-((tert-Butoxycarbonyl)amino)cyclopropyl)-5-methylthiophene-2-carboxylic acid (100 mg), tetrahydro-2H-pyran-4-amine (0.042 mL) and triethylamine (0.117 mL) were dissolved in DMF (5 mL), O-(7-azabenzotriazol-1-yl)-N,N,N',N'-tetramethyluronium hexafluorophosphate (153 mg) was added, and the mixture was stirred at room temperature overnight. Water was added to the reaction mixture, and the mixture was extracted with ethyl acetate. The organic layer was successively washed with water and saturated brine, dried over anhydrous sodium sulfate, and purified by silica gel column chromatography (ethyl acetate/hexane) to give the title compound (114 mg).

MS: [M-HCl+H]$^+$ 381.3.

B) 4-((1S,2R)-2-aminocyclopropyl)-5-methyl-N-(tetrahydro-2H-pyran-4-yl)thiophene-2-carboxamide hydrochloride To a solution of tert-butyl ((1R,2S)-2-(2-methyl-5-((tetrahydro-2H-pyran-4-yl)carbamoyl)thiophen-3-yl)cyclopropyl)carbamate (110 mg) in ethyl acetate (3 mL) was added 4 mol/L hydrogen chloride/ethyl acetate solution (0.723 mL), and the mixture was stirred at room temperature overnight. The precipitated solid was collected by filtration and washed with ethyl acetate to give the title compound (92 mg).

MS: [M-HCl+H]$^+$ 281.2.

C) 4-((1S,2R)-2-(cyclobutylamino)cyclopropyl)-5-methyl-N-(tetrahydro-2H-pyran-4-yl)thiophene-2-carboxamide hydrochloride To a mixture of 4-((1S,2R)-2-aminocyclopropyl)-5-methyl-N-(tetrahydro-2H-pyran-4-yl)thiophene-2-carboxamide hydrochloride (35.0 mg), sodium hydrogen carbonate (13.9 mg), THF (1.5 mL) and methanol (1.5 mL) was added cyclobutanone (9.94 μL). Under a nitrogen atmosphere, the reaction mixture was stirred at 60° C. for 1.5 hr and at room temperature for 30 min, sodium borohydride (6.27 mg) was added under ice-cooling, and the reaction mixture was stirred at room temperature for 1 hr. The reaction mixture was diluted with ethyl acetate, water and saturated aqueous sodium hydrogen carbonate solution were added, and the mixture was extracted with ethyl acetate. The extract was successively washed with water and saturated brine, and dried over anhydrous sodium sulfate. The solvent was evaporated under reduced pressure. The obtained residue was purified by silica gel column chromatography (ethyl acetate/methanol), and to the obtained fraction was added 4 mol/L hydrogen chloride/ethyl acetate solution. The mixture was stirred overnight, and the precipitated solid was collected by filtration and washed with ethyl acetate to give the title compound (29.7 mg).

$^1$H NMR (300 MHz, DMSO-d$_6$) δ 1.10-1.19 (1H, m), 1.43-1.59 (3H, m), 1.67-1.87 (4H, m), 2.14-2.30 (4H, m), 2.34-2.43 (1H, m), 2.44 (3H, s), 2.69-2.81 (1H, m), 3.35-3.40 (1H, m), 3.76-3.97 (4H, m), 7.30-7.39 (1H, m), 8.08 (1H, d, J=7.95 Hz), 9.56 (2H, brs).

Example 109

4-((1R,2S)-2-(cyclobutylamino)cyclopropyl)-5-methyl-N-(tetrahydro-2H-pyran-4-yl)thiophene-2-carboxamide hydrochloride The title compound could be produced according to the production methods described in the present specification, a method shown in the Examples, or a method analogous thereto.

The compounds of Examples 110 and 111 could be produced according to the production methods described in the present specification, a method shown in the Examples, or a method analogous thereto.

Example 110

4-((((1R,2R)-2-(4-((4,4-difluorocyclohexyl)carbamoyl)-2-thienyl)cyclopropyl)amino)methyl)benzoic acid Example 111

5-((1R,2R)-2-(((5-amino-1,3,4-oxadiazol-2-yl)methyl)amino)cyclopropyl)-N-(4,4-difluorocyclohexyl)thiophene-3-carboxamide Example 112

5-((1R,2R)-2-((cyclobutylmethyl)amino)cyclopropyl)-N-(tetrahydro-2H-pyran-4-yl)thiophene-3-carboxamide To a mixture of 5-((1R,2R)-2-aminocyclopropyl)-N-(tetrahydro-2H-pyran-4-yl)thiophene-3-carboxamide dihydrochloride (40 mg), triethylamine (0.055 mL), THF (1 mL) and methanol (1 mL) was added cyclobutanecarbaldehyde (13.33 mg) at room temperature. The reaction mixture was stirred at room temperature for 5 min, and sodium borohydride (7.5 mg) was added at 0° C. The reaction mixture was stirred at room temperature for 10 min. To the reaction mixture were added water, ethyl acetate and saturated aqueous sodium hydrogen carbonate solution, and the mixture was extracted with ethyl acetate. The extract was washed with water and saturated brine, and dried over anhydrous sodium sulfate. The solvent was evaporated under reduced pressure. The residue was purified by silica gel column chromatography (ethyl acetate/methanol), and to the obtained fraction was added 4 mol/L hydrogen chloride/ethyl acetate solution. The reaction mixture was concentrated under reduced pressure, and the obtained residue was washed with ethyl acetate to give the title compound (31 mg).

$^1$H NMR (300 MHz, DMSO-d$_6$) δ 1.21-1.35 (1H, m), 1.44-1.65 (3H, m), 1.82 (6H, d, J=7.2 Hz), 1.98-2.14 (2H, m), 2.57-2.79 (2H, m), 2.88-2.98 (1H, m), 3.06-3.16 (2H, m), 3.35-3.42 (2H, m), 3.80-4.00 (3H, m), 7.28 (1H, s), 7.95 (1H, d, J=1.5 Hz), 8.06 (1H, d, J=7.6 Hz), 9.01-9.34 (2H, m).

Example 113

5-((1R,2R)-2-((cyclopropylmethyl)amino)cyclopropyl)-N-(tetrahydro-2H-pyran-4-yl)thiophene-3-carboxamide malate To a suspension of L-(−)-malic acid (50.2 mg, 0.37 mmol) in ethyl acetate (2 mL) was added a solution of 5-((1R,2R)-2-((cyclopropylmethyl)amino)cyclopropyl)-N-(tetrahydro-2H-pyran-4-yl)thiophene-3-carboxamide (120 mg, 0.37 mmol) in ethanol (1 mL) at 60° C. The reaction mixture was stirred at room temperature for 1 hr, and concentrated under reduced pressure. To the residue were added ethyl acetate (2 mL) and ethanol (0.5 mL), and ethyl acetate (2 mL) was further added. The precipitate was collected by filtration to give the title compound (106 mg). The obtained title compound (106 mg) was recrystallized from ethanol (0.3 mL) and ethyl acetate (1.2 mL) to give the title compound (65.0 mg).

$^1$H NMR (300 MHz, DMSO-d$_6$) δ 0.12-0.25 (2H, m), 0.37-0.54 (2H, m), 0.82-1.12 (2H, m), 1.23 (1H, dt, J=9.6, 4.9 Hz), 1.41-1.62 (2H, m), 1.72 (2H, dd, J=12.9, 2.3 Hz), 2.14-2.29 (1H, m), 2.33-2.43 (1H, m), 2.52-2.73 (4H, m), 3.17-3.46 (2H, m), 3.81-4.00 (3H, m), 4.06 (1H, dd, J=7.6, 6.1 Hz), 7.18 (1H, d, J=0.8 Hz), 7.84 (1H, d, J=1.1 Hz), 7.99 (1H, d, J=8.0 Hz).

Example 114

5-((1R,2R)-2-((cyclopropylmethyl)amino) cyclopropyl)-N-(tetrahydro-2H-pyran-4-yl)thiophene-3-carboxamide succinate To a solution of succinic acid (36.9 mg, 0.31 mmol) in ethanol (3 mL) was added 5-((1R,2R)-2-((cyclopropylmethyl)amino) cyclopropyl)-N-(tetrahydro-2H-pyran-4-yl)thiophene-3-carboxamide (100 mg, 0.31 mmol) at 60° C. The reaction mixture was stirred at room temperature for 1 hr and concentrated under reduced pressure. To the residue were added ethyl acetate (2 mL) and ethanol (0.5 mL), and ethyl acetate (2 mL) was further added. The precipitate was collected by filtration to give the title compound (105 mg). The obtained title compound (105 mg) was recrystallized from ethanol (0.8 mL) and ethyl acetate (1.2 mL) to give the title compound (62.0 mg).
$^1$H NMR (300 MHz, DMSO-d$_6$) δ 0.06-0.19 (2H, m), 0.34-0.49 (2H, m), 0.78-1.15 (3H, m), 1.41-1.61 (2H, m), 1.64-1.78 (2H, m), 1.97-2.07 (1H, m), 2.32-2.43 (5H, m), 2.50-2.54 (2H, m), 3.30-3.52 (2H, m), 3.75-4.01 (3H, m), 7.13 (1H, d, J=0.8 Hz), 7.79 (1H, d, J=1.1 Hz), 7.97 (1H, d, J=8.0 Hz).

Example 115

5-((1R,2R)-2-((cyclopropylmethyl)amino) cyclopropyl)-N-(tetrahydro-2H-pyran-4-yl)thiophene-3-carboxamide fumarate To a solution of fumaric acid (42.7 mg, 0.37 mmol) in ethanol (1 mL) was added a solution of 5-((1R,2R)-2-((cyclopropylmethyl)amino)cyclopropyl)-N-(tetrahydro-2H-pyran-4-yl)thiophene-3-carboxamide (118 mg, 0.37 mmol) in ethyl acetate (3 mL) at 60° C. To the reaction mixture was added ethyl acetate (2 mL), the mixture was stirred at room temperature, and the precipitate was collected by filtration to give the title compound (122 mg). The obtained title compound (122 mg) was recrystallized from ethanol (1.08 mL) and ethyl acetate (1.8 mL) to give the title compound (85 mg).
$^1$H NMR (300 MHz, DMSO-d$_6$) δ 0.06-0.17 (2H, m), 0.36-0.48 (2H, m), 0.82-1.18 (3H, m), 1.52 (2H, qd, J=11.9, 4.4 Hz), 1.66-1.80 (2H, m), 2.00-2.12 (1H, m), 2.35-2.44 (1H, m), 2.50-2.57 (2H, m), 3.36 (2H, td, J=11.5, 1.9 Hz), 3.75-4.01 (3H, m), 6.59 (2H, s), 7.13 (1H, s), 7.80 (1H, d, J=1.5 Hz), 7.98 (1H, d, J=8.0 Hz).

Example 116

4-((1S,2R)-2-(cyclobutylamino)cyclopropyl)-N-(5-methyl-1,3,4-thiadiazol-2-yl)thiophene-2-carboxamide phosphate To a mixture of 4-((1S,2R)-2-(cyclobutylamino)cyclopropyl)-N-(5-methyl-1,3,4-thiadiazol-2-yl)thiophene-2-carboxamide (100 mg) and ethanol (4 mL) was added 1 mol/l aqueous phosphoric acid solution (0.329 mL) at room temperature, and the mixture was stirred at room temperature for 3 hr. The precipitated solid was collected by filtration, and crystallized from ethanol/water/diisopropyl ether to give the title compound (97.0 mg).
$^1$H NMR (300 MHz, DMSO-d$_6$) δ 0.90-1.12 (2H, m), 1.52-1.74 (2H, m), 1.77-1.94 (2H, m), 1.95-2.21 (3H, m), 2.32-2.39 (1H, m), 2.62 (3H, s), 3.34-3.50 (1H, m), 7.56 (1H, s), 7.98-8.04 (1H, m).

Example 117

4-((1S,2R)-2-(cyclobutylamino)cyclopropyl)-N-(5-methyl-1,3,4-thiadiazol-2-yl)thiophene-2-carboxamide succinate To a mixture of 4-((1S,2R)-2-(cyclobutylamino)cyclopropyl)-N-(5-methyl-1,3,4-thiadiazol-2-yl)thiophene-2-carboxamide (100 mg) and ethyl acetate (4 mL) was added a mixture of succinic acid (35.3 mg) and ethanol (1 mL) at 70° C., and the mixture was stirred at room temperature for 2 hr. The precipitated solid was collected by filtration, and crystallized from ethanol/water/diisopropyl ether to give the title compound (78.2 mg).
$^1$H NMR (300 MHz, DMSO-d$_6$) δ 0.83-1.02 (2H, m), 1.49-1.82 (4H, m), 1.82-1.91 (1H, m), 2.03-2.19 (2H, m), 2.20-2.30 (1H, m), 2.40 (4H, s), 2.62 (3H, s), 3.31 (2H, dt, J=15.52, 7.76 Hz), 7.51 (1H, d, J=1.14 Hz), 7.96 (1H, d, J=1.14 Hz), 10.00 (2H, brs).

Example 118

4-((1S,2R)-2-(cyclobutylamino)cyclopropyl)-N-(5-methyl-1,3,4-thiadiazol-2-yl)thiophene-2-carboxamide sulfate A) 4-((1S,2R)-2-(cyclobutylamino)cyclopropyl)-N-(5-methyl-1,3,4-thiadiazol-2-yl)thiophene-2-carboxamide To a suspension of 4-((1S,2R)-2-aminocyclopropyl)-N-(5-methyl-1,3,4-thiadiazol-2-yl)thiophene-2-carboxamide dihydrochloride (13.3 g), THF (120 mL) and methanol (120 mL) were added triethylamine (15.7 mL), triethyl orthoformate (8.32 mL) and cyclobutanone (3.39 mL) at room temperature, and the mixture was stirred at room temperature overnight. Sodium borohydride (2.14 g) was added under ice-cooling, and the reaction mixture was stirred at room temperature for 1 hr. To the reaction mixture was added saturated aqueous ammonium chloride solution at 0° C., and the mixture was stirred at 0° C. for 30 min. The organic solvent was evaporated under reduced pressure. To the residue were added saturated aqueous sodium hydrogen carbonate solution and THF, and the mixture was extracted with ethyl acetate. The extract was successively washed with water and saturated brine, and dried over anhydrous sodium sulfate. The solvent was evaporated under reduced pressure. The obtained residue was purified by silica gel column chromatography (ethyl acetate/methanol) to give the title compound (6.35 g).
MS: [M+H]$^+$ 335.0.

B) 4-((1S,2R)-2-(cyclobutylamino)cyclopropyl)-N-(5-methyl-1,3,4-thiadiazol-2-yl)thiophene-2-carboxamide sulfate To a mixture of 4-((1S,2R)-2-(cyclobutylamino)cyclopropyl)-N-(5-methyl-, 3,4-thiadiazol-2-yl)thiophene-2-carboxamide (9.51 g) and THF (150 mL) was added 10% aqueous sulfuric acid solution (27.4 mL) at room temperature, and the mixture was stirred at room temperature overnight. To the reaction mixture was added ethyl acetate (100 mL), and the mixture was further stirred for 1 hr. The precipitated solid was collected by filtration, and washed with ethyl acetate. The obtained solid (10.8 g) was dissolved in ethanol (100 mL) and water (65 mL) at 65° C., and the mixture was stirred at 65° C. for 30 min. To the reaction mixture was added dropwise ethyl acetate (250 mL). The reaction mixture was slowly cooled to room temperature, and stirred at room temperature overnight. The precipitated solid was collected by filtration, and washed with ethyl acetate to give the title compound (9.46 g).

$^1$H NMR (300 MHz, DMSO-$d_6$) δ 1.21-1.32 (1H, m), 1.42 (1H, ddd, J=10.22, 6.06, 4.54 Hz), 1.74-1.92 (2H, m), 2.06-2.31 (4H, m), 2.39-2.48 (1H, m), 2.63 (3H, s), 2.84 (1H, dt, J=7.48, 4.02 Hz), 3.87 (1H, quin, J=8.05 Hz), 7.74 (1H, d, J=1.14 Hz), 8.04 (1H, d, J=1.14 Hz)

Example 119

4-((1S,2R)-2-(cyclobutylamino)cyclopropyl)-N-(5-methyl-1,3,4-thiadiazol-2-yl)thiophene-2-carboxamide To 4-((1S,2R)-2-(cyclobutylamino)cyclopropyl)-N-(5-methyl-1,3,4-thiadiazol-2-yl)thiophene-2-carboxamide dihydrochloride (650 mg) were added ethyl acetate and saturated aqueous sodium hydrogen carbonate solution, and the mixture was extracted with ethyl acetate. The extract was washed with water and saturated brine, dried over anhydrous sodium sulfate, and concentrated under reduced pressure to give the title compound (523 mg).

$^1$H NMR (300 MHz, DMSO-$d_6$) δ 0.82-1.00 (2H, m), 1.48-1.88 (5H, m), 2.01-2.17 (2H, m), 2.18-2.25 (1H, m), 2.62 (3H, s), 3.20-3.41 (3H, m), 7.48 (1H, d, J=1.14 Hz), 7.94 (1H, d, J=1.14 Hz).

Example 120

5-((1R,2R)-2-((cyclopropylmethyl)amino)cyclopropyl)-N-(tetrahydro-2H-pyran-4-yl)thiophene-3-carboxamide To 5-((1R,2R)-2-((cyclopropylmethyl)amino)cyclopropyl)-N-(tetrahydro-2H-pyran-4-yl)thiophene-3-carboxamide hydrochloride (600 mg) were added ethyl acetate and saturated aqueous sodium hydrogen carbonate solution, and the mixture was extracted with ethyl acetate. The extract was washed with saturated brine, dried over magnesium sulfate, and concentrated under reduced pressure to give the title compound (520 mg).

$^1$H NMR (300 MHz, CDCl$_3$) δ 0.06-0.17 (2H, m), 0.42-0.55 (2H, m), 0.86-1.04 (2H, m), 1.10-1.22 (1H, m), 1.44-1.57 (2H, m), 1.91-2.13 (3H, m), 2.37-2.50 (1H, m), 2.53-2.66 (2H, m), 3.45-3.61 (2H, m), 3.93-4.05 (2H, m), 4.06-4.25 (1H, m), 5.62-5.77 (1H, m), 6.92-6.98 (1H, m), 7.52 (1H, d, J=1.5 Hz).

The compounds of Examples 121 and 122 could be produced according to the production methods described in the present specification, a method shown in the Examples, or a method analogous thereto.

Example 121

4-((1S,2R)-2-((cyclobutylmethyl)amino)cyclopropyl)-5-methyl-N-(1-methyl-1H-pyrazol-4-yl)thiophene-2-carboxamide dihydrochloride Example 122

4-((1S,2R)-2-((cyclobutylmethyl)amino)cyclopropyl)-5-methyl-N-(tetrahydro-2H-pyran-4-yl)thiophene-2-carboxamide hydrochloride Example 123

4-((1S,2R)-2-(cyclobutylamino)cyclopropyl)-5-methyl-N-(1-methyl-1H-pyrazol-4-yl)thiophene-2-carboxamide hydrochloride A) methyl 4-((1S,2R)-2-((tert-butoxycarbonyl)amino)cyclopropyl)-5-methylthiophene-2-carboxylate Methyl 4-(trans-2-((tert-butoxycarbonyl)amino) cyclopropyl)-5-methylthiophene-2-carboxylate (8 g) was fractionated by SFC (column: CHIRALPAK AD, 20 mmID×250 mmL, manufactured by Daicel Corporation, mobile phase: carbon dioxide/methanol=900/100), and the obtained fraction was concentrated under reduced pressure to give methyl 4-((1S,2R)-2-((tert-butoxycarbonyl)amino)cyclopropyl)-5-methylthiophene-2-carboxylate (optical isomer, retention time short) (3.68 g) and methyl 4-((1R,2S)-2-((tert-butoxycarbonyl)amino)cyclopropyl)-5-methylthiophene-2-carboxylate (optical isomer, retention time long) (3.72 g).
methyl 4-((1S,2R)-2-((tert-butoxycarbonyl)amino)cyclopropyl)-5-methylthiophene-2-carboxylate (optical isomer, retention time short)

HPLC retention time 4.834 min (column: CHIRALPAK ADH, 4.6 mmID×150 mmL, mobile phase: carbon dioxide/methanol=900/100, flow rate: 2.5 mL/min, temperature: 35° C., detection: UV 220 nm, concentration: 0.5 mg/mL, injection volume: 0.005 mL).

MS: [M-tBu+2H]$^+$ 256.1.

methyl 4-((1R,2S)-2-((tert-butoxycarbonyl)amino) cyclopropyl)-5-methylthiophene-2-carboxylate (Optical Isomer, Retention Time Long)

HPLC retention time 6.885 min (column: CHIRALPAK ADH, 4.6 mmID×150 mmL, mobile phase: carbon dioxide/methanol=900/100, flow rate: 2.5 mL/min, temperature: 35° C., detection: UV 220 nm, concentration: 0.5 mg/mL, injection volume: 0.005 mL).

MS: [M-tBu+2H]$^+$ 256.1.

B) 4-((1S,2R)-2-((tert-butoxycarbonyl)amino)cyclopropyl)-5-methylthiophene-2-carboxylic acid Methyl 4-((1S,2R)-2-((tert-butoxycarbonyl)amino)cyclopropyl)-5-methylthiophene-2-carboxylate (3.2 g) was dissolved in methanol (20 mL) and tetrahydrofuran (10 mL), 2 mol/L aqueous sodium hydroxide solution (12.9 mL) was added at 0° C., and the mixture was stirred at room temperature overnight. The reaction mixture was acidified with 1 mol/L hydrochloric acid, and extracted with ethyl acetate. The extract was washed with water and saturated brine, dried over anhydrous sodium sulfate, and concentrated under reduced pressure to give the title compound (3.06 g).
MS: [M−H]⁻ 296.0.

C) tert-butyl ((1R,2S)-2-(2-methyl-5-((1-methyl-1H-pyrazol-4-yl)carbamoyl)thiophen-3-yl)cyclopropyl)carbamate 4-((1S,2R)-2-((tert-Butoxycarbonyl)amino)cyclopropyl)-5-methylthiophene-2-carboxylic acid (3.06 g), l-methyl-1H-pyrazol-4-amine hydrochloride (1.37 g) and triethylamine (5.73 mL) were dissolved in DMF (30 mL), O-(7-azabenzotriazol-1-yl)-N,N,N',N'-tetramethyluronium hexafluorophosphate (4.69 g) was added, and the mixture was stirred at 40° C. overnight. Water was added to the reaction mixture, and the mixture was extracted with ethyl acetate. The extract was washed with saturated aqueous sodium hydrogen carbonate solution, water and saturated brine, dried over anhydrous sodium sulfate, and concentrated under reduced pressure. The residue was purified by silica gel column chromatography (hexane/ethyl acetate and methanol/ethyl acetate) to give the title compound (3.7 g).
MS: [M+H]⁺ 377.1

D) 4-((1S,2R)-2-aminocyclopropyl)-5-methyl-N-(1-methyl-1H-pyrazol-4-yl)thiophene-2-carboxamide dihydrochloride To a suspension of tert-butyl ((1R,2S)-2-(2-methyl-5-((1-methyl-1H-pyrazol-4-yl)carbamoyl)thiophen-3-yl)cyclopropyl)carbamate (3.7 g) in ethyl acetate (45 mL) and methanol (25 mL) was added 4 mol/L hydrogen chloride/ethyl acetate solution (49.1 mL) at 0° C., and the mixture was stirred at room temperature overnight. The precipitated solid was collected by filtration, and washed with ethyl acetate to give the title compound (3 g).
MS: [M+H−2HCl]⁺ 277.1.

E) 4-((1S,2R)-2-(cyclobutylamino)cyclopropyl)-5-methyl-N-(1-methyl-1H-pyrazol-4-yl)thiophene-2-carboxamide To a suspension of 4-((1S,2R)-2-aminocyclopropyl)-5-methyl-N-(1-methyl-1H-pyrazol-4-yl)thiophene-2-carboxamide dihydrochloride (3 g) in methanol (40 mL) were added triethylamine (2.99 mL, 21.5 mmol), trimethoxymethane (1.90 mL, 17.2 mmol) and cyclobutanone (0.77 mL, 10.3 mmol) at room temperature. The reaction mixture was stirred at room temperature overnight, and sodium borohydride (487 mg) was added under cooling at −40° C. The reaction mixture was stirred at −40° C. for 1 hr, saturated aqueous ammonium chloride solution was added, and the mixture was concentrated under reduced pressure. To the residue was added saturated aqueous sodium hydrogen carbonate solution, and the mixture was extracted with ethyl acetate. The extract was washed with saturated brine, and dried over anhydrous magnesium sulfate. The solvent was evaporated under reduced pressure and the residue was purified by silica gel column chromatography (ethyl acetate/methanol) to give the title compound (2 g).
MS: [M+H]⁺ 331.1.

F) 4-((1S,2R)-2-(cyclobutylamino)cyclopropyl)-5-methyl-N-(1-methyl-1H-pyrazol-4-yl)thiophene-2-carboxamide hydrochloride 4N Hydrogen chloride/ethyl acetate solution (6.08 mL, 24.33 mmol) was added to a solution of 4-((1S,2R)-2-(cyclobutylamino)cyclopropyl)-5-methyl-N-(1-methyl-1H-pyrazol-4-yl)thiophene-2-carboxamide (2.68 g, 8.11 mmol) in ethyl acetate (20 mL) at 0° C. The precipitate was collected by filtration, and washed with ethyl acetate to give a white solid. The obtained white solid was recrystallized from ethanol, water and ethyl acetate to give the title compound (1.920 g) as a white solid.
¹H NMR (300 MHz, DMSO-d₆) δ 1.10-1.26 (1H, m), 1.51-1.55 (1H, m), 1.66-1.94 (2H, m), 2.14-2.36 (4H, m), 2.39-2.50 (4H, m), 2.76-2.81 (1H, m), 3.70-3.93 (4H, m), 7.50-7.57 (2H, m), 7.92 (1H, s), 9.68 (2H, brs), 10.33 (1H, s).

The compounds of Examples 124 and 125 could be produced according to the production methods described in the present specification, a method shown in the Examples, or a method analogous thereto.

Example 124

4-((1S,2R)-2-aminocyclopropyl)-N-(5-methyl-1,3,4-thiadiazol-2-yl)thiophene-2-carboxamide dihydrochloride Example 125

5-((1S,2S)-2-((cyclopropylmethyl)amino)cyclopropyl)-N-(tetrahydro-2H-pyran-4-yl)thiophene-3-carboxamide hydrochloride Example compounds are shown in the following Tables. MS in the Tables shows measured values.

TABLE 1

| Ex. No. | IUPAC name | structure | salt | MS |
|---|---|---|---|---|
| 1 | 4-(trans-2-aminocyclopropyl)-5-methyl-N-(5-methyl-1,3,4-thiadiazol-2-yl)thiophene-2-carboxamide | 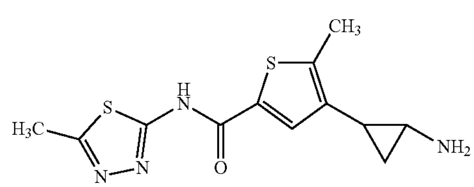 [SMILES: Cc1nnc(NC(=O)c2cc(C3CC3N)c(C)s2)s1] | 2HCl | 295.0 |

TABLE 1-continued

| Ex. No. | IUPAC name | structure | salt | MS |
|---|---|---|---|---|
| 2 | 4-(trans-2-((cyclo-propylmethyl)amino)-cyclopropyl)-5-methyl-N-(5-methyl-1,3,4-thiadiazol-2-yl)thiophene-2-carboxamide | 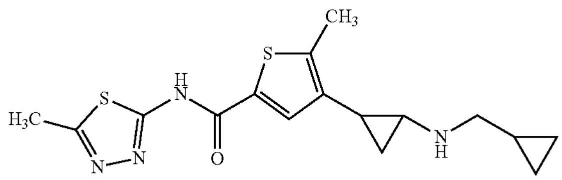 [SMILES: Cc1nnc(NC(=O)c2cc(C3CC3NCC3CC3)c(C)s2)s1] | 2HCl | 349.1 |
| 3 | 5-(trans-2-((cyclo-propylmethyl)amino)-cyclopropyl)-N-(4,4-difluorocyclohexyl)-1-methyl-1H-pyrazole-3-carboxamide | 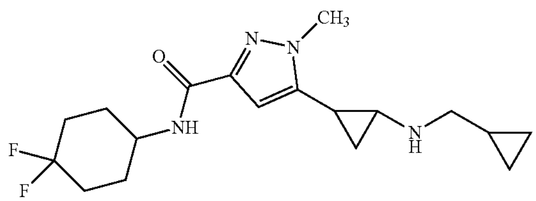 [SMILES: Cn1nc(C(=O)NC2CCC(F)(F)CC2)cc1C1CC1NCC1CC1] | HCl | 353.1 |
| 4 | 5-(trans-2-aminocyclopropyl)-N-(4,4-difluorocyclohexyl)-1-methyl-1H-pyrazole-3-carboxamide | 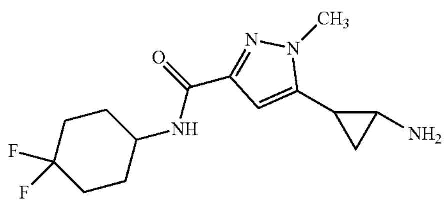 [SMILES: Cn1nc(C(=O)NC2CCC(F)(F)CC2)cc1C1CC1N] | HCl | 299.1 |
| 5 | 4-(trans-2-aminocyclopropyl)-N-(5-methyl-1,3,4-thiadiazol-2-yl)-2-naphthamide | 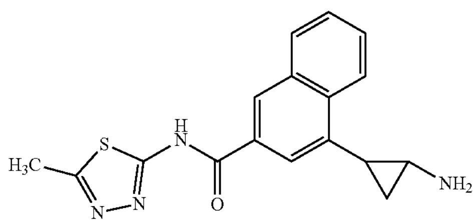 [SMILES: Cc1nnc(NC(=O)c2cc(C3CC3N)c3ccccc3c2)s1] | 2HCl | 325.1 |
| 6 | N-(5-methyl-1,3,4-thiadiazol-2-yl)-4-(trans-2-((tetrahydro-2H-pyran-4-ylmethyl)amino)-cyclopropyl)-2-naphthamide | 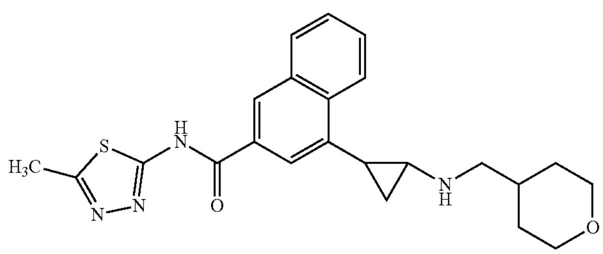 [SMILES: Cc1nnc(NC(=O)c2cc(C3CC3NCC3CCOCC3)c3ccccc3c2)s1] | HCl | 421.1 |
| 7 | 4-(trans-2-((cyclo-propylmethyl)amino)-cyclopropyl)-N-(5-methyl-1,3,4-thiadiazol-2-yl)-2-naphthamide | 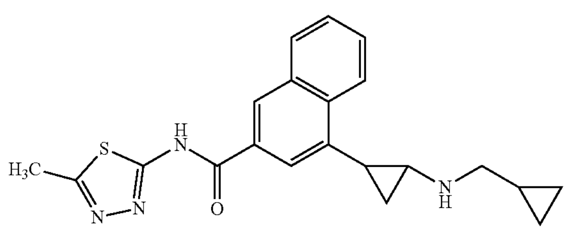 [SMILES: Cc1nnc(NC(=O)c2cc(C3CC3NCC3CC3)c3ccccc3c2)s1] | 2HCl | 379.2 |
| 8 | N-(4,4-difluorocyclohexyl)-5-methyl-4-(trans-2-((tetrahydro-2H-pyran-4-ylmethyl)-amino)cyclopropyl)-thiophene-2-carboxamide | 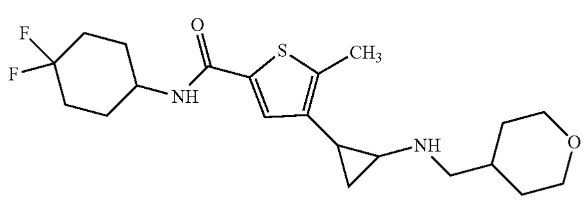 [SMILES: Cc1sc(C(=O)NC2CCC(F)(F)CC2)cc1C1CC1NCC1CCOCC1] | HCl | 413.2 |

TABLE 1-continued

| Ex. No. | IUPAC name | structure | salt | MS |
|---|---|---|---|---|
| 9 | 7-(trans-2-aminocyclopropyl)-N-(5-methyl-1,3,4-thiadiazol-2-yl)-2,3-dihydro-1-benzofuran-5-carboxamide | 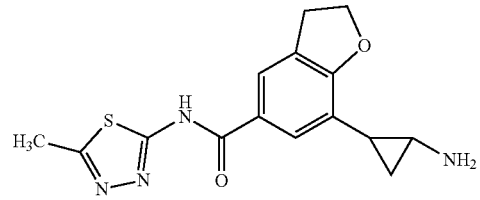 [SMILES: Cc1nnc(NC(=O)c2cc3c(c(C4CC4N)c2)OCC3)s1] | 2HCl | 317.0 |
| 10 | 7-(trans-2-((cyclopropylmethyl)amino)cyclopropyl)-N-(5-methyl-1,3,4-thiadiazol-2-yl)-2,3-dihydro-1-benzofuran-5-carboxamide | 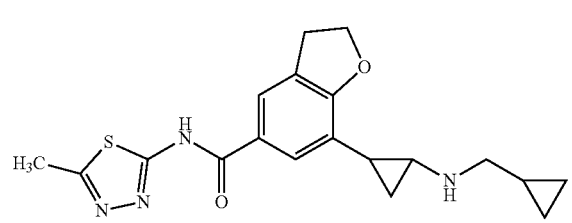 [SMILES: Cc1nnc(NC(=O)c2cc3c(c(C4CC4NCC4CC4)c2)OCC3)s1] | 2HCl | 371.1 |
| 11 | 7-(trans-2-((cyclopropylmethyl)amino)cyclopropyl)-N-(4,4-difluorocyclohexyl)-2,3-dihydro-1-benzofuran-5-carboxamide | 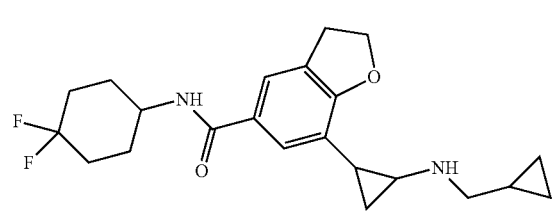 [SMILES: O=C(NC1CCC(F)(F)CC1)c1cc2c(c(C3CC3NCC3CC3)c1)OCC2] | HCl | 391.2 |
| 12 | N-(4,4-difluorocyclohexyl)-7-(trans-2-((tetrahydro-2H-pyran-4-ylmethyl)amino)cyclopropyl)-2,3-dihydro-1-benzofuran-5-carboxamide | 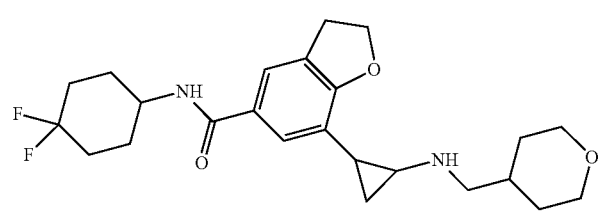 [SMILES: O=C(NC1CCC(F)(F)CC1)c1cc2c(c(C3CC3NCC3CCOCC3)c1)OCC2] | HCl | 435.2 |
| 13 | 5-(trans-2-aminocyclopropyl)-N-(4,4-difluorocyclohexyl)-6-methylnicotinamide | 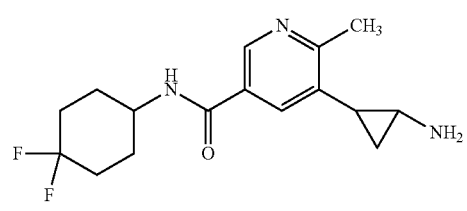 [SMILES: Cc1ncc(C(=O)NC2CCC(F)(F)CC2)cc1C1CC1N] | 2HCl | 310.2 |
| 14 | 5-(trans-2-((cyclopropylmethyl)amino)cyclopropyl)-N-(4,4-difluorocyclohexyl)-6-methylnicotinamide | 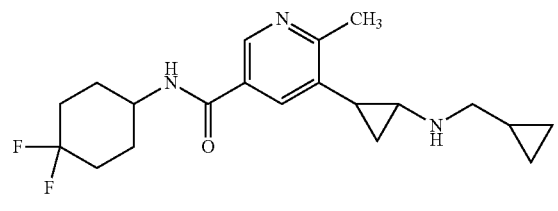 [SMILES: Cc1ncc(C(=O)NC2CCC(F)(F)CC2)cc1C1CC1NCC1CC1] | 2HCl | 364.2 |
| 15 | 3-(trans-2-aminocyclopropyl)-N-(5-methyl-1,3,4-thiadiazol-2-yl)-1-naphthamide | 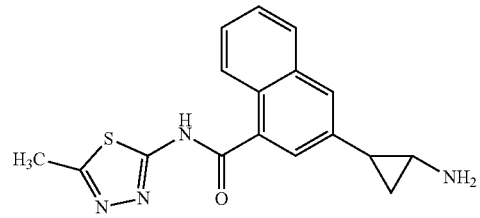 [SMILES: Cc1nnc(NC(=O)c2cc(C3CC3N)cc3ccccc23)s1] | 2HCl | 325.1 |

TABLE 1-continued

| Ex. No. | IUPAC name | structure | salt | MS |
|---|---|---|---|---|
| 16 | N-(5-methyl-1,3,4-thiadiazol-2-yl)-3-(trans-2-((tetrahydro-2H-pyran-4-ylmethyl)amino)-cyclopropyl)-1-naphthamide | 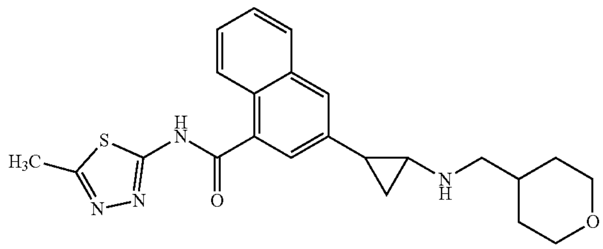 [SMILES: Cc1nnc(NC(=O)c2cc(C3CC3NCC3CCOCC3)cc3ccccc23)s1] | 2HCl | 423.2 |
| 17 | 4-(trans-2-(cyclobutylamino)-cyclopropyl)-5-methyl-N-(5-methyl-1,3,4-thiadiazol-2-yl)thiophene-2-carboxamide | 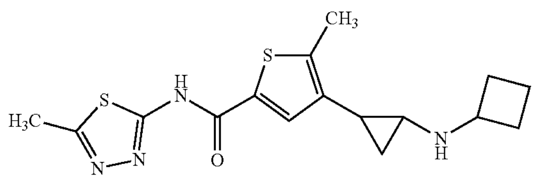 [SMILES: Cc1nnc(NC(=O)c2cc(C3CC3NC3CCC3)c(C)s2)s1] | 1/2 fumarate | 349.1 |
| 18 | 4-(trans-2-((cyclopropylmethyl)amino)-cyclopropyl)-N-(4,4-difluorocyclohexyl)-5-methylthiophene-2-carboxamide | 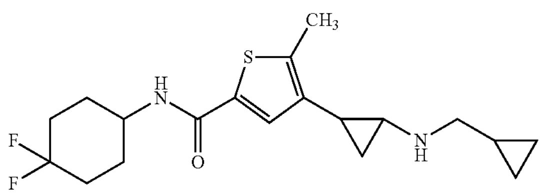 [SMILES: Cc1sc(C(=O)NC2CCC(F)(F)CC2)cc1C1CC1NCC1CC1] | fumarate | 369.1 |
| 19 | 4-(trans-2-((cyclopropylmethyl)amino)-cyclopropyl)-5-methyl-N-(tetrahydro-2H-pyran-4-yl)thiophene-2-carboxamide | 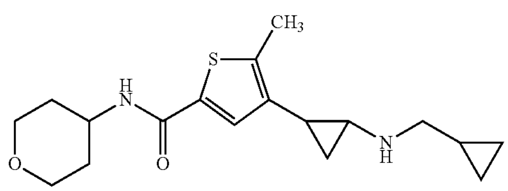 [SMILES: Cc1sc(C(=O)NC2CCOCC2)cc1C1CC1NCC1CC1] | fumarate | 335.1 |
| 20 | 5-methyl-N-(5-methyl-1,3,4-thiadiazol-2-yl)-4-(trans-2-((tetrahydro-2H-pyran-4-ylmethyl)-amino)cyclopropyl)-thiophene-2-carboxamide | 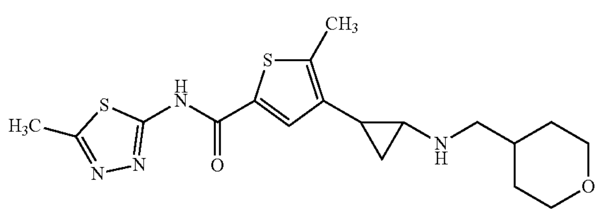 [SMILES: Cc1nnc(NC(=O)c2cc(C3CC3NCC3CCOCC3)c(C)s2)s1] | 2HCl | 391.1 |
| 21 | N-(4,4-difluoro-cyclohexyl)-5-methyl-4-(trans-2-(tetrahydro-2H-pyran-4-ylamino)-cyclopropyl)thiophene-2-carboxamide | 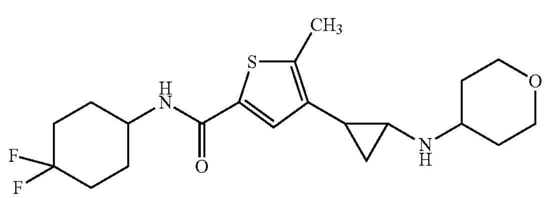 [SMILES: Cc1sc(C(=O)NC2CCC(F)(F)CC2)cc1C1CC1NC1CCOCC1] | fumarate | 399.2 |
| 22 | 4-(trans-2-(cyclobutylamino)-cyclopropyl)-5-methyl-N-(1-methyl-1H-pyrazol-4-yl)thiophene-2-carboxamide | 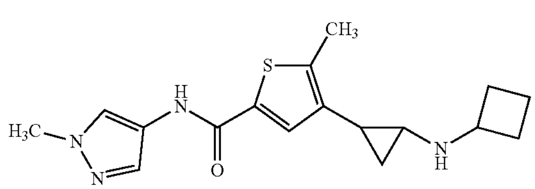 [SMILES: Cc1sc(C(=O)Nc2cnn(C)c2)cc1C1CC1NC1CCC1] | 2HCl | 331.3 |

TABLE 1-continued

| Ex. No. | IUPAC name | structure | salt | MS |
|---|---|---|---|---|
| 23 | 5-(trans-2-((cyclo-propylmethyl)amino)-cyclopropyl)-N-(5-methyl-1,3,4-thiadiazol-2-yl)thiophene-3-carboxamide | 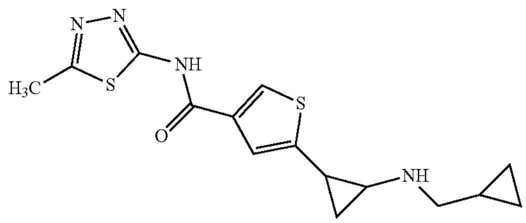 [SMILES: Cc1nnc(NC(=O)c2csc(C3CC3NCC3CC3)c2)s1] | 2HCl | 335.1 |
| 24 | N-(4,4-difluorocyclohexyl)-5-(trans-2-((tetrahydro-2H-pyran-4-ylmethyl)-amino)cyclopropyl)-thiophene-3-carboxamide | 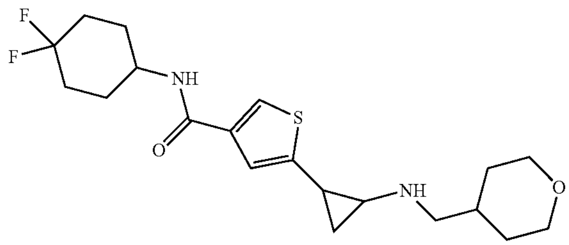 [SMILES: O=C(NC1CCC(F)(F)CC1)c1csc(C2CC2NCC2CCOCC2)c1] | HCl | 399.2 |
| 25 | 4-(trans-2-aminocyclopropyl)-5-methyl-N-(1-methyl-1H-pyrazol-4-yl)thiophene-2-carboxamide | 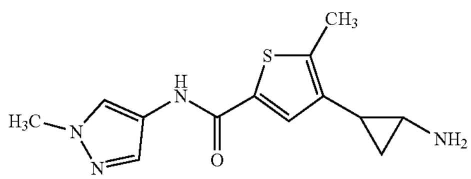 [SMILES: Cc1sc(C(=O)Nc2cnn(C)c2)cc1C1CC1N] | 2HCl | 277.1 |
| 26 | 4-(trans-2-((cyclo-propylmethyl)amino)-cyclopropyl)-5-methyl-N-(5-methyl-1,3,4-thiadiazol-2-yl)thiophene-2-carboxamide | 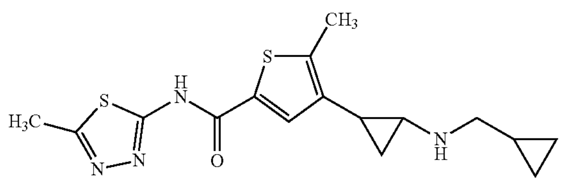 [SMILES: Cc1nnc(NC(=O)c2cc(C3CC3NCC3CC3)c(C)s2)s1] | fumarate | 349.1 |
| 27 | 4-(trans-2-((cyclo-propylmethyl)amino)-cyclopropyl)-N-(5-methyl-1,3,4-thiadiazol-2-yl)thiophene-2-carboxamide | 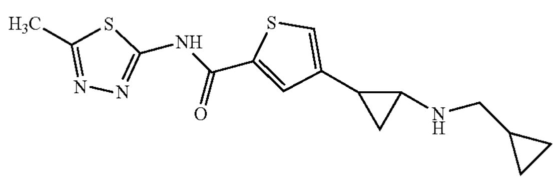 [SMILES: Cc1nnc(NC(=O)c2cc(C3CC3NCC3CC3)cs2)s1] | 2HCl | 335.1 |
| 28 | 4-(trans-2-((cyclo-propylmethyl)amino)-cyclopropyl)-N-(4,4-difluorocyclohexyl)-thiophene-2-carboxamide | 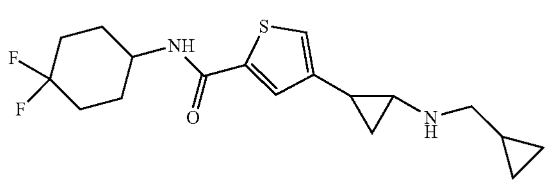 [SMILES: O=C(NC1CCC(F)(F)CC1)c1cc(C2CC2NCC2CC2)cs1] | HCl | 355.2 |
| 29 | N-(4,4-difluorocyclohexyl)-4-(trans-2-(tetrahydro-2H-pyran-4-ylamino)-cyclopropyl)thio-phene-2-carboxamide | 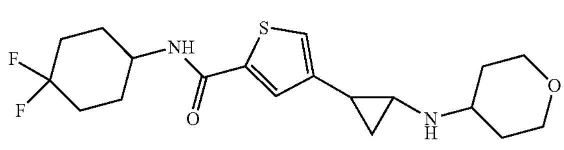 [SMILES: O=C(NC1CCC(F)(F)CC1)c1cc(C2CC2NC2CCOCC2)cs1] | HCl | 385.1 |

TABLE 1-continued

| Ex. No. | IUPAC name | structure | salt | MS |
|---|---|---|---|---|
| 30 | 5-(trans-2-((cyclopropylmethyl)amino)-cyclopropyl)-N-(4,4-difluorocyclohexyl)-thiophene-3-carboxamide | 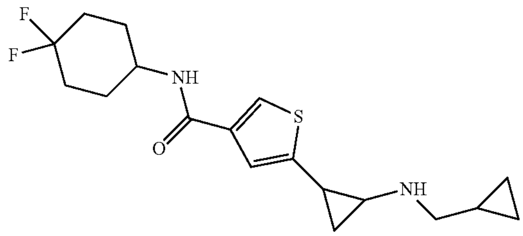 [SMILES: O=C(NC1CCC(F)(F)CC1)c1csc(C2CC2NCC2CC2)c1] | HCl | 355.2 |
| 31 | N-(4,4-difluoro-cyclohexyl)-5-(trans-2-(tetrahydro-2H-pyran-4-ylamino)-cyclopropyl)thiophene-3-carboxamide | 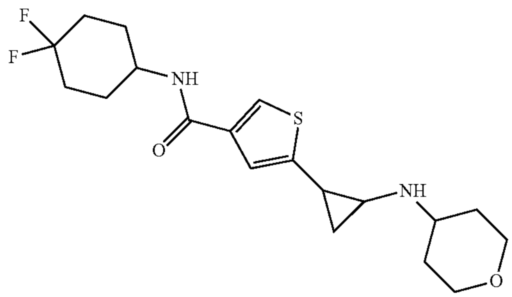 [SMILES: O=C(NC1CCC(F)(F)CC1)c1csc(C2CC2NC2CCOCC2)c1] | HCl | 385.1 |
| 32 | 5-(trans-2-((cyclopropylmethyl)amino)-cyclopropyl)-N-(tetrahydro-2H-pyran-4-yl)thiophene-3-carboxamide | 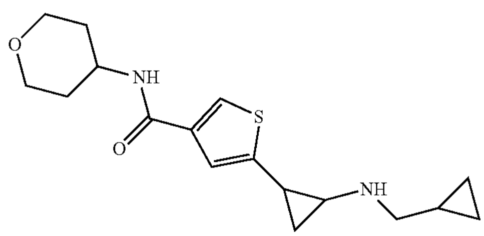 [SMILES: O=C(NC1CCOCC1)c1csc(C2CC2NCC2CC2)c1] | HCl | 321.1 |
| 33 | 5-(trans-2-(cyclobutylamino)cyclopropyl)-N-(5-methyl-1,3,4-thiadiazol-2-yl)thiophene-3-carboxamide | 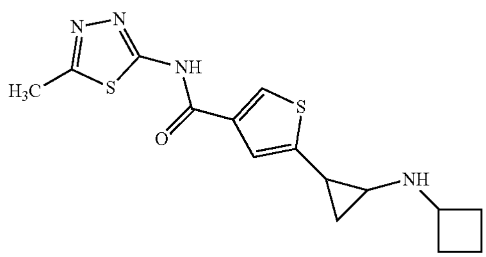 [SMILES: Cc1nnc(NC(=O)c2csc(C3CC3NC3CCC3)c2)s1] | 2HCl | 335.1 |
| 34 | 5-(trans-2-(cyclobutylamino)cyclopropyl)-N-(1-methyl-1H-pyrazol-4-yl)thiophene-3-carboxamide | 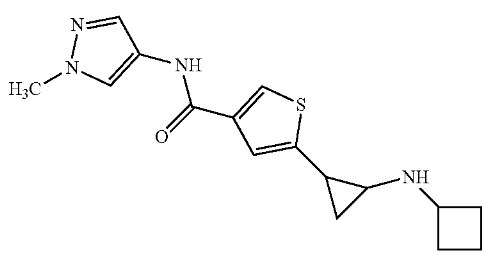 [SMILES: Cn1cc(NC(=O)c2csc(C3CC3NC3CCC3)c2)cn1] | HCl | 317.2 |
| 35 | 4-(trans-2-((cyclopropylmethyl)amino)-cyclopropyl)-N-(4,4-difluorocyclohexyl)-thiazole-2-carboxamide | 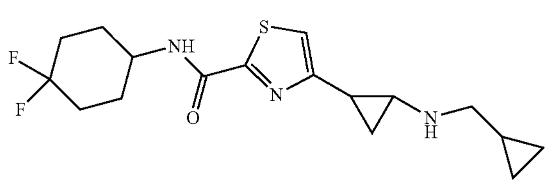 [SMILES: O=C(NC1CCC(F)(F)CC1)c1nc(C2CC2NCC2CC2)cs1] | HCl | 356.2 |

TABLE 1-continued

| Ex. No. | IUPAC name | structure | salt | MS |
|---|---|---|---|---|
| 36 | 5-(trans-2-((cyclo-propylmethyl)amino)-cyclopropyl)-N-(4,4-difluorocyclohexyl)-thiophene-2-carboxamide | 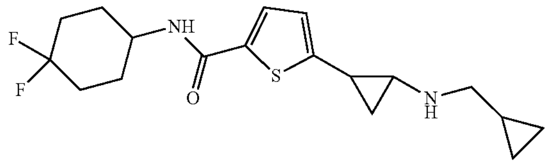 [SMILES: O=C(NC1CCC(F)(F)CC1)c1ccc(C2CC2NCC2CC2)s1] | HCl | 355.1 |
| 37 | 5-(trans-2-((cyclo-propylmethyl)amino)-cyclopropyl)-N-(5-methyl-1,3,4-thiadiazol-2-yl)thiophene-2-carboxamide | 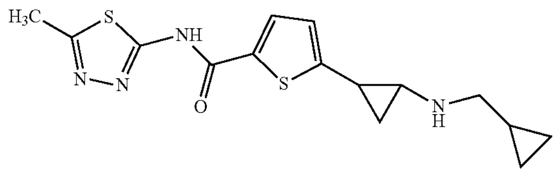 [SMILES: Cc1nnc(NC(=O)c2ccc(C3CC3NCC3CC3)s2)s1] | 2HCl | 335.1 |
| 38 | N-cyclopentyl-5-((1R,2R)-2-(tetrahydro-2H-pyran-4-ylamino)-cyclopropyl)thio-phene-3-carboxamide | 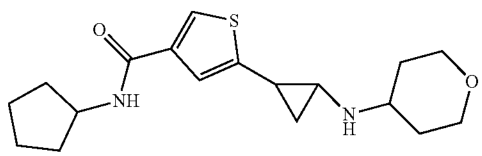 [SMILES: O=C(NC1CCCC1)c1csc(C2CC2NC2CCOCC2)c1] | HCl | 335.1 |
| 39 | N-cyclopentyl-5-((1S,2S)-2-(tetrahydro-2H-pyran-4-ylamino)-cyclopropyl)thio-phene-3-carboxamide | 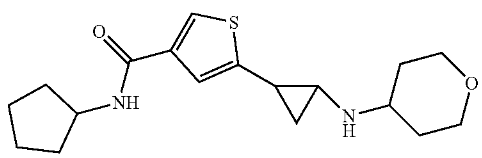 [SMILES: O=C(NC1CCCC1)c1csc(C2CC2NC2CCOCC2)c1] | HCl | 335.1 |
| 40 | N-(5-methyl-1,3,4-thiadiazol-2-yl)-5-((1R,2R)-2-((tetrahydro-2H-pyran-4-ylmethyl)-amino)cyclopropyl)-thiophene-3-carboxamide | 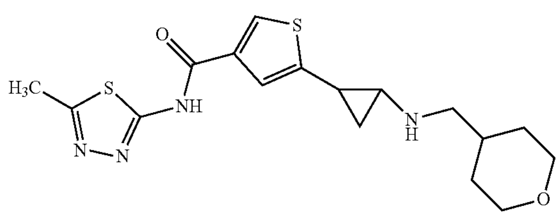 [SMILES: Cc1nnc(NC(=O)c2csc(C3CC3NCC3CCOCC3)c2)s1] | 2HCl | 379.1 |
| 41 | N-(5-methyl-1,3,4-thiadiazol-2-yl)-5-((1S,2S)-2-((tetrahydro-2H-pyran-4-ylmethyl)-amino)cyclopropyl)-thiophene-3-carboxamide | 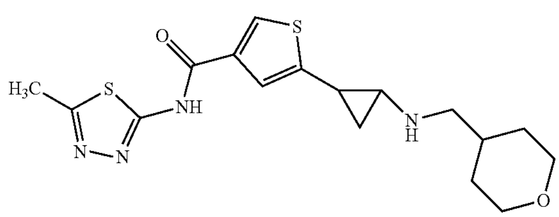 [SMILES: Cc1nnc(NC(=O)c2csc(C3CC3NCC3CCOCC3)c2)s1] | 2HCl | 379.1 |
| 42 | 5-((1R,2R)-2-(cyclobutylamino)-cyclopropyl)-N-(tetrahydro-2H-pyran-4-yl)thiophene-3-carboxamide | 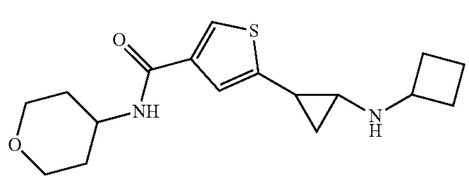 [SMILES: O=C(NC1CCOCC1)c1csc(C2CC2NC2CCC2)c1] | HCl | 321.1 |
| 43 | 5-((1S,2S)-2-(cyclo-butylamino)cyclo-propyl)-N-(tetrahydro-2H-pyran-4-yl)thiophene-3-carboxamide | 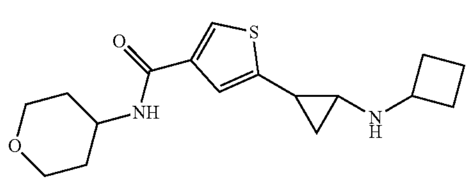 [SMILES: O=C(NC1CCOCC1)c1csc(C2CC2NC2CCC2)c1] | HCl | 321.1 |

TABLE 1-continued

| Ex. No. | IUPAC name | structure | salt | MS |
|---|---|---|---|---|
| 44 | N-(4,4-difluorocyclohexyl)-5-((1R,2R)-2-(tetrahydro-2H-pyran-4-ylamino)-cyclopropyl)thiophene-3-carboxamide | 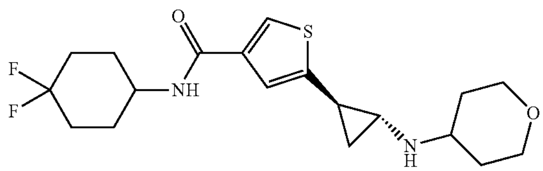 [SMILES: O=C(NC1CCC(F)(F)CC1)c1csc([C@@H]2C[C@H]2NC2CCOCC2)c1] | HCl | 385.0 |
| 45 | 5-((1R,2R)-2-(cis-(4-aminocyclohexyl)-amino)cyclopropyl)-N-(4,4-difluorocyclohexyl)-thiophene-3-carboxamide or 5-((1R,2R)-2-(trans-(4-aminocyclohexyl)-amino)cyclopropyl)-N-(4,4-difluorocyclohexyl)-thiophene-3-carboxamide | 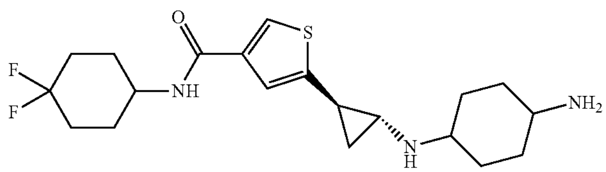 [SMILES: NC1CCC(N[C@@H]2C[C@H]2c2cc(C(=O)NC3CCC(F)(F)CC3)cs2)CC1] | 2HCl | 398.1 |
| 46 | 5-((1R,2R)-2-(cis-(4-aminocyclohexyl)amino)cyclopropyl)-N-(4,4-difluorocyclohexyl)-thiophene-3-carboxamide or 5-((1R,2R)-2-(trans-(4-aminocyclohexyl)-amino)cyclopropyl)-N-(4,4-difluorocyclohexyl)-thiophene-3-carboxamide | 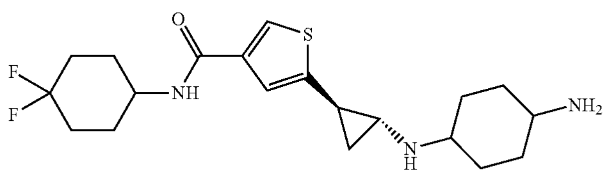 [SMILES: NC1CCC(N[C@@H]2C[C@H]2c2cc(C(=O)NC3CCC(F)(F)CC3)cs2)CC1] | 2HCl | 398.1 |
| 47 | 5-((1R,2R)-2-((4,4-difluorocyclohexyl)-amino)cyclopropyl)-N-(tetrahydro-2H-pyran-4-yl)thiophene-3-carboxamide | 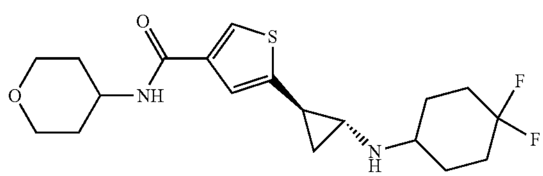 [SMILES: O=C(NC1CCOCC1)c1csc([C@@H]2C[C@H]2NC2CCC(F)(F)CC2)c1] | HCl | 385.0 |
| 48 | 5-((1R,2R)-2-((1-cyclopropylpiperidin-4-yl)amino)-cyclopropyl)-N-(5-methyl-1,3,4-thiadiazol-2-yl)thiophene-3-carboxamide | 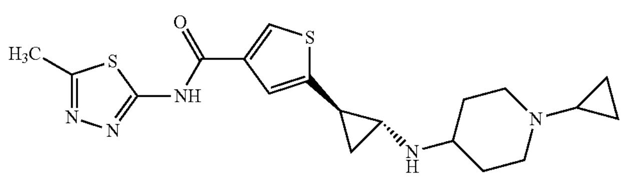 [SMILES: Cc1nnc(NC(=O)c2csc([C@@H]3C[C@H]3NC3CCN(C4CC4)CC3)c2)s1] | 2HCl | 403.9 |
| 49 | N-(5-methyl-1,3,4-thiadiazol-2-yl)-5-((1R,2R)-2-(tetrahydro-2H-pyran-4-ylamino)-cyclopropyl)thiophene-3-carboxamide | 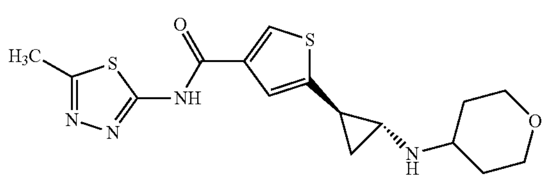 [SMILES: Cc1nnc(NC(=O)c2csc([C@@H]3C[C@H]3NC3CCOCC3)c2)s1] | HCl | 364.9 |
| 50 | N-(2-methyl-1,3-thiazol-5-yl)-5-((1R,2R)-2-(tetrahydro-2H-pyran-4-ylamino)-cyclopropyl)thiophene-3-carboxamide | 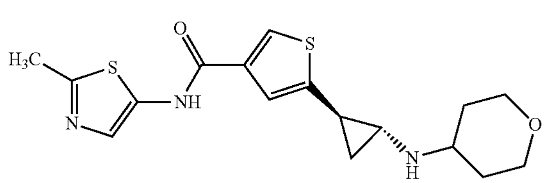 [SMILES: Cc1ncc(NC(=O)c2csc([C@@H]3C[C@H]3NC3CCOCC3)c2)s1] | HCl | 364.0 |

TABLE 1-continued

| Ex. No. | IUPAC name | structure | salt | MS |
|---|---|---|---|---|
| 51 | N-(4,4-difluorocyclohexyl)-5-((1R,2R)-2-((tetrahydro-2H-pyran-4-ylmethyl)-amino)cyclopropyl)-thiophene-3-carboxamide | 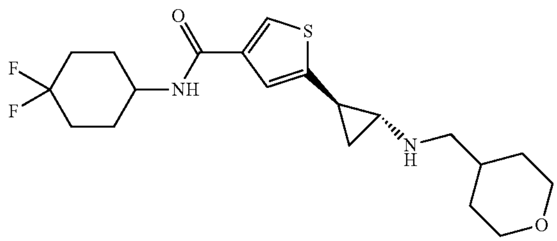 [SMILES: O=C(NC1CCC(F)(F)CC1)c1csc([C@@H]2C[C@H]2NCC2CCOCC2)c1] | HCl | 399.0 |
| 52 | 5-((1R,2R)-2-((tetrahydro-2H-pyran-4-ylmethyl)-amino)cyclopropyl)-N-(1-(2,2,2-trifluoroethyl)-piperidin-4-yl)thiophene-3-carboxamide | 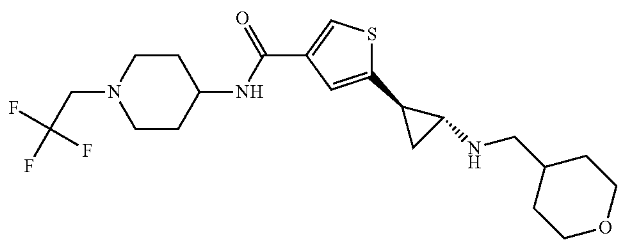 [SMILES: O=C(NC1CCN(CC(F)(F)F)CC1)c1csc([C@@H]2C[C@H]2NCC2CCOCC2)c1] | HCl | 446.1 |
| 53 | N-(2-methyl-1,3-thiazol-5-yl)-5-((1R,2R)-2-((tetrahydro-2H-pyran-4-ylmethyl)-amino)cyclopropyl)-thiophene-3-carboxamide | 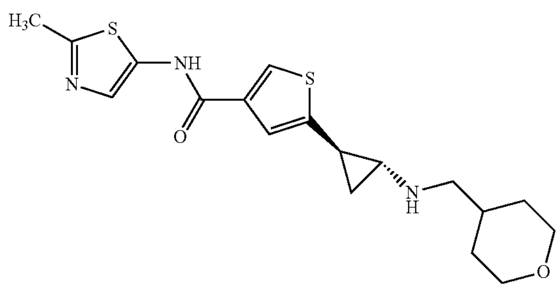 [SMILES: Cc1ncc(NC(=O)c2csc([C@@H]3C[C@H]3NCC3CCOCC3)c2)s1] | 2HCl | 378.0 |
| 54 | N-(1,3-dimethyl-1H-pyrazol-4-yl)-5-((1R,2R)-2-((tetrahydro-2H-pyran-4-ylmethyl)-amino)cyclopropyl)-thiophene-3-carboxamide | 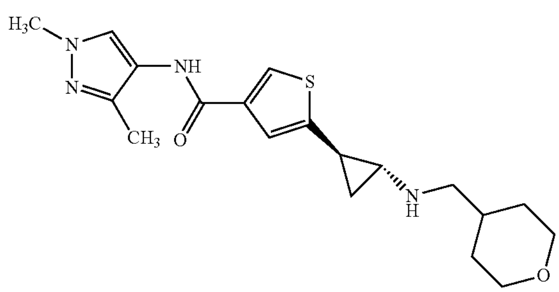 [SMILES: Cc1nn(C)cc1NC(=O)c1csc([C@@H]2C[C@H]2NCC2CCOCC2)c1] | 2HCl | 375.0 |
| 55 | N-(1,5-dimethyl-1H-pyrazol-4-yl)-5-((1R,2R)-2-((tetrahydro-2H-pyran-4-ylmethyl)-amino)cyclopropyl)-thiophene-3-carboxamide | 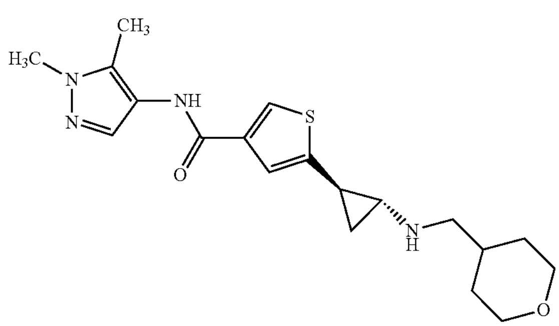 [SMILES: Cc1c(NC(=O)c2csc([C@@H]3C[C@H]3NCC3CCOCC3)c2)cnn1C] | 2HCl | 375.1 |

TABLE 1-continued

| Ex. No. | IUPAC name | structure | salt | MS |
|---|---|---|---|---|
| 56 | N-cyclopropyl-5-((1R,2R)-2-((tetrahydro-2H-pyran-4-ylmethyl)-amino)cyclopropyl)-thiophene-3-carboxamide | 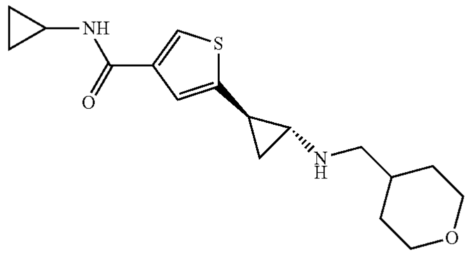 [SMILES: O=C(NC1CC1)c1csc([C@@H]2C[C@H]2NCC2CCOCC2)c1] | HCl | 321.0 |
| 57 | 4-(trans-2-(cyclobutylamino)-cyclopropyl)-N-(5-methyl-1,3,4-thiadiazol-2-yl)thiophene-2-carboxamide | 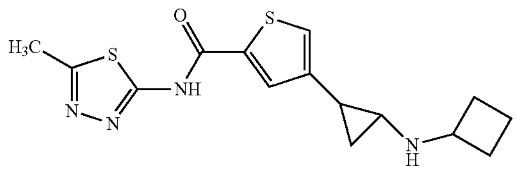 [SMILES: Cc1nnc(NC(=O)c2cc(C3CC3NC3CCC3)cs2)s1] | HCl | 335.0 |
| 58 | N-(5-methyl-1,3,4-thiadiazol-2-yl)-4-(trans-2-((tetrahydro-2H-pyran-4-ylmethyl)-amino)cyclopropyl)-thiophene-2-carboxamide | 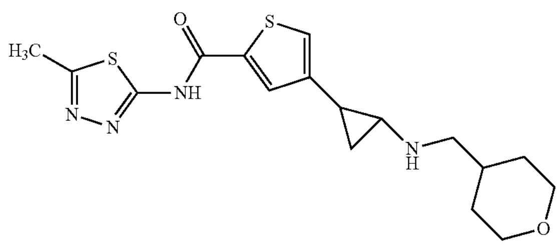 [SMILES: Cc1nnc(NC(=O)c2cc(C3CC3NCC3CCOCC3)cs2)s1] | HCl | 379.1 |
| 59 | 4-(trans-2-((1-cyclopropyl-piperidin-4-yl)-amino)cyclopropyl)-N-(5-methyl-1,3,4-thiadiazol-2-yl)thiophene-2-carboxamide | 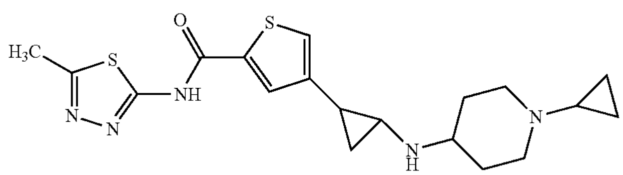 [SMILES: Cc1nnc(NC(=O)c2cc(C3CC3NC3CCN(C4CC4)CC3)cs2)s1] | 2HCl | 404.2 |
| 60 | 3-(4-((((1R,2R)-2-(4-((5-methyl-1,3,4-thiadiazol-2-yl)-carbamoyl)-2-thienyl)cyclopropyl)amino)methyl)-piperidin-1-yl)propanoic acid | 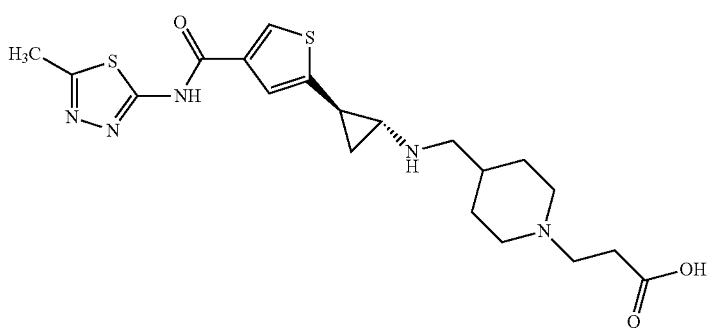 [SMILES: Cc1nnc(NC(=O)c2csc([C@@H]3C[C@H]3NCC3CCN(CCC(=O)O)CC3)c2)s1] | 3HCl | 450.0 |
| 61 | 4-(trans-2-(cyclobutylamino)-cyclopropyl)-N-(1-methyl-1H-pyrazol-4-yl)thiophene-2-carboxamide | 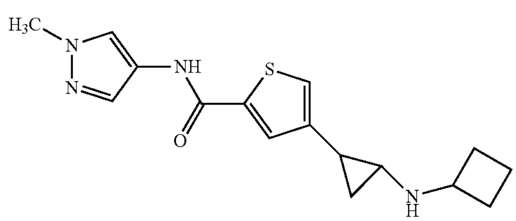 [SMILES: Cn1cc(NC(=O)c2cc(C3CC3NC3CCC3)cs2)cn1] | 2HCl | 317.1 |

TABLE 1-continued

| Ex. No. | IUPAC name | structure | salt | MS |
|---|---|---|---|---|
| 62 | 4-(trans-2-((cyclopropylmethyl)amino)-cyclopropyl)-N-(1-methyl-1H-pyrazol-4-yl)thiophene-2-carboxamide | 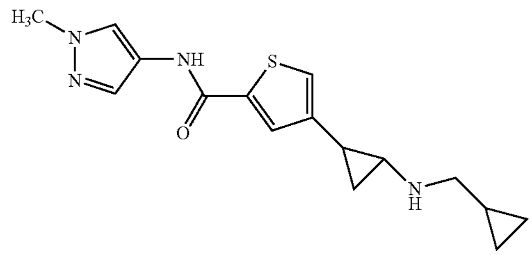 [SMILES: Cn1cc(NC(=O)c2cc(C3CC3NCC3CC3)cs2)cn1] | 2HCl | 317.0 |
| 63 | 4-(trans-2-(cyclobutylamino)-cyclopropyl)-N-(tetrahydro-2H-pyran-4-yl)thiophene-2-carboxamide | 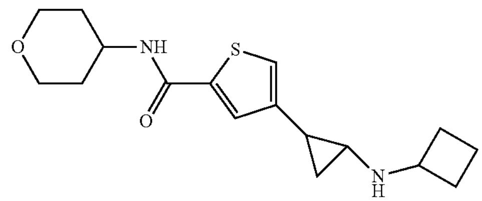 [SMILES: O=C(NC1CCOCC1)c1cc(C2CC2NC2CCC2)cs1] | HCl | 321.0 |
| 64 | 4-(trans-2-((cyclopropylmethyl)amino)-cyclopropyl)-N-(tetrahydro-2H-pyran-4-yl)thiophene-2-carboxamide | 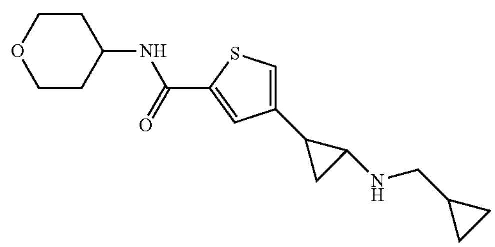 [SMILES: O=C(NC1CCOCC1)c1cc(C2CC2NCC2CC2)cs1] | HCl | 321.0 |
| 65 | 5-(trans-2-((cyclopropylmethyl)amino)-cyclopropyl)-N-(4,4-difluorocyclohexyl)-2-methylthiophene-3-carboxamide | 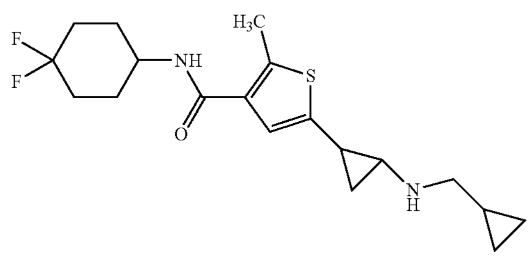 [SMILES: Cc1sc(C2CC2NCC2CC2)cc1C(=O)NC1CCC(F)(F)CC1] | HCl | 369.1 |
| 66 | N-(4,4-difluorocyclohexyl)-2-methyl-5-(trans-2-((tetrahydro-2H-pyran-4-ylmethyl)-amino)cyclopropyl)-thiophene-3-carboxamide | 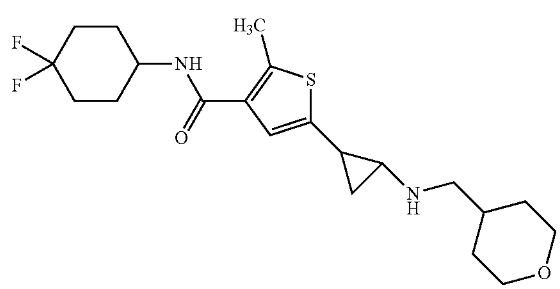 [SMILES: Cc1sc(C2CC2NCC2CCOCC2)cc1C(=O)NC1CCC(F)(F)CC1] | HCl | 413.1 |
| 67 | N-(4,4-difluoro-cyclohexyl)-2-methyl-5-(trans-2-(tetrahydro-2H-pyran-4-ylamino)-cyclopropyl)thiophene-3-carboxamide | 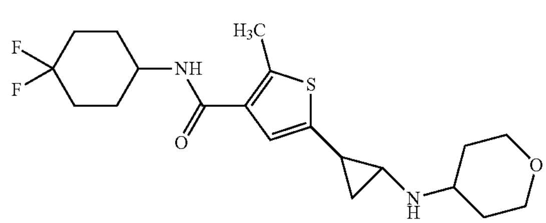 [SMILES: Cc1sc(C2CC2NC2CCOCC2)cc1C(=O)NC1CCC(F)(F)CC1] | HCl | 399.0 |

TABLE 1-continued

| Ex. No. | IUPAC name | structure | salt | MS |
|---|---|---|---|---|
| 68 | 5-(trans-2-((cyclopropylmethyl)amino)-cyclopropyl)-2-methyl-N-(tetrahydro-2H-pyran-4-yl)thiophene-3-carboxamide | 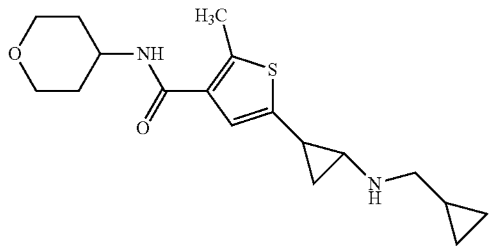 [SMILES: Cc1sc(C2CC2NCC2CC2)cc1C(=O)NC1CCOCC1] | HCl | 335.1 |
| 69 | 5-(trans-2-((cyclopropylmethyl)amino)-cyclopropyl)-2-methyl-N-(5-methyl-1,3,4-thiadiazol-2-yl)thiophene-3-carboxamide | 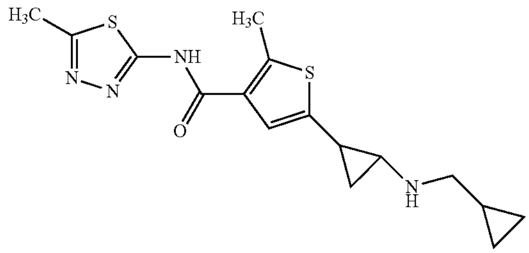 [SMILES: Cc1nnc(NC(=O)c2cc(C3CC3NCC3CC3)sc2C)s1] | 2HCl | 349.0 |
| 70 | 2-methyl-N-(5-methyl-1,3,4-thiadiazol-2-yl)-5-(trans-2-((tetrahydro-2H-pyran-4-ylmethyl)-amino)cyclopropyl)-thiophene-3-carboxamide | 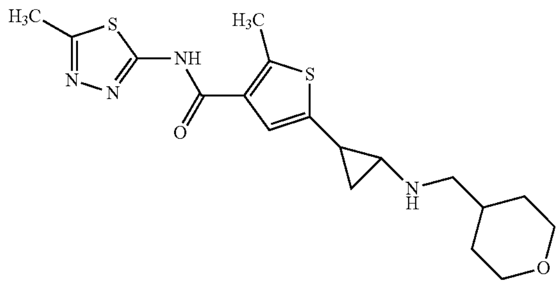 [SMILES: Cc1nnc(NC(=O)c2cc(C3CC3NCC3CCOCC3)sc2C)s1] | 2HCl | 393.0 |
| 71 | 5-((1R,2R)-2-((cyclopropylmethyl)amino)-cyclopropyl)-N-(tetrahydro-2H-pyran-4-yl)thiophene-3-carboxamide | 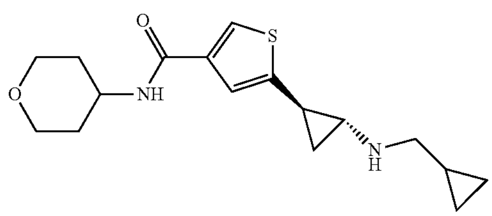 [SMILES: O=C(NC1CCOCC1)c1csc([C@@H]2C[C@H]2NCC2CC2)c1] | HCl | 321.0 |
| 72 | N-(5-methyl-1,3,4-thiadiazol-2-yl)-4-((1S,2R)-2-((tetrahydro-2H-pyran-4-ylmethyl)-amino)cyclopropyl)-thiophene-2-carboxamide | 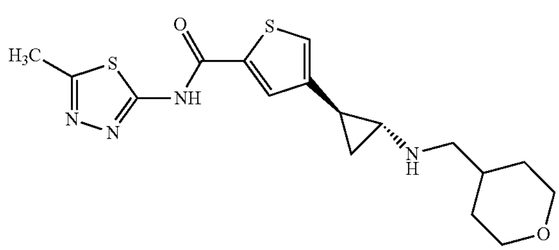 [SMILES: Cc1nnc(NC(=O)c2cc([C@@H]3C[C@H]3NCC3CCOCC3)cs2)s1] | HCl | 377.0 |
| 73 | 4-((1R,2S)-2-(cyclobutylamino)cyclopropyl)-N-(tetrahydro-2H-pyran-4-yl)thiophene-2-carboxamide | 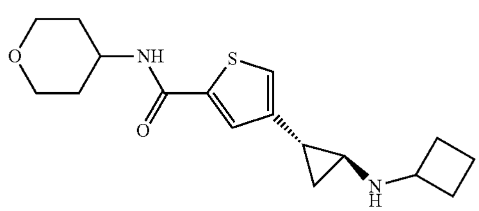 [SMILES: O=C(NC1CCOCC1)c1cc([C@H]2C[C@@H]2NC2CCC2)cs1] | HCl | 321.0 |

TABLE 1-continued

| Ex. No. | IUPAC name | structure | salt | MS |
|---|---|---|---|---|
| 74 | N-(5-methyl-1,3,4-thiadiazol-2-yl)-4-((1R,2S)-2-((tetrahydro-2H-pyran-4-ylmethyl)amino)cyclopropyl)-thiophene-2-carboxamide | 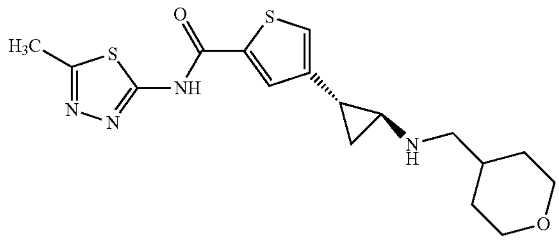 [SMILES: Cc1nnc(NC(=O)c2cc([C@H]3C[C@@H]3NCC3CCOCC3)cs2)s1] | HCl | 379.0 |
| 75 | 4-((1R,2S)-2-((cyclopropylmethyl)amino)cyclopropyl)-N-(tetrahydro-2H-pyran-4-yl)thiophene-2-carboxamide | 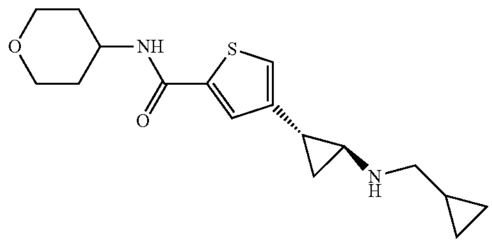 [SMILES: O=C(NC1CCOCC1)c1cc([C@H]2C[C@@H]2NCC2CC2)cs1] | HCl | 321.0 |
| 76 | 4-((1S,2R)-2-(cyclobutylamino)cyclopropyl)-N-(tetrahydro-2H-pyran-4-yl)thiophene-2-carboxamide | 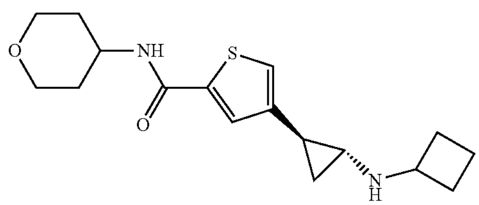 [SMILES: O=C(NC1CCOCC1)c1cc([C@@H]2C[C@H]2NC2CCC2)cs1] | HCl | 321.0 |
| 77 | 4-((1S,2R)-2-((cyclopropylmethyl)amino)cyclopropyl)-N-(tetrahydro-2H-pyran-4-yl)thiophene-2-carboxamide | 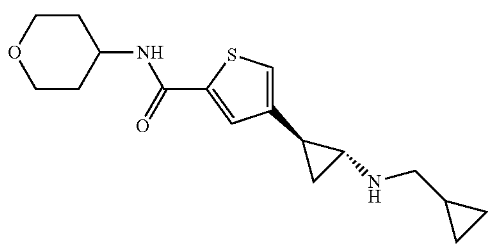 [SMILES: O=C(NC1CCOCC1)c1cc([C@@H]2C[C@H]2NCC2CC2)cs1] | HCl | 321.0 |
| 78 | 4-((1S,2R)-2-((1-cyclopropylpiperidin-4-yl)amino)cyclopropyl)-N-(5-methyl-1,3,4-thiadiazol-2-yl)thiophene-2-carboxamide | 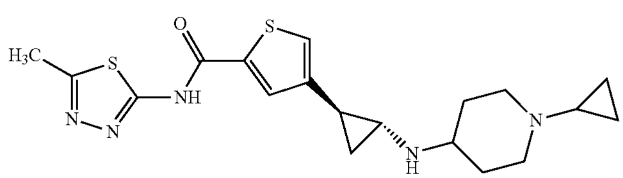 [SMILES: Cc1nnc(NC(=O)c2cc([C@@H]3C[C@H]3NC3CCN(C4CC4)CC3)cs2)s1] | 2HCl | 404.0 |
| 79 | 4-((1R,2S)-2-((1-cyclopropylpiperidin-4-yl)amino)cyclopropyl)-N-(5-methyl-1,3,4-thiadiazol-2-yl)thiophene-2-carboxamide | 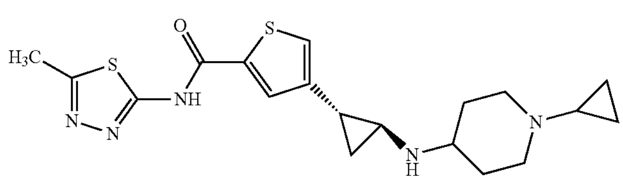 [SMILES: Cc1nnc(NC(=O)c2cc([C@H]3C[C@@H]3NC3CCN(C4CC4)CC3)cs2)s1] | 2HCl | 404.0 |
| 80 | 5-((1R,2R)-2-((1-cyclopropylpiperidin-4-yl)amino)cyclopropyl)-N-(4,4-difluorocyclohexyl)thiophene-3-carboxamide | 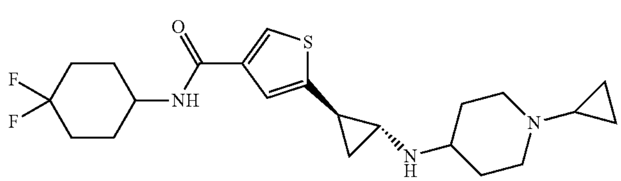 [SMILES: O=C(NC1CCC(F)(F)CC1)c1csc([C@@H]2C[C@H]2NC2CCN(C3CC3)CC2)c1] | HCl | 424.0 |

TABLE 1-continued

| Ex. No. | IUPAC name | structure | salt | MS |
|---|---|---|---|---|
| 81 | N-5-methyl-1,2-oxazol-3-yl)-5-((1R,2R)-2-((tetrahydro-2H-pyran-4-ylmethyl)-amino)cyclopropyl)-thiophene-3-carboxamide | 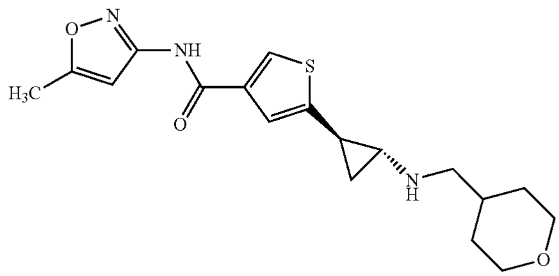 [SMILES: Cc1cc(NC(=O)c2csc([C@@H]3C[C@H]3NCC3CCOCC3)c2)no1] | HCl | 362.0 |
| 82 | 4-((1S,2R)-2-((cyclopropylmethyl)amino)-cyclopropyl)-N-(5-methyl-1,3,4-thiadiazol-2-yl)thiophene-2-carboxamide | 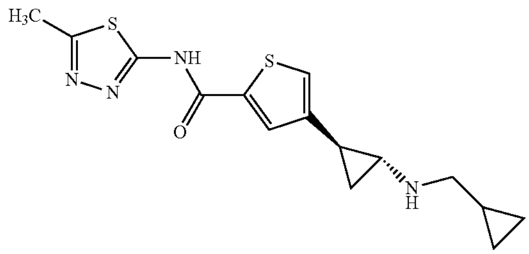 [SMILES: Cc1nnc(NC(=O)c2cc([C@@H]3C[C@H]3NCC3CC3)cs2)s1] | 2HCl | 335.0 |
| 83 | 4-((1R,2S)-2-((cyclopropylmethyl)amino)-cyclopropyl)-N-(5-methyl-1,3,4-thiadiazol-2-yl)thiophene-2-carboxamide | 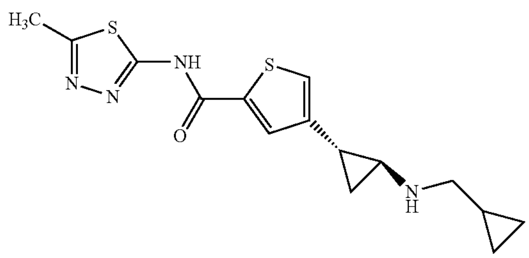 [SMILES: Cc1nnc(NC(=O)c2cc([C@H]3C[C@@H]3NCC3CC3)cs2)s1] | 2HCl | 335.0 |
| 84 | 4-((1S,2R)-2-(cyclobutylamino)-cyclopropyl)-N-(5-methyl-1,3,4-thiadiazol-2-yl)thiophene-2-carboxamide | 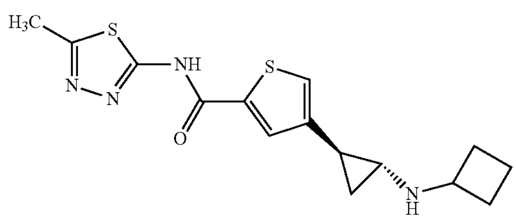 [SMILES: Cc1nnc(NC(=O)c2cc([C@@H]3C[C@H]3NC3CCC3)cs2)s1] | 2HCl | 335.0 |
| 85 | 4-((1R,2S)-2-(cyclobutylamino)-cyclopropyl)-N-(5-methyl-1,3,4-thiadiazol-2-yl)thiophene-2-carboxamide | 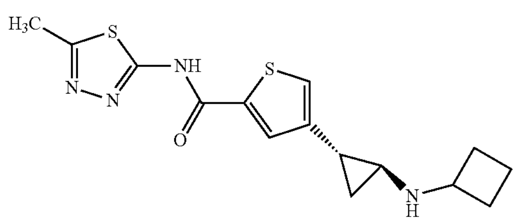 [SMILES: Cc1nnc(NC(=O)c2cc([C@H]3C[C@@H]3NC3CCC3)cs2)s1] | 2HCl | 335.0 |
| 86 | N-(1-ethyl-1H-pyrazol-4-yl)-5-((1R,2R)-2-((tetrahydro-2H-pyran-4-ylmethyl)-amino)cyclopropyl)-thiophene-3-carboxamide | 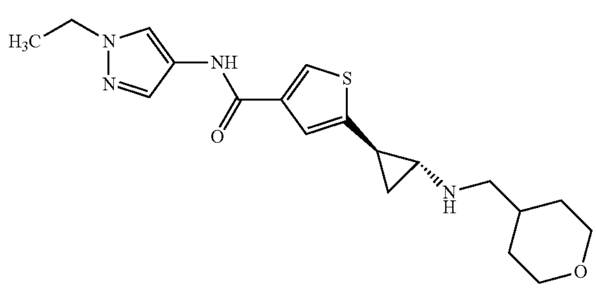 [SMILES: CCn1cc(NC(=O)c2csc([C@@H]3C[C@H]3NCC3CCOCC3)c2)cn1] | 2HCl | 375.1 |

TABLE 1-continued

| Ex. No. | IUPAC name | structure | salt | MS |
|---|---|---|---|---|
| 87 | 4-((1S,2R)-2-((cyclopropylmethyl)amino)cyclopropyl)-N-(1-methyl-1H-pyrazol-4-yl)thiophene-2-carboxamide | 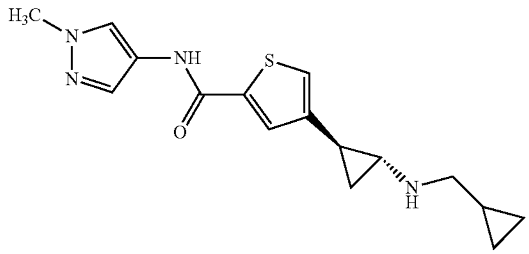 [SMILES: Cn1cc(NC(=O)c2cc([C@@H]3C[C@H]3NCC3CC3)cs2)cn1] | 2HCl | 317.1 |
| 88 | 4-((1R,2S)-2-((cyclopropylmethyl)amino)cyclopropyl)-N-(1-methyl-1H-pyrazol-4-yl)thiophene-2-carboxamide | 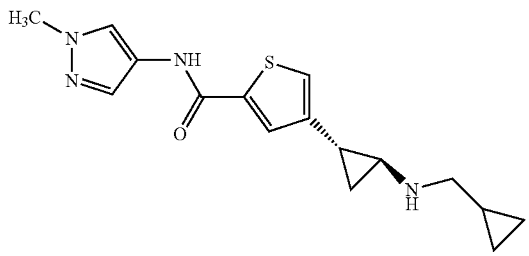 [SMILES: Cn1cc(NC(=O)c2cc([C@H]3C[C@@H]3NCC3CC3)cs2)cn1] | 2HCl | 317.1 |
| 89 | 4-((1S,2R)-2-(cyclobutylamino)cyclopropyl)-N-(1-methyl-1H-pyrazol-4-yl)thiophene-2-carboxamide | 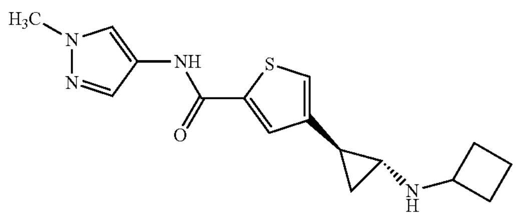 [SMILES: Cn1cc(NC(=O)c2cc([C@@H]3C[C@H]3NC3CCC3)cs2)cn1] | 2HCl | 317.1 |
| 90 | 4-((1R,2S)-2-(cyclobutylamino)cyclopropyl)-N-(1-methyl-1H-pyrazol-4-yl)thiophene-2-carboxamide | 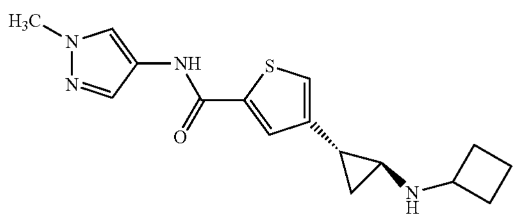 [SMILES: Cn1cc(NC(=O)c2cc([C@H]3C[C@@H]3NC3CCC3)cs2)cn1] | 2HCl | 317.0 |
| 91 | 5-((1R,2R)-2-((1-acetylpiperidin-4-yl)amino)cyclopropyl)-N-(4,4-difluorocyclohexyl)thiophene-3-carboxamide | 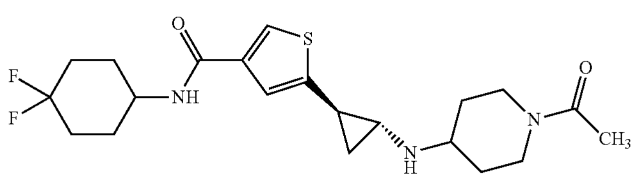 [SMILES: CC(=O)N1CCC(N[C@@H]2C[C@H]2c2cc(C(=O)NC3CCC(F)(F)CC3)cs2)CC1] | HCl | 426.1 |
| 92 | 5-((1R,2R)-2-((1-(cyclopropylcarbonyl)piperidin-4-yl)amino)cyclopropyl)-N-(4,4-difluorocyclohexyl)thiophene-3-carboxamide | 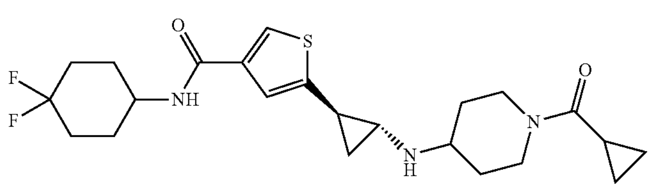 [SMILES: O=C(NC1CCC(F)(F)CC1)c1csc([C@@H]2C[C@H]2NC2CCN(C(=O)C3CC3)CC2)c1] | HCl | 452.1 |
| 93 | N-(4,4-difluorocyclohexyl)-5-methyl-4-((1S,2R)-2-(tetrahydro-2H-pyran-4-ylamino)cyclopropyl)thiophene-2-carboxamide | 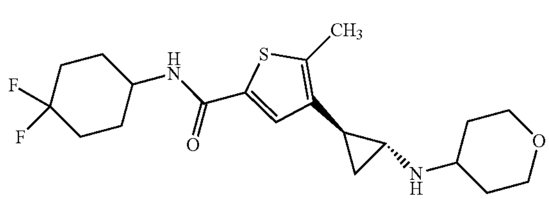 [SMILES: Cc1sc(C(=O)NC2CCC(F)(F)CC2)cc1[C@@H]1C[C@H]1NC1CCOCC1] | fumarate | 399.0 |

TABLE 1-continued

| Ex. No. | IUPAC name | structure | salt | MS |
|---|---|---|---|---|
| 94 | N-(4,4-difluorocyclohexyl)-5-methyl-4-((1R,2S)-2-(tetrahydro-2H-pyran-4-ylamino)cyclopropyl)thiophene-2-carboxamide | 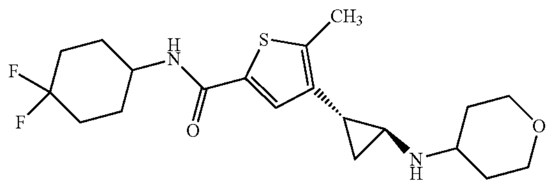 [SMILES: Cc1sc(C(=O)NC2CCC(F)(F)CC2)cc1[C@H]1C[C@@H]1NC1CCOCC1] | fumarate | 399.0 |
| 95 | 4-((1S,2R)-2-((cyclopropylmethyl)amino)cyclopropyl)-5-methyl-N-(5-methyl-1,3,4-thiadiazol-2-yl)thiophene-2-carboxamide | 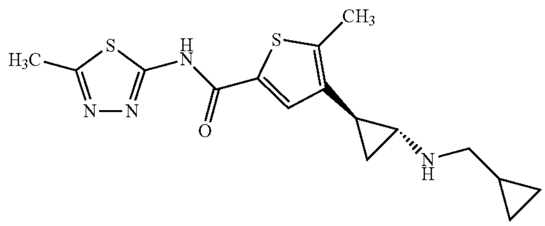 [SMILES: Cc1nnc(NC(=O)c2cc([C@@H]3C[C@H]3NCC3CC3)c(C)s2)s1] | fumarate | 349.0 |
| 96 | 4-((1R,2S)-2-((cyclopropylmethyl)amino)cyclopropyl)-5-methyl-N-(5-methyl-1,3,4-thiadiazol-2-yl)thiophene-2-carboxamide | 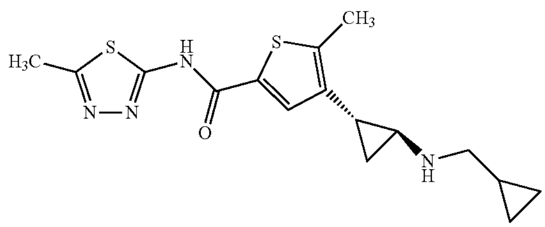 [SMILES: Cc1nnc(NC(=O)c2cc([C@H]3C[C@@H]3NCC3CC3)c(C)s2)s1] | fumarate | 349.0 |
| 97 | 5-methyl-N-(5-methyl-1,3,4-thiadiazol-2-yl)-4-((1S,2R)-2-((tetrahydro-2H-pyran-4-ylmethyl)amino)cyclopropyl)thiophene-2-carboxamide | 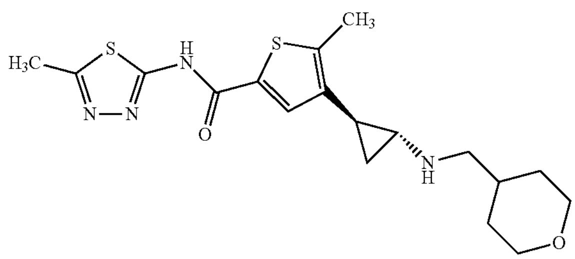 [SMILES: Cc1nnc(NC(=O)c2cc([C@@H]3C[C@H]3NCC3CCOCC3)c(C)s2)s1] | HCl | 391.0 |
| 98 | 5-methyl-N-(5-methyl-1,3,4-thiadiazol-2-yl)-4-((1R,2S)-2-((tetrahydro-2H-pyran-4-ylmethyl)amino)cyclopropyl)thiophene-2-carboxamide | 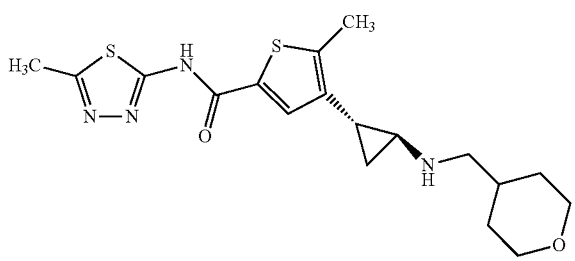 [SMILES: Cc1nnc(NC(=O)c2cc([C@H]3C[C@@H]3NCC3CCOCC3)c(C)s2)s1] | HCl | 391.0 |
| 99 | 4-((1S,2R)-2-(cyclobutylamino)cyclopropyl)-5-methyl-N-(5-methyl-1,3,4-thiadiazol-2-yl)thiophene-2-carboxamide | 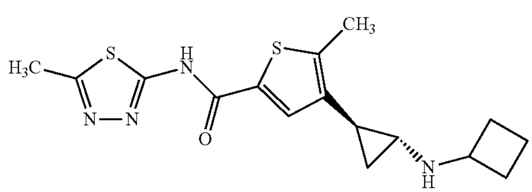 [SMILES: Cc1nnc(NC(=O)c2cc([C@@H]3C[C@H]3NC3CCC3)c(C)s2)s1] | HCl | 349.0 |
| 100 | 4-((1R,2S)-2-(cyclobutylamino)cyclopropyl)-5-methyl-N-(5-methyl-1,3,4-thiadiazol-2-yl)thiophene-2-carboxamide | 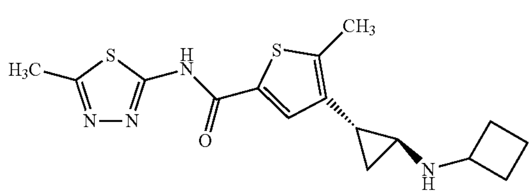 [SMILES: Cc1nnc(NC(=O)c2cc([C@H]3C[C@@H]3NC3CCC3)c(C)s2)s1] | HCl | 349.0 |

TABLE 1-continued

| Ex. No. | IUPAC name | structure | salt | MS |
|---|---|---|---|---|
| 101 | 4-((4-((((1R,2R)-2-(4-((4,4-difluorocyclohexyl)-carbamoyl)-2-thienyl)cyclopropyl)amino)methyl)piperidin-1-yl)methyl)benzoic acid | 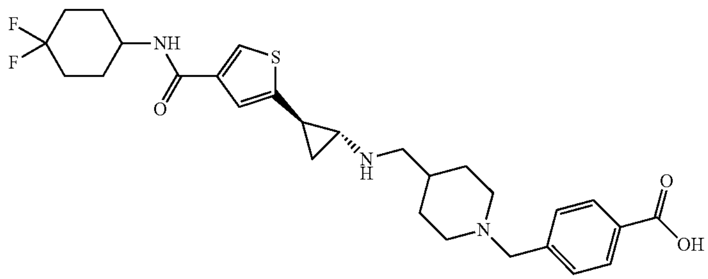 [SMILES: O=C(O)c1ccc(CN2CCC(CN[C@@H]3C[C@H]3c3cc(C(=O)NC4CCC(F)(F)CC4)cs3)CC2)cc1] | 2HCl | 532.1 |
| 102 | 4-((1S,2R)-2-((cyclopropylmethyl)amino)cyclopropyl)-5-methyl-N-(1-methyl-1H-pyrazol-4-yl)thiophene-2-carboxamide | 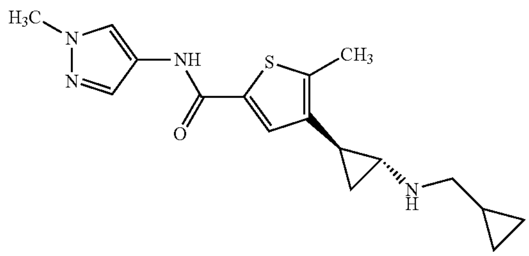 [SMILES: Cc1sc(C(=O)Nc2cnn(C)c2)cc1[C@@H]1C[C@H]1NCC1CC1] | 2HCl | 331.1 |
| 103 | 4-((1R,2S)-2-((cyclopropylmethyl)amino)cyclopropyl)-5-methyl-N-(1-methyl-1H-pyrazol-4-yl)thiophene-2-carboxamide | 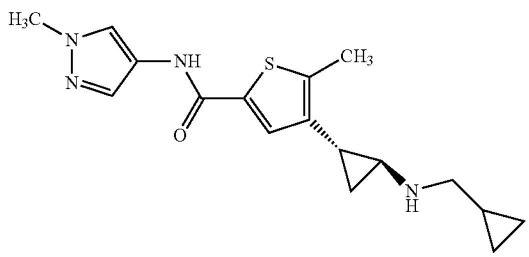 [SMILES: Cc1sc(C(=O)Nc2cnn(C)c2)cc1[C@H]1C[C@@H]1NCC1CC1] | 2HCl | 331.1 |
| 104 | 4-((1S,2R)-2-(cyclobutylamino)cyclopropyl)-5-methyl-N-(1-methyl-1H-pyrazol-4-yl)thiophene-2-carboxamide | 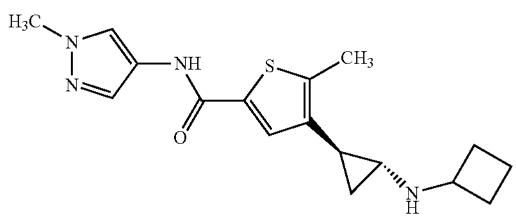 [SMILES: Cc1sc(C(=O)Nc2cnn(C)c2)cc1[C@@H]1C[C@H]1NC1CCC1] | 2HCl | 331.1 |
| 105 | 4-((1R,2S)-2-(cyclobutylamino)cyclopropyl)-5-methyl-N-(1-methyl-1H-pyrazol-4-yl)thiophene-2-carboxamide | 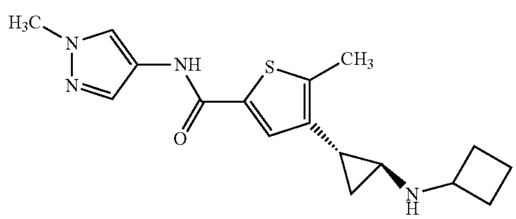 [SMILES: Cc1sc(C(=O)Nc2cnn(C)c2)cc1[C@H]1C[C@@H]1NC1CCC1] | 2HCl | 331.1 |
| 106 | 4-((1S,2R)-2-((cyclopropylmethyl)amino)cyclopropyl)-5-methyl-N-(tetrahydro-2H-pyran-4-yl)thiophene-2-carboxamide | 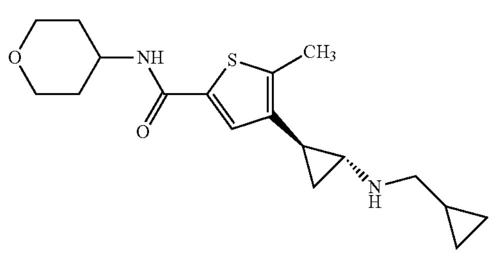 [SMILES: Cc1sc(C(=O)NC2CCOCC2)cc1[C@@H]1C[C@H]1NCC1CC1] | HCl | 335.0 |

TABLE 1-continued

| Ex. No. | IUPAC name | structure | salt | MS |
|---|---|---|---|---|
| 107 | 4-((1R,2S)-2-((cyclopropylmethyl)amino)cyclopropyl)-5-methyl-N-(tetrahydro-2H-pyran-4-yl)thiophene-2-carboxamide | 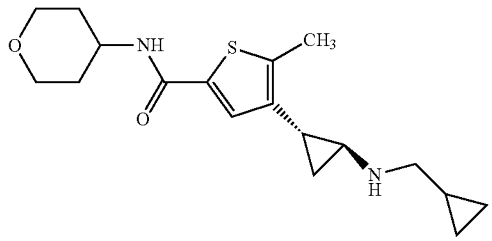 [SMILES: Cc1sc(C(=O)NC2CCOCC2)cc1[C@H]1C[C@@H]1NCC1CC1] | HCl | 335.0 |
| 108 | 4-((1S,2R)-2-(cyclobutylamino)cyclopropyl)-5-methyl-N-(tetrahydro-2H-pyran-4-yl)thiophene-2-carboxamide | 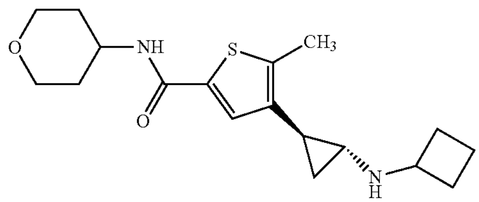 [SMILES: Cc1sc(C(=O)NC2CCOCC2)cc1[C@@H]1C[C@H]1NC1CCC1] | HCl | 335.0 |
| 109 | 4-((1R,2S)-2-(cyclobutylamino)cyclopropyl)-5-methyl-N-(tetrahydro-2H-pyran-4-yl)thiophene-2-carboxamide | 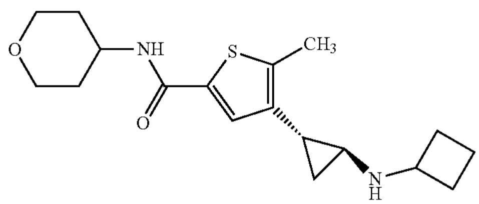 [SMILES: Cc1sc(C(=O)NC2CCOCC2)cc1[C@H]1C[C@@H]1NC1CCC1] | HCl | 335.0 |
| 110 | 4-((((1R,2R)-2-(4-((4,4-difluorocyclohexyl)carbamoyl)-2-thienyl)cyclopropyl)amino)methyl)benzoic acid | 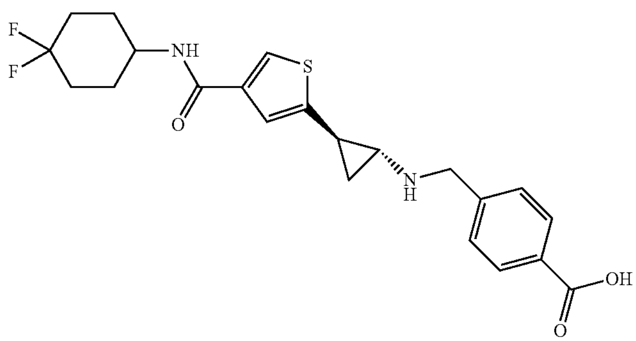 [SMILES: O=C(O)c1ccc(CN[C@@H]2C[C@H]2c2cc(C(=O)NC3CCC(F)(F)CC3)cs2)cc1] | HCl | 435.0 |
| 111 | 5-((1R,2R)-2-(((5-amino-1,3,4-oxadiazol-2-yl)methyl)amino)cyclopropyl)-N-(4,4-difluorocyclohexyl)thiophene-3-carboxamide | 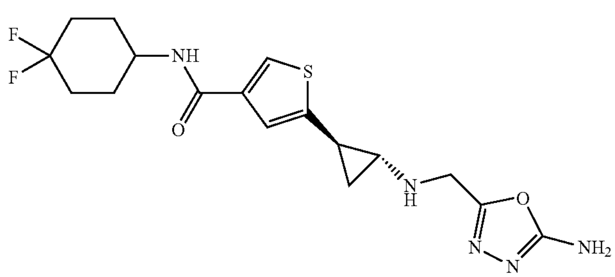 [SMILES: Nc1nnc(CN[C@@H]2C[C@H]2c2cc(C(=O)NC3CCC(F)(F)CC3)cs2)o1] | 2HCl | 398.0 |
| 112 | 5-((1R,2R)-2-((cyclobutylmethyl)amino)cyclopropyl)-N-(tetrahydro-2H-pyran-4-yl)thiophene-3-carboxamide | 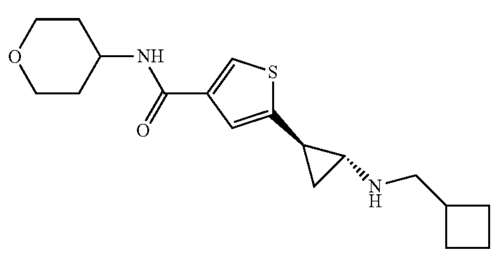 [SMILES: O=C(NC1CCOCC1)c1csc([C@@H]2C[C@H]2NCC2CCC2)c1] | HCl | 335.1 |

TABLE 1-continued

| Ex. No. | IUPAC name | structure | salt | MS |
|---|---|---|---|---|
| 113 | 5-((1R,2R)-2-((cyclopropylmethyl)amino)cyclopropyl)-N-(tetrahydro-2H-pyran-4-yl)thiophene-3-carboxamide | 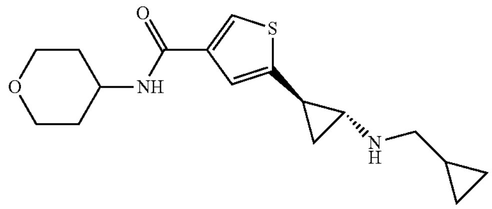 [SMILES: O=C(NC1CCOCC1)c1csc([C@@H]2C[C@H]2NCC2CC2)c1] | L-malate | 321.2 |
| 114 | 5-((1R,2R)-2-((cyclopropylmethyl)amino)cyclopropyl)-N-(tetrahydro-2H-pyran-4-yl)thiophene-3-carboxamide | 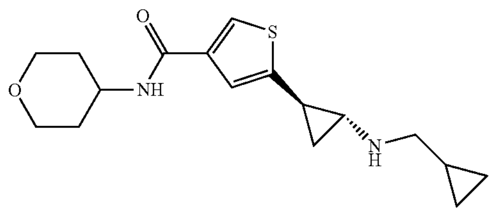 [SMILES: O=C(NC1CCOCC1)c1csc([C@@H]2C[C@H]2NCC2CC2)c1] | succinate | 321.2 |
| 115 | 5-((1R,2R)-2-((cyclopropylmethyl)amino)cyclopropyl)-N-(tetrahydro-2H-pyran-4-yl)thiophene-3-carboxamide | 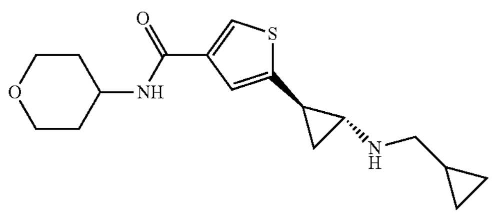 [SMILES: O=C(NC1CCOCC1)c1csc([C@@H]2C[C@H]2NCC2CC2)c1] | fumarate | 321.1 |
| 116 | 4-((1S,2R)-2-(cyclobutylamino)cyclopropyl)-N-(5-methyl-1,3,4-thiadiazol-2-yl)thiophene-2-carboxamide | 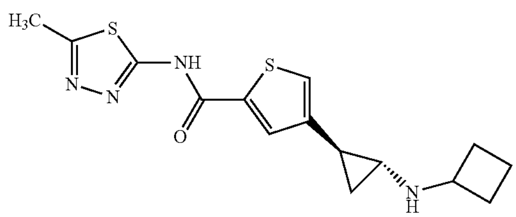 [SMILES: Cc1nnc(NC(=O)c2cc([C@@H]3C[C@H]3NC3CCC3)cs2)s1] | $H_3PO_4$ | 335.1 |
| 117 | 4-((1S,2R)-2-(cyclobutylamino)cyclopropyl)-N-(5-methyl-1,3,4-thiadiazol-2-yl)thiophene-2-carboxamide | 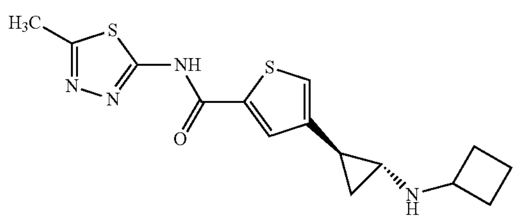 [SMILES: Cc1nnc(NC(=O)c2cc([C@@H]3C[C@H]3NC3CCC3)cs2)s1] | succinate | 335.1 |
| 118 | 4-((1S,2R)-2-(cyclobutylamino)cyclopropyl)-N-(5-methyl-1,3,4-thiadiazol-2-yl)thiophene-2-carboxamide | 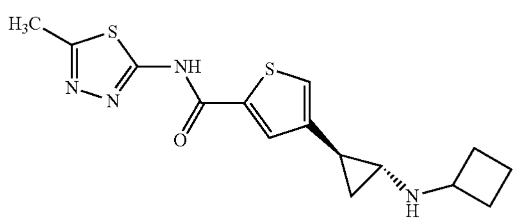 [SMILES: Cc1nnc(NC(=O)c2cc([C@@H]3C[C@H]3NC3CCC3)cs2)s1] | $H_2SO_4$ | 335.1 |
| 119 | 4-((1S,2R)-2-(cyclobutylamino)cyclopropyl)-N-(5-methyl-1,3,4-thiadiazol-2-yl)thiophene-2-carboxamide | 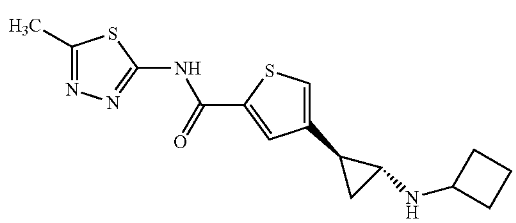 [SMILES: Cc1nnc(NC(=O)c2cc([C@@H]3C[C@H]3NC3CCC3)cs2)s1] | | 335.0 |

TABLE 1-continued

| Ex. No. | IUPAC name | structure | salt | MS |
|---|---|---|---|---|
| 120 | 5-((1R,2R)-2-((cyclopropylmethyl)amino)cyclopropyl)-N-(tetrahydro-2H-pyran-4-yl)thiophene-3-carboxamide | 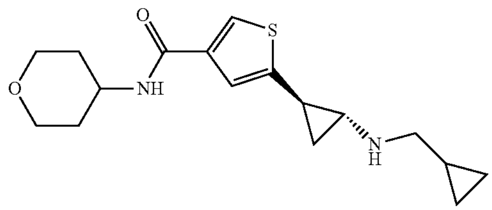 [SMILES: O=C(NC1CCOCC1)c1csc([C@@H]2C[C@H]2NCC2CC2)c1] | | 321.1 |
| 121 | 4-((1S,2R)-2-((cyclobutylmethyl)amino)cyclopropyl)-5-methyl-N-(1-methyl-1H-pyrazol-4-yl)thiophene-2-carboxamide | 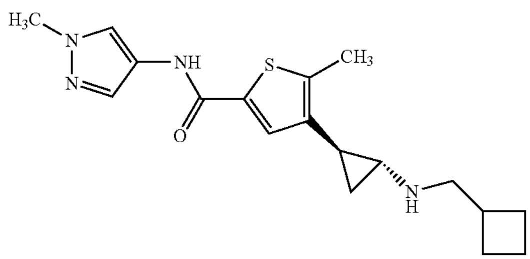 [SMILES: Cc1sc(C(=O)Nc2cnn(C)c2)cc1[C@@H]1C[C@H]1NCC1CCC1] | 2HCl | 345.1 |
| 122 | 4-((1S,2R)-2-((cyclobutylmethyl)amino)cyclopropyl)-5-methyl-N-(tetrahydro-2H-pyran-4-yl)thiophene-2-carboxamide | 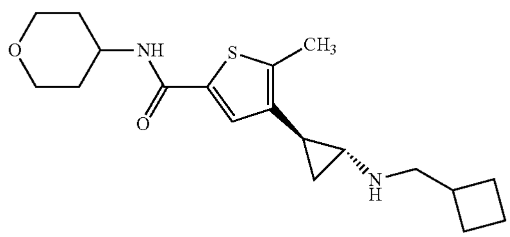 [SMILES: Cc1sc(C(=O)NC2CCOCC2)cc1[C@@H]1C[C@H]1NCC1CCC1] | HCl | 349.1 |
| 123 | 4-((1S,2R)-2-(cyclobutylamino)cyclopropyl)-5-methyl-N-(1-methyl-1H-pyrazol-4-yl)thiophene-2-carboxamide | 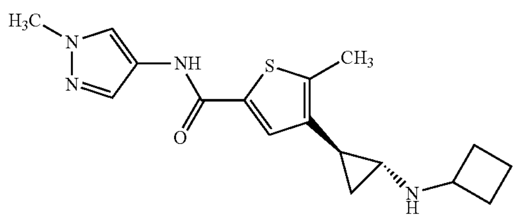 [SMILES: Cc1sc(C(=O)Nc2cnn(C)c2)cc1[C@@H]1C[C@H]1NC1CCC1] | HCl | 331.2 |
| 124 | 4-((1S,2R)-2-aminocyclopropyl)-N-(5-methyl-1,3,4-thiadiazol-2-yl)thiophene-2-carboxamide | 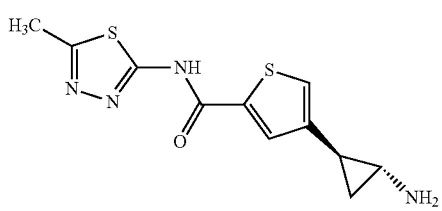 [SMILES: Cc1nnc(NC(=O)c2cc([C@@H]3C[C@H]3N)cs2)s1] | 2HCl | 281.1 |
| 125 | 5-((1S,2S)-2-((cyclopropylmethyl)amino)cyclopropyl)-N-(tetrahydro-2H-pyran-4-yl)thiophene-3-carboxamide | 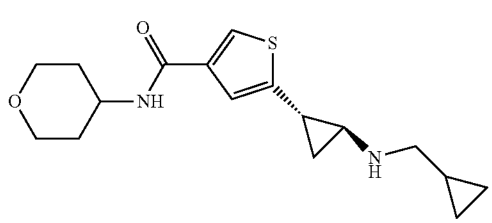 [SMILES: O=C(NC1CCOCC1)c1csc([C@H]2C[C@@H]2NCC2CC2)c1] | HCl | 321.2 |

Other preferable specific examples of the compound represented by the formula (I) include the following compounds shown in the Examples, an optically active form thereof, and a mixture of optically active forms thereof. The following compounds shown in the Examples, an optically active form thereof, and a mixture of optically active forms thereof can be produced according to the aforementioned production methods, a method shown in the Examples, or a method analogous thereto. The relative configuration of the substituent on the cyclopropane ring is cis or trans, preferably trans.

Example A1

4-(2-(cyclobutylamino)cyclopropyl)-N-(1,3-dimethyl-1H-pyrazol-4-yl)thiophene-2-carboxamide Example A2

4-(2-(cyclobutylamino)cyclopropyl)-N-(1-ethyl-1H-pyrazol-4-yl)thiophene-2-carboxamide Example A3

4-(2-(cyclobutylamino)cyclopropyl)-N-(1,3-dimethyl-1H-pyrazol-5-yl)thiophene-2-carboxamide Example A4

4-(2-(cyclobutylamino)cyclopropyl)-N-(tetrahydro-2H-pyran-4-yl)thiophene-2-carboxamide Example A5

4-(2-(cyclobutylamino)cyclopropyl)-N-cyclopentyl-thiophene-2-carboxamide

Example A6

4-(2-(cyclobutylamino)cyclopropyl)-N-(4,4-difluorocyclohexyl)thiophene-2-carboxamide Example A7

4-(2-(cyclobutylamino)cyclopropyl)-N-(1-(2,2,2-trifluoroethyl)piperidin-4-yl)thiophene-2-carboxamide Example A8

4-(2-(cyclobutylamino)cyclopropyl)-N-(5-methyl-1,2-oxazol-3-yl)thiophene-2-carboxamide Example A9

4-(2-(cyclobutylamino)cyclopropyl)-N-(3-methyl-1,2-oxazol-5-yl)thiophene-2-carboxamide Example A10

4-(2-(cyclobutylamino)cyclopropyl)-N-(2-methyl-1,3-thiazol-5-yl)thiophene-2-carboxamide Example A11

4-(2-((cyclopropylmethyl)amino) cyclopropyl)-N-(1-methyl-1H-pyrazol-4-yl)thiophene-2-carboxamide Example A12

4-(2-((cyclopropylmethyl)amino)cyclopropyl)-N-(1,3-dimethyl-1H-pyrazol-4-yl)thiophene-2-carboxamide Example A13

4-(2-((cyclopropylmethyl)amino)cyclopropyl)-N-(1-ethyl-1H-pyrazol-4-yl)thiophene-2-carboxamide Example A14

4-(2-((cyclopropylmethyl)amino)cyclopropyl)-N-(1,3-dimethyl-1H-pyrazol-5-yl)thiophene-2-carboxamide Example A15

N-cyclopentyl-4-(2-((cyclopropylmethyl)amino)cyclopropyl)thiophene-2-carboxamide Example A16

4-(2-((cyclopropylmethyl)amino)cyclopropyl)-N-(1-(2,2,2-trifluoroethyl)piperidin-4-yl)thiophene-2-carboxamide Example A17

4-(2-((cyclopropylmethyl)amino)cyclopropyl)-N-(5-methyl-1,2-oxazol-3-yl)thiophene-2-carboxamide Example A18

4-(2-((cyclopropylmethyl)amino)cyclopropyl)-N-(3-methyl-1,2-oxazol-5-yl)thiophene-2-carboxamide Example A19

4-(2-((cyclopropylmethyl)amino)cyclopropyl)-N-(2-methyl-1,3-thiazol-5-yl)thiophene-2-carboxamide

Example A20

4-(2-((cyclopropylmethyl)amino)cyclopropyl)-N-(oxetan-3-yl)thiophene-2-carboxamide

Example A21

4-(2-((cyclopropylmethyl)amino)cyclopropyl)-N-(3,3-difluorocyclobutyl)thiophene-2-carboxamide

Example A22

4-(2-((cyclopropylmethyl)amino)cyclopropyl)-N-(5-methyl-1,3,4-oxadiazol-2-yl)thiophene-2-carboxamide

Example A23

4-(2-((cyclopropylmethyl)amino)cyclopropyl)-N-(5-methyl-2-thienyl)thiophene-2-carboxamide

Example A24

4-(2-((cyclopropylmethyl)amino)cyclopropyl)-N-(pyridin-4-yl)thiophene-2-carboxamide

Example A25

4-(2-((cyclopropylmethyl)amino)cyclopropyl)-N-(2-methyl-1,3-oxazol-5-yl)thiophene-2-carboxamide

Example A26

4-(2-((cyclopropylmethyl)amino)cyclopropyl)-N-(5-(trifluoromethyl)-1,3,4-thiadiazol-2-yl)thiophene-2-carboxamide

Example A27

4-(2-((cyclopropylmethyl)amino)cyclopropyl)-N-(3-methyloxetan-3-yl)thiophene-2-carboxamide

Example A28

N-cyclopropyl-4-(2-((cyclopropylmethyl)amino)cyclopropyl)thiophene-2-carboxamide

Example A29

N-cyclopentyl-4-(2-(tetrahydro-2H-pyran-4-ylamino)cyclopropyl)thiophene-2-carboxamide

Example A30

N-(2-methyl-1,3-thiazol-5-yl)-4-(2-(tetrahydro-2H-pyran-4-ylamino)cyclopropyl)thiophene-2-carboxamide

Example A31

4-(2-((1-cyclopropylpiperidin-4-yl)amino)cyclopropyl)-N-(5-methyl-1,3,4-thiadiazol-2-yl)thiophene-2-carboxamide

Example A32

4-(2-((1-cyclopropylpiperidin-4-yl)amino)cyclopropyl)-N-(1-ethyl-1H-pyrazol-4-yl)thiophene-2-carboxamide

Example A33

4-(2-((1-cyclopropylpiperidin-4-yl)amino)cyclopropyl)-N-(1,3-dimethyl-1H-pyrazol-5-yl)thiophene-2-carboxamide

Example A34

N-cyclopentyl-4-(2-((1-cyclopropylpiperidin-4-yl)amino)cyclopropyl)thiophene-2-carboxamide

Example A35

4-(2-((1-cyclopropylpiperidin-4-yl)amino)cyclopropyl)-N-(4,4-difluorocyclohexyl)thiophene-2-carboxamide

Example A36

4-(2-((1-cyclopropylpiperidin-4-yl)amino)cyclopropyl)-N-(1-(2,2,2-trifluoroethyl)piperidin-4-yl)thiophene-2-carboxamide

Example A37

4-(2-((1-cyclopropylpiperidin-4-yl)amino)cyclopropyl)-N-(5-methyl-1,2-oxazol-3-yl)thiophene-2-carboxamide

Example A38

4-(2-((1-cyclopropylpiperidin-4-yl)amino)cyclopropyl)-N-(3-methyl-1,2-oxazol-5-yl)thiophene-2-carboxamide

Example A39

4-(2-((1-cyclopropylpiperidin-4-yl)amino)cyclopropyl)-N-(2-methyl-1,3-thiazol-5-yl)thiophene-2-carboxamide

Example A40

N-(1,3-dimethyl-1H-pyrazol-4-yl)-4-(2-((tetrahydro-2H-pyran-4-ylmethyl)amino)cyclopropyl)thiophene-2-carboxamide

Example A41

N-(1-ethyl-1H-pyrazol-4-yl)-4-(2-((tetrahydro-2H-pyran-4-ylmethyl)amino)cyclopropyl)thiophene-2-carboxamide

Example A42

N-(1,3-dimethyl-1H-pyrazol-5-yl)-4-(2-((tetrahydro-2H-pyran-4-ylmethyl)amino)cyclopropyl)thiophene-2-carboxamide

Example A43

N-cyclopentyl-4-(2-((tetrahydro-2H-pyran-4-ylmethyl)amino)cyclopropyl)thiophene-2-carboxamide

Example A44

4-(2-((tetrahydro-2H-pyran-4-ylmethyl)amino)cyclopropyl)-N-(1-(2,2,2-trifluoroethyl)piperidin-4-yl)thiophene-2-carboxamide

Example A45

N-(5-methyl-1,2-oxazol-3-yl)-4-(2-((tetrahydro-2H-pyran-4-ylmethyl)amino)cyclopropyl)thiophene-2-carboxamide

Example A46

N-(3-methyl-1,2-oxazol-5-yl)-4-(2-((tetrahydro-2H-pyran-4-ylmethyl)amino)cyclopropyl)thiophene-2-carboxamide

Example A47

N-(2-methyl-1,3-thiazol-5-yl)-4-(2-((tetrahydro-2H-pyran-4-ylmethyl)amino)cyclopropyl)thiophene-2-carboxamide

Example A48

N-(5-methyl-1,3,4-thiadiazol-2-yl)-4-(2-((1-(2,2,2-trifluoroethyl)piperidin-4-yl)amino)cyclopropyl)thiophene-2-carboxamide

Example A49

N-(1-methyl-1H-pyrazol-4-yl)-4-(2-((1-(2,2,2-trifluoroethyl)piperidin-4-yl)amino)cyclopropyl)thiophene-2-carboxamide

Example A50

N-(1-ethyl-1H-pyrazol-4-yl)-4-(2-((1-(2,2,2-trifluoroethyl)piperidin-4-yl)amino)cyclopropyl)thiophene-2-carboxamide

Example A51

N-(1,3-dimethyl-1H-pyrazol-5-yl)-4-(2-((1-(2,2,2-trifluoroethyl)piperidin-4-yl)amino)cyclopropyl)thiophene-2-carboxamide

Example A52

N-cyclopentyl-4-(2-((1-(2,2,2-trifluoroethyl)piperidin-4-yl)amino)cyclopropyl)thiophene-2-carboxamide

Example A53

N-(4,4-difluorocyclohexyl)-4-(2-((1-(2,2,2-trifluoroethyl)piperidin-4-yl)amino)cyclopropyl)thiophene-2-carboxamide

Example A54

N-(1-(2,2,2-trifluoroethyl)piperidin-4-yl)-4-(2-((1-(2,2,2-trifluoroethyl)piperidin-4-yl)amino)cyclopropyl)thiophene-2-carboxamide

Example A55

N-(5-methyl-1,2-oxazol-3-yl)-4-(2-((1-(2,2,2-trifluoroethyl)piperidin-4-yl)amino)cyclopropyl)thiophene-2-carboxamide

Example A56

N-(3-methyl-1,2-oxazol-5-yl)-4-(2-((1-(2,2,2-trifluoroethyl)piperidin-4-yl)amino)cyclopropyl)thiophene-2-carboxamide

Example A57

N-(2-methyl-1,3-thiazol-5-yl)-4-(2-((1-(2,2,2-trifluoroethyl)piperidin-4-yl)amino)cyclopropyl)thiophene-2-carboxamide

Example A58

4-(2-(cyclobutylamino)cyclopropyl)-N-(5-methyl-1,3,4-thiadiazol-2-yl)thiophene-2-carboxamide

Example A59

4-(2-(cyclobutylamino)cyclopropyl)-N-(1-methyl-1H-pyrazol-4-yl)thiophene-2-carboxamide

Example A60

N-(5-methyl-1,3,4-thiadiazol-2-yl)-4-(2-((tetrahydro-2H-pyran-4-ylmethyl)amino)cyclopropyl)thiophene-2-carboxamide

Example A61

N-(4,4-difluorocyclohexyl)-4-(2-((tetrahydro-2H-pyran-4-ylmethyl)amino)cyclopropyl)thiophene-2-carboxamide

Example A62

4-(2-((cyclopropylmethyl)amino)cyclopropyl)-N-(tetrahydro-2H-pyran-4-yl)thiophene-2-carboxamide

Example B1

4-(2-(cyclobutylamino)cyclopropyl)-N-(1,3-dimethyl-1H-pyrazol-4-yl)-5-methylthiophene-2-carboxamide

Example B2

4-(2-(cyclobutylamino)cyclopropyl)-N-(1-ethyl-1H-pyrazol-4-yl)-5-methylthiophene-2-carboxamide

Example B3

4-(2-(cyclobutylamino)cyclopropyl)-N-(1,3-dimethyl-1H-pyrazol-5-yl)-5-methylthiophene-2-carboxamide

Example B4

4-(2-(cyclobutylamino)cyclopropyl)-5-methyl-N-(tetrahydro-2H-pyran-4-yl)thiophene-2-carboxamide

Example B5

4-(2-(cyclobutylamino)cyclopropyl)-N-cyclopentyl-5-methylthiophene-2-carboxamide

Example B6

4-(2-(cyclobutylamino)cyclopropyl)-N-(4,4-difluorocyclohexyl)-5-methylthiophene-2-carboxamide

Example B7

4-(2-(cyclobutylamino)cyclopropyl)-5-methyl-N-(1-(2,2,2-trifluoroethyl)piperidin-4-yl)thiophene-2-carboxamide

Example B8

4-(2-(cyclobutylamino)cyclopropyl)-5-methyl-N-(5-methyl-1,2-oxazol-3-yl)thiophene-2-carboxamide

Example B9

4-(2-(cyclobutylamino)cyclopropyl)-5-methyl-N-(3-methyl-1,2-oxazol-5-yl)thiophene-2-carboxamide

Example B10

4-(2-(cyclobutylamino)cyclopropyl)-5-methyl-N-(2-methyl-1,3-thiazol-5-yl)thiophene-2-carboxamide

Example B11

4-(2-((cyclopropylmethyl)amino)cyclopropyl)-5-methyl-N-(1-methyl-1H-pyrazol-4-yl)thiophene-2-carboxamide

Example B12

4-(2-((cyclopropylmethyl)amino)cyclopropyl)-N-(1,3-dimethyl-1H-pyrazol-4-yl)-5-methylthiophene-2-carboxamide

Example B13

4-(2-((cyclopropylmethyl)amino)cyclopropyl)-N-(1-ethyl-1H-pyrazol-4-yl)-5-methylthiophene-2-carboxamide

Example B14

4-(2-((cyclopropylmethyl)amino)cyclopropyl)-N-(1,3-dimethyl-1H-pyrazol-5-yl)-5-methylthiophene-2-carboxamide

Example B15

N-cyclopentyl-4-(2-((cyclopropylmethyl)amino)cyclopropyl)-5-methylthiophene-2-carboxamide

Example B16

4-(2-((cyclopropylmethyl)amino)cyclopropyl)-5-methyl-N-(1-(2,2,2-trifluoroethyl)piperidin-4-yl)thiophene-2-carboxamide

Example B17

4-(2-((cyclopropylmethyl)amino)cyclopropyl)-5-methyl-N-(5-methyl-1,2-oxazol-3-yl)thiophene-2-carboxamide

Example B18

4-(2-((cyclopropylmethyl)amino)cyclopropyl)-5-methyl-N-(3-methyl-1,2-oxazol-5-yl)thiophene-2-carboxamide

Example B19

4-(2-((cyclopropylmethyl)amino)cyclopropyl)-5-methyl-N-(2-methyl-1,3-thiazol-5-yl)thiophene-2-carboxamide

Example B20

4-(2-((cyclopropylmethyl)amino)cyclopropyl)-5-methyl-N-(oxetan-3-yl)thiophene-2-carboxamide

Example B21

4-(2-((cyclopropylmethyl)amino)cyclopropyl)-N-(3,3-difluorocyclobutyl)-5-methylthiophene-2-carboxamide

Example B22

4-(2-((cyclopropylmethyl)amino)cyclopropyl)-5-methyl-N-(5-methyl-1,3,4-oxadiazol-2-yl)thiophene-2-carboxamide

Example B23

4-(2-((cyclopropylmethyl)amino)cyclopropyl)-5-methyl-N-(5-methyl-2-thienyl)thiophene-2-carboxamide

Example B24

4-(2-((cyclopropylmethyl)amino)cyclopropyl)-5-methyl-N-(pyridin-4-yl)thiophene-2-carboxamide

Example B25

4-(2-((cyclopropylmethyl)amino)cyclopropyl)-5-methyl-N-(2-methyl-1,3-oxazol-5-yl)thiophene-2-carboxamide

Example B26

4-(2-((cyclopropylmethyl)amino)cyclopropyl)-5-methyl-N-(5-(trifluoromethyl)-1,3,4-thiadiazol-2-yl)thiophene-2-carboxamide

Example B27

4-(2-((cyclopropylmethyl)amino)cyclopropyl)-5-methyl-N-(3-methyloxetan-3-yl)thiophene-2-carboxamide

Example B28

N-cyclopropyl-4-(2-((cyclopropylmethyl)amino)cyclopropyl)-5-methylthiophene-2-carboxamide

Example B29

N-cyclopentyl-5-methyl-4-(2-(tetrahydro-2H-pyran-4-ylamino)cyclopropyl)thiophene-2-carboxamide

Example B30

5-methyl-N-(2-methyl-1,3-thiazol-5-yl)-4-(2-(tetrahydro-2H-pyran-4-ylamino)cyclopropyl)thiophene-2-carboxamide

Example B31

4-(2-((1-cyclopropylpiperidin-4-yl)amino)cyclopropyl)-5-methyl-N-(5-methyl-1,3,4-thiadiazol-2-yl)thiophene-2-carboxamide

Example B32

4-(2-((1-cyclopropylpiperidin-4-yl)amino) cyclopropyl)-N-(1-ethyl-1H-pyrazol-4-yl)-5-methylthiophene-2-carboxamide

Example B33

4-(2-((1-cyclopropylpiperidin-4-yl)amino)cyclopropyl)-N-(1,3-dimethyl-1H-pyrazol-5-yl)-5-methylthiophene-2-carboxamide

Example B34

N-cyclopentyl-4-(2-((1-cyclopropylpiperidin-4-yl)amino)cyclopropyl)-5-methylthiophene-2-carboxamide

Example B35

4-(2-((1-cyclopropylpiperidin-4-yl)amino)cyclopropyl)-N-(4,4-difluorocyclohexyl)-5-methylthiophene-2-carboxamide

Example B36

4-(2-((1-cyclopropylpiperidin-4-yl)amino)cyclopropyl)-5-methyl-N-(1-(2,2,2-trifluoroethyl)piperidin-4-yl)thiophene-2-carboxamide

Example B37

4-(2-((1-cyclopropylpiperidin-4-yl)amino)cyclopropyl)-5-methyl-N-(5-methyl-1,2-oxazol-3-yl)thiophene-2-carboxamide

Example B38

4-(2-((1-cyclopropylpiperidin-4-yl)amino)cyclopropyl)-5-methyl-N-(3-methyl-1,2-oxazol-5-yl)thiophene-2-carboxamide

Example B39

4-(2-((1-cyclopropylpiperidin-4-yl)amino)cyclopropyl)-5-methyl-N-(2-methyl-1,3-thiazol-5-yl)thiophene-2-carboxamide

Example B40

N-(1,3-dimethyl-1H-pyrazol-4-yl)-5-methyl-4-(2-((tetrahydro-2H-pyran-4-ylmethyl)amino)cyclopropyl)thiophene-2-carboxamide

Example B41

N-(1-ethyl-1H-pyrazol-4-yl)-5-methyl-4-(2-((tetrahydro-2H-pyran-4-ylmethyl)amino)cyclopropyl)thiophene-2-carboxamide

Example B42

N-(1,3-dimethyl-1H-pyrazol-5-yl)-5-methyl-4-(2-((tetrahydro-2H-pyran-4-ylmethyl)amino)cyclopropyl)thiophene-2-carboxamide

Example B43

N-cyclopentyl-5-methyl-4-(2-((tetrahydro-2H-pyran-4-ylmethyl)amino)cyclopropyl)thiophene-2-carboxamide

Example B44

5-methyl-4-(2-((tetrahydro-2H-pyran-4-ylmethyl)amino)cyclopropyl)-N-(1-(2,2,2-trifluoroethyl)piperidin-4-yl)thiophene-2-carboxamide

Example B45

5-methyl-N-(5-methyl-1,2-oxazol-3-yl)-4-(2-((tetrahydro-2H-pyran-4-ylmethyl)amino)cyclopropyl)thiophene-2-carboxamide

Example B46

5-methyl-N-(3-methyl-1,2-oxazol-5-yl)-4-(2-((tetrahydro-2H-pyran-4-ylmethyl)amino)cyclopropyl)thiophene-2-carboxamide

Example B47

5-methyl-N-(2-methyl-1,3-thiazol-5-yl)-4-(2-((tetrahydro-2H-pyran-4-ylmethyl)amino)cyclopropyl)thiophene-2-carboxamide

Example B48

5-methyl-N-(5-methyl-1,3,4-thiadiazol-2-yl)-4-(2-((1-(2,2,2-trifluoroethyl)piperidin-4-yl)amino)cyclopropyl)thiophene-2-carboxamide

Example B49

5-methyl-N-(1-methyl-1H-pyrazol-4-yl)-4-(2-((1-(2,2,2-trifluoroethyl)piperidin-4-yl)amino)cyclopropyl)thiophene-2-carboxamide

Example B50

N-(1-ethyl-1H-pyrazol-4-yl)-5-methyl-4-(2-((1-(2,2,2-trifluoroethyl)piperidin-4-yl)amino)cyclopropyl)thiophene-2-carboxamide

Example B51

N-(1,3-dimethyl-1H-pyrazol-5-yl)-5-methyl-4-(2-((1-(2,2,2-trifluoroethyl)piperidin-4-yl)amino)cyclopropyl)thiophene-2-carboxamide

Example B52

N-cyclopentyl-5-methyl-4-(2-((1-(2,2,2-trifluoro-ethyl)piperidin-4-yl)amino)cyclopropyl)thiophene-2-carboxamide

Example B53

N-(4,4-difluorocyclohexyl)-5-methyl-4-(2-((1-(2,2,2-trifluoroethyl)piperidin-4-yl)amino)cyclopropyl)thiophene-2-carboxamide

Example B54

5-methyl-N-(1-(2,2,2-trifluoroethyl)piperidin-4-yl)-4-(2-((1-(2,2,2-trifluoroethyl)piperidin-4-yl)amino)cyclopropyl)thiophene-2-carboxamide

Example B55

5-methyl-N-(5-methyl-1,2-oxazol-3-yl)-4-(2-((1-(2,2,2-trifluoroethyl)piperidin-4-yl)amino)cyclopropyl)thiophene-2-carboxamide

Example B56

5-methyl-N-(3-methyl-1,2-oxazol-5-yl)-4-(2-((1-(2,2,2-trifluoroethyl)piperidin-4-yl)amino)cyclopropyl)thiophene-2-carboxamide

Example B57

5-methyl-N-(2-methyl-1,3-thiazol-5-yl)-4-(2-((1-(2,2,2-trifluoroethyl)piperidin-4-yl)amino)cyclopropyl)thiophene-2-carboxamide

Example C1

5-(2-(cyclobutylamino)cyclopropyl)-N-(1,3-dimethyl-1H-pyrazol-4-yl)thiophene-3-carboxamide

Example C2

5-(2-(cyclobutylamino)cyclopropyl)-N-(1-ethyl-1H-pyrazol-4-yl)thiophene-3-carboxamide

Example C3

5-(2-(cyclobutylamino)cyclopropyl)-N-(1,3-dimethyl-1H-pyrazol-5-yl)thiophene-3-carboxamide

Example C4

5-(2-(cyclobutylamino)cyclopropyl)-N-(tetrahydro-2H-pyran-4-yl)thiophene-3-carboxamide

Example C5

5-(2-(cyclobutylamino)cyclopropyl)-N-cyclopentyl-thiophene-3-carboxamide

Example C6

5-(2-(cyclobutylamino)cyclopropyl)-N-(4,4-difluorocyclohexyl)thiophene-3-carboxamide

Example C7

5-(2-(cyclobutylamino)cyclopropyl)-N-(1-(2,2,2-trifluoroethyl)piperidin-4-yl)thiophene-3-carboxamide

Example C8

5-(2-(cyclobutylamino)cyclopropyl)-N-(5-methyl-1,2-oxazol-3-yl)thiophene-3-carboxamide

Example C9

5-(2-(cyclobutylamino)cyclopropyl)-N-(3-methyl-1,2-oxazol-5-yl)thiophene-3-carboxamide

Example C10

5-(2-(cyclobutylamino)cyclopropyl)-N-(2-methyl-1,3-thiazol-5-yl)thiophene-3-carboxamide

Example C11

5-(2-((cyclopropylmethyl)amino)cyclopropyl)-N-(1-methyl-1H-pyrazol-4-yl)thiophene-3-carboxamide

Example C12

5-(2-((cyclopropylmethyl)amino)cyclopropyl)-N-(1,3-dimethyl-1H-pyrazol-4-yl)thiophene-3-carboxamide

Example C13

5-(2-((cyclopropylmethyl)amino)cyclopropyl)-N-(1-ethyl-1H-pyrazol-4-yl)thiophene-3-carboxamide

Example C14

5-(2-((cyclopropylmethyl)amino)cyclopropyl)-N-(1,3-dimethyl-1H-pyrazol-5-yl)thiophene-3-carboxamide

Example C15

N-cyclopentyl-5-(2-((cyclopropylmethyl)amino)cyclopropyl)thiophene-3-carboxamide

Example C16

5-(2-((cyclopropylmethyl)amino)cyclopropyl)-N-(1-(2,2,2-trifluoroethyl)piperidin-4-yl)thiophene-3-carboxamide

Example C17

5-(2-((cyclopropylmethyl)amino)cyclopropyl)-N-(5-methyl-1,2-oxazol-3-yl)thiophene-3-carboxamide

Example C18

5-(2-((cyclopropylmethyl)amino)cyclopropyl)-N-(3-methyl-1,2-oxazol-5-yl)thiophene-3-carboxamide

Example C19

5-(2-((cyclopropylmethyl)amino)cyclopropyl)-N-(2-methyl-1,3-thiazol-5-yl)thiophene-3-carboxamide

Example C20

5-(2-((cyclopropylmethyl)amino)cyclopropyl)-N-(oxetan-3-yl)thiophene-3-carboxamide

Example C21

5-(2-((cyclopropylmethyl)amino) cyclopropyl)-N-(3,3-difluorocyclobutyl)thiophene-3-carboxamide

Example C22

5-(2-((cyclopropylmethyl)amino)cyclopropyl)-N-(5-methyl-1,3,4-oxadiazol-2-yl)thiophene-3-carboxamide

Example C23

5-(2-((cyclopropylmethyl)amino)cyclopropyl)-N-(5-methyl-2-thienyl)thiophene-3-carboxamide

Example C24

5-(2-((cyclopropylmethyl)amino)cyclopropyl)-N-(pyridin-4-yl)thiophene-3-carboxamide

Example C25

5-(2-((cyclopropylmethyl)amino)cyclopropyl)-N-(2-methyl-1,3-oxazol-5-yl)thiophene-3-carboxamide

Example C26

5-(2-((cyclopropylmethyl)amino) cyclopropyl)-N-(5-(trifluoromethyl)-1,3,4-thiadiazol-2-yl)thiophene-3-carboxamide

Example C27

5-(2-((cyclopropylmethyl)amino)cyclopropyl)-N-(3-methyloxetan-3-yl)thiophene-3-carboxamide

Example C28

N-cyclopropyl-5-(2-((cyclopropylmethyl)amino)cyclopropyl)thiophene-3-carboxamide

Example C29

N-cyclopentyl-5-(2-(tetrahydro-2H-pyran-4-ylamino)cyclopropyl)thiophene-3-carboxamide

Example C30

N-(2-methyl-1,3-thiazol-5-yl)-5-(2-(tetrahydro-2H-pyran-4-ylamino)cyclopropyl)thiophene-3-carboxamide

Example C31

5-(2-((1-cyclopropylpiperidin-4-yl)amino)cyclopropyl)-N-(5-methyl-1,3,4-thiadiazol-2-yl)thiophene-3-carboxamide

Example C32

5-(2-((1-cyclopropylpiperidin-4-yl)amino)cyclopropyl)-N-(1-ethyl-1H-pyrazol-4-yl)thiophene-3-carboxamide

Example C33

5-(2-((1-cyclopropylpiperidin-4-yl)amino)cyclopropyl)-N-(1,3-dimethyl-1H-pyrazol-5-yl)thiophene-3-carboxamide

Example C34

N-cyclopentyl-5-(2-((1-cyclopropylpiperidin-4-yl)amino)cyclopropyl)thiophene-3-carboxamide

Example C35

5-(2-((1-cyclopropylpiperidin-4-yl)amino)cyclopropyl)-N-(4,4-difluorocyclohexyl)thiophene-3-carboxamide

Example C36

5-(2-((1-cyclopropylpiperidin-4-yl)amino)cyclopropyl)-N-(1-(2,2,2-trifluoroethyl)piperidin-4-yl)thiophene-3-carboxamide

Example C37

5-(2-((1-cyclopropylpiperidin-4-yl)amino)cyclopropyl)-N-(5-methyl-1,2-oxazol-3-yl)thiophene-3-carboxamide

Example C38

5-(2-((1-cyclopropylpiperidin-4-yl)amino)cyclopropyl)-N-(3-methyl-1,2-oxazol-5-yl)thiophene-3-carboxamide

Example C39

5-(2-((1-cyclopropylpiperidin-4-yl)amino)cyclopropyl)-N-(2-methyl-1,3-thiazol-5-yl)thiophene-3-carboxamide

Example C40

N-(1,3-dimethyl-1H-pyrazol-4-yl)-5-(2-((tetrahydro-2H-pyran-4-ylmethyl)amino)cyclopropyl)thiophene-3-carboxamide

Example C41

N-(1-ethyl-1H-pyrazol-4-yl)-5-(2-((tetrahydro-2H-pyran-4-ylmethyl)amino)cyclopropyl)thiophene-3-carboxamide

Example C42

N-(1,3-dimethyl-1H-pyrazol-5-yl)-5-(2-((tetrahydro-2H-pyran-4-ylmethyl)amino)cyclopropyl)thiophene-3-carboxamide

Example C43

N-cyclopentyl-5-(2-((tetrahydro-2H-pyran-4-ylmethyl)amino)cyclopropyl)thiophene-3-carboxamide

Example C44

5-(2-((tetrahydro-2H-pyran-4-ylmethyl)amino)cyclopropyl)-N-(1-(2,2,2-trifluoroethyl)piperidin-4-yl)thiophene-3-carboxamide

Example C45

N-(5-methyl-1,2-oxazol-3-yl)-5-(2-((tetrahydro-2H-pyran-4-ylmethyl)amino)cyclopropyl)thiophene-3-carboxamide

Example C46

N-(3-methyl-1,2-oxazol-5-yl)-5-(2-((tetrahydro-2H-pyran-4-ylmethyl)amino)cyclopropyl)thiophene-3-carboxamide

Example C47

N-(2-methyl-1,3-thiazol-5-yl)-5-(2-((tetrahydro-2H-pyran-4-ylmethyl)amino)cyclopropyl)thiophene-3-carboxamide

Example C48

N-(5-methyl-1,3,4-thiadiazol-2-yl)-5-(2-((1-(2,2,2-trifluoroethyl)piperidin-4-yl)amino)cyclopropyl)thiophene-3-carboxamide

Example C49

N-(1-methyl-1H-pyrazol-4-yl)-5-(2-((1-(2,2,2-trifluoroethyl)piperidin-4-yl)amino)cyclopropyl)thiophene-3-carboxamide

Example C50

N-(1-ethyl-1H-pyrazol-4-yl)-5-(2-((1-(2,2,2-trifluoroethyl)piperidin-4-yl)amino)cyclopropyl)thiophene-3-carboxamide

Example C51

N-(1,3-dimethyl-1H-pyrazol-5-yl)-5-(2-((1-(2,2,2-trifluoroethyl)piperidin-4-yl)amino)cyclopropyl)thiophene-3-carboxamide

Example C52

N-cyclopentyl-5-(2-((1-(2,2,2-trifluoroethyl)piperidin-4-yl)amino)cyclopropyl)thiophene-3-carboxamide

Example C53

N-(4,4-difluorocyclohexyl)-5-(2-((1-(2,2,2-trifluoroethyl)piperidin-4-yl)amino)cyclopropyl)thiophene-3-carboxamide

Example C54

N-(1-(2,2,2-trifluoroethyl)piperidin-4-yl)-5-(2-((1-(2,2,2-trifluoroethyl)piperidin-4-yl)amino)cyclopropyl)thiophene-3-carboxamide

Example C55

N-(5-methyl-1,2-oxazol-3-yl)-5-(2-((1-(2,2,2-trifluoroethyl)piperidin-4-yl)amino)cyclopropyl)thiophene-3-carboxamide

Example C56

N-(3-methyl-1,2-oxazol-5-yl)-5-(2-((1-(2,2,2-trifluoroethyl)piperidin-4-yl)amino)cyclopropyl)thiophene-3-carboxamide

Example C57

N-(2-methyl-1,3-thiazol-5-yl)-5-(2-((1-(2,2,2-trifluoroethyl)piperidin-4-yl)amino)cyclopropyl)thiophene-3-carboxamide

Example D1

5-(2-(cyclobutylamino)cyclopropyl)-N-(1,3-dimethyl-1H-pyrazol-4-yl)-2-methylthiophene-3-carboxamide

Example D2

5-(2-(cyclobutylamino)cyclopropyl)-N-(1-ethyl-1H-pyrazol-4-yl)-2-methylthiophene-3-carboxamide

Example D3

5-(2-(cyclobutylamino)cyclopropyl)-N-(1,3-dimethyl-1H-pyrazol-5-yl)-2-methylthiophene-3-carboxamide

Example D4

5-(2-(cyclobutylamino)cyclopropyl)-2-methyl-N-(tetrahydro-2H-pyran-4-yl)thiophene-3-carboxamide

Example D5

5-(2-(cyclobutylamino)cyclopropyl)-N-cyclopentyl-2-methylthiophene-3-carboxamide

Example D6

5-(2-(cyclobutylamino)cyclopropyl)-N-(4,4-difluorocyclohexyl)-2-methylthiophene-3-carboxamide

Example D7

5-(2-(cyclobutylamino)cyclopropyl)-2-methyl-N-(1-(2,2,2-trifluoroethyl)piperidin-4-yl)thiophene-3-carboxamide

Example D8

5-(2-(cyclobutylamino)cyclopropyl)-2-methyl-N-(5-methyl-1,2-oxazol-3-yl)thiophene-3-carboxamide

Example D9

5-(2-(cyclobutylamino)cyclopropyl)-2-methyl-N-(3-methyl-1,2-oxazol-5-yl)thiophene-3-carboxamide

Example D10

5-(2-(cyclobutylamino)cyclopropyl)-2-methyl-N-(2-methyl-1,3-thiazol-5-yl)thiophene-3-carboxamide

Example D11

5-(2-((cyclopropylmethyl)amino)cyclopropyl)-2-methyl-N-(1-methyl-1H-pyrazol-4-yl)thiophene-3-carboxamide

Example D12

5-(2-((cyclopropylmethyl)amino)cyclopropyl)-N-(1,3-dimethyl-1H-pyrazol-4-yl)-2-methylthiophene-3-carboxamide

Example D13

5-(2-((cyclopropylmethyl)amino)cyclopropyl)-N-(1-ethyl-1H-pyrazol-4-yl)-2-methylthiophene-3-carboxamide

Example D14

5-(2-((cyclopropylmethyl)amino)cyclopropyl)-N-(1,3-dimethyl-1H-pyrazol-5-yl)-2-methylthiophene-3-carboxamide

Example D15

N-cyclopentyl-5-(2-((cyclopropylmethyl)amino)cyclopropyl)-2-methylthiophene-3-carboxamide Example D16

5-(2-((cyclopropylmethyl)amino)cyclopropyl)-2-methyl-N-(1-(2,2,2-trifluoroethyl)piperidin-4-yl)thiophene-3-carboxamide Example D17

5-(2-((cyclopropylmethyl)amino)cyclopropyl)-2-methyl-N-(5-methyl-1,2-oxazol-3-yl)thiophene-3-carboxamide Example D18

5-(2-((cyclopropylmethyl)amino)cyclopropyl)-2-methyl-N-(3-methyl-1,2-oxazol-5-yl)thiophene-3-carboxamide Example D19

5-(2-((cyclopropylmethyl)amino)cyclopropyl)-2-methyl-N-(2-methyl-1,3-thiazol-5-yl)thiophene-3-carboxamide Example D20

5-(2-((cyclopropylmethyl)amino)cyclopropyl)-2-methyl-N-(oxetan-3-yl)thiophene-3-carboxamide Example D21

5-(2-((cyclopropylmethyl)amino)cyclopropyl)-N-(3,3-difluorocyclobutyl)-2-methylthiophene-3-carboxamide Example D22

5-(2-((cyclopropylmethyl)amino)cyclopropyl)-2-methyl-N-(5-methyl-1,3,4-oxadiazol-2-yl)thiophene-3-carboxamide Example D23

5-(2-((cyclopropylmethyl)amino)cyclopropyl)-2-methyl-N-(5-methyl-2-thienyl)thiophene-3-carboxamide Example D24

5-(2-((cyclopropylmethyl)amino)cyclopropyl)-2-methyl-N-(pyridin-4-yl)thiophene-3-carboxamide Example D25

5-(2-((cyclopropylmethyl)amino)cyclopropyl)-2-methyl-N-(2-methyl-1,3-oxazol-5-yl)thiophene-3-carboxamide Example D26

5-(2-((cyclopropylmethyl)amino)cyclopropyl)-2-methyl-N-(5-(trifluoromethyl)-1,3,4-thiadiazol-2-yl)thiophene-3-carboxamide Example D27

5-(2-((cyclopropylmethyl)amino)cyclopropyl)-2-methyl-N-(3-methyloxetan-3-yl)thiophene-3-carboxamide Example D28

N-cyclopropyl-5-(2-((cyclopropylmethyl)amino)cyclopropyl)-2-methylthiophene-3-carboxamide Example D29

N-cyclopentyl-2-methyl-5-(2-(tetrahydro-2H-pyran-4-ylamino)cyclopropyl)thiophene-3-carboxamide Example D30

2-methyl-N-(2-methyl-1,3-thiazol-5-yl)-5-(2-(tetrahydro-2H-pyran-4-ylamino)cyclopropyl)thiophene-3-carboxamide Example D31

5-(2-((1-cyclopropylpiperidin-4-yl)amino)cyclopropyl)-2-methyl-N-(5-methyl-1,3,4-thiadiazol-2-yl)thiophene-3-carboxamide Example D32

5-(2-((1-cyclopropylpiperidin-4-yl)amino)cyclopropyl)-N-(1-ethyl-1H-pyrazol-4-yl)-2-methylthiophene-3-carboxamide Example D33

5-(2-((1-cyclopropylpiperidin-4-yl)amino)cyclopropyl)-N-(1,3-dimethyl-1H-pyrazol-5-yl)-2-methylthiophene-3-carboxamide

Example D34

N-cyclopentyl-5-(2-((1-cyclopropylpiperidin-4-yl)amino)cyclopropyl)-2-methylthiophene-3-carboxamide

Example D35

5-(2-((1-cyclopropylpiperidin-4-yl)amino)cyclopropyl)-N-(4,4-difluorocyclohexyl)-2-methylthiophene-3-carboxamide

Example D36

5-(2-((1-cyclopropylpiperidin-4-yl)amino)cyclopropyl)-2-methyl-N-(1-(2,2,2-trifluoroethyl)piperidin-4-yl)thiophene-3-carboxamide

Example D37

5-(2-((1-cyclopropylpiperidin-4-yl)amino)cyclopropyl)-2-methyl-N-(5-methyl-1,2-oxazol-3-yl)thiophene-3-carboxamide

Example D38

5-(2-((1-cyclopropylpiperidin-4-yl)amino)cyclopropyl)-2-methyl-N-(3-methyl-1,2-oxazol-5-yl)thiophene-3-carboxamide

Example D39

5-(2-((1-cyclopropylpiperidin-4-yl)amino)cyclopropyl)-2-methyl-N-(2-methyl-1,3-thiazol-5-yl)thiophene-3-carboxamide

Example D40

N-(1,3-dimethyl-1H-pyrazol-4-yl)-2-methyl-5-(2-((tetrahydro-2H-pyran-4-ylmethyl)amino)cyclopropyl)thiophene-3-carboxamide

Example D41

N-(1-ethyl-1H-pyrazol-4-yl)-2-methyl-5-(2-((tetrahydro-2H-pyran-4-ylmethyl)amino)cyclopropyl)thiophene-3-carboxamide

Example D42

N-(1,3-dimethyl-1H-pyrazol-5-yl)-2-methyl-5-(2-((tetrahydro-2H-pyran-4-ylmethyl)amino)cyclopropyl)thiophene-3-carboxamide

Example D43

N-cyclopentyl-2-methyl-5-(2-((tetrahydro-2H-pyran-4-ylmethyl)amino)cyclopropyl)thiophene-3-carboxamide

Example D44

2-methyl-5-(2-((tetrahydro-2H-pyran-4-ylmethyl)amino)cyclopropyl)-N-(1-(2,2,2-trifluoroethyl)piperidin-4-yl)thiophene-3-carboxamide

Example D45

2-methyl-N-(5-methyl-1,2-oxazol-3-yl)-5-(2-((tetrahydro-2H-pyran-4-ylmethyl)amino)cyclopropyl)thiophene-3-carboxamide

Example D46

2-methyl-N-(3-methyl-1,2-oxazol-5-yl)-5-(2-((tetrahydro-2H-pyran-4-ylmethyl)amino)cyclopropyl)thiophene-3-carboxamide

Example D47

2-methyl-N-(2-methyl-1,3-thiazol-5-yl)-5-(2-((tetrahydro-2H-pyran-4-ylmethyl)amino)cyclopropyl)thiophene-3-carboxamide

Example D48

2-methyl-N-(5-methyl-1,3,4-thiadiazol-2-yl)-5-(2-((1-(2,2,2-trifluoroethyl)piperidin-4-yl)amino)cyclopropyl)thiophene-3-carboxamide

Example D49

2-methyl-N-(1-methyl-1H-pyrazol-4-yl)-5-(2-((1-(2,2,2-trifluoroethyl)piperidin-4-yl)amino)cyclopropyl)thiophene-3-carboxamide

Example D50

N-(1-ethyl-1H-pyrazol-4-yl)-2-methyl-5-(2-((1-(2,2,2-trifluoroethyl)piperidin-4-yl)amino)cyclopropyl)thiophene-3-carboxamide

Example D51

N-(1,3-dimethyl-1H-pyrazol-5-yl)-2-methyl-5-(2-((1-(2,2,2-trifluoroethyl)piperidin-4-yl)amino)cyclopropyl)thiophene-3-carboxamide

Example D52

N-cyclopentyl-2-methyl-5-(2-((1-(2,2,2-trifluoroethyl)piperidin-4-yl)amino)cyclopropyl)thiophene-3-carboxamide

Example D53

N-(4,4-difluorocyclohexyl)-2-methyl-5-(2-((1-(2,2,2-trifluoroethyl)piperidin-4-yl)amino)cyclopropyl)thiophene-3-carboxamide

Example D54

2-methyl-N-(1-(2,2,2-trifluoroethyl)piperidin-4-yl)-5-(2-((1-(2,2,2-trifluoroethyl)piperidin-4-yl)amino)cyclopropyl)thiophene-3-carboxamide

Example D55

2-methyl-N-(5-methyl-1,2-oxazol-3-yl)-5-(2-((1-(2,2,2-trifluoroethyl)piperidin-4-yl)amino)cyclopropyl)thiophene-3-carboxamide

Example D56

2-methyl-N-(3-methyl-1,2-oxazol-5-yl)-5-(2-((1-(2,2,2-trifluoroethyl)piperidin-4-yl)amino)cyclopropyl)thiophene-3-carboxamide

Example D57

2-methyl-N-(2-methyl-1,3-thiazol-5-yl)-5-(2-((1-(2,2,2-trifluoroethyl)piperidin-4-yl)amino)cyclopropyl)thiophene-3-carboxamide

Example D58

5-(2-(cyclobutylamino)cyclopropyl)-2-methyl-N-(5-methyl-1,3,4-thiadiazol-2-yl)thiophene-3-carboxamide

Example D59

5-(2-((cyclopropylmethyl)amino)cyclopropyl)-2-methyl-N-(5-methyl-1,3,4-thiadiazol-2-yl)thiophene-3-carboxamide

Example D60

2-methyl-N-(5-methyl-1,3,4-thiadiazol-2-yl)-5-(2-((tetrahydro-2H-pyran-4-ylmethyl)amino)cyclopropyl)thiophene-3-carboxamide

Example D61

5-(2-((cyclopropylmethyl)amino)cyclopropyl)-N-(4,4-difluorocyclohexyl)-2-methylthiophene-3-carboxamide

Example D62

N-(4,4-difluorocyclohexyl)-2-methyl-5-(2-(tetrahydro-2H-pyran-4-ylamino)cyclopropyl)thiophene-3-carboxamide

Example D63

N-(4,4-difluorocyclohexyl)-2-methyl-5-(2-((tetrahydro-2H-pyran-4-ylmethyl)amino)cyclopropyl)thiophene-3-carboxamide

Example D64

5-(2-((cyclopropylmethyl)amino)cyclopropyl)-2-methyl-N-(tetrahydro-2H-pyran-4-yl)thiophene-3-carboxamide

Example E1

4-(2-((3-aminocyclobutyl)amino)cyclopropyl)-N-(5-methyl-1,3,4-thiadiazol-2-yl)thiophene-2-carboxamide

Example E2

4-(2-((3-aminocyclobutyl)amino)cyclopropyl)-5-methyl-N-(5-methyl-1,3,4-thiadiazol-2-yl)thiophene-2-carboxamide

Example E3

5-(2-((3-aminocyclobutyl)amino) cyclopropyl)-2-methyl-N-(5-methyl-1,3,4-thiadiazol-2-yl)thiophene-3-carboxamide

Example E4

5-(2-((3-aminocyclobutyl)amino)cyclopropyl)-N-(5-methyl-1,3,4-thiadiazol-2-yl)thiophene-3-carboxamide

Example E5

4-(2-((4-aminocyclohexyl)amino)cyclopropyl)-N-(5-methyl-1,3,4-thiadiazol-2-yl)thiophene-2-carboxamide

Example E6

4-(2-((4-aminocyclohexyl)amino)cyclopropyl)-5-methyl-N-(5-methyl-1,3,4-thiadiazol-2-yl)thiophene-2-carboxamide

Example E7

5-(2-((4-aminocyclohexyl)amino)cyclopropyl)-2-methyl-N-(5-methyl-1,3,4-thiadiazol-2-yl)thiophene-3-carboxamide

Example E8

5-(2-((4-aminocyclohexyl)amino)cyclopropyl)-N-(5-methyl-1,3,4-thiadiazol-2-yl)thiophene-3-carboxamide

Example E9

4-(2-((3-aminocyclobutyl)amino)cyclopropyl)-N-(-ethyl-1H-pyrazol-4-yl)thiophene-2-carboxamide

Example E10

4-(2-((3-aminocyclobutyl)amino) cyclopropyl)-N-(1-ethyl-1H-pyrazol-4-yl)-5-methylthiophene-2-carboxamide

Example E11

5-(2-((3-aminocyclobutyl)amino)cyclopropyl)-N-(1-ethyl-H-pyrazol-4-yl)-2-methylthiophene-3-carboxamide

Example E12

5-(2-((3-aminocyclobutyl)amino)cyclopropyl)-N-(1-ethyl-1H-pyrazol-4-yl)thiophene-3-carboxamide

Example E13

4-(2-((4-aminocyclohexyl)amino) cyclopropyl)-N-(1-ethyl-1H-pyrazol-4-yl)thiophene-2-carboxamide

Example E14

4-(2-((4-aminocyclohexyl)amino)cyclopropyl)-N-(1-ethyl-1H-pyrazol-4-yl)-5-methylthiophene-2-carboxamide

Example E15

5-(2-((4-aminocyclohexyl)amino)cyclopropyl)-N-(1-ethyl-1H-pyrazol-4-yl)-2-methylthiophene-3-carboxamide

Example E16

5-(2-((4-aminocyclohexyl)amino)cyclopropyl)-N-(1-ethyl-1H-pyrazol-4-yl)thiophene-3-carboxamide

Example E17

4-(2-((3-aminocyclobutyl)amino)cyclopropyl)-N-(1-methyl-TH-pyrazol-4-yl)thiophene-2-carboxamide

Example E18

4-(2-((3-aminocyclobutyl)amino)cyclopropyl)-5-methyl-N-(1-methyl-1H-pyrazol-4-yl)thiophene-2-carboxamide

Example E19

5-(2-((3-aminocyclobutyl)amino)cyclopropyl)-2-methyl-N-(1-methyl-1H-pyrazol-4-yl)thiophene-3-carboxamide

Example E20

5-(2-((3-aminocyclobutyl)amino)cyclopropyl)-N-(1-methyl-TH-pyrazol-4-yl)thiophene-3-carboxamide

Example E21

4-(2-((4-aminocyclohexyl)amino)cyclopropyl)-N-(1-methyl-1H-pyrazol-4-yl)thiophene-2-carboxamide

Example E22

4-(2-((4-aminocyclohexyl)amino)cyclopropyl)-5-methyl-N-(1-methyl-1H-pyrazol-4-yl)thiophene-2-carboxamide

Example E23

5-(2-((4-aminocyclohexyl)amino)cyclopropyl)-2-methyl-N-(1-methyl-1H-pyrazol-4-yl)thiophene-3-carboxamide

Example E24

5-(2-((4-aminocyclohexyl)amino)cyclopropyl)-N-(1-methyl-1H-pyrazol-4-yl)thiophene-3-carboxamide

Example E25

4-(2-((3-aminocyclobutyl)amino)cyclopropyl)-N-(1,3-dimethyl-1H-pyrazol-4-yl)thiophene-2-carboxamide

Example E26

4-(2-((3-aminocyclobutyl)amino)cyclopropyl)-N-(1,3-dimethyl-1H-pyrazol-4-yl)-5-methylthiophene-2-carboxamide

Example E27

5-(2-((3-aminocyclobutyl)amino)cyclopropyl)-N-(1,3-dimethyl-1H-pyrazol-4-yl)-2-methylthiophene-3-carboxamide

Example E28

5-(2-((3-aminocyclobutyl)amino)cyclopropyl)-N-(1,3-dimethyl-1H-pyrazol-4-yl)thiophene-3-carboxamide

Example E29

4-(2-((4-aminocyclohexyl)amino)cyclopropyl)-N-(1,3-dimethyl-1H-pyrazol-4-yl)thiophene-2-carboxamide

Example E30

4-(2-((4-aminocyclohexyl)amino)cyclopropyl)-N-(1,3-dimethyl-1H-pyrazol-4-yl)-5-methylthiophene-2-carboxamide

Example E31

5-(2-((4-aminocyclohexyl)amino)cyclopropyl)-N-(1,3-dimethyl-1H-pyrazol-4-yl)-2-methylthiophene-3-carboxamide

Example E32

5-(2-((4-aminocyclohexyl)amino)cyclopropyl)-N-(1,3-dimethyl-1H-pyrazol-4-yl)thiophene-3-carboxamide

Example E33

4-(2-((3-aminocyclobutyl)amino)cyclopropyl)-N-(1,3-dimethyl-1H-pyrazol-5-yl)thiophene-2-carboxamide

Example E34

4-(2-((3-aminocyclobutyl)amino)cyclopropyl)-N-(1,3-dimethyl-1H-pyrazol-5-yl)-5-methylthiophene-2-carboxamide

Example E35

5-(2-((3-aminocyclobutyl)amino)cyclopropyl)-N-(1,3-dimethyl-1H-pyrazol-5-yl)-2-methylthiophene-3-carboxamide

Example E36

5-(2-((3-aminocyclobutyl)amino)cyclopropyl)-N-(1,3-dimethyl-1H-pyrazol-5-yl)thiophene-3-carboxamide

Example E37

4-(2-((4-aminocyclohexyl)amino)cyclopropyl)-N-(1,3-dimethyl-1H-pyrazol-5-yl)thiophene-2-carboxamide

Example E38

4-(2-((4-aminocyclohexyl)amino)cyclopropyl)-N-(1,3-dimethyl-1H-pyrazol-5-yl)-5-methylthiophene-2-carboxamide

Example E39

5-(2-((4-aminocyclohexyl)amino) cyclopropyl)-N-(1,3-dimethyl-1H-pyrazol-5-yl)-2-methylthiophene-3-carboxamide

Example E40

5-(2-((4-aminocyclohexyl)amino)cyclopropyl)-N-(1,3-dimethyl-1H-pyrazol-5-yl)thiophene-3-carboxamide

Example E41

4-(2-((3-aminocyclobutyl)amino)cyclopropyl)-N-(4,4-difluorocyclohexyl)thiophene-2-carboxamide

Example E42

4-(2-((3-aminocyclobutyl)amino)cyclopropyl)-N-(4,4-difluorocyclohexyl)-5-methylthiophene-2-carboxamide

Example E43

5-(2-((3-aminocyclobutyl)amino) cyclopropyl)-N-(4,4-difluorocyclohexyl)-2-methylthiophene-3-carboxamide Example E44

5-(2-((3-aminocyclobutyl)amino) cyclopropyl)-N-(4,4-difluorocyclohexyl)thiophene-3-carboxamide Example E45

4-(2-((4-aminocyclohexyl)amino)cyclopropyl)-N-(4,4-difluorocyclohexyl)thiophene-2-carboxamide Example E46

4-(2-((4-aminocyclohexyl)amino)cyclopropyl)-N-(4,4-difluorocyclohexyl)-5-methylthiophene-2-carboxamide Example E47

5-(2-((4-aminocyclohexyl)amino)cyclopropyl)-N-(4,4-difluorocyclohexyl)-2-methylthiophene-3-carboxamide Example E48

5-(2-((4-aminocyclohexyl)amino)cyclopropyl)-N-(4,4-difluorocyclohexyl)thiophene-3-carboxamide Example E49

4-(2-((3-aminocyclobutyl)amino)cyclopropyl)-N-(5-methyl-1,2-oxazol-3-yl)thiophene-2-carboxamide Example E50

4-(2-((3-aminocyclobutyl)amino)cyclopropyl)-5-methyl-N-(5-methyl-1,2-oxazol-3-yl)thiophene-2-carboxamide Example E51

5-(2-((3-aminocyclobutyl)amino)cyclopropyl)-2-methyl-N-(5-methyl-1,2-oxazol-3-yl)thiophene-3-carboxamide Example E52

5-(2-((3-aminocyclobutyl)amino)cyclopropyl)-N-(5-methyl-1,2-oxazol-3-yl)thiophene-3-carboxamide Example E53

4-(2-((4-aminocyclohexyl)amino)cyclopropyl)-N-(5-methyl-1,2-oxazol-3-yl)thiophene-2-carboxamide Example E54

4-(2-((4-aminocyclohexyl)amino)cyclopropyl)-5-methyl-N-(5-methyl-1,2-oxazol-3-yl)thiophene-2-carboxamide Example E55

5-(2-((4-aminocyclohexyl)amino)cyclopropyl)-2-methyl-N-(5-methyl-1,2-oxazol-3-yl)thiophene-3-carboxamide Example E56

5-(2-((4-aminocyclohexyl)amino)cyclopropyl)-N-(5-methyl-1,2-oxazol-3-yl)thiophene-3-carboxamide Example E57

4-(2-((3-aminocyclobutyl)amino)cyclopropyl)-N-(2-methyl-, 3-thiazol-5-yl)thiophene-2-carboxamide Example E58

4-(2-((3-aminocyclobutyl)amino)cyclopropyl)-5-methyl-N-(2-methyl-1,3-thiazol-5-yl)thiophene-2-carboxamide Example E59

5-(2-((3-aminocyclobutyl)amino)cyclopropyl)-2-methyl-N-(2-methyl-1,3-thiazol-5-yl)thiophene-3-carboxamide Example E60

5-(2-((3-aminocyclobutyl)amino) cyclopropyl)-N-(2-methyl-1,3-thiazol-5-yl)thiophene-3-carboxamide Example E61

4-(2-((4-aminocyclohexyl)amino)cyclopropyl)-N-(2-methyl-1,3-thiazol-5-yl)thiophene-2-carboxamide Example E62

4-(2-((4-aminocyclohexyl)amino)cyclopropyl)-5-methyl-N-(2-methyl-1,3-thiazol-5-yl)thiophene-2-carboxamide Example E63

5-(2-((4-aminocyclohexyl)amino)cyclopropyl)-2-methyl-N-(2-methyl-1,3-thiazol-5-yl)thiophene-3-carboxamide

Example E64

5-(2-((4-aminocyclohexyl)amino)cyclopropyl)-N-(2-methyl-1,3-thiazol-5-yl)thiophene-3-carboxamide

Example E65

4-(2-((4,4-difluorocyclohexyl)amino)cyclopropyl)-N-(tetrahydro-2H-pyran-4-yl)thiophene-2-carboxamide

Example E66

4-(2-((4,4-difluorocyclohexyl)amino)cyclopropyl)-5-methyl-N-(tetrahydro-2H-pyran-4-yl)thiophene-2-carboxamide

Example E67

5-(2-((4,4-difluorocyclohexyl)amino)cyclopropyl)-2-methyl-N-(tetrahydro-2H-pyran-4-yl)thiophene-3-carboxamide

Example E68

5-(2-((4,4-difluorocyclohexyl)amino) cyclopropyl)-N-(tetrahydro-2H-pyran-4-yl)thiophene-3-carboxamide

Example E69

4-(2-((4,4-difluorocyclohexyl)amino)cyclopropyl)-N-(tetrahydro-2H-pyran-4-yl)thiophene-2-carboxamide

Example E70

4-(2-((4,4-difluorocyclohexyl)amino)cyclopropyl)-5-methyl-N-(tetrahydro-2H-pyran-4-yl)thiophene-2-carboxamide

Example E71

5-(2-((4,4-difluorocyclohexyl)amino)cyclopropyl)-2-methyl-N-(tetrahydro-2H-pyran-4-yl)thiophene-3-carboxamide

Example E72

5-(2-((4,4-difluorocyclohexyl)amino)cyclopropyl)-N-(tetrahydro-2H-pyran-4-yl)thiophene-3-carboxamide

Experimental Example 1

The genetic engineering method described below was performed according to the method described in a book (Maniatis et al., Molecular Cloning, Cold Spring Harbor Laboratory, 1989) or the method described in the protocol attached to the reagent.

(1) Construction of GST-Tagged Expression Vector Having TEV Protease Cleavage Sequence A GST-tagged expression vector having TEV Protease cleavage sequence was constructed by successive 2 times of PCR method. Firstly, PCR was performed using pGEX6P1 (GE Healthcare) as a template, two primers

```
GST-Sw-F:
                                      [SEQ ID NO: 1]
5'-AGAATCATTTAAATGGTGATCATGTAACCCATCCT-3'

GST-Tv-R1:
                                      [SEQ ID NO: 2]
5'-CGCCCTGAAAGTACAGGTTCTCATCCGATTTTGGAGGATGGTCG-3'
``` and PrimeStar GXL DNA Polymerase (Takara Bio Inc.). Template DNA 0.5 µL, PrimeStar GXL DNA Polymerase Buffer 10 µL, 2.5 mM dNTP solution 4 µL, 10 µM primer solution each 1.5 µL, PrimeStar GXL DNA Polymerase 1 µL, and sterilized distilled water 31.5 µL were mixed. After a treatment at 98° C. for 1 min, the PCR was started with 35 repeats of reactions at 98° C. for 10 seconds, at 65° C. for 5 seconds, and at 72° C. for 25 seconds, followed by a reaction at 72° C. for 1 min. Then, PCR was performed using the obtained PCR product as a template, two primers

```
GST-Sw-F:
                                      [SEQ ID NO: 1]
5'-AGAATCATTTAAATGGTGATCATGTAACCCATCCT-3'

GST-Tv-R2:
                                      [SEQ ID NO: 3]
5'-ATAATAGGATCCGCCCTGAA2GTACAGGTTCTC-3'
``` and PrimeStar GXL DNA Polymerase. Template DNA 0.5 µL, PrimeStar GXL DNA Polymerase Buffer 10 µL, 2.5 mM dNTP solution 4 µL, 10 µM primer solution each 1.5 µL, PrimeStar GXL DNA Polymerase 1 µL, and sterilized distilled water 31.5 µL were mixed. After a treatment at 98° C. for 1 min, the PCR was started with 25 repeats of reactions at 98° C. for 10 seconds, at 65° C. for 5 seconds, and at 72° C. for 25 seconds, followed by a reaction at 72° C. for 1 min. The obtained PCR product was electrophoresed on agarose gel (1%), and an about 0.3 kbp DNA fragment containing a part of the GST gene was recovered from the gel. The recovered DNA fragment was cleaved with restriction enzymes Swa I (New England Biolabs) and Bam HI (Takara Bio Inc.), and inserted into the Swa I/Bam HI site of pGEX6P1 to construct an expression vector pGEX7V1.

(2) Cloning of Human LSD1 (AOF2) cDNA

Human LSD1 cDNA was cloned by PCR method using brain cDNA Library (Takara Bio Inc.) as a template, two primers

```
hLSD1-NheI-ko-F:
                                      [SEQ ID NO: 4]
5'-TATTATGCTAGCGCCACCATGTTATCTGGGAAGAAGGCGGCAGC--3' hLSD1-St-NotI-R:
                                      [SEQ ID NO: 5]
5'-TATTATGCGGCCGCTCACATGCTTGGGGACTGCTGTGC-3'
``` and Pyrobest DNA Polymerase (Takara Bio Inc.). Template DNA 0.5 µL, Pyrobest DNA Polymerase Buffer 5 µL, 2.5 mM dNTP solution 4 µL, 10 µM primer solution each 2.5 µL, Pyrobest DNA Polymerase 0.5 µL, and sterilized distilled water 35 μL were mixed. After a reaction at 98° C. for 1 min, the PCR was started with 35 repeats of reactions at 98° C. for 10 seconds, at 68° C. for 5 seconds, and at 72° C. for 2.5 min, followed by a reaction at 72° C. for 1 min. The obtained PCR product was electrophoresed on agarose gel (1%), and an about 2.5 kbp DNA fragment containing the human LSD1 cDNA was recovered from the gel. The recovered DNA fragment was cleaved with restriction enzymes Nhe I and Not I (Takara Bio Inc.), and inserted into the Nhe I/Not I site of pcDNA3.1(+) (Invitrogen) to construct an expression plasmid pcDNA3.1/hLSD1.

(3) Construction of Expression Plasmid for Human LSD1 (172-833) in *Escherichia coli*

A plasmid for expression of human LSD1(172-833) in *Escherichia coli* was constructed by PCR method using pcDNA3.1/hLSD1 as a template, two primers

```
hLSD1-172aa-Bgl2-F:
                                           [SEQ ID NO: 6]
5'-ATAATAAGATCTTCGGGTGTGGAGGGCGCAGCTT-3' hLSD1-833aa-St-NotI-R:
                                           [SEQ ID NO: 7]
5'-ATAATAGOGGCCGCCATGGCCCCCAAAAACTGGTCTGCA-3'
``` and PrimeStar MAX DNA Polymerase (Takara Bio Inc.). Template DNA 1 μL, PrimeStar MAX DNA Polymerase Enzyme PreMix 25 μL, 10 μM primer solution each 1.5 μL, and sterilized distilled water 21 μL were mixed. After a reaction at 98° C. for 1 min, the PCR was started with 25 repeats of reactions at 98° C. for 10 seconds and at 68° C. for 8 seconds, followed by a reaction at 72° C. for 1 min. The obtained PCR product was electrophoresed on agarose gel (1%), and an about 2 kbp DNA fragment containing human LSD1(172-833) cDNA was recovered from the gel. The recovered DNA fragment was cleaved with restriction enzymes Bgl II and Not I (Takara Bio Inc.), and inserted into the Bam HI/Not I site of pGEX7V1 to construct an expression plasmid pGEX7V1/GST-hLSD1(172-833).

(4) Preparation of LSD1

*Escherichia coli* C43(DE3) pLysS was transformed with the expression plasmid pGEX7V1/GST-hLSD1(172-833). The obtained recombinant *Escherichia coli* was inoculated in a TB medium (1.2% tryptone, 2.4% yeast extract, 0.4% glycerol, 17 mM potassium dihydrogen phosphate and 72 mM dipotassium hydrogen phosphate) added with 100 mg/L ampicillin and 35 mg/L chloramphenicol, and cultured at 37° C. When the turbidity reached 500 Klett units, the culture temperature was changed to 16° C., IPTG (Isopropyl β-D-1-thiogalactopyranoside) having a final concentration of 0.5 mM was added to induce expression, and the cells were cultured further for 14 hr. The culture medium was centrifuged at 6,000 g for 15 min, and *Escherichia coli* pellets were recovered.

*Escherichia coli* pellets for 12 L of the culture medium were suspended in 1000 mL of PBS (Immuno-Biological Laboratories Co., Ltd.), 0.15 M NaCl, 5% (V/V) Glycerol (Buffer A), and 5000 units Benzonase (Merck), 1000 mg Lysozyme, and 10 tablets of Protease Inhibitor (Roche) were added. Using Branson ultrasonic disintegrator, the suspension was disrupted by ultrasonication for 3 min, and centrifuged at 33,000 g for 60 min, and the supernatant was recovered. The supernatant was applied to two GSTrap 4B 5 mL columns (GE Healthcare) equilibrated in advance with 0.1 M Tris (pH 8.0), 0.15 M NaCl, 5% (V/V) Glycerol (Buffer B), and the columns were each washed with 30 mL of Buffer B. GST-hLSD1(172-833) was eluted from each column with Buffer B added with 13 mL of GSH with the final concentration 20 mM, applied to two HiLoad 26/60 Superdex 200 pg columns (GE Healthcare) equilibrated in advance with Buffer B, and eluted with 380 mL of Buffer B. Total 60 mL of GST-hLSD1(172-833)-containing fraction was diluted 5-fold with 20 mM Tris (pH 8.0) (Buffer C), applied to Mono Q 10/100 GL column (GE Healthcare) equilibrated in advance with Buffer C, and 0-500 mM NaCl gradient elution was performed to give purified GST-hLSD1 (172-833). 3.4 mg of His-TEV protease was added to about 34 mg of GST-hLSD1(172-833), and the mixture was treated with 50 mM Tris (pH 8.0), 0.5 mM EDTA, 1 mM DTT at 4° C. for 16 hr to cleave the GST tag. The reaction mixture after the cleavage reaction was applied to two series-coupled columns with Ni-NTA Superflow Cartridges 1 mL (QIAGEN), and GSTrap 4B 5 mL column (GE Healthcare) equilibrated in advance with Buffer A added with Imidazole at a final concentration of 20 mM, and a flow-through fraction containing hLSD1(172-833) free of GST-tag was recovered. It was concentrated to 10 mL with AmiconUltra 15 (NWCO 30K) (Millipore Japan), and purified with HiLoad 26/60 Superdex 200 pg column (GE Healthcare) equilibrated with Buffer A to give hLSD1 purified product (8.4 mg). The protein concentration of hLSD1 was measured by BCA Protein Assay Kit (Thermo Fisher Scientific K.K.) using bovine serum albumin as the standard.

(5) Measurement of LSD1 Inhibitory Activity

A test compound dissolved in DMSO was added by to a reaction solution (50 mM Tris-HCl (pH 8.0), 0.1% BSA, 1 mM DTT) containing LSD1 enzyme, and the mixture was reacted at room temperature for 60 min. Biotin-histone H3 mono methylated K4 peptide solution (NH2-ART(me-K) QTARKSTGGKAPRKQLAGGK(Biotin)-CONH2) was added to start the reaction. After reaction at room temperature for 5 min, 2-PCPA solution was added to terminate the reaction. A detection solution (800 mM potassium fluoride, 0.1% BSA) containing europium-labeled anti-histone H3 antibody (Wako Pure Chemical Industries, Ltd.) and Streptavidin-XL665 (Cisbio) was further added, and the mixture was left standing for 60 min. A time-resolved fluorescence (excitation 320 nm, emission 615 nm, 665 nm) was measured by Envision (PerkinElmer). The LSD1 inhibitory rate (%) of the test compound was calculated by the following formula.

inhibitory rate (%)=(1−(test compound count−blank) ÷(control−blank))×100

The count of the LSD1 enzyme reaction mixture under compound non-addition conditions is indicated as control, and the count under compound non-addition and LSD1 enzyme non-addition conditions is indicated as blank. A concentration necessary for achieving 50% inhibitory rate was taken as $IC_{50}$ value. The results are shown in Table 2.

Experimental Example 2

(1) Measurement of MAO-A Inhibitory Activity

The MAO-A inhibitory activity evaluation described below followed the protocol of MAO-Glo (registered trademark) Assay of Promega KK.

A test compound dissolved in DMSO was added to a reaction solution (100 mM HEPES (pH 7.5), 5% glycerol) containing MAO-A enzyme (Sigma-Aldrich Co. LLC.), and the mixture was reacted at room temperature for 15 min. MAO substrate (Promega KK) was added to start the reaction. After reaction at room temperature for 60 min, Luciferine detection reagent (Promega KK) was added to terminate the reaction. After reaction at room temperature for 20 min with stirring, the luminescence was measured by Envision (PerkinElmer). The MAO-A inhibitory rate (%) of the test compound was calculated by the following formula.

inhibitory rate (%)=(1−(test compound count−blank)
÷(control−blank))×100

The count of the MAO-A enzyme reaction mixture under compound non-addition conditions is indicated as control, and the count under compound non-addition and MAO-A enzyme non-addition conditions is indicated as blank. A concentration necessary for achieving 50% inhibitory rate was taken as $IC_{50}$ value. The results are shown in Table 2.

(2) Measurement of MAO-B Inhibitory Activity

The MAO-B inhibitory activity evaluation described below followed the protocol of MAO-Glo (registered trademark) Assay of Promega KK.

A test compound dissolved in DMSO was added to a reaction solution (100 mM HEPES (pH 7.5), 5% glycerol, 10% DMSO) containing MAO-B enzyme (Sigma-Aldrich Co. LLC.), and the mixture was reacted at room temperature for 15 min. MAO substrate (Promega KK) was added to start the reaction. After reaction at room temperature for 60 min, Luciferine detection reagent (Promega KK) (50 µL) was added to terminate the reaction. After reaction at room temperature for 20 min with stirring, the luminescence was measured by Envision (PerkinElmer). The MAO-B inhibitory rate (%) of the test compound was calculated by the following formula.

inhibitory rate (%)=(1−(test compound count−blank)
÷(control−blank))×100

The count of the MAO-B enzyme reaction mixture under compound non-addition conditions is indicated as control, and the count under compound non-addition and MAO-B enzyme non-addition conditions is indicated as blank. A concentration necessary for achieving 50% inhibitory rate was taken as $IC_{50}$ value. The results are shown in Table 2.

TABLE 2

| Example No. | LSD1 $IC_{50}$ value (µM) | MAO-A $IC_{50}$ value (µM) | MAO-B $IC_{50}$ value (µM) |
| --- | --- | --- | --- |
| 1 | 1.3 | >100 | >100 |
| 2 | 0.33 | >100 | >100 |
| 3 | 0.29 | >100 | >100 |
| 4 | 1.7 | >100 | >100 |
| 5 | 4.6 | >100 | >100 |
| 6 | 0.11 | >100 | >100 |
| 7 | 0.26 | 82 | >100 |
| 8 | 0.25 | >100 | >100 |
| 9 | 3.0 | >100 | >100 |
| 10 | 0.23 | >100 | >100 |
| 11 | 0.18 | >100 | >100 |
| 12 | <0.1 | >100 | >100 |
| 13 | 12 | >100 | 93 |
| 14 | 2.4 | >100 | 28 |
| 15 | 0.73 | 89 | 66 |
| 16 | <0.1 | >100 | >100 |
| 17 | 0.22 | >100 | >100 |
| 18 | 0.26 | >100 | >100 |
| 19 | 0.65 | >100 | >100 |
| 20 | <0.1 | >100 | >100 |
| 21 | 0.23 | >100 | 88 |
| 22 | 0.14 | >100 | >100 |
| 23 | <0.1 | >100 | >100 |
| 24 | <0.1 | >100 | >100 |
| 25 | 3.0 | >100 | >100 |
| 26 | 0.50 | >100 | >100 |
| 27 | 0.33 | >100 | >100 |
| 28 | <0.1 | >100 | >100 |
| 29 | 0.40 | >100 | >100 |
| 30 | <0.1 | >100 | >100 |
| 31 | <0.1 | >100 | >100 |
| 32 | <0.1 | >100 | >100 |
| 33 | <0.1 | >100 | >100 |
| 34 | <0.1 | >100 | >100 |
| 35 | 0.68 | >100 | >100 |
| 36 | 3.8 | 22 | 6.0 |
| 37 | 99 | 85 | 90 |
| 38 | <0.1 | >100 | >100 |
| 39 | <0.1 | 23 | >100 |
| 40 | <0.1 | >100 | >100 |
| 41 | <0.1 | 67 | >100 |
| 42 | <0.1 | >100 | >100 |
| 43 | 0.13 | >100 | >100 |
| 44 | <0.1 | >100 | 100 |
| 45 | <0.1 | >100 | >100 |
| 46 | <0.1 | >100 | >100 |
| 47 | <0.1 | >100 | >100 |
| 48 | <0.1 | 31 | >100 |
| 49 | <0.1 | >100 | >100 |
| 50 | <0.1 | >100 | >100 |
| 51 | <0.1 | >100 | >100 |
| 52 | <0.1 | >100 | >100 |
| 53 | <0.1 | 61 | 96 |
| 54 | <0.1 | >100 | >100 |
| 55 | <0.1 | >100 | >100 |
| 56 | <0.1 | >100 | >100 |
| 57 | 0.44 | >100 | >100 |
| 58 | <0.1 | >100 | >100 |
| 59 | <0.1 | >100 | >100 |
| 60 | <0.1 | >100 | >100 |
| 61 | <0.1 | >100 | >100 |
| 62 | <0.1 | >100 | >100 |
| 63 | 0.32 | >100 | >100 |
| 64 | 0.30 | >100 | >100 |
| 65 | <0.1 | 25 | >100 |
| 66 | <0.1 | 98 | >100 |
| 67 | 0.10 | 76 | >100 |
| 68 | 0.14 | >100 | >100 |
| 69 | <0.1 | 33 | >100 |
| 70 | <0.1 | 10 | 23 |
| 71 | <0.1 | >100 | >100 |
| 72 | <0.1 | >100 | >100 |
| 73 | 0.58 | >100 | >100 |
| 74 | <0.1 | >100 | >100 |
| 75 | 0.34 | >100 | >100 |
| 76 | 0.20 | >100 | >100 |
| 77 | 0.36 | >100 | >100 |
| 78 | <0.1 | >100 | >100 |
| 79 | 0.27 | >100 | >100 |
| 80 | <0.1 | >100 | >100 |
| 81 | <0.1 | 36 | >100 |
| 82 | 0.24 | >100 | >100 |
| 83 | 0.28 | >100 | >100 |
| 84 | 0.23 | >100 | >100 |
| 85 | 0.81 | >100 | >100 |
| 86 | <0.1 | 87 | >100 |
| 87 | 0.18 | >100 | >100 |
| 88 | <0.1 | >100 | >100 |
| 89 | <0.1 | >100 | >100 |
| 90 | 0.10 | >100 | >100 |
| 91 | <0.1 | >100 | >100 |
| 92 | <0.1 | >100 | >100 |
| 93 | 0.16 | >100 | >100 |
| 94 | 0.21 | >100 | >100 |
| 95 | 0.18 | >100 | >100 |
| 96 | 0.59 | >100 | >100 |
| 97 | <0.1 | >100 | >100 |
| 98 | 0.27 | >100 | >100 |
| 99 | <0.1 | >100 | >100 |
| 100 | 0.82 | >100 | >100 |
| 101 | <0.1 | >100 | >100 |
| 102 | 0.21 | >100 | >100 |
| 103 | 0.15 | >100 | >100 |
| 104 | <0.1 | >100 | >100 |
| 105 | 0.21 | >100 | >100 |

TABLE 2-continued

| Example No. | LSD1 IC$_{50}$ value (µM) | MAO-A IC$_{50}$ value (µM) | MAO-B IC$_{50}$ value (µM) |
|---|---|---|---|
| 106 | 0.44 | >100 | >100 |
| 107 | 1.40 | >100 | >100 |
| 108 | 0.34 | >100 | >100 |
| 109 | 2.30 | >100 | >100 |
| 110 | <0.1 | 49 | >100 |
| 111 | 0.10 | 61 | >100 |
| 112 | <0.1 | >100 | >100 |
| 113 | <0.1 | >100 | >100 |
| 114 | <0.1 | >100 | >100 |
| 115 | <0.1 | >100 | >100 |
| 116 | 0.29 | >100 | >100 |
| 117 | 0.26 | >100 | >100 |
| 118 | 0.24 | >100 | >100 |
| 119 | 0.19 | >100 | >100 |
| 120 | <0.1 | >100 | >100 |
| 121 | 0.12 | >100 | >100 |
| 122 | 0.17 | >100 | >100 |
| 123 | 0.10 | >100 | >100 |
| 124 | 1.90 | >100 | >100 |
| 125 | <0.1 | >100 | >100 |

As shown in Table 2, the compound of the present invention has a superior LSD1 inhibitory activity. In addition, the MAO-A inhibitory activity and MAO-B inhibitory activity of the compound of the present invention are low, and the compound of the present invention has a selective LSD1 inhibitory activity.

Experimental Example 3

Gad1 H3K4 Methylation Induction Activity in Rat Primary Culture Neurons
Experimental Method Hippocampus and cerebral cortex were isolated from fetal SD rat at embryonic day 19, a cell suspension was prepared using Nerve Cell Dissociation Medium (SUMITOMO BAKELITE, MS-0006L), and plated on a poly L-lysine-coated 6-well plate (SUMITOMO BAKELITE, MS-0006L) at a density of 900000 cells/well. Under the conditions of 37° C. and 5% CO$_2$, the cells were cultured in a neurobasal medium (Invitrogen, #211103049) containing B27 supplement (Invitrogen, #17504044, 1:50 dilution), 2 mM L-glutamine (Lonza, #B76053), 100 U/mL penicillin/100 µg/mL streptomycin (Lonza, #17-602E), and 20 µg/mL gentamicin sulfate (Lonza, #17-519Z) for 10 days.

Thereafter, the compound was added to final concentrations of 10 µM, the cells were further cultured for 3 days, and chromatin immunoprecipitation was performed. Chromatin immunoprecipitation was performed by using ChIP-IT Express Enzymatic (Active Motif, #53009) and H3K4me2 antibody (Millipore, #07-030). The culture supernatant was aspirated, ice-cold PBS was added, and the cell suspension was collected on ice using CELL SCRAPER (IWAKI). The supernatant was removed by centrifugation at 3000 rpm, 4° C. for 5 min. Lysis buffer (500 µL) was added to the precipitate, and the cells were lysed by incubating for 30 min on ice. Thereafter, the suspension was centrifuged at 2400 g, 4° C. for 10 min, the supernatant was removed, the pellet was suspended in cell lysis buffer [60 mM KCl, 15 mM NaCl, 5 mM MgCl$_2$, 0.1 mM EGTA, 15 mM Tris-HCl (pH 7.6), 1.2 M sucrose, 0.5 mM DTT, protease inhibitor (Roche, #4693132)] (500 µL), and the suspension was centrifuged at 10000 g, 4° C. for 10 min. The supernatant was removed, and the pellet was suspended in Digestion buffer (120 µL) and preincubated at 37° C. for 5 min. Shearing cocktail was added, and the mixture was incubated at 37° C. for 20 min. 0.5 M EDTA (2.4 µL) was added, and the mixture was incubated for 10 min on ice and centrifuged at 18000 rpm, 4° C. for 10 min. The supernatant was collected as a chromatin fraction and subjected to immunoprecipitation.

Using the DNA obtained by the chromatin immunoprecipitation as a template, quantitative PCR of the Gad1 gene upstream genomic region was performed, and the measurement value was taken as the Gad1 H3K4me2 level. The quantitative PCR was performed by ABI PRISM 7900HT Sequence Detection System (Applied Biosystems) using forward primer: 5'-TGATCTTTTCCCTGCTGTCA-3' (SEQ ID NO: 8), reverse primer: 5'-TCCCATGAGTAATCCA-GAACG-3' (SEQ ID NO: 9), and SYBR Green Realtime PCR Master Mix-Plus-(TOYOBO, #QPK-212). The Gad1 H3K4me2 induction by the compound was expressed by the H3K4me2 level when the compound was added, as compared to the H3K4me2 level of the control (without addition of the compound) as 100%.

Gad1 H3K4me2 induction activity (%) (H3K4me2 induction expressed as percentage of control)= (H3K4me2 level with addition of compound÷H3K4me2 level without addition of compound)×100

The Gad1 H3K4me2 induction activity by each compound as measured by the above-mentioned method is shown in Table 3.

TABLE 3

| Example No. | Gad1 H3K4me2 induction activity (%) 10 µM |
|---|---|
| 102 | 153 |
| 82 | 115 |
| 123 | 143 |
| 99 | 146 |
| 97 | 184 |
| 71 | 182 |
| 118 | 233 |

From the results of Table 3, it was clarified that the compound of the present invention has an inductive effect on H3K4 methylation.

Experimental Example 4

Evaluation of Blood Cell Number in Mouse
Experimental Method

Male ICR mice (hereinafter mice) were acclimated for at least one week in a rearing facility. The mice were raised in a rearing room with controlled temperature and humidity under a 12:12 hour light-dark cycle, and allowed free ingestion of feed and water.

The compounds were suspended in 0.5% methylcellulose/ 0.5% citric acid/distilled water and orally administered. All compounds were repeatedly administered to the mice at a dose of 1 mg/kg, 10 mg/kg or 100 mg/kg (body weight) for 7 or 9 days. One day after the final administration of the compound, the whole blood was collected.

Using Sysmex XT-1800i (Sysmex Corporation), the white blood cell number, red blood cell number, and platelet number in the collected whole blood per unit volume were measured. The influence of each compound on each blood cell number was determined by calculating the number with the mean of each blood cell number of the mouse without administration of the compound (0 mg/kg group), and the mean of each blood cell number in the whole blood of a mouse with the administration of the compound. The values of the blood cell numbers measured by the above-mentioned method are shown in Table 4.

TABLE 4

| Example No. | 0 mg/kg | | 1 mg/kg | | 10 mg/kg | | 100 mg/kg | |
|---|---|---|---|---|---|---|---|---|
| | Mean | S.E. | Mean | S.E. | Mean | S.E. | Mean | S.E. |
| White blood cells (10 cells) | | | | | | | | |
| 102 | 457 | 71 | 335 | 40 | 425 | 34 | 361 | 50 |
| 99 | 340 | 30 | 399 | 46 | 378 | 40 | 347 | 28 |
| 97 | 397 | 59 | 377 | 43 | 366 | 44 | 332 | 34 |
| 71 | 275 | 15 | 275 | 29 | 276 | 20 | 323 | 16 |
| 82 | 322 | 17 | 403 | 47 | 424 | 51 | 329 | 21 |
| 84 | 312 | 44 | 370 | 30 | 339 | 41 | 313 | 38 |
| 118 | 275 | 15 | 299 | 51 | 312 | 34 | 245 | 12 |
| 123 | 389 | 42 | 390 | 47 | 368 | 22 | 380 | 24 |
| 104 | 375 | 22 | 373 | 44 | 397 | 28 | — | — |
| 95 | 375 | 22 | 422 | 46 | 408 | 27 | — | — |
| Red blood cells ($10^4$ cells) | | | | | | | | |
| 102 | 888 | 16 | 903 | 12 | 929 | 18 | 929 | 16 |
| 99 | 863 | 17 | 892 | 17 | 915 | 20 | 876 | 19 |
| 97 | 902 | 12 | 902 | 12 | 890 | 25 | 929 | 18 |
| 71 | 830 | 32 | 873 | 23 | 817 | 20 | 853 | 8 |
| 82 | 872 | 11 | 899 | 20 | 926 | 21 | 903 | 19 |
| 84 | 884 | 25 | 910 | 18 | 880 | 24 | 900 | 12 |
| 118 | 830 | 32 | 853 | 17 | 907 | 19 | 881 | 13 |
| 123 | 829 | 13 | 846 | 14 | 854 | 13 | 866 | 7 |
| 104 | 883 | 8 | 870 | 16 | 872 | 16 | — | — |
| 95 | 883 | 8 | 888 | 15 | 898 | 12 | — | — |
| Platelets ($10^3$ cells) | | | | | | | | |
| 102 | 1401 | 53 | 1387 | 56 | 1499 | 43 | 1417 | 61 |
| 99 | 1468 | 71 | 1442 | 65 | 1380 | 49 | 1519 | 99 |
| 97 | 1466 | 22 | 1462 | 65 | 1483 | 78 | 1533 | 55 |
| 71 | 1148 | 63 | 1178 | 76 | 1197 | 67 | 1322 | 91 |
| 82 | 1389 | 35 | 1399 | 44 | 1445 | 38 | 1411 | 58 |
| 84 | 1515 | 60 | 1533 | 43 | 1627 | 58 | 1665 | 107 |
| 118 | 1148 | 63 | 1051 | 71 | 1158 | 66 | 1176 | 60 |
| 123 | 1130 | 58 | 1086 | 79 | 1234 | 68 | 1333 | 75 |
| 104 | 1345 | 33 | 1370 | 32 | 1404 | 77 | — | — |
| 95 | 1345 | 33 | 1352 | 66 | 1482 | 66 | — | — |

From the results of Table 4, it was clarified that the compound of the present invention reduces an influence on the white blood cell number, red blood cell number and platelet number.

Experimental Example 5

Evaluation of Hippocampal Distribution in Mouse
Experimental Method

Male ICR mice (hereinafter mice) were acclimated for at least one week in a rearing facility. The mice were raised in a rearing room with controlled temperature and humidity under a 12:12 hour light-dark cycle, and allowed free ingestion of feed and water.

The compounds were suspended in 0.5% methylcellulose/0.5% citric acid/distilled water and orally administered. All compounds were administered to the mice at a dose of 10 mg/kg (body weight).

Blood samples were collected at 0.5 hr or 1 hr from compound administration, and the hippocampus was isolated simultaneously. The plasma concentration and hippocampus concentration of each test compound were measured by the LC/MS/MS method, the ratio (hippocampus/plasma concentration ratio) was calculated, and distribution into hippocampus was evaluated. The results are shown in Table 5.

TABLE 5

| Example No. | time after administration (h) | Concentration (μg/mL or μg/g) | | | | Ratio (hippocampus/plasma) | |
|---|---|---|---|---|---|---|---|
| | | Plasma | | Hippocampus | | | |
| | | Mean | S.D. | Mean | S.D. | Mean | S.D. |
| 102 | 1 | 0.348 | 0.008 | 0.104 | 0.021 | 0.298 | 0.062 |
| 99 | 1 | 2.948 | 0.934 | 0.640 | 0.168 | 0.223 | 0.047 |
| 97 | 1 | 0.978 | 0.182 | 0.194 | 0.012 | 0.205 | 0.051 |
| 71 | 1 | 0.229 | 0.027 | 0.082 | 0.015 | 0.358 | 0.063 |
| 82 | 1 | 1.327 | 0.115 | 0.170 | 0.021 | 0.128 | 0.015 |
| 84 | 1 | 0.523 | 0.120 | 0.177 | 0.040 | 0.339 | 0.014 |
| 118 | 1 | 0.405 | 0.113 | 0.151 | 0.022 | 0.384 | 0.061 |
| 123 | 0.5 | 1.107 | 0.123 | 0.369 | 0.089 | 0.333 | 0.070 |

As shown in Table 5, the compounds of the present invention were all confirmed to have distributed into the hippocampus.

Formulation Example 1

A medicament containing the compound of the present invention as an active ingredient can be produced, for example, according to the following formulation.

1. Capsule

| | |
|---|---|
| (1) compound obtained in Example 1 | 10 mg |
| (2) lactose | 90 mg |
| (3) crystalline cellulose | 70 mg |
| (4) magnesium stearate | 10 mg |
| 1 capsule | 180 mg |

The total amount of the above-mentioned (1), (2) and (3) and 5 mg of (4) are blended, and the mixture is granulated. Thereto is added the remaining 5 mg of (4), and the whole is sealed in a gelatin capsule.

2. Tablet

| | |
|---|---|
| (1) compound obtained in Example 1 | 10 mg |
| (2) lactose | 35 mg |
| (3) cornstarch | 150 mg |
| (4) crystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended, and the mixture is granulated. Thereto are added the remaining 10 mg of (4) and 2.5 mg of (5), and the mixture is compression-molded to give a tablet.

INDUSTRIAL APPLICABILITY

The compound of the present invention has a superior LSD1 inhibitory action, and is useful as a medicament such as a prophylactic or therapeutic agent for cancer, schizophrenia, developmental disorders, particularly diseases having intellectual disability (e.g., autistic spectrum disorders, Rett syndrome, Down's syndrome, Kabuki syndrome, fragile X syndrome, Kleefstra syndrome, neurofibromatosis type 1, Noonan syndrome, tuberous sclerosis), neurodegenerative diseases (e.g., Alzheimer's disease, Parkinson's disease, spinocerebellar degeneration (e.g., dentatorubural pallidoluysian atrophy) and Huntington's disease (Huntington chorea)), epilepsy (e.g., Dravet syndrome) or drug dependence, and the like.

This application is based on patent application No. 2014-82057 filed in Japan, the entire contents of which are incorporated by reference herein.

The invention claimed is:

1. A method for the treatment of autistic spectrum disorders, in a mammal, comprising administering an effective amount of 5-((1R,2R)-2-((cyclopropylmethyl)amino)cyclopropyl)-N-(tetrahydro-2H-pyran-4-yl)thiophene-3-carboxamide or a salt thereof to the mammal.

* * * * *